US009989536B2

(12) United States Patent
Grabulovski et al.

(10) Patent No.: US 9,989,536 B2
(45) **Date of Patent: *Jun. 5, 2018**

(54) SPECIFIC AND HIGH AFFINITY BINDING PROTEINS COMPRISING MODIFIED SH3 DOMAINS OF FYN KINASE

(71) Applicant: EIDGENOESSISCHE TECHNISCHE HOCHSCHULE ZURICH, Zurich (CH)

(72) Inventors: Dragan Grabulovski, Zurich (CH); Dario Neri, Buchs (CH)

(73) Assignee: EIDGENOESSISCHE TECHNISCHE HOCHSCHULE ZURICH, Zurich (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/601,353

(22) Filed: May 22, 2017

(65) Prior Publication Data

US 2017/0307628 A1 Oct. 26, 2017

Related U.S. Application Data

(60) Continuation of application No. 15/252,938, filed on Aug. 31, 2016, now Pat. No. 9,689,879, which is a division of application No. 14/490,953, filed on Sep. 19, 2014, now Pat. No. 9,513,296, which is a continuation-in-part of application No. 12/310,315, filed as application No. PCT/EP2007/007324 on Aug. 20, 2007, now abandoned.

(30) Foreign Application Priority Data

Aug. 21, 2006 (EP) .................................... 06017336

(51) Int. Cl.
*G01N 33/68* (2006.01)
*C40B 30/04* (2006.01)

(52) U.S. Cl.
CPC ... *G01N 33/6845* (2013.01); *G01N 2333/912* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | | | |
|---|---|---|---|---|
| 6,326,469 | B1 | 12/2001 | Ullrich et al. | |
| 9,689,879 | B2 * | 6/2017 | Grabulovski | G01N 33/6845 |

FOREIGN PATENT DOCUMENTS

| | | | |
|---|---|---|---|
| CN | 1415012 | A | 4/2003 |
| CN | 1816564 | A | 8/2006 |
| EP | 1 541 694 | A1 | 6/2005 |
| JP | 2005-516605 | A | 6/2005 |
| WO | 01/62298 | A2 | 8/2001 |
| WO | 03/013523 | A1 | 2/2003 |
| WO | 03/065984 | A2 | 8/2003 |
| WO | 2004/023973 | A2 | 3/2004 |
| WO | 2004/042022 | A2 | 5/2004 |
| WO | 2005/019258 | A2 | 3/2005 |
| WO | 2007/030426 | A2 | 3/2007 |
| WO | 2007/030594 | A2 | 3/2007 |

OTHER PUBLICATIONS

Skerra, Arne, "Engineered Protein Scaffolds for Molecular Recognition", Journal of Molecular Recognition, vol. 13, pp. 167-187, 2000.
Borchert, T.V., et al., "The Crystal Structure of Human CskSH3: Structural Diversity Near the RT-Src and n-Src Loop", FEBS Letters, vol. 341, pp. 79-85, 1994.
Brack, Simon, et al., "A Bispecific HER2-Targeting FynomAb with Superior Antitumor Activity and Novel Mode of Action", Molecular Cancer Therapeutics, vol. 13, pp. 2030-2039, 2014.
"FYN SH3-Derived Proteins (Fynomers) Binding to GST", Covagen Advanced Biopharmaceuticals.
Koide, Akiko, et al., "The Fibronectin Type III Domain as a Scaffold for Novel Binding Proteins", Journal of Molecular Biology, vol. 284, pp. 1141-1151, 1998.
Canadian Intellectual Property Office; Office Action dated Jun. 6, 2012 for CA 2,661,160; four (4) pages.
State Intellectual Property Office of People's Republic China; Search Report dated Jan. 20, 2014 for CN 201310010977.7; two (2) pages.
Japanese Patent Office; Office Action dated Jul. 12, 2011 for JP 2009-524142; seven (7) pages.
Ferguson et al., Directed discovery of bivalent peptide ligands to an SH3 domain, Prot. Sci (13), 626-632 (2004).
Tomlinson, Next-generation protein drugs, Nature Biotech (5), 521-522 (2004).
Banner et al., Mapping the conformational space accessible to BACE2 using surface mutants and cocrystals with Fab fragments, Fynomers and Xaperones, Acta Cryst. (D69), 1124-1137 (2013).
Schlatter et al., Generation, characterization and structural data of chymase binding proteins based on the human Fyn kinase SH3 domain, http:dx.doi.org/10.4161/mabs.20452 (2012).
Grabulovski et al., A Novel, Non-immunogenic Fyn SH3-derived Binding Protein with Tumor Vascular Targeting Properties, J. Biol. Chem. (282), 3196-3204 (2007).
Hoogenboom et al., By-passing Immunisation: Human Antibodies from Synthetic Repertoires of Germline VH Gene Segments Rearranged in Vitro, J. Mol. Biol. (227), 381-388 (1992).
Niissim et al., Antibody fragments from a 'single pot' phage display library as immunochemical reagents, EMBO J. (13), 692-698 (1994).

(Continued)

*Primary Examiner* — Channing S Mahatan
(74) *Attorney, Agent, or Firm* — Nath, Goldberg & Meyer; Tanya E. Harkins; Joshua B. Goldberg

(57) ABSTRACT

The present invention relates to a method for the production of a library comprising recombinant derivatives of the SH3 domain of the Fyn kinase of SEQ ID NO: 1 as well as a method for selecting from a library comprising recombinant derivatives of the SH3 domain of the Fyn kinase of SEQ ID NO: 1 one or more of said derivatives having a specific binding affinity to a protein or peptide.

7 Claims, 57 Drawing Sheets

(56) References Cited

OTHER PUBLICATIONS

Hoogenboom, Designing and optimizing library selection strategies for generating high-affinity antibodies, Tibtech (15), 62-70 (1997).
Beste et al., Small antibody-like proteins with prescribed ligand specificities derived from the lipocalin fold, Proc. Natl. Acad. Sci. (96), 1898-1903 (1999).
Nygren et al., Binding proteins from alternative scaffolds, J. Immunological Methods (290), 3-28 (2004).
Silacci et al., Design, construction, and characterization of a large synthetic human antibody phage display library, Proteomics (5), 2340-2350 (2005).
Hoogenboom, Selecting and screening recombinant antibody libraries, Nature Biotech. (23), 1105-1116 (2005).
Locher et al., COVA322: A Novel, Bispecific Tumor-Necrosis-Factor-Alpha / Interleukin-17A (TNF/IL-17A) Inhibitor With Excellent Pharmacokinetic Properties in Mice and Cynomolgus Monkeys, ACR meeting, Abstract No. 2225 (2013).
Grabulovski et al., Bispecific Fynomer-antibody fusion proteins targeting two epitopes on HER2, Cancer Res. (72, 24 Suppl) (2012).
Binz, H Kaspar et al., "Engineering novel binding proteins from nonimmunoglobulin domains", Nature Biotechnology, 2005, pp. 1257-1268, vol. 23, No. 10.
Cohen, George B. et al., "Modular Binding Domains in Signal Transduction Proteins", Cell, 1995, pp. 237-248, vol. 80.
Erpel, Thorsten et al., "Mutational analysis of the Src SH3 domain: the same residues of the ligand binding surface are important for intra- and intermolecular interactions", The EMBO Journal, 1995, pp. 963-975, vol. 14, No. 4.
Hiipakka, Marita et al., "SH3 Domains with High Affinity and Engineered Ligand Specificities Targeted to HIV-1 Nef", J. Mol. Biol., 1999, pp. 1097-1106, vol. 293.
Lee, Chi-Hon et al., "A single amino acid in the SH3 domain of Hck determines its high affinity and specificity in binding to HIV-1 Nef protein", The EMBO Journal, 1995, pp. 5006-5015, vol. 14, No. 20.
Hosse, Ralf J. et al., "A new generation of protein display scaffolds for molecular recognition", Protein Science, 2006, pp. 14-27, vol. 15, Cold Spring Harbor Laboratory Press.
Semba, Kentaro et al., "yes-related protooncogene, syn, belongs to the protein-tyrosine kinase family", Proc. Natl. Acad. Sci. USA, 1986, pp. 5459-5463, vol. 83.
Kawakami, Toshiaki et al., "Isolation and Oncogenic Potential of a Novel Human src-Like Gene", Molecular and Cellular Biology, 1986, pp. 4195-4201, vol. 6, No. 12.
Cooke, Michael P. et al., "Expression of a Novel Form of the fyn Proto-Oncogene in Hematopoietic Cells", The New Biologist, 1989, pp. 66-74, vol. 1, No. 1.
Resh, Marilyn D., "Molecules in focus: Fyn, a Src family tyrosine kinase", The International Journal of Biochemistry & Cell Biology, 1998, pp. 1159-1162, vol. 30.
Huang, Xiaoqiu, "A Time-Efficient, Linear-Space Local Similarity Algorithm", Advances in Applied Mathematics, 1991, pp. 337-357, vol. 12.
Thompson, Julie D. et al., "CLUSTAL W: improving the sensitivity of progressive multiple sequence alignment through sequence weighting, position-specific gap penalties and weight matrix choice", Nucleic Acids Research, 1994, pp. 4673-4680, vol. 22, No. 22.
Neri, Dario et al., "Tumour Vascular Targeting", Nature Reviews Cancer, 2005, pp. 436-446, vol. 5.
Berlier, Judith E. et al., "Quantitative Comparison of Long-wavelength Alexa Fluor Dyes to Cy Dyes: Fluorescence of the Dyes and Their Bioconjugates", The Journal of Histochemistry & Cytochemistry, 2003, pp. 1699-1712, vol. 51, No. 12.
Hoogenboom, Hennie R. et al., "Multi-subunit proteins on the surface of filamentous phage: methodologies for displaying antibody (Fab) heavy and light chains", Nucleic Acids Research, 1991, pp. 4133-4137, vol. 19, No. 15.
Zardi, Luciano et al., "Transformed human cells produce a new fibronectin isoform by preferential alternative splicing of a previously unobserved exon", The EMBO Journal, 1987, pp. 2337-2342, vol. 6, No. 8.
Menrad, Andreas et al., "ED-B fibronectin as a target for antibody-based cancer treatments", Expert Opin. Ther. Targets, 2005, pp. 491-500, vol. 9, No. 3.
Kaspar, et al., "Fibronectin as target for tumor therapy," Int. J. Cancer, (2006), vol. 118, pp. 1331-1339.
Panni, et al., "In Vitro Evolution of Recognition Specificity Mediated by SH3 Domains Reveals Target Recognition Rules," The Journal of Biological Chemistry, (2002), vol. 277, No. 24, pp. 21666-21674.

* cited by examiner

A

| | maximal effect (% viability) |
|---|---|
| anti-HER2 mAb 1 | 82 |
| COVA201 | 61 |
| COVA202 | 67 |

B

| | maximal effect (% viability) |
|---|---|
| anti-HER2 mAb 1 | 81 |
| COVA207 | 52 |
| COVA208 | 37 |

SDS-PAGE

MW: molecular weight marker
lane 1: anti-HER2 mAb 1
lane 2: anti-HER2 mAb 1 (reduced)
lane 3: COVA208
lane 4: COVA208 (reduced)

Size exclusion chromatography of COVA208

C

A

B

D

E

A

B

SPECIFIC AND HIGH AFFINITY BINDING PROTEINS COMPRISING MODIFIED SH3 DOMAINS OF FYN KINASE

This is a Continuation Application of U.S. patent application Ser. No. 15/252,938, filed Aug. 31, 2016, which was a Divisional of Ser. No. 14/490,953, filed Sep. 19, 2014, which was a Continuation-In-Part Application of U.S. patent application Ser. No. 12/310,315, filed Feb. 20, 2009, which was a national phase application under 371 of PCT/EP2007/007324 with an international filing date of Aug. 20, 2007 and claimed priority to European Patent Application No. 06017336.6 filed Aug. 21, 2006, the content of each which is hereby incorporated by reference in its entirety.

FIELD OF THE INVENTION

The present invention relates to a method for the production of a library comprising recombinant derivatives of the SH3 domain of the Fyn kinase of SEQ ID NO: 1 as well as a method for selecting from a library comprising recombinant derivatives of the SH3 domain of the Fyn kinase of SEQ ID NO: 1 one or more of said derivatives having a specific binding affinity to a protein or peptide.

The Sequence Listing submitted in text format (.txt) filed on Aug. 31, 2016, named "S1236 US1 Sequenzprotokoll 4010961.txt", (created on Sep. 11, 2014, 364 KB), is incorporated herein by reference.

BACKGROUND OF THE INVENTION

Specific and high-affinity binding agents are indispensable tools for biological and medical research and also have utility for medical diagnosis, prophylaxis and treatment. At present, monoclonal antibodies are the predominant class of binding molecules that can be rapidly isolated with high affinity and specificity to virtually any target. However, immunoglobulins have limitations that are based mostly on their general biophysical properties and their rather complicated molecular structure. Therefore, already in the 1990's several research groups have explored small globular proteins as substitutes for antibodies. The idea behind this concept is the transfer of a universal binding site from an antibody structure to alternative protein frameworks, the so-called scaffolds. So far more than 40 scaffolds have been described, among them two SH3 domains, the SH3 domains of the Abl and the Src kinase (see Binz et al., Nature Biotechnology, Vol. 23, No. 10, 1257-1268, 2005).

SH3 domains are found in many different proteins involved in intracellular signalling and cytoskeletal organization (Cohen et al., "Modular binding domains in signal transduction proteins." Cell 80(2): 237-48, 1995). Despite the variability in their primary structures these SH3 domains share a very similar overall structure and mode of binding to proteins sharing the minimal consensus sequence PxxP that is a critical determinant for natural SH3 binding. An important function of SH3 domains is to participate in highly selective protein-protein interactions.

Erpel et al. ("Mutational analysis of the Src SH3 domain: the same residues of the ligand binding surface are important for intra- and intermolecular interactions." Embo J. 14(5): 963-75, 1995) investigated the influence of mutations in the RT and n-Src loops of Src SH3 domains and demonstrated that mutations in both loops which are adjacent to the hydrophobic surface could influence the ability of this domain to participate in inter- and intramolecular associations.

Hiipakka et al. ("SH3 domains with high affinity and engineered ligand specificities targeted to HIV-1 Nef." J. Mol. Biol. 293(5): 1097-106, 1999) investigated the ability of the RT-loop of the Hck SH3 domain to act as a versatile specificity and affinity determinant. The authors constructed a phage library of Hck domains, where 6 amino acids of the RT-Loop were randomized (termed RRT-SH3). Using this strategy they identified individual RRT-SH3 domains that can bind to HIV-1 Nef up to 40 times better than Hck-Sh3. The authors indicate the importance of the RT loop in SH3 ligand selection as a general strategy for creating SH3 domains with desired binding properties.

Lee et al. ("A single amino acid in the SH3 domain of Hck determines its high affinity and specificity in binding to HIV-1 Nef protein." Embo. J. 14(20): 5006-15, 1995) investigated the structural basis of the different SH3 binding affinities and specificities of Hck to the HIV-1 Nef protein and were able to transfer the binding property of Hck SH3 towards Nef to the Fyn SH3 domain by a single mutation in the RT loop of the Fyn SH3 domain (R96I).

Hosse et al. ("A new generation of protein display scaffolds for molecular recognition", Protein Science, 15:14-27, 2006) specifically address the requirements for binding proteins suitable for therapeutic applications. The authors note the importance of some characteristics for therapeutically useful binding proteins such as serum stability, tissue penetration, blood clearance, target retention and immune response. In the latter respect it is noted that non-human therapeutic proteins should be made as similar to their human counterparts as possible and a human scaffold might be less immunogenic right from the start. These authors conclude:

> "However, even an entirely human scaffold is no guarantee for a protein that does not elicit a human immune response, especially if it is an intracellular protein. Randomization of amino acids during library construction can potentially introduce novel T-cell epitopes. Even single point mutations can render a human protein immunogenic. Furthermore, most human scaffolds cause some autoimmune response."

Today, the SH3 domains of Abl and Hck kinases are acknowledged as protein scaffolds for generating protein binders with prescribed specificity, even though only binders towards known ligands like the Nef proteins or synthetic peptides have been identified so far (see Binz et al. above).

The SH3 domain of the Fyn kinase (Fyn SH3) comprises 63 residues (aa 83-145 of the sequence reported by Semba et al. ("yes-related protooncogene, syn, belongs to the protein-tyrosine kinase family." Proc. Natl. Acad. Sci. USA 83(15): 5459-63, 1986) and Kawakami et al. ("Isolation and oncogenic potential of a novel human src-like gene." *Mol* Cell Biol. 6(12): 4195-201, 1986). Fyn is a 59 kDa member of the Src family of tyrosine kinases. As a result of alternative splicing the Fyn protein exists in two different isoforms differing in their kinase domains; one form is found in thymocytes, splenocytes and some hematolymphoid cell lines, while a second form accumulates principally in brain (Cooke and Perlmutter, "Expression of a novel form of the Fyn proto-oncogene in hematopoietic cells." New Biol. 1(1): 66-74, 1989). The biological functions of Fyn are diverse and include signalling via the T cell receptor, regulation of brain function as well as adhesion mediated signalling (Resh, M. D. "Fyn, a Src family tyrosine kinase." Int. J. Biochem. Cell Biol. 30(11): 1159-62, 1998). It is an intracellular protein. SEQ ID NO: 1 shows the Fyn SH3 sequence (aa 83-145 of Fyn kinase as reported by Kawakami et al. and Semba et al. in 1986, see above):

(SEQ ID NO: 1)
GVTLFVALYDYEARTEDDLSFHKGEKFQILNSSEGDWWEARSLTTGETGY

IPSNYVAPVDSIQ

The sequence of the RT-Src and the n-Src loop are underlined and double-underlined, respectively.

The amino acid sequence of Fyn SH3 is fully conserved among man, mouse, rat and monkey (gibbon). Chicken Fyn SH3 differs in one, the one of *Xenopus laevis* in two amino acid positions from the corresponding human domain. Just as other SH3 domains the Fyn SH3 is composed of two antiparallel β-sheets and contains two flexible loops (called RT-Src and n-Src-loops) in order to interact with other proteins.

In summary, the prior art teaches protein frameworks, the so-called scaffolds, as alternatives to established antibody structures. The Src homology 3 domain (SH3) is one of these about 40 or more scaffolds. Among the many different SH3 domains (about 300 in the human genome and several thousands described so far in nature) the Fyn SH3 is one, which has been used once before in order to elucidate SH3 binding specificity and affinity in general. The skilled person is also aware that intracellular proteins are particularly prone to produce immune responses and, therefore, are typically less useful or even useless for in vivo applications like therapy and diagnosis.

The object underlying the present invention is to provide improved target specific and high affinity binding proteins that are suitable as research, and in particular, as diagnostic and medical agents. Furthermore, these binding proteins should be stable and soluble under physiological conditions, elicit little or no immune effects in humans receiving these, and provide a binding structure that is also accessible by large target structures, i.e. that is not masked by steric hindrance.

DESCRIPTION OF THE INVENTION

It was surprisingly found that the SH3 domain of the Fyn kinase of the Src family provides excellent properties for designing recombinant binding domains with specificity and high affinity to selected targets. In particular, it was found that the target specificity can be designed by mutating the RT loop and/or the src loop resulting in higher variability and improved binding properties for many targets.

Moreover, it was unexpectedly found that not only the native Fyn SH3 binding protein but also mutated Fyn SH3-derived binding proteins were not immunogenic in vivo. Therefore, recombinant mutant Fyn SH3 binding proteins are particularly useful for the development of non-immunogenic protein therapeutics and/or diagnostics.

As a result of the above, a first aspect the present invention relates to a recombinant binding protein comprising at least one derivative of the Src homology 3 domain (SH3) of the Fyn kinase, wherein (a) at least one amino acid in or positioned up to two amino acids adjacent to the src loop and/or (b) at least one amino acid in or positioned up to two amino acids adjacent to the RT loop is substituted, deleted or added, wherein the SH3 domain derivative has an amino acid sequence having at least 70, preferably at least 80, more preferably at least 90 and most preferred at least 95% sequence identity to the amino acid sequence of SEQ ID NO: 1, preferably with the proviso that the recombinant binding protein does not comprise the amino acid sequence of SEQ ID NO: 2, and preferably that the recombinant protein is not a natural SH3 domain containing protein existing in nature.

The amino acid sequence of SEQ ID NO: 2 (the Fyn SH3 variant R96I of Lee et al., see above) is provided below.

(SEQ ID NO: 2)
GVTLFVALYDYEAITEDDLSFHKGEKFQILNSSEGDWWEARSLTTGETGY

IPSNYVAPVDSIQ

In the context of this invention the RT loop of the Fyn kinase (sometimes also designated RT-Src-loop) consists of the amino acids E A R T E D that are located in positions 12 to 17 in SEQ ID NO: 1. The positions to be substituted, deleted and/or added, i.e. to be mutated, in or adjacent to the RT loop are amino acids 10 to 19, preferably 11 to 18, more preferably 12 to 17.

In the context of this invention the src loop of the FYN kinase (sometimes also designated n-Src-loop) consists of the amino acids N S S E that are located in positions 31 to 34 in SEQ ID NO: 1. The positions to be substituted, deleted and/or added, i.e. to be mutated, in or adjacent to the src loop are amino acids 29 to 36, preferably 30 to 35, more preferably 31 to 34.

The recombinant protein of the invention is preferably not a natural SH3 domain containing protein existing in or isolated from nature. In other words, the scope of the invention preferably excludes wild type SH3 domain containing proteins. There are abundant SH3 domain containing proteins in nature. These natural SH3 proteins have a binding affinity to their natural ligands. Most if not all of these natural SH3 ligands have a PxxP motif. However, the recombinant proteins of the invention are engineered proteins designed for having affinities to non-natural targets, i.e. non-natural targets being any target, e.g. in nature, preferably in a mammalian, more preferably in a human, excluding natural (wild-type) SH3 ligands. More preferably, the recombinant proteins of the invention essentially have no binding affinity to any natural SH3 binding ligands, most preferably not to any natural SH3 binding ligand having a PxxP motif.

Preferably, the number of amino acids to be added into one and/or both loops is 1 to 20, more preferably 1 to 10 or 1 to 5 amino acids, and most preferably no amino acids are added into the loops.

In another preferred embodiment, the portions of the SH3 domain derivative that lie outside the RT and src loops are conserved as much as possible in order not to introduce immunogenic motifs.

It is preferred that the recombinant proteins of the invention essentially do not elicit an immunogenic reaction in mammals, preferably in mouse, rat and/or human, most preferably in human. Of course, the immunogenicity of the complete recombinant protein of the invention will not only depend on the SH3 domain derivative portion but can be influenced by other portions of the whole protein.

In a preferred embodiment of the invention, at least the SH3 domain derivative portion of the recombinant protein is essentially non-immunogenic in mammals, preferably in mouse, rat and/or human, most preferably in human.

For example, the person skilled in the art can determine immunogenic reactions of the recombinant protein or its SH3 domain derivative portion by standard and routine techniques, e.g. by administering (e.g. i.v. injection) a recombinant protein of interest or its SH3 domain derivative to a mammal such as a mouse and analysing the response of immunogenic blood cells and/or factors (e.g. interleukins) after an appropriate time for an immune reaction to occur.

In a more preferred embodiment the binding protein according to the invention is one, wherein said SH3 domain derivative has at least 70 or at least 85, preferably at least 90, more preferably at least 95, most preferably at least 98 to 100% identity to the Src homology 3 domain (SH3) of the FYN kinase outside the src and RT loops.

In a preferred embodiment mutations are introduced in both the RT and src loops.

In a further more preferred embodiment the binding protein of the invention comprises one or preferably two altered residues in positions 37 and/or 50 of the SH3 domain derivative, preferably two hydrophobic altered residues, more preferably Trp37 and/or Tyr50, Trp37 and Tyr50 being most preferred. As demonstrated in FIG. 3*b* below their randomization can increase the affinity.

The term "derivative of the Src homology 3 domain (SH3) of the FYN kinase", as it is used herein, is meant to encompass an amino acid sequence having at least 70, preferably at least 80, more preferably at least 90 and most preferred at least 95% sequence identity to the amino acid sequence of SEQ ID NO: 1. The same meaning holds true for an SH3 domain derivative having at least 70 or at least 85, preferably at least 90, more preferably at least 95, most preferably at least 98% identity to the Src homology 3 domain (SH3) of the FYN kinase outside the src and RT loops, except that the amino acids forming said loops are excluded when determining the sequence identity.

For the purpose of determining the extent of sequence identity of a derivative of the Fyn SH3 domain to the amino acid sequence of SEQ ID NO: 1, for example, the SIM Local similarity program can be employed (Xiaoquin Huang and Webb Miller, "A Time-Efficient, Linear-Space Local Similarity Algorithm." Advances in Applied Mathematics, vol. 12: 337-357, 1991.), freely available from the authors and their institute (see also the world wide web: http://www.expasy.org/tools/sim-prot.html); for multiple alignment analysis ClustalW can be used (Thompson et al., "CLUSTAL W: improving the sensitivity of progressive multiple sequence alignment through sequence weighting, position-specific gap penalties and weight matrix choice.", Nucleic Acids Res., 22(22): 4673-4680, 1994.). Preferably, the extent of the sequence identity of the derivative to SEQ ID NO: 1 is determined relative to the complete sequence of SEQ ID NO: 1.

In a preferred embodiment the binding protein of the invention comprises at least two derivatives of the Fyn SH3 domain. More preferably, it is a bivalent binding protein. The at least two derivatives of the SH3 domain may be the same or different. Preferably, they are the same.

The binding protein of the invention can be designed to have any specific binding affinity to a given target. In a preferred embodiment, the target is an amino acid-based target such as a peptide or protein, more preferably one comprising a PxxP motif. Of course, only a minority of natural and physiologically relevant target proteins contains a PxxP motif. The examples below demonstrate that binding proteins according to the invention for targets (e.g. ED-B domain of fibronectin, interleukin (IL) 17A, the serine protease chymase (E.C. 3.4.21.39), human epidermal growth factor receptor 2 (Her-2), human serum albumin, the transmembrane receptor CD33, epidermal growth factor receptor (EGFR) and the membrane-bound aspartic protease BACE (UniProt Q95YZ0)) with motifs other than PxxP are available. Therefore, the binding protein of the invention is by no means limited to the PxxP motif and can have a specific binding affinity to any given target, e.g. sugars, polypeptides, etc.

More preferably, the binding protein according to the invention has a specific binding affinity to a target of $10^{-7}$ to $10^{-12}$ M, preferably $10^{-8}$ to $10^{-12}$ M, preferably a therapeutically and/or diagnostically relevant target, more preferably an amino acid-based target comprising a PxxP motif.

In a most preferred aspect, the binding protein according to the invention has a specific (in vivo and/or in vitro) binding affinity of $10^{-7}$ to $10^{-12}$ M, preferably $10^{-8}$ to $10^{-12}$ M, to the extracellular domain of oncofetal fibronectin (ED-B).

In a preferred embodiment, the present invention relates to a recombinant binding protein, comprising at least one derivative of the Src homology 3 domain (SH3) of the FYN kinase, wherein (a) at least one amino acid in or positioned up to two amino acids adjacent to the src loop and/or (b) at least one amino acid in or positioned up to two amino acids adjacent to the RT loop, is substituted, deleted or added, wherein the SH3 domain derivative has an amino acid sequence having at least 70, preferably at least 80, more preferably at least 90 and most preferred at least 95% sequence identity to the amino acid sequence of SEQ ID NO: 1, preferably with the proviso that the recombinant binding protein does not comprise the amino acid sequence of SEQ ID NO: 2, and preferably with the proviso that the recombinant protein is not a natural SH3 domain containing protein existing in nature, wherein said binding protein has a specific (in vivo and/or in vitro) binding affinity of preferably $10^{-7}$ to $10^{-12}$ M, more preferably $10^{-8}$ to $10^{-12}$ M, to the extracellular domain of oncofetal fibronectin (ED-B).

In a more preferred embodiment said SH3 domain derivative has at least 85, preferably at least 90, more preferably at least 95, most preferably at least 98 to 100% identity to the Src homology 3 domain (SH3) of the FYN kinase outside the src and RT loops.

In another more preferred embodiment the above ED-B-specific binding protein comprises at least two derivatives of the SH3 domain, preferably it is a bivalent binding protein.

Preferably, said ED-B-specific binding protein has one or more, preferably two, altered, preferably hydrophobic, residues in positions 37 and/or 50 of the SH3 domain derivative, in particular Trp37 and/or Tyr50, Trp37 and Tyr50 being most preferred.

Next to a specific binding affinity to polypeptide and protein targets, the binding protein of the invention can also have a specific binding affinity to a small organic or non-amino-acid based compound, e.g. a sugar, oligo- or polysaccharide, fatty acid, etc.

A number of antibody-cytokine fusion proteins have already been investigated for applications in, e.g. arthritis or cancer therapy, often with impressive results. For example, the human antibody L19 specific to the ED-B domain of fibronectin (a marker of angiogenesis) has been used to deliver pro-inflammatory cytokines (such as IL-2, IL-12 or TNF) to solid tumours, sometimes with striking therapeutic benefits [for a review and corresponding references see Neri & Bicknell, Nat. Rev. Cancer (2005) 5: 436-446, and also WO 01/62298].

The binding protein of the present invention now allows for substituting antibodies in prior art fusion proteins and also for designing new and less immunogenic fusion proteins for in vivo and in vitro pharmaceutical and diagnostic applications.

In a second aspect, the invention relates to a fusion protein comprising a binding protein of the invention fused to a pharmaceutically and/or diagnostically active component.

A fusion protein of the invention may comprise non-polypeptide components, e.g. non-peptidic linkers, non-peptidic ligands, e.g. for therapeutically or diagnostically relevant radionuclides.

Preferably, said active component is a cytokine, preferably a cytokine selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta.

More preferably, said active component is a toxic compound, preferably a small organic compound or a polypeptide, preferably a toxic compound selected from the group consisting of calicheamicin, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and recombinant gelonin.

In another preferred embodiment, the fusion protein according to invention is one, wherein said active component is a chemokine, preferably a chemokine selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, Eotaxin, Eotaxin-2, 1-309, MPIF-1, 6Ckine, CTACK, MEC, Lymphotactin and Fractalkine.

In a further preferred embodiment the binding protein according to the invention contains artificial amino acids.

In further preferred embodiments of the fusion protein of the present invention said active component is a fluorescent dye, preferably a component selected from the groups of Alexa Fluor or Cy dyes (Berlier et al., "Quantitative Comparison of Long-wavelength Alexa Fluor Dyes to Cy Dyes: Fluorescence of the Dyes and Their Bioconjugates", J Histochem Cytochem. 51 (12): 1699-1712, 2003.); a photosensitizer, preferably bis(triethanolamine)Sn(IV) chlorin $e_6$ ($SnChe_6$); a pro-coagulant factor, preferably tissue factor; an enzyme for pro-drug activation, preferably an enzyme selected from the group consisting of carboxy-peptidases, glucuronidases and glucosidases; a radionuclide either from the group of gamma-emitting isotopes, preferably $^{99m}$Tc, $^{123}$I, $^{111}$In, or from the group of positron emitters, preferably $^{18}$F, $^{64}$Cu, $^{68}$Ga, $^{86}$Y, $^{124}$I, or from the group of beta-emitter, preferably $^{131}$I, $^{90}$Y, $^{177}$Lu, $^{67}$Cu, or from the group of alpha-emitter, preferably $^{213}$Bi, $^{211}$At; and/or a functional Fc domain, preferably a human functional Fc domain.

The above mentioned functional Fc domain will allow for directing a mammal's immune response to a site of specific target binding of the binding protein component of the fusion protein, e.g. in therapeutic, prophylactic and/or diagnostic applications.

A further preferred embodiment relates to fusion proteins according to the invention as mentioned above, further comprising a component modulating serum half-life, preferably a component selected from the group consisting of polyethylene glycol (PEG), immunoglobulin and albumin-binding peptides.

In a most preferred embodiment, the fusion protein of the invention as mentioned above comprises a binding protein of the invention having a specific (in vivo and/or in vitro) binding affinity of $10^7$ to $10^{-12}$ M, preferably $10^{-8}$ to $10^{-12}$ M, to the extra domain of oncofetal fibronectin (ED-B). Preferably, said ED-B-specific binding protein has one or more, preferably two hydrophobic residues in positions 37 and/or 50 of the SH3 domain derivative, in particular Trp37 and/or Tyr50, Trp37 and Tyr50 being most preferred.

Binding and fusion proteins according to the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

Further aspects of the present invention are directed to (i) a polynucleotide coding for a binding protein or fusion protein according to the invention, (ii) a vector comprising said polynucleotide, (iii) a host cell comprising said polynucleotide and/or said vector.

Polynucleotides can be DNA, RNA, PNA and any other analogues thereof. The vectors and host cells may be any conventional type that fits the purpose, e.g. production of binding and fusion proteins of the invention, therapeutically useful vectors and host cells, e.g. for gene therapy. The skilled person will be able to select those polynucleotides, vectors and host cells from an abundant prior art and confirm their particular suitability for the desired purpose by routine methods and without undue burden.

The binding and fusion proteins of the present invention do not elicit a strong and preferably have essentially no immune response in mammals, in particular in humans and mice, as was demonstrated for mice and is analogously expected to hold true for humans, too, because the Fyn SH3 is identical in both mammalian species. It was surprisingly found that neither native Fyn SH3 nor mutated Fyn SH3 causes an immune response in mice injected i.v. with either one. This was unexpected because Fyn kinase is an intracellular protein and does not participate in neonatal B cell selection. Therefore, Fyn SH3-derived binding and fusion proteins with designed target specificity and affinity are particularly well suited for therapeutic, prophylactic and/or diagnostic applications in vivo.

Hence, a highly relevant aspect of the present invention relates to the use of a binding or fusion protein according to the invention for preparing a medicament.

In a further aspect, the binding or fusion protein of the invention is used for preparing a diagnostic means, in particular for in vivo applications.

Preferably, an ED-B specific binding or fusion protein as described above is used for preparing a medicament or diagnostic means for the treatment or diagnosis of cancer.

Another aspect of the present invention relates to a pharmaceutical composition comprising a binding or fusion protein of the invention and optionally a pharmaceutically acceptable excipient.

Another aspect of the present invention relates to a diagnostic composition, preferably for in vivo applications, comprising a binding or fusion protein of the invention and optionally a pharmaceutically acceptable excipient.

Preferably, the pharmaceutical or diagnostic composition comprises an ED-B specific binding or fusion protein of the invention and optionally a pharmaceutically acceptable excipient.

Pharmaceutical compositions and diagnostic means for in vivo applications of the present invention typically comprise a therapeutically or diagnostically effective amount of a binding and/or fusion protein according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilizers, antioxidants, pH-regulating substances, controlled-release excipients. The pharmaceutical preparation of the invention may be adapted, for example, for parenteral use and may be administered to the patient in the form of solutions or the like.

Finally, another aspect of the present invention concerns a method of treatment or diagnosis, wherein an effective amount of the above pharmaceutical or diagnostic composition is administered to a patient in need thereof, preferably a patient suffering or suspected of suffering from cancer and/or inflammatory diseases.

In effecting treatment or diagnosis of a subject suffering from diseases, a binding or fusion protein of the present invention can be administered in any form or mode which makes the therapeutic or diagnostic compound bioavailable in an effective amount, including oral or parenteral routes. For example, compositions of the present invention can be administered subcutaneously, intramuscularly, intravenously and the like. One skilled in the art in the field of preparing formulations can readily select the proper form and mode of administration depending upon the particular characteristics of the product selected, the disease or condition to be treated or diagnosed, the stage of the disease or condition and other relevant circumstances (see. e.g. Remington's Pharmaceutical Sciences, Mack Publishing Co. (1990)). The compositions of the present invention can be administered alone or in the form of a pharmaceutical or diagnostic preparation in combination with pharmaceutically acceptable carriers or excipients, the proportion and nature of which are determined by the solubility and chemical properties of the product selected, the chosen route of administration and standard pharmaceutical and diagnostic practice. The products of the present invention, while effective themselves, may be formulated and administered in the form of their pharmaceutically acceptable salts, such as acid addition salts or base addition salts, for purposes of stability, convenience of crystallization, increased solubility and the like.

FIGURES

FIG. 1A illustrates a dot blot analysis for FynSH3 mutants with randomized RT-Src-loop. The percentage of clones expressing a detectable amount of soluble Fyn SH3 mutants was determined by dot blot analysis of bacterial cell lysates using anti-HIS-HRP antibody conjugate (Sigma) as detecting reagent. Peroxidase activity was detected using the ECL plus Western blotting detection system (Amersham).

FIG. 1B illustrates a dot blot analysis for FynSH3 mutants with an extended (4→6) and randomized n-Src-loop. The percentage of clones expressing a detectable amount of soluble Fyn SH3 mutants was determined by dot blot analysis of bacterial cell lysates using anti-HIS-HRP antibody conjugate (Sigma) as detecting reagent. Peroxidase activity was detected using the ECL plus Western blotting detection system (Amersham).

FIG. 1C illustrates a dot blot analysis for FynSH3 with RT- and n-Src randomized loops. The percentage of clones expressing a detectable amount of soluble Fyn SH3 mutants was determined by dot blot analysis of bacterial cell lysates using anti-HIS-HRP antibody conjugate (Sigma) as detecting reagent. Peroxidase activity was detected using the ECL plus Western blotting detection system (Amersham).

FIG. 2 illustrates a monoclonal phage-ELISA. After the third round of panning against MSA monoclonal bacterial supernatants containing phages displaying Fyn SH3 mutants were tested by ELISA using MaxiSorp plates (Nunc) coated with MSA (100 μg/ml overnight, 100 μl per well). Bound phages were detected using anti M-13-HRP antibody conjugates (Amersham).

Figure 4:
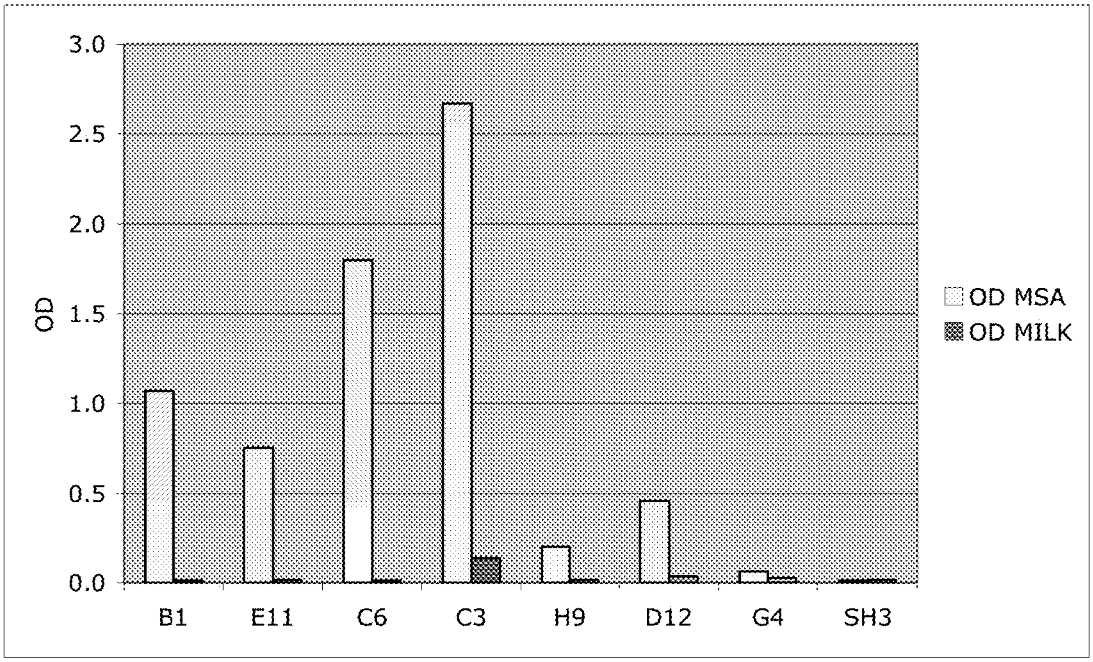

FIG. 4 shows the soluble ELISA (using MaxiSorp plates (Nunc) coated with MSA (100 μg/ml overnight, 100 μl per well) of several MSA binding clones, after cloning (pQE-12 vector), expression and purification of the soluble protein, according to the manufacturer's instructions (Qiagen, native conditions). As detecting agents anti-HIS-HRP antibody conjugates were used. As a control the same binding proteins were added to wells blocked with 4% MPBS only.

Figure 5:
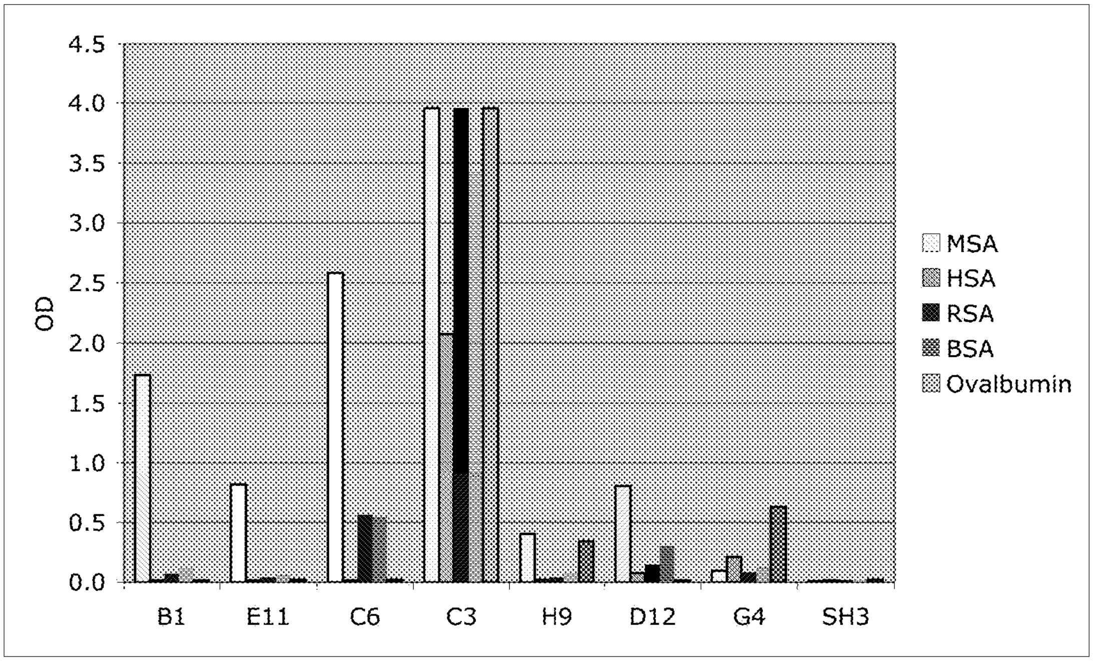

FIG. 5 Specificity ELISA of soluble protein. Selected MSA binding Fyn SH3 mutants were tested for binding against human serum albumin (HSA), rat serum albumin (RSA), bovine serum albumin (BSA) and ovalbumin using MaxiSorp plates (Nunc) coated with the different albumins (each 100 μg/ml overnight, 100 μl per well).

Figure 6:
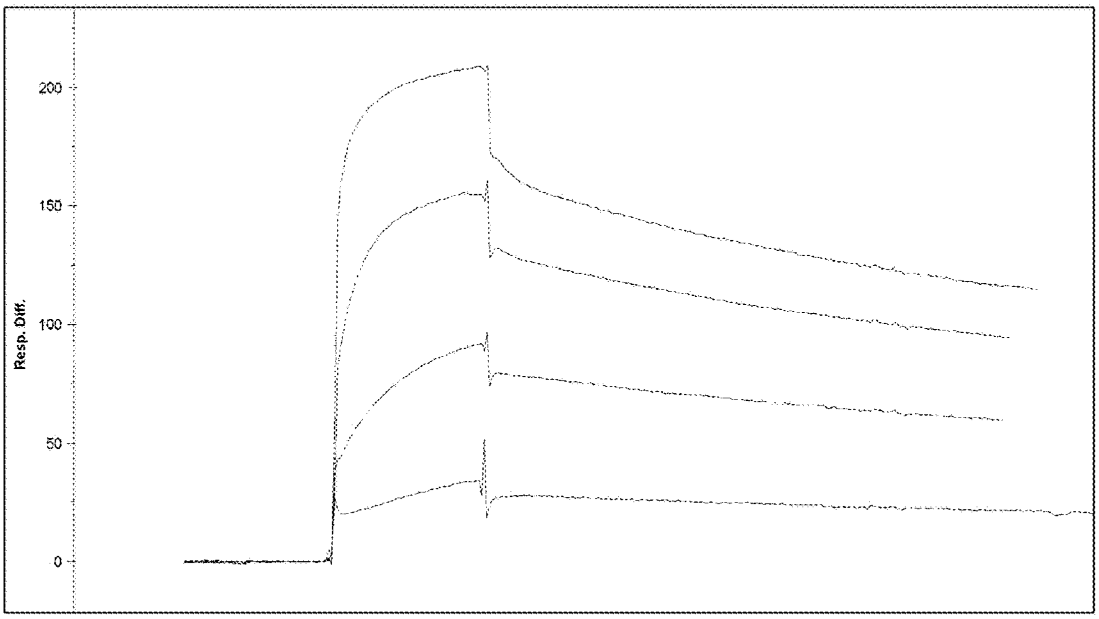

FIG. 6 BIACore analysis of D3. Used concentrations: 4, 2, 1, and 0.5 μM (from top).

Figure 7A:
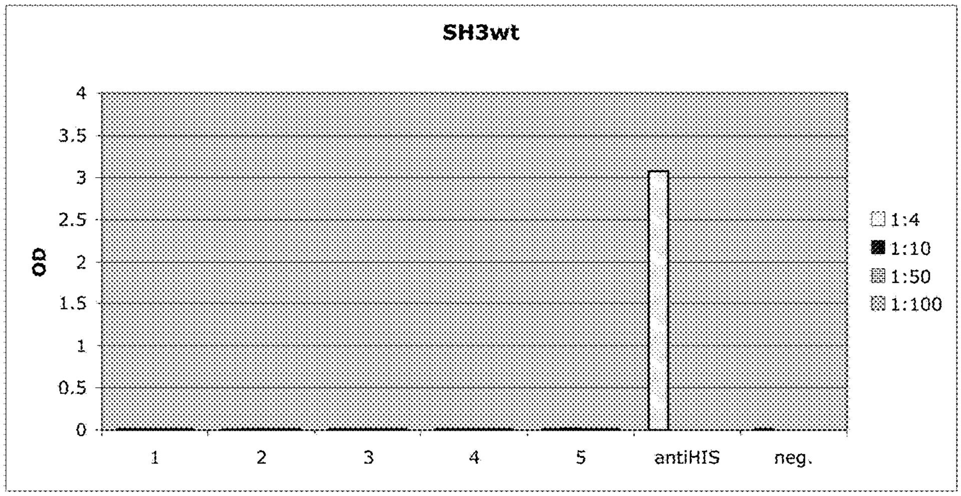

FIG. 7A ELISA analysis of blood samples for the presence of murine antibodies. MaxiSorp plates (Nunc) were coated with Fyn SH3 (20 μg/ml overnight, 100 μl per well). Blood samples (ranging from 75-200 μl) of each of the 5 mice were applied in dilution series (from 1:4 to 1:100). Detection of antibodies was performed using anti-mouse-IgG-HRP antibody conjugate (Sigma). As a control of the coating efficiency anti-HIS-HRP-conjugates (Sigma) were used.

Figure 7B:
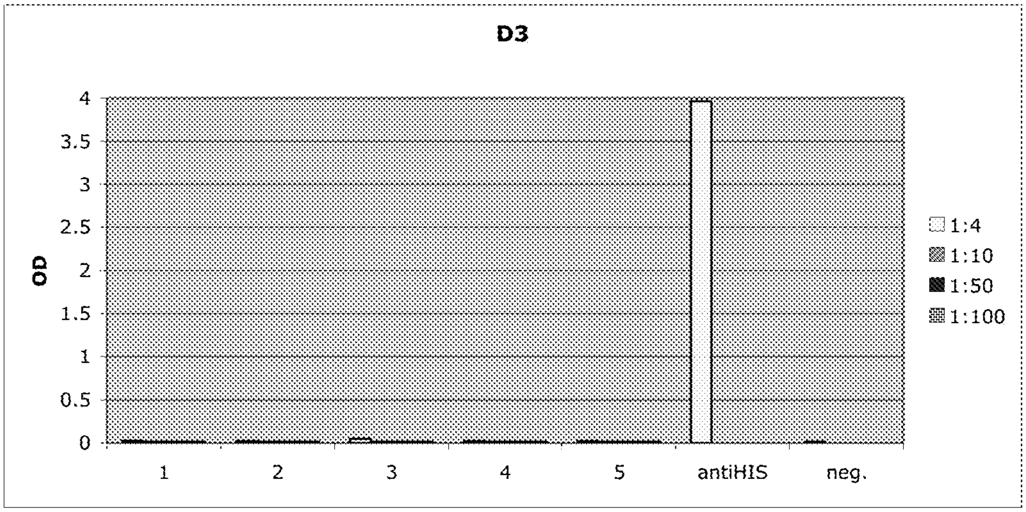

FIG. 7B ELISA analysis of blood samples for the presence of murine antibodies. MaxiSorp plates (Nunc) were coated with Fyn SH3 D3 (20 μg/ml overnight, 100 μl per well). Blood samples (ranging from 75-200 μl) of each of the 5 mice were applied in dilution series (from 1:4 to 1:100). Detection of antibodies was performed using anti-mouse IgG-HRP antibody conjugate (Sigma). As a control of the coating efficiency anti-HIS-HRP-conjugates (Sigma) were used.

Figure 7C:
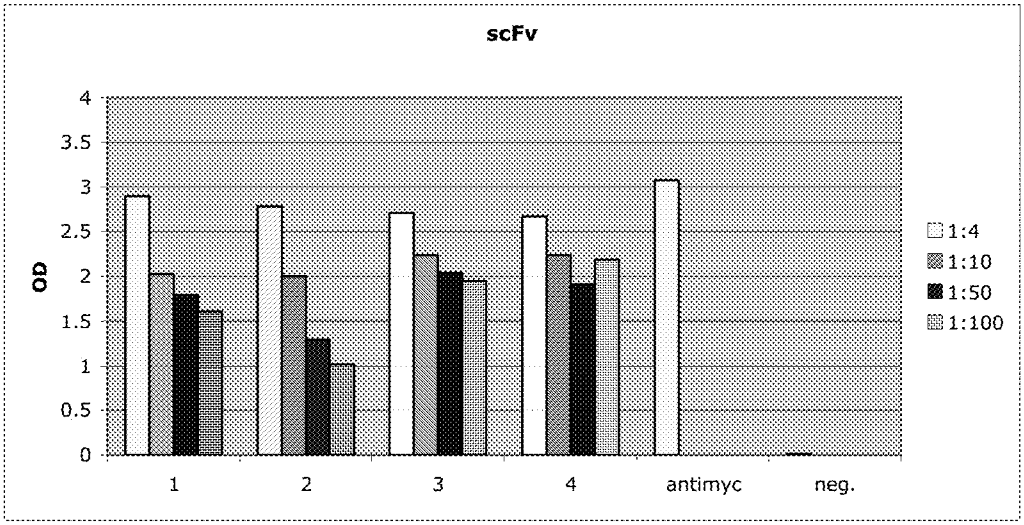

FIG. 7C ELISA analysis of blood samples for the presence of murine antibodies. MaxiSorp plates (Nunc) were coated with scFv (60 μg/ml overnight, 100 μl per well). Blood samples (ranging from 75-200 μl) of each of the 4 mice were applied in dilution series (from 1:4 to 1:100). Detection of antibodies was performed using anti-mouse-IgG-HRP antibody conjugate (Sigma). As a control of the coating efficiency, anti-myc-HRP-conjugates (Roche) were used.

Figure 8A:
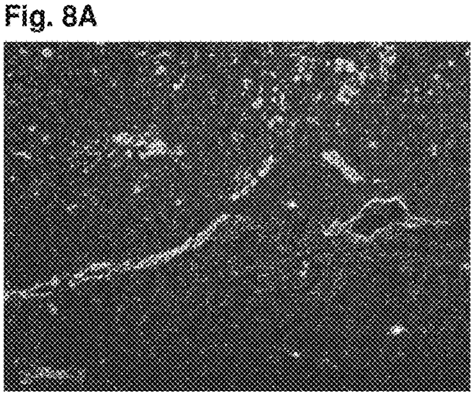

FIG. 8A shows immunofluorescence of D3 on F9 murine teratocarcinoma histological sections.

Figure 8B:
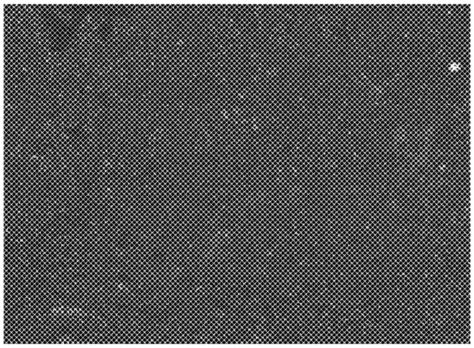

FIG. 8B shows the corresponding negative control of FIG. 8A on F9 murine teratocarcinoma histological sections.

Figure 8C:
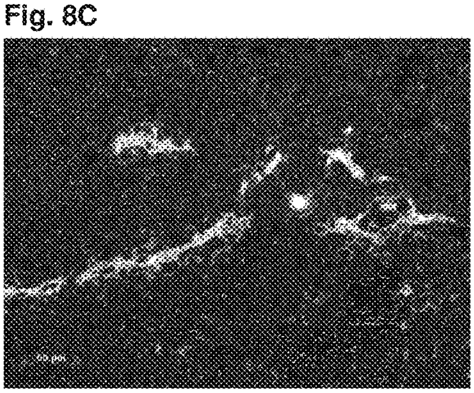

FIG. 8C shows the anti-CD31 staining on F9 murine teratocarcinoma histological sections.

Figure 8D:
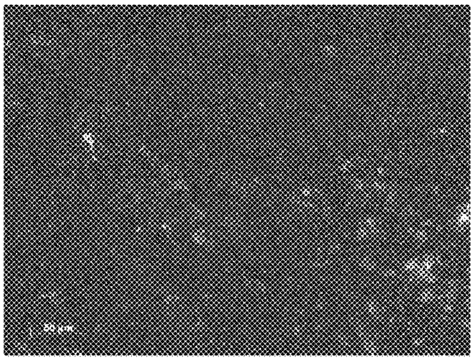

FIG. 8D shows the corresponding negative control of FIG. 8C on F9 murine teratocarcinoma histological sections.

Figure 9A:
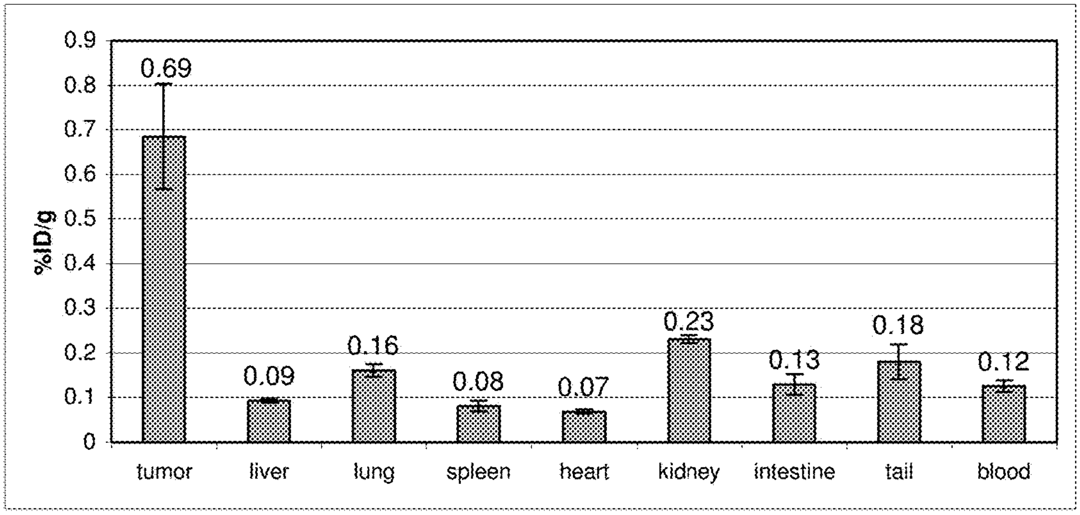

FIG. 9A shows the tumor retention of Fyn SH3-D3. Targeting results are expressed as % injected dose of $^{125}$I-labeled protein retained per g of tissue (% ID/g).

Figure 9B:
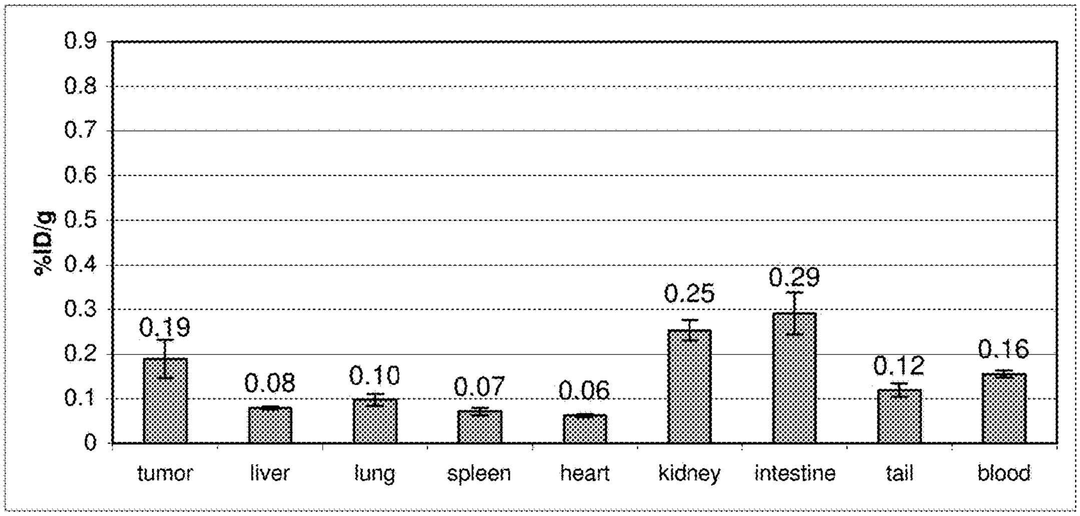

FIG. 9B shows that no accumulation could be observed for Fyn SH3 wt. Targeting results are expressed as % injected dose of $^{125}$I-labeled protein retained per g of tissue (% ID/g).

Figure 10A:
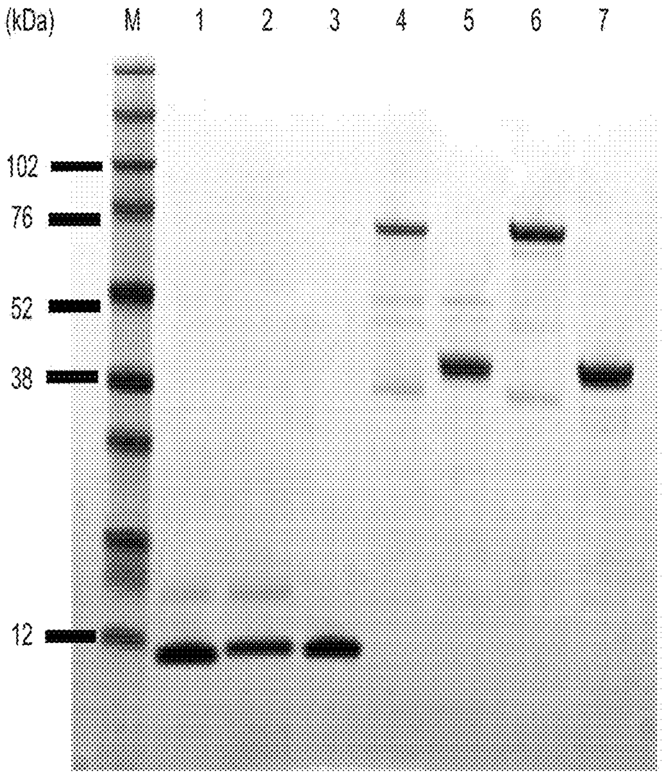
Figure 10B:
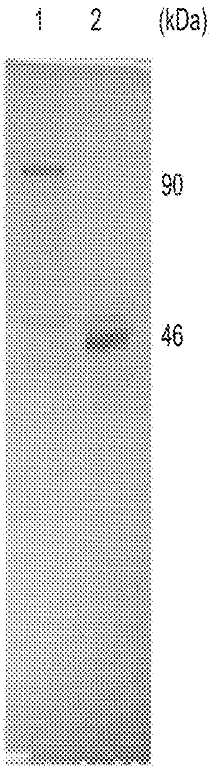

FIG. 10. shows the SDS PAGE analysis of embodiments of IL-17-binding polypeptides of the invention: (a) SDS PAGE of B1_2 (SEQ ID No: 42) (lane 1), E4 (SEQ ID NO: 60) (lane 2), 2C1 (SEQ ID NO: 110) (lane 3), E4-Fc (SEQ ID NO: 120) (lane 4: non-reducing conditions, lane 5: reducing conditions), 2C1-Fc (SEQ ID NO: 121) (lane 6: non-reducing conditions, lane 7: reducing conditions); (b) SDS PAGE of [(2C1)2-Fc] (SEQ ID NO: 122) (lane 1: non-reducing conditions, lane 2: reducing conditions). The molecular weight of (2C1)2-Fc is estimated from the reference molecular weight full range marker (not shown).

Figure 11:
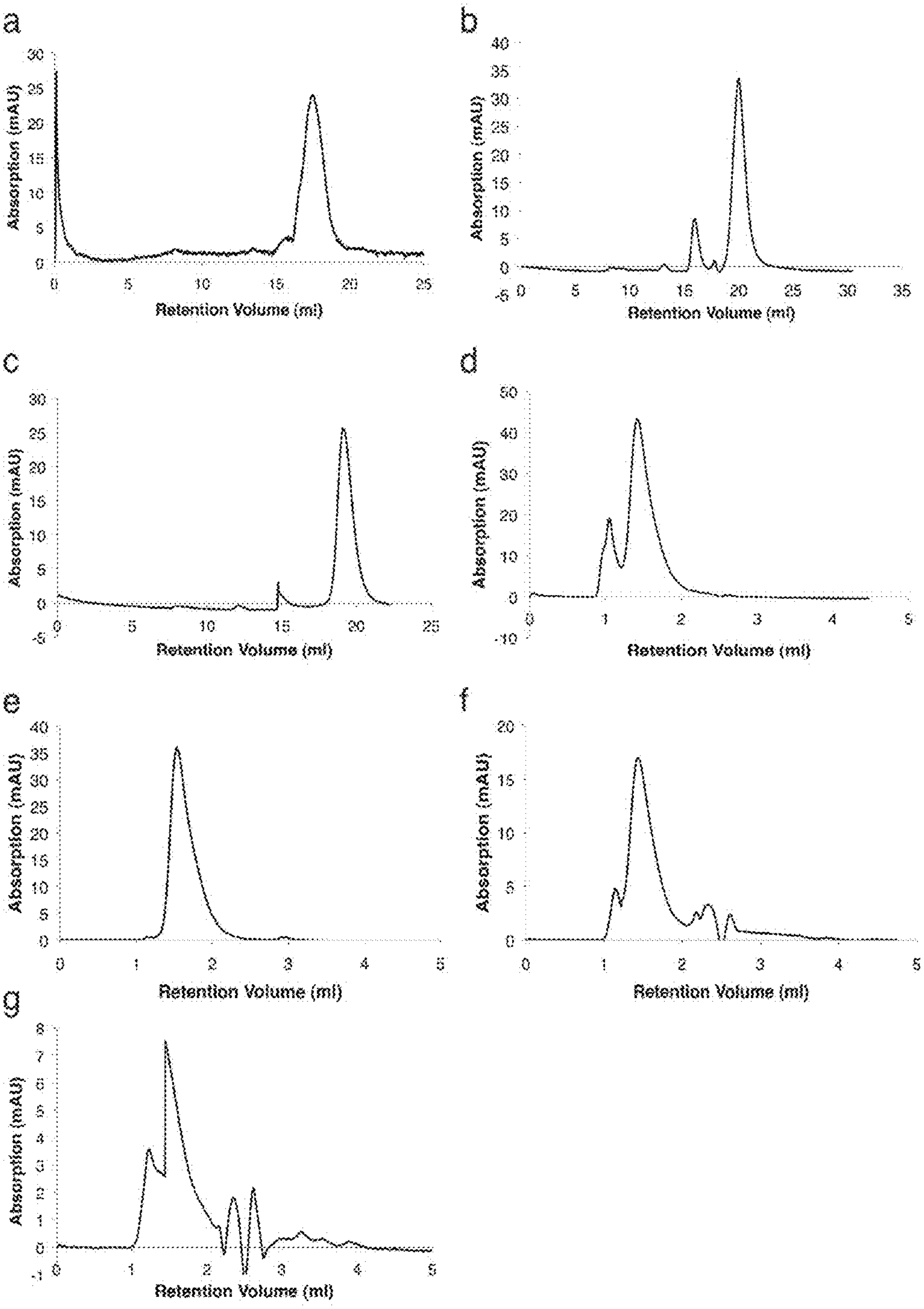
Figure 12A:
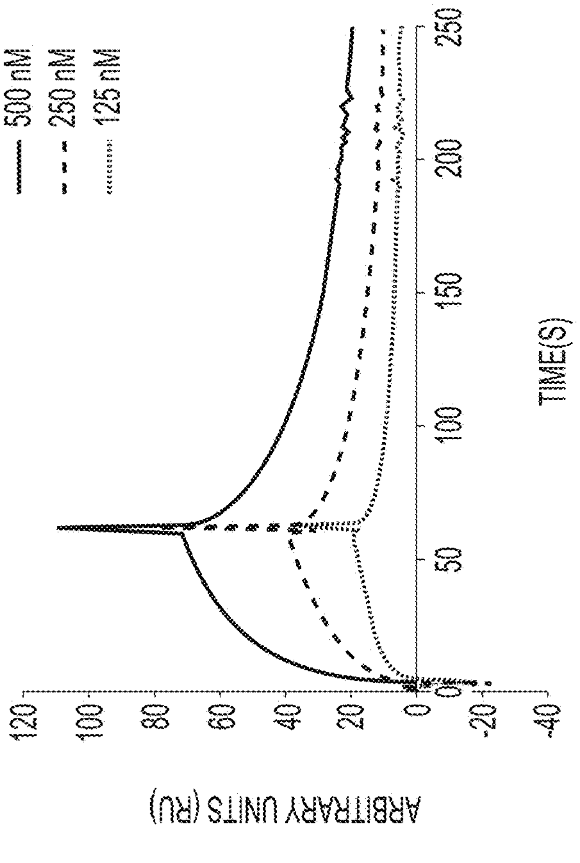
Figure 12B:
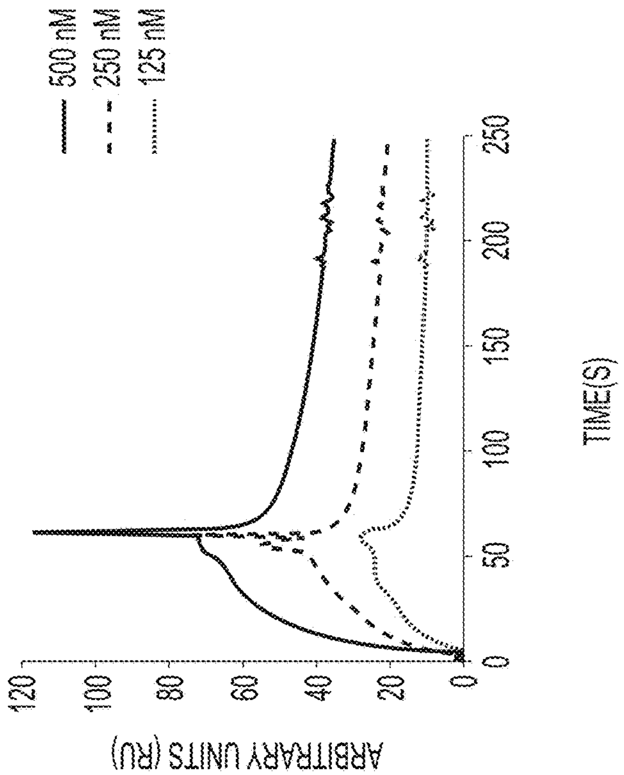
Figure 12D:
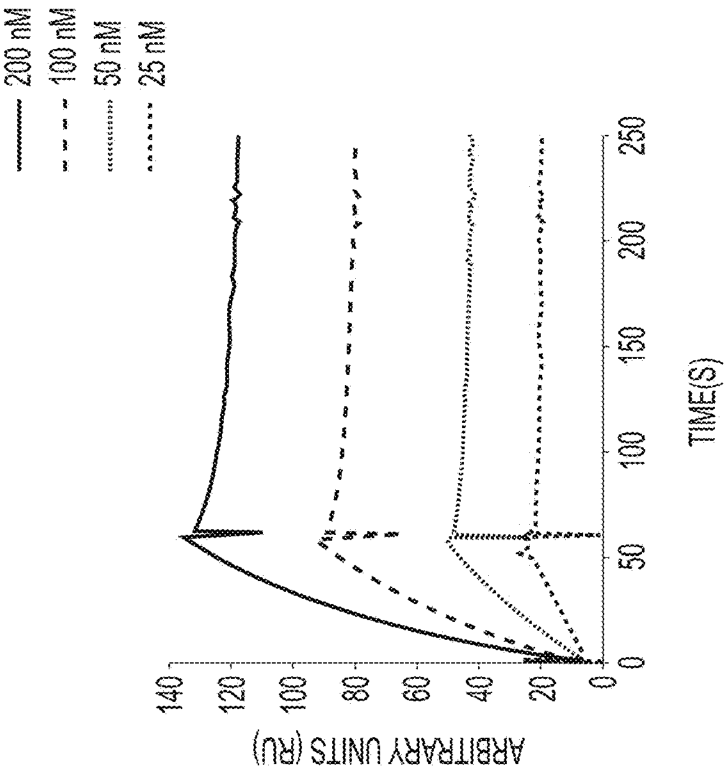
Figure 12C:
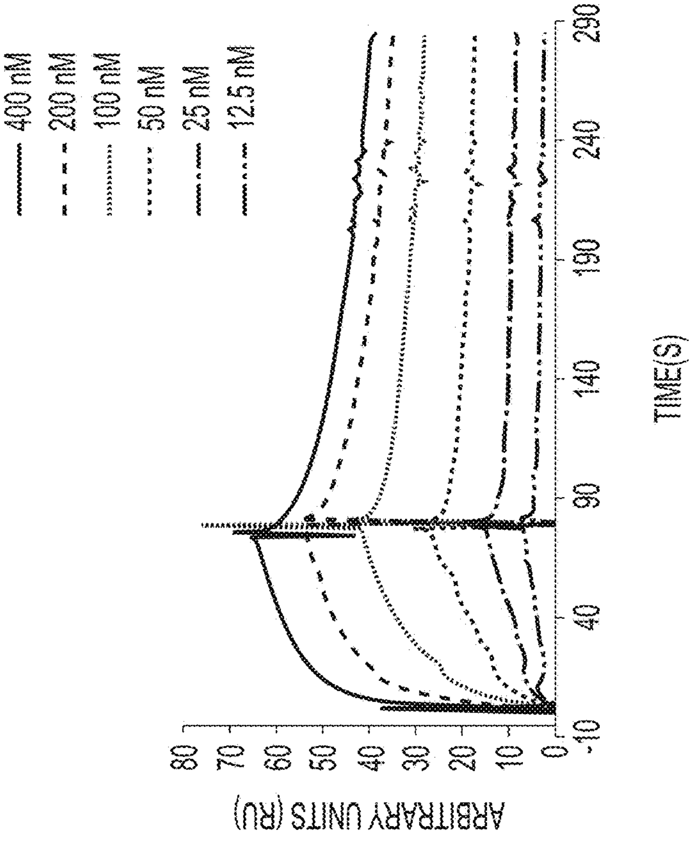
Figure 12F:
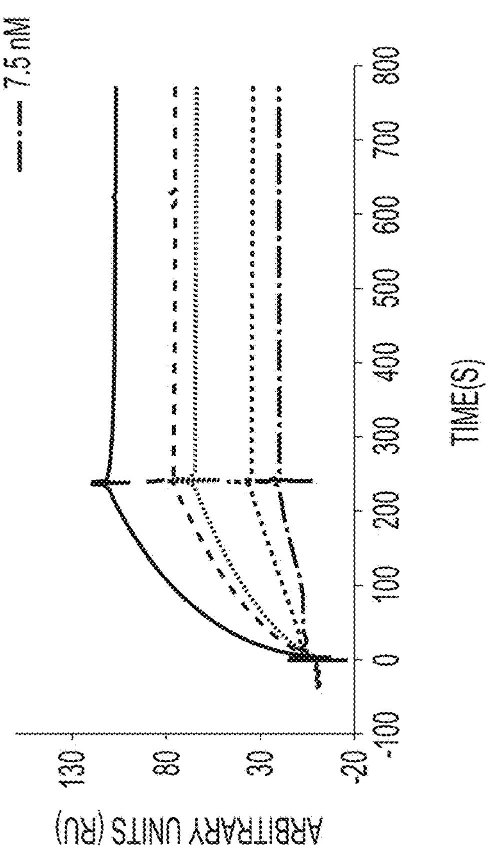
Figure 12E:
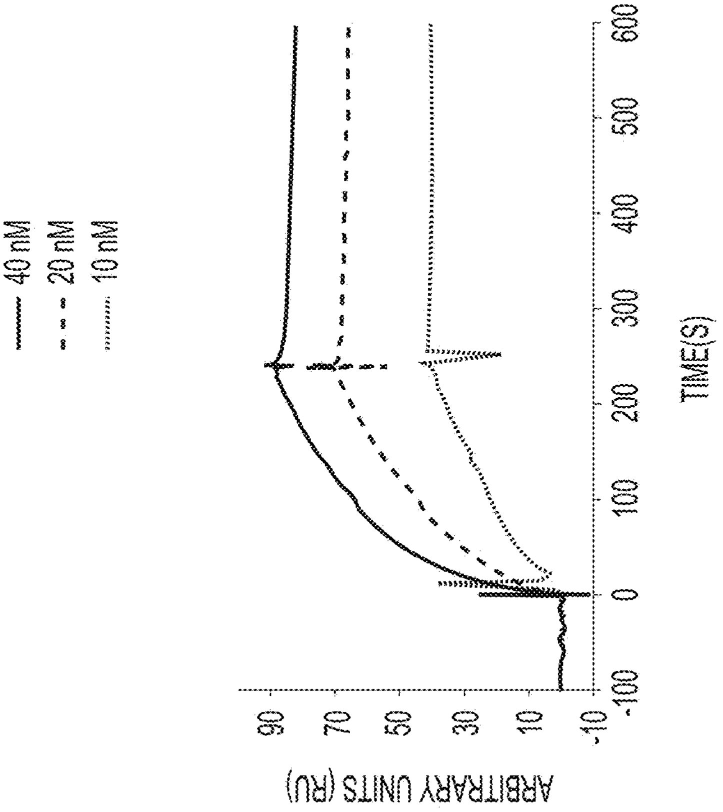

FIG. 11 shows size exclusion chromatograms (SEC) of IL-17A-binding polypeptides of the invention: (a) Clone B1_2 (SEQ ID NO: 42), (b) E4 (SEQ ID NO: 60), (c) 2C1 (SEQ ID NO: 110), (d) E4-Fc (SEQ ID NO: 120), (e) SEC-peak purified E4-Fc, analyzed after 40 days after purification and storage in PBS at 4° C., (f) 2C1-Fc (SEQ ID NO: 121), (g) (2C1)2-Fc (SEQ ID NO: 122).

FIG. 12 depicts BIAcore sensograms of IL-17A-binding polypeptides of the invention: (a) Clone B1_2 (SEQ ID NO: 42), (b) E4 (SEQ ID NO: 60), (c) 2C1 (SEQ ID NO: 110), (d) E4-Fc (SEQ ID NO: 120), (e) 2C1-Fc (SEQ ID NO: 121), f) $(2C1)_2$-Fc (SEQ ID NO: 122).

Figure 13:
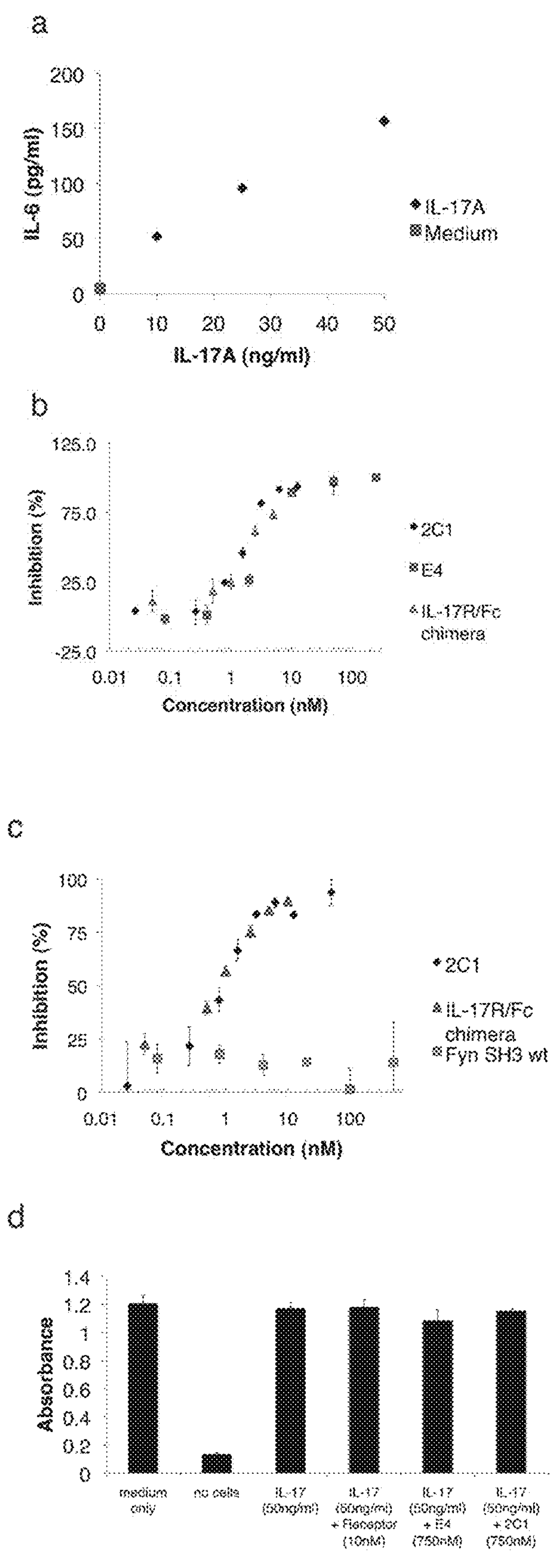

FIG. 13 depicts the results of an IL-17A inhibition cell assay: (a) Dose-dependent induction of IL-6 after incubation of NHDF cells with IL-17A. (b) Dose-dependent inhibition of IL-17A-induced IL-6 production in NHDF cells by Fyn SH3 derived IL-17 binders and IL-17A receptor-Fc chimera. (c) same as b), Fyn SH3 wt protein was used as a control protein with no IL-17A binding affinity. (d) XTT-assay: viable cells are able to metabolize the tetrazolium salt XTT to a coloured product. In our experiment, all cells were viable after 24 hours incubation with IL-17A, IL-17A and Fyn SH3 binders, or IL-17A and IL-17R-Fc chimera.

Figure 14:
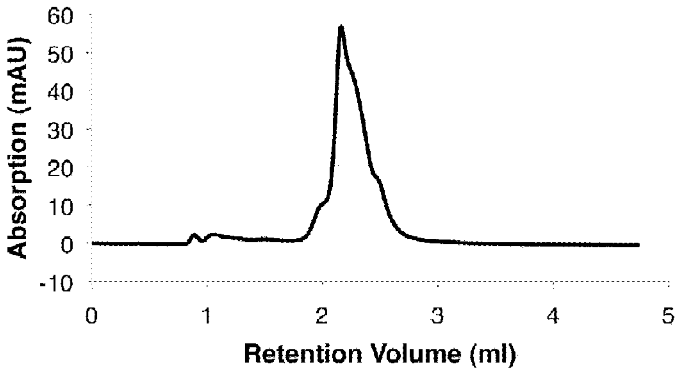

FIG. 14 depicts a size exclusion chromatography with an IL-17A-binding polypeptide of the invention designated G3 (SEQ ID NO: 37) one day after purification (stored in PBS at 4° C.). The chromatography was performed using a Superdex 75 (GE Healthcare) column.

Figure 15A:
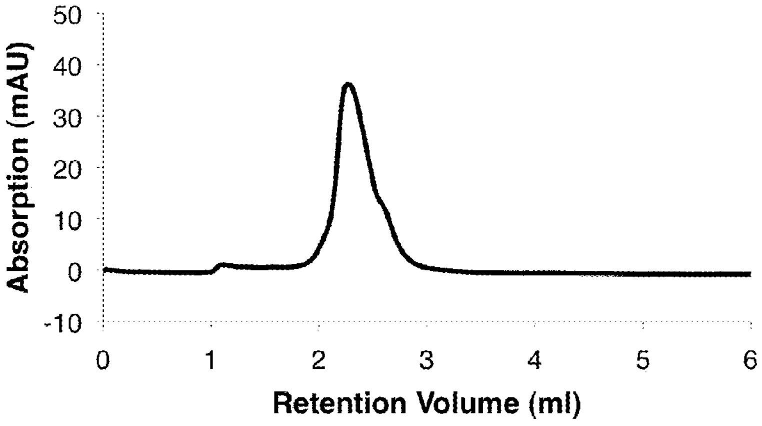

FIG. 15A depicts a size exclusion chromatography with an IL-17A-binding polypeptide of the invention designated G3 (SEQ ID NO: 37) stored for more than six months at 4° C.

Figure 15B:
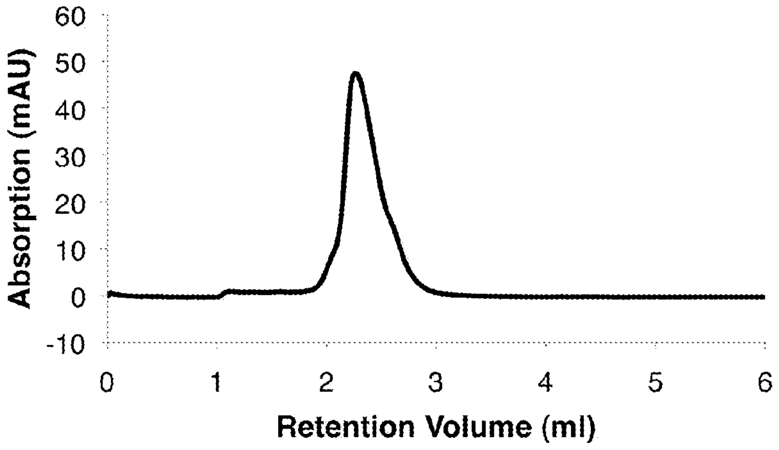

FIG. 15B depicts a size exclusion chromatography with an IL-17A-binding polypeptide of the invention designated G3 (SEQ ID NO: 37) stored for more than six months at −20° C.

Figure 16A:
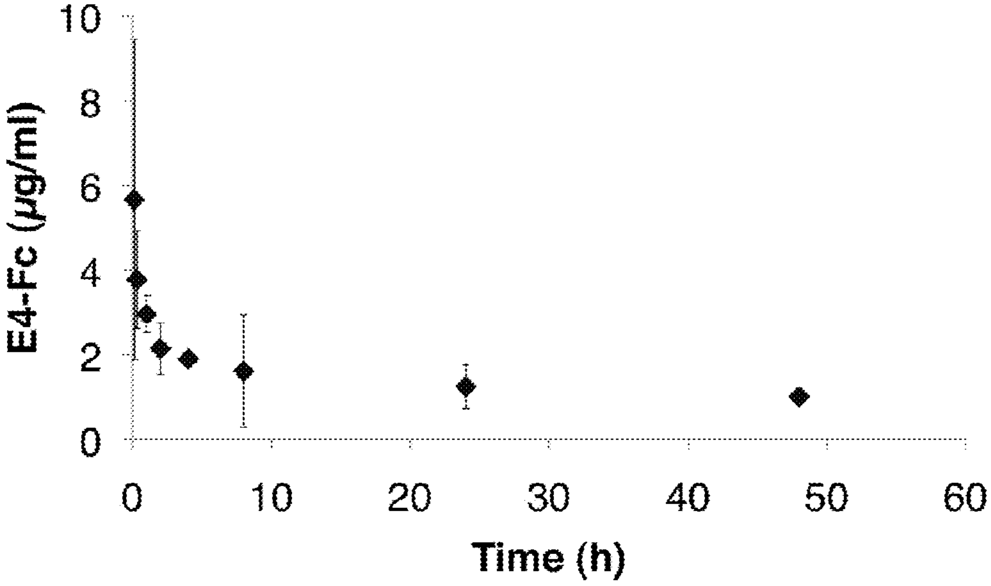

FIG. 16A shows the pharmacokinetic data of an IL-17A-binding polypeptide of the invention designated E4-Fc (SEQ ID NO: 120) in mice, where E4-Fc concentration in serum is plotted versus time after intravenous injection. The last four time points were used to calculate the terminal half-life of 50.6 hours.

Figure 16B:
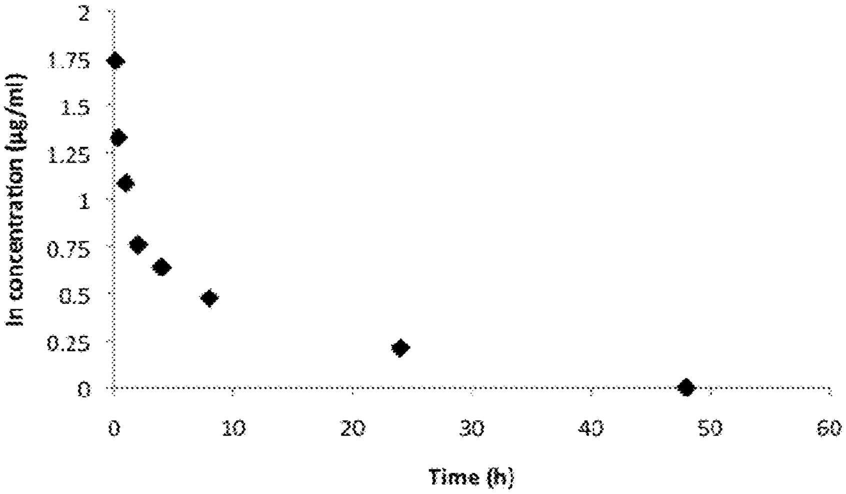

FIG. 16B shows the pharmacokinetic data of an IL-17A-binding polypeptide of the invention designated E4-Fc (SEQ ID NO: 120) in mice, where E4-Fc concentration in serum is plotted versus time after intravenous injection, but with a semi-logarithmic display. The last four time points were used to calculate the terminal half-life of 50.6 hours.

Figure 17:
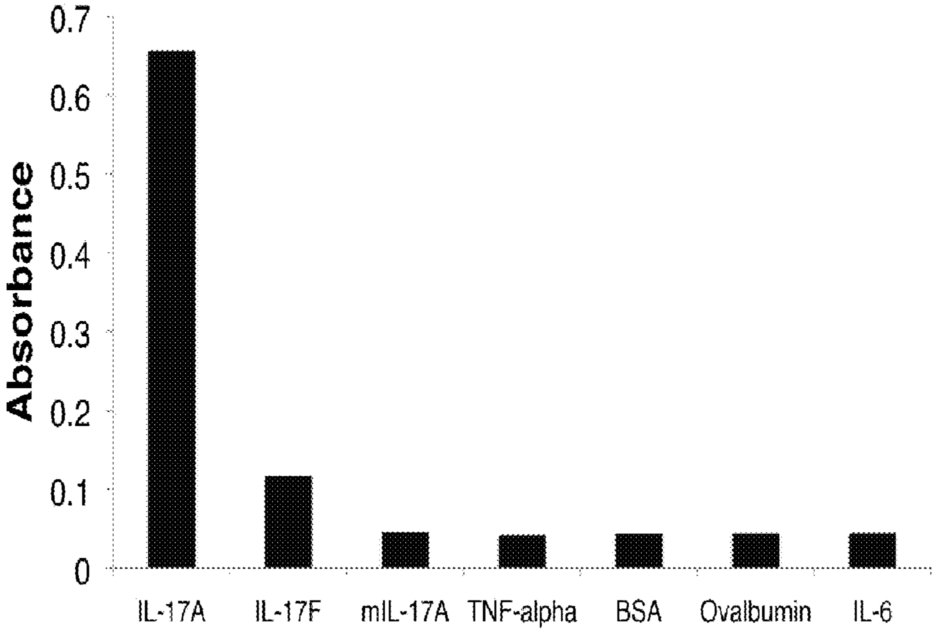

FIG. 17 shows a table of the binding specificity of a polypeptide of the invention designated 2C1 (SEQ ID NO: 110). The absorbance results relate to an ELISA performed using different target proteins: human IL-17A, human IL-17F, mIL-17A (murine IL-17 A), TNF-alpha (human tumor necrosis factor alpha), BSA (bovine serum albumin), Ovalbumin (hen egg white), IL-6 (human interleukin 6).

Figure 18:
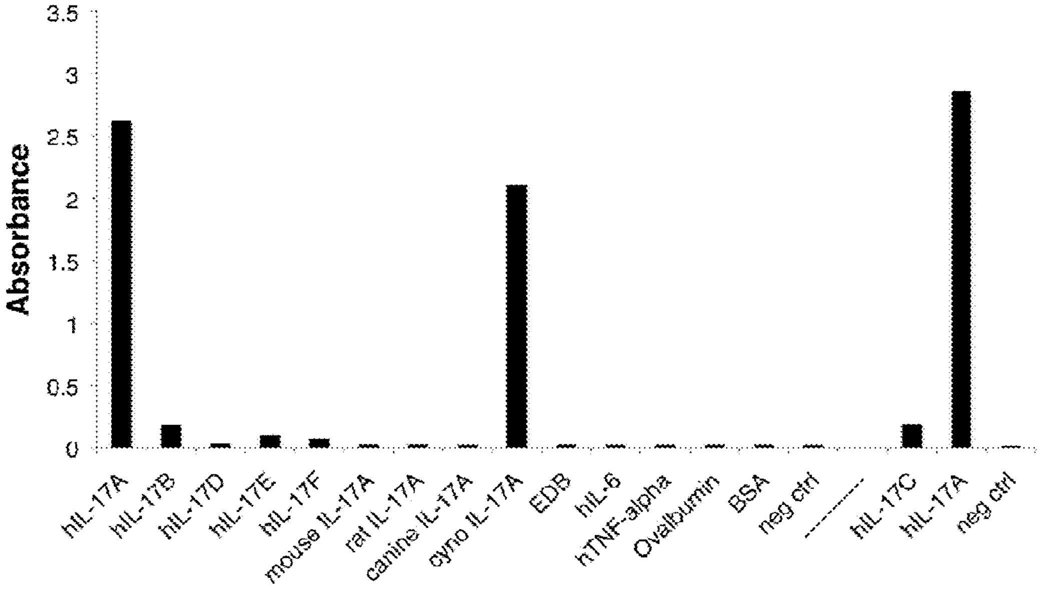

FIG. 18 shows the specificity of the Fyn SH3-derived polypeptide of the invention 2C1 (SEQ ID NO: 110). Different IL-17 family members, IL-17A of different species and other unrelated antigens were used in ELISA with the Fyn SH3-derived polypeptide of the invention 2C1 (SEQ ID NO: 110) as binding agent. Fyn SH3-derived polypeptide of the invention 2C1 (SEQ ID NO: 110) only binds to human and cynomolgus IL-17A. No binding to any of the other antigens could be detected. On the right side of the Figure (right side of the dashed line) the ELISA signal to human IL-17C is shown, which was determined on another day with the human IL-17A control. Legend: hIL-17A: human Interleukin 17A, hIL-17B: human Interleukin 17B, hIL-17D: human Interleukin 17D, hIL-17E: human Interleukin 17E, hIL-17F: human Interleukin 17F, mouse IL-17A: mouse Interleukin 17A, rat IL-17A: rat Interleukin 17A, canine IL-17A: canine Interleukin 17A, cyno II-17A: cynomolgus Interleukin 17A, EDB: extra domain B of fibronectin, hIL-6: human Interleukin 6, hTNF alpha: human Tumor Necrosis Factor alpha, Ovalbumin: Albumin from chicken egg white, BSA: Bovine Serum Albumin neg ctrl: no antigen was used for coating, hIL-17C: human Interleukin 17C.

Figure 19:
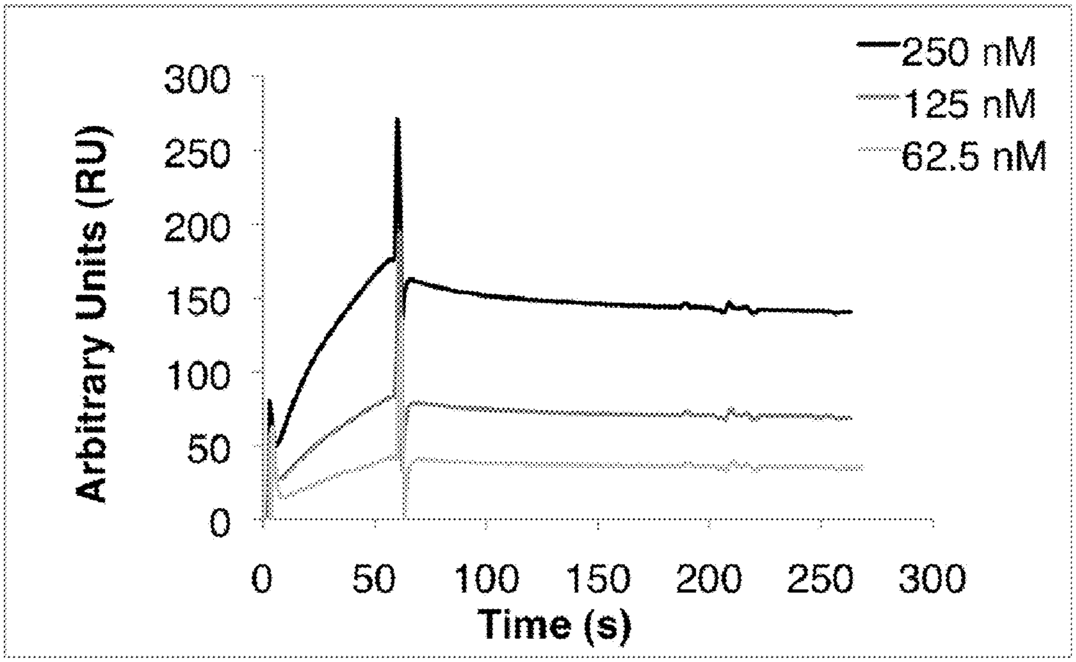

FIG. 19 depicts the Biacore sensogram of the Fyn SH3-derived polypeptide of the invention 2C1 (SEQ ID NO: 110) on a chip coated with cynomolgus IL-17A refolded from inclusion bodies.

Figure 20:
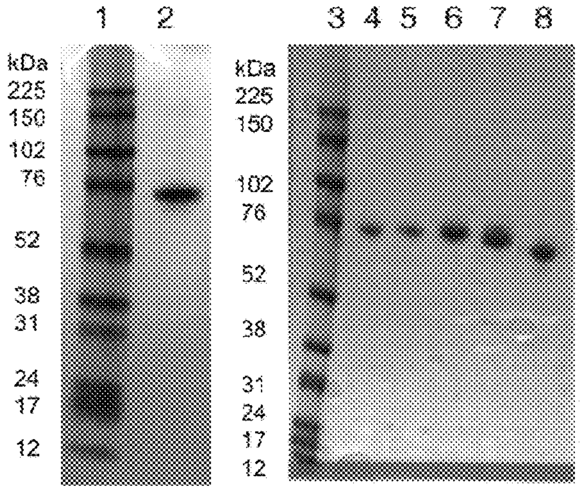

FIG. 20 shows SDS PAGE analysis of Fc fusion proteins. Lane 1: full range rainbow marker (GE Healthcare), lane 2: 2C1-Fc (SEQ ID NO: 133), lane 3: full range rainbow marker (GE Healthcare), lane 4: 2C1-m5-Fc(LALA) (SEQ ID NO: 136), lane 5: 2C1-m10-Fc(LALA) (SEQ ID NO: 137), lane 6: 2C1-m15-Fc(LALA) (SEQ ID NO: 138), lane 7: 2C1-m5E-Fc(LALA) (SEQ ID NO: 135), lane 8: 2C1-Fc(LALA) (SEQ ID NO: 134).

Figure 21:
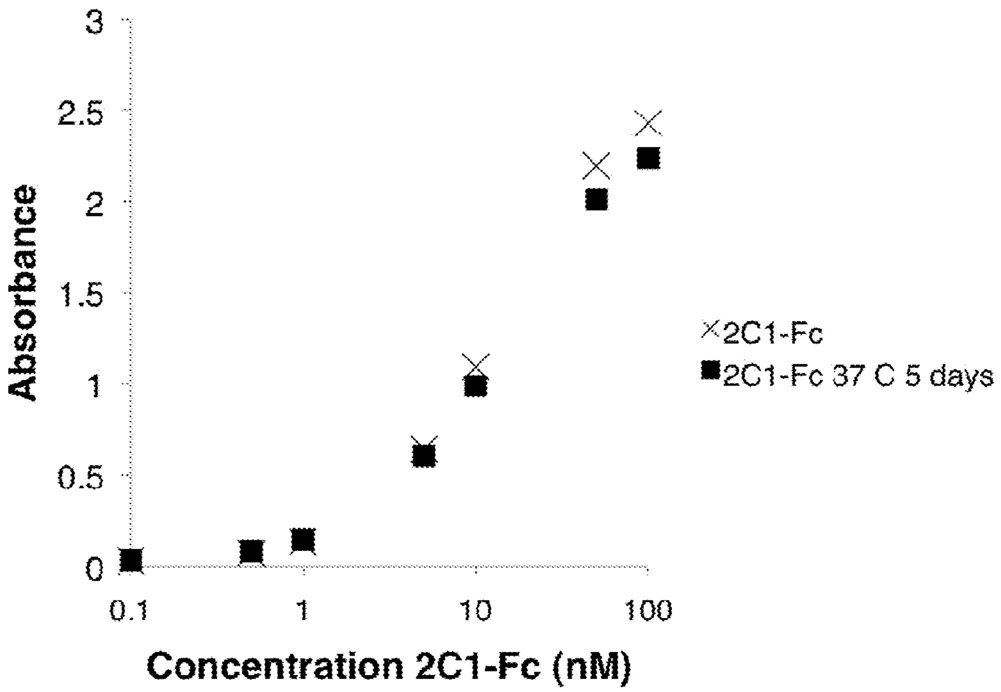

FIG. 21 shows the ELISA of 2C1-Fc (SEQ ID NO: 133) binding to IL-17A after storage for 5 days at 37° C. in human serum (■) compared to the standard control 2C1-Fc (SEQ ID NO: 133) stored at 4° C. in PBS (x).

Figure 22:
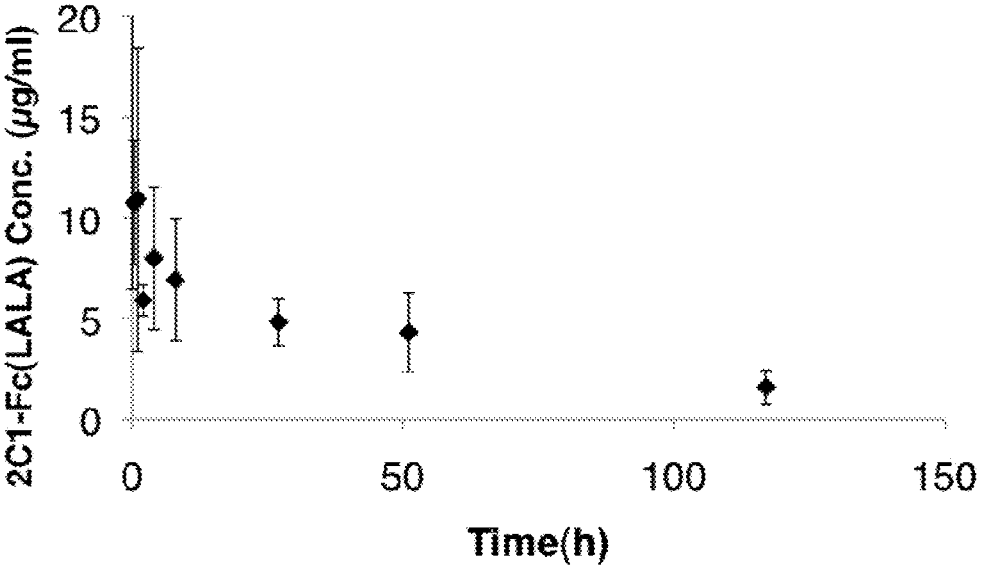

FIG. 22 shows the serum concentration at different time-points of 2C1-Fc(LALA) (SEQ ID NO: 134) after a single i.v. injection into mice. 2C1-Fc(LALA) fusion protein (SEQ ID NO: 134) produced in mammalian cells was injected (40 μg per animal) intravenously (iv) (n=5) in mice. The last four time points of the PK profile were used to calculate a terminal half-life of 2C1-Fc fusion protein of 53 hours.

Figure 23:
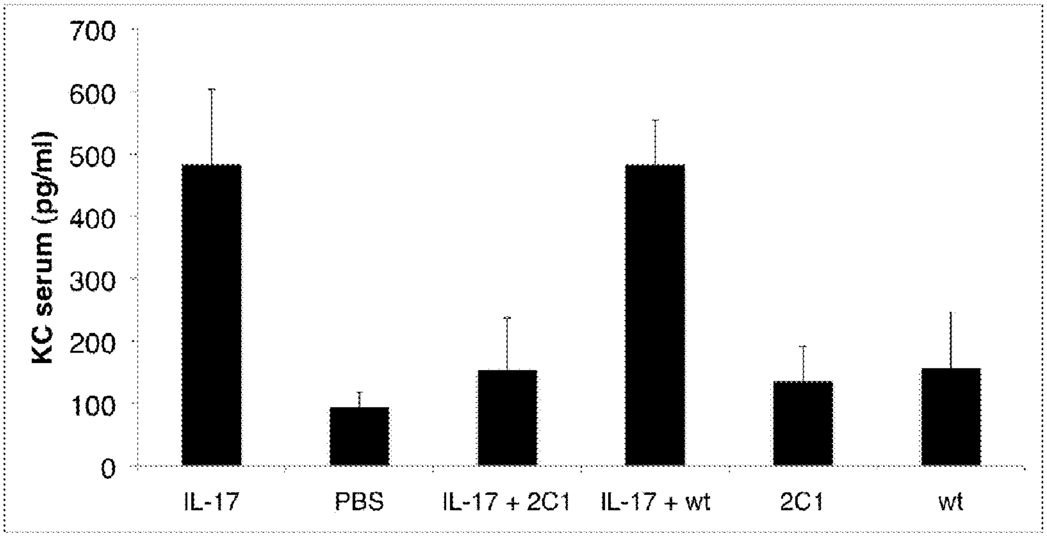

FIG. 23 shows the inhibition of human IL-17A induced KC production by the anti-IL-17 Fyn SH3-derived polypeptide 2C1 (SEQ ID NO: 110) of the invention in an acute inflammation model. Two hours after s.c. injection of either 3 μg human IL-17A (IL-17), PBS (PBS), 3 μg human IL-17A with 17 μg monomeric Fyn SH3-derived polypeptide 2C1 (SEQ ID NO: 110) of the invention (IL-17+2C1), 3 μg human IL-17A with 16 μg wild-type Fyn SH3 monomer (IL-17+wt), 17 μg monomeric Fyn SH3-derived polypeptide 2C1 (SEQ ID NO: 110) of the invention alone (2C1), or 16 μg wild-type Fyn SH3 monomer alone (wt), blood samples were taken and KC levels in mouse-serum were quantified. Mean KC levels of 4 mice per group are shown (±SD), with the exception of the wild-type control groups (Fyn SH3 without and with IL-17A), where mean levels of 3 mice are shown (±SD).

Figure 24:
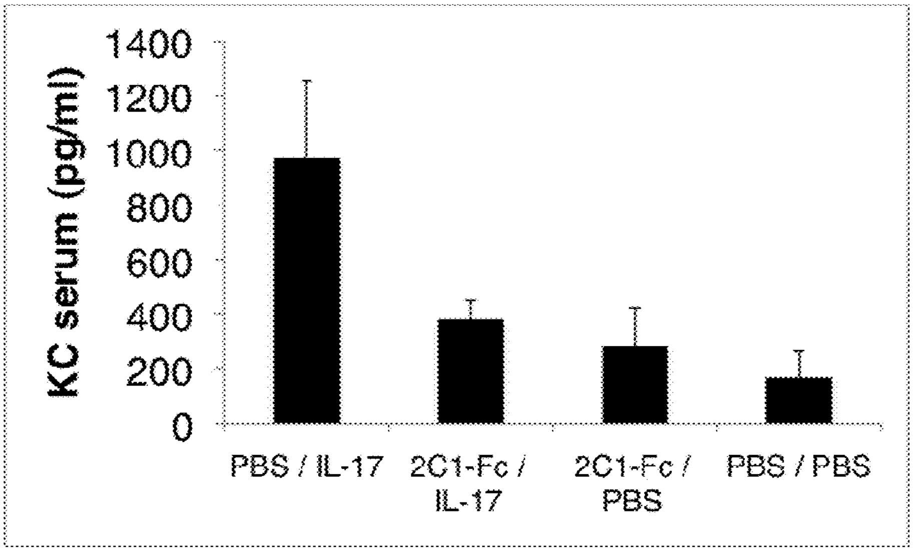

FIG. 24 depicts the inhibition of human IL-17A induced KC production by 2C1-Fc fusion protein (SEQ ID NO: 133) in an acute inflammation model. 2C1-Fc/IL-17: 44 μg of 2C1-Fc (SEQ ID NO: 133) was injected i.v. followed by s.c. injection of 3 μg human IL-17A. Two hours after administration of IL-17A, blood samples were taken from the mice and KC serum levels were measured by ELISA. Control experiments were performed as follows: PBS/IL-17: i.v. injection of PBS followed by s.c. injection of IL-17; 2C1-Fc/PBS: i.v. injection of 2C1-Fc (SEQ ID NO: 133) followed by s.c. injection of PBS; PBS/PBS: i.v. injection of PBS followed by s.c. injection of PBS. Mean KC levels of 3-5 mice per group are shown (±SD).

Figure 25:
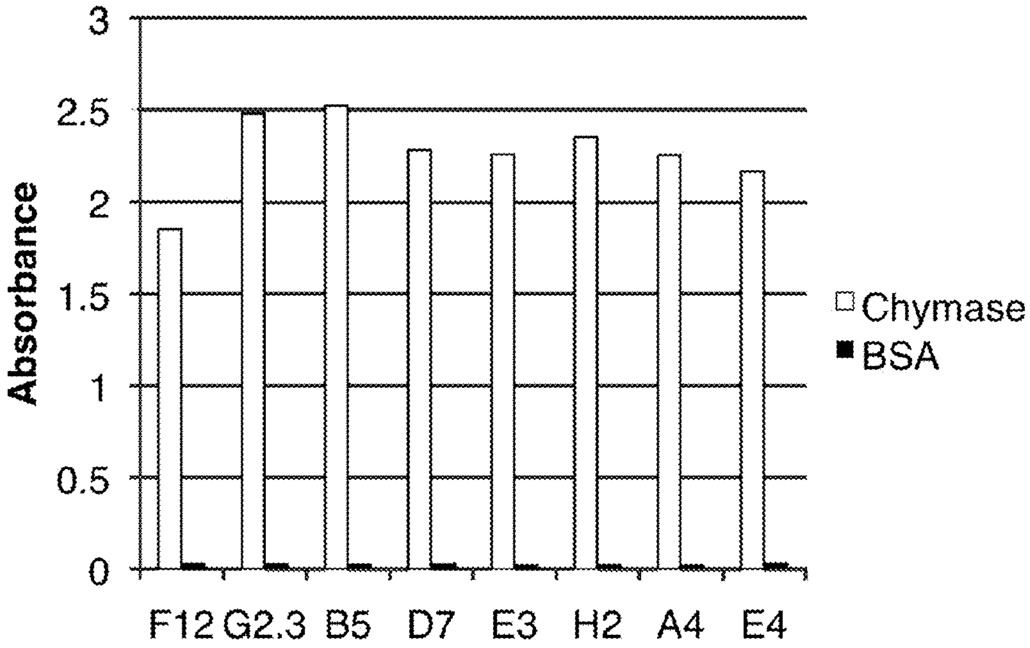

FIG. 25 shows the ELISA signals for binding of the indicated Fyn SH3-derived polypeptides of the invention to chymase. No ELISA signals could be detected for the binding to the irrelevant protein bovine serum albumin (BSA).

Figure 26:
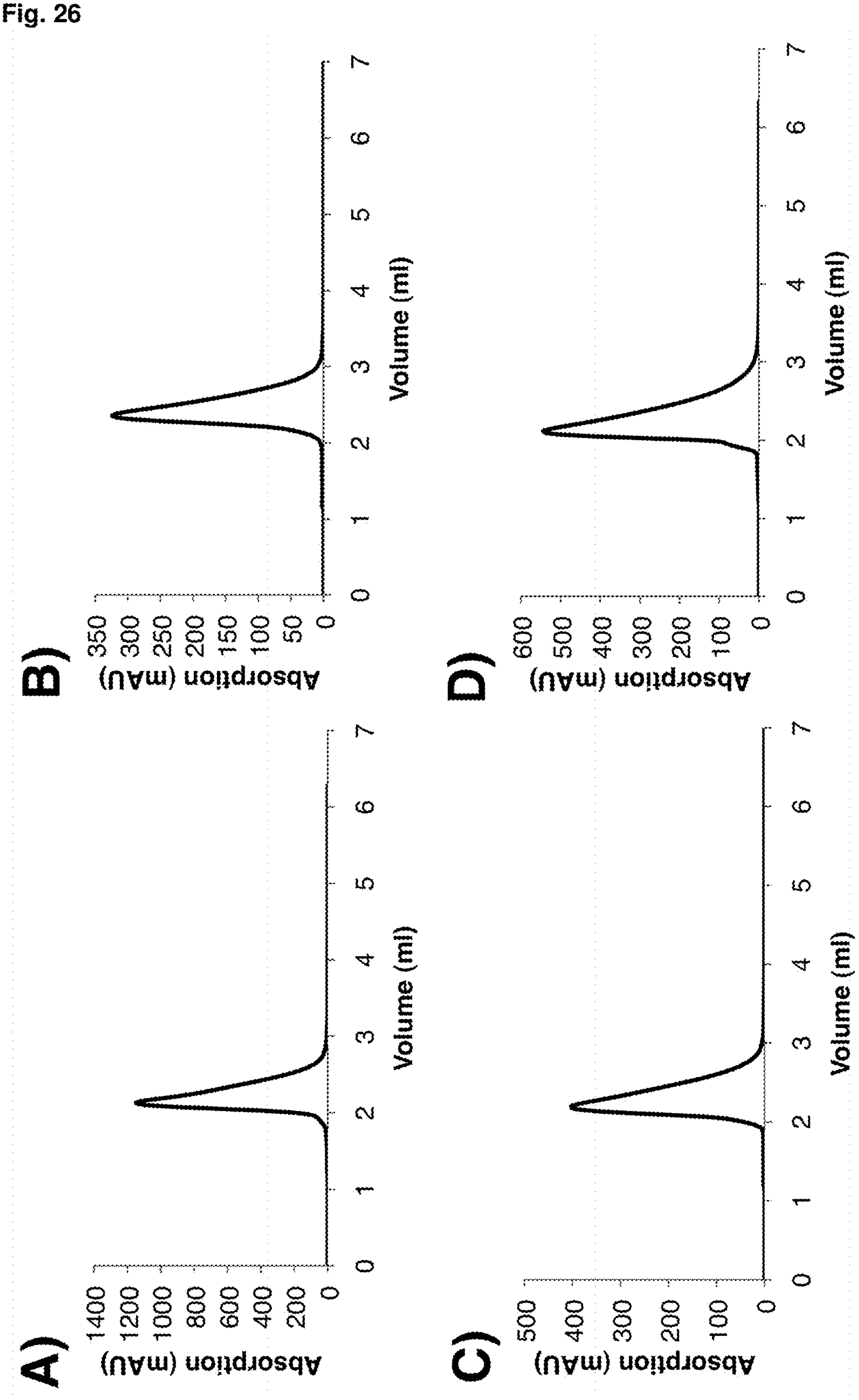
Figure 26:
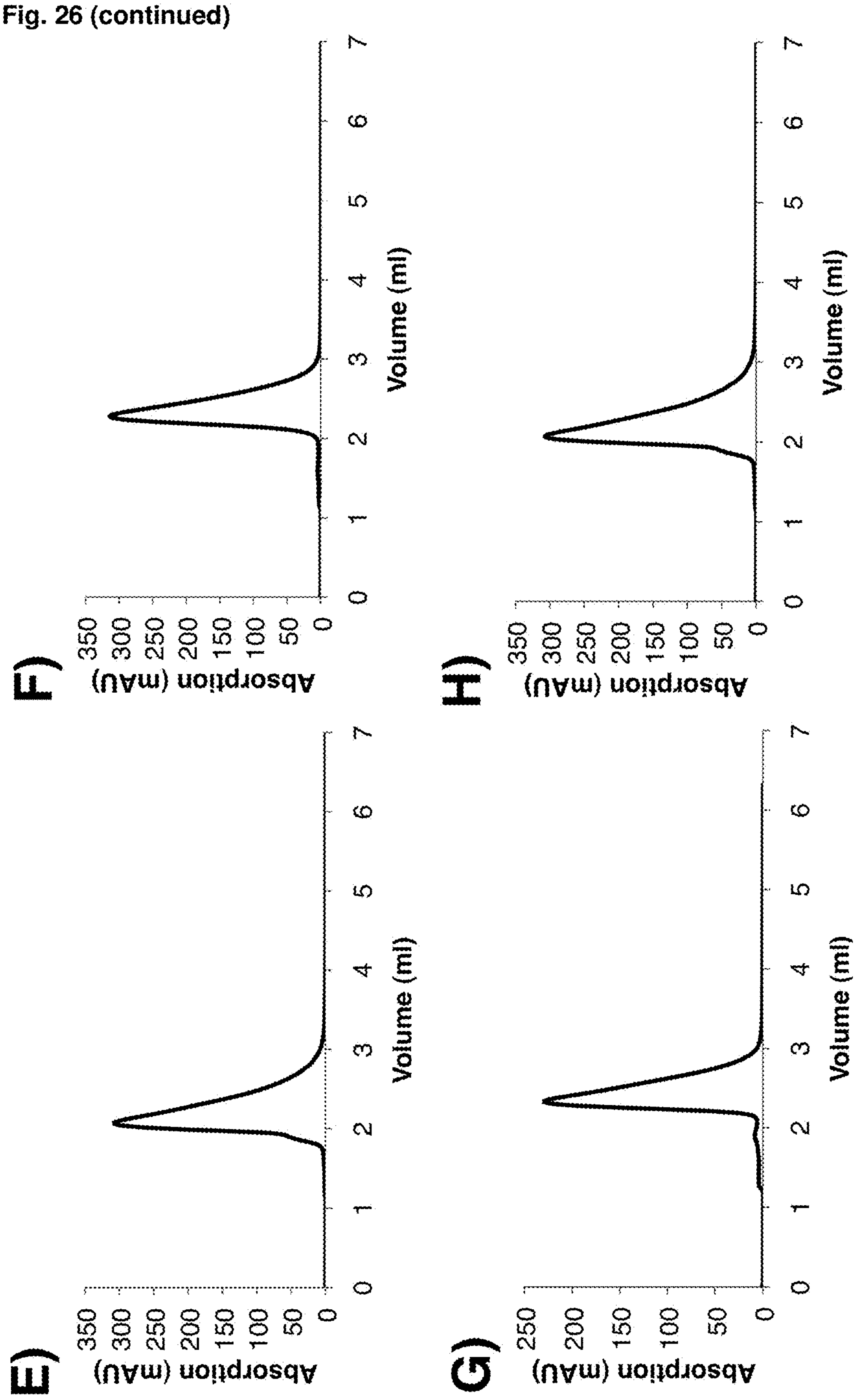

FIG. 26 shows the monomeric size exclusions profiles of the following Fyn SH3-derived polypeptides of the invention: A) Fyn SH3-derived polypeptide of the invention F12 (SEQ ID NO: 5), B) Fyn SH3-derived polypeptide of the invention G2.3 (SEQ ID NO: 157), C) Fyn SH3-derived polypeptide of the invention E3 (SEQ ID NO: 160), D) Fyn SH3-derived polypeptide of the invention B5 (SEQ ID NO: 154), E) Fyn SH3-derived polypeptide of the invention D7 (SEQ ID NO: 158), F) Fyn SH3-derived polypeptide of the invention E4 (SEQ ID NO: 153), G) Fyn SH3-derived polypeptide of the invention H2 (SEQ ID NO: 159), H) Fyn SH3-derived polypeptide of the invention A4 (SEQ ID NO: 155)

Figure 27:
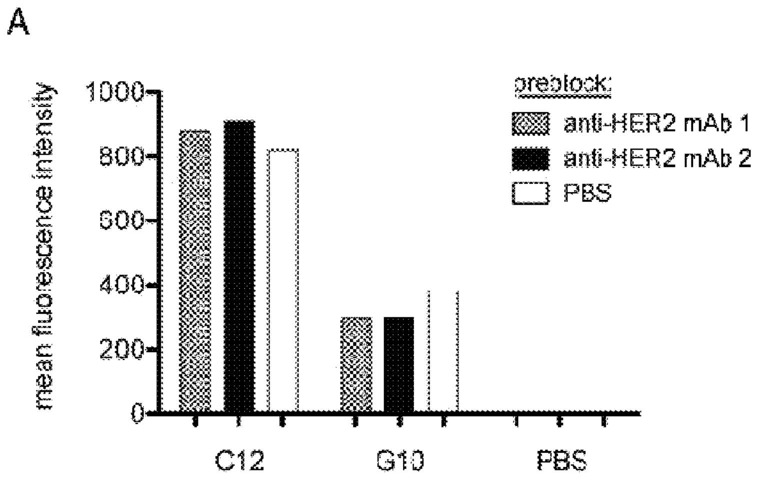
Figure 27:
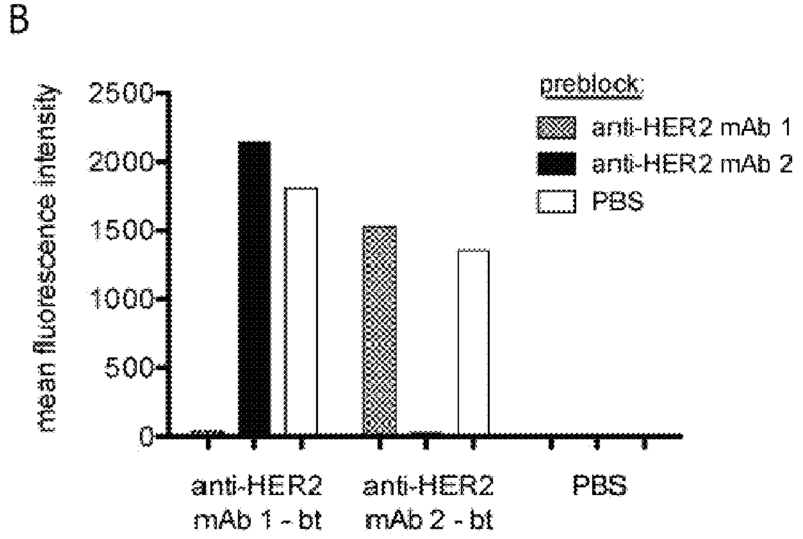

FIG. 27 FACS binding experiments using HER2 overexpressing BT-474 cells.

(A) Binding of Fyn SH3 derived polypeptides C12 (SEQ ID NO: 167) and G10 (SEQ ID NO: 168) on HER2 with or without pre-blocking of the epitope of the anti-HER2 antibody 1 (anti-HER2 mAb 1; wherein the heavy chain has the amino acid sequence of SEQ ID NO: 320 and the light chain has the amino acid sequence of SEQ ID NO: 321; exemplary nucleic acid molecules encoding the heavy and light chain are shown in SEQ ID NO: 331 and 332) and anti-HER2 antibody 2 (anti-HER2 mAb 2; wherein the heavy chain has the amino acid sequence of SEQ ID NO: 326 and the light chain has the amino acid sequence of SEQ ID NO: 329; exemplary nucleic acid molecules encoding the heavy and light chain are shown in SEQ ID NO: 334 and 335). PBS, phosphate buffered saline, represents the negative control.

(B) Binding of biotinylated anti-HER2 antibody 1 and biotinylated anti-HER2 antibody 2 (biotinylated antibodies are indicated with the abbreviation "bt") with or without pre-blocking of the epitope of the anti-HER2 antibody 1 and anti-HER2 antibody 2. PBS, phosphate buffered saline, represents the negative control.

Figure 28A:
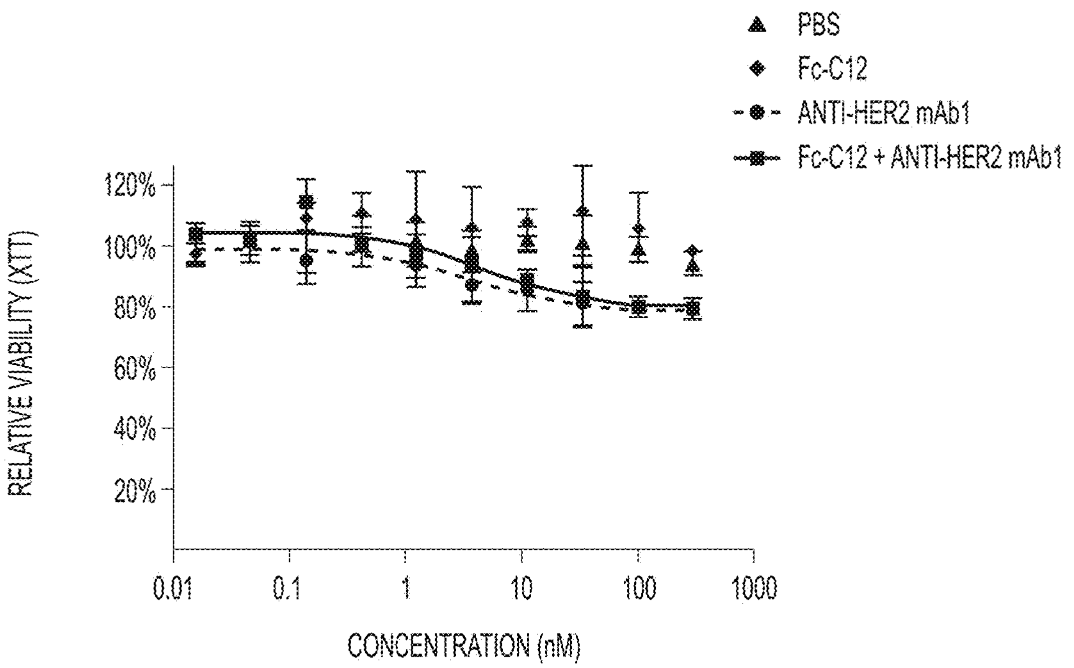
Figure 28B:
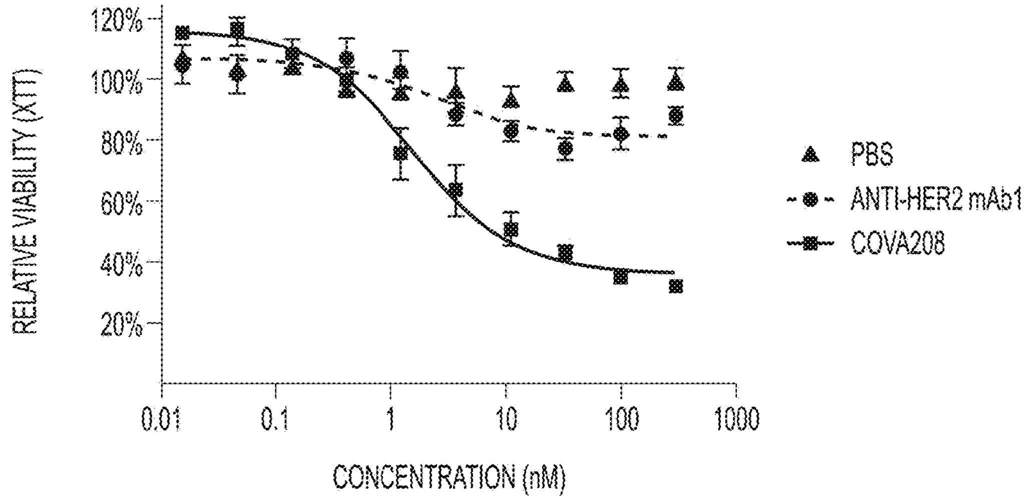
Figure 28:
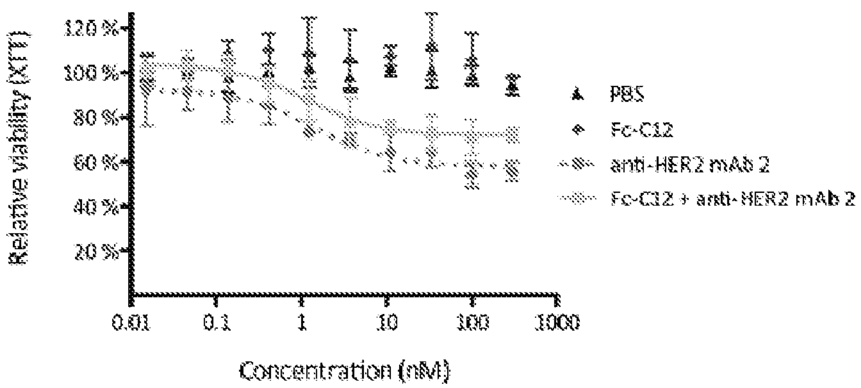
Figure 28:
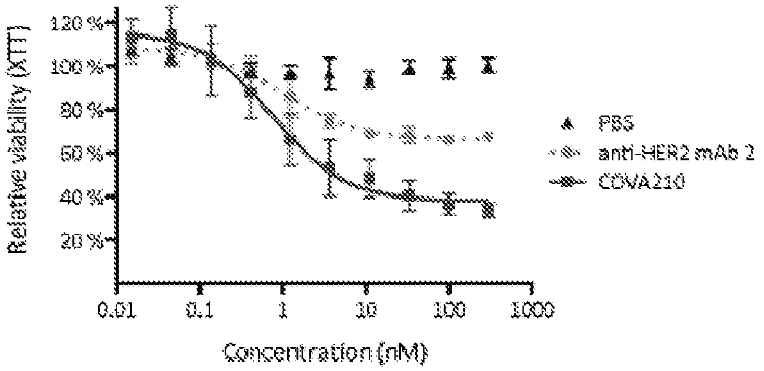

FIG. 28 In vitro proliferation assays with HER2 overexpressing gastric cancer cell line NCI-N87.

Fyn SH3-derived polypeptide C12 (SEQ ID NO: 167) was fused to the Fc part of a human IgG1 to create the monospecific bivalent protein called Fc-C12 (SEQ ID NO: 319). The combination mixture of Fynomer C12-Fc with the anti-HER2 antibody 1 (anti-HER2 mAb 1) (shown in FIG. 28A) and with the anti-HER2 antibody 2 (anti-HER2 mAb 2) (shown in FIG. 28C) did not reduce proliferation rate of NCI-N87 cells more effectively than the corresponding anti-HER2 antibodies alone. However, the anti-proliferative activity of the binding molecules COVA208 (SEQ ID NO: 319 & 325) (shown in FIG. 28B) and COVA210 (SEQ ID NO: 326 & 327; an exemplary nucleic acid molecule encoding SEQ ID NO: 327 is shown in SEQ ID NO: 336) (FIG. 28D) was higher than the activity of the corresponding unmodified antibody. COVA 208 consists of the fusion of C12 (SEQ ID NO: 167) to the N-terminus of the light chain of antibody 1 (SEQ ID NO: 320 and 321) and COVA210 consists of the fusion of C12 (SEQ ID NO: 167) to the N-terminus of the light chain of antibody 2 (SEQ ID NO: 226 and 329), see also FIG. 36.

Figure 29:
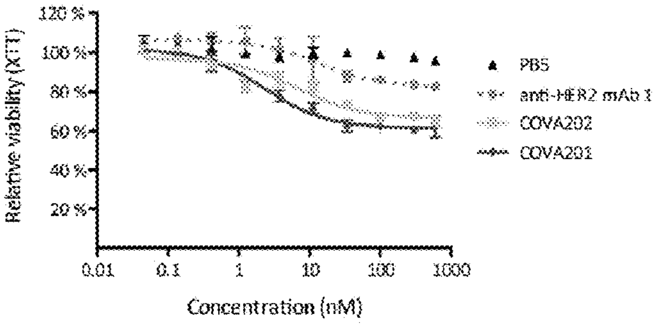
Figure 29:
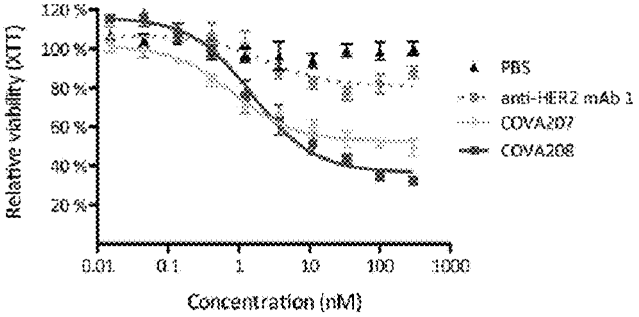

FIG. 29 The anti-proliferative activity of anti-HER2 Fynomer-antibody fusions varies depending on the relative orientation of the Fynomer and the binding site of the antibody.

The anti-proliferative activities of the different Fynomer-antibody fusion proteins in a proliferation cell assay with NCI-N87 gastric cancer cells showed variations (A) and (B), and COVA208 showed the best anti-proliferative effects on this cell line (B). The maximal effects are indicated in the tables and given in percentage of viability. COVA201 (SEQ ID NOs: 322 and 321), COVA202 (SEQ ID NOs: 320 and 323), COVA207 (SEQ ID NOs: 324 and 321) and COVA208 (SEQ ID NOs: 320 and 325) are all fusion proteins of the Fyn SH3 derived polypeptide C12 (SEQ ID NO: 167) and anti-HER2 antibody 1 (anti-HER2 mAb 1) (SEQ ID NOs: 320 and 321). COVA201 consists of the C-terminal heavy chain fusion, COV202 represents the C-terminal light chain fusion, COVA 207 consists of the N-terminal heavy chain fusion and COVA208 represents the N-terminal light chain fusion.

Figure 30:
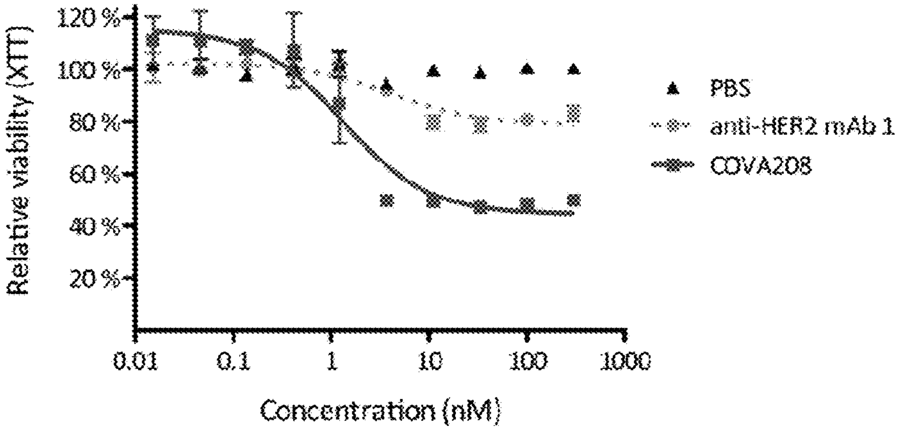

FIG. 30 The anti-proliferative activity of COVA208 (SEQ ID NOs: 321 and 325) (fusion of Fynomer C12 to the N-terminus of the light chain of anti-HER2 antibody 1 (anti-HER2 mAb 1, SEQ ID NOs: 320 and 321)) was determined in a cell assay with the HER2 overexpressing breast cancer cell line BT-474. COVA208 exhibited superior anti-proliferative activity as compared to the unmodified antibody.

Figure 31:
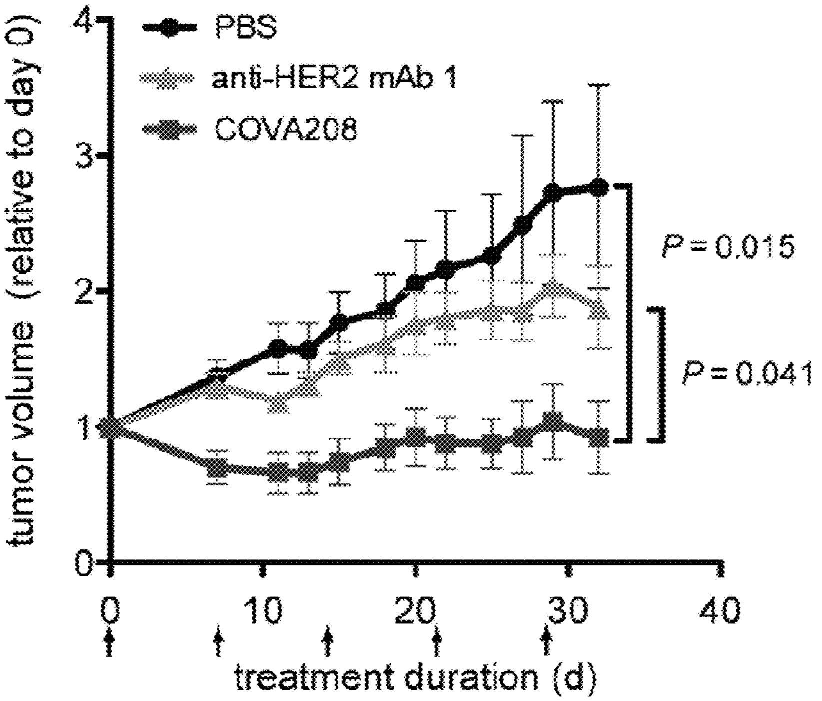

FIG. 31 depicts an animal study with a NCI-N87 gastric cancer xenograft mouse model. NCI-N87 gastric cancer cells were inoculated subcutaneously in CD1 Nude mice (n=6 per treatment group). When tumors reached a size of about 140 $mm^3$, animals were treated with a loading dose of 30 mg/kg COVA208 (SEQ ID NOs: 320 and 325), anti-HER2 antibody 1 (anti-HER2 mAb 1 (SEQ ID NOs: 320 and 321)) or placebo (PBS). Treatment was continued with four weekly i.p. injections (15 mg/kg) (indicated with the arrows) and size of tumors was measured with a caliper. COVA208 was found to inhibit tumor growth significantly better than the monospecific anti-HER2 antibody 1 or placebo (PBS). Mean tumor volumes of 6 mice are shown (relative to day 0 when the treatment was started)±standard error of the mean (SEM).

Figure 32:
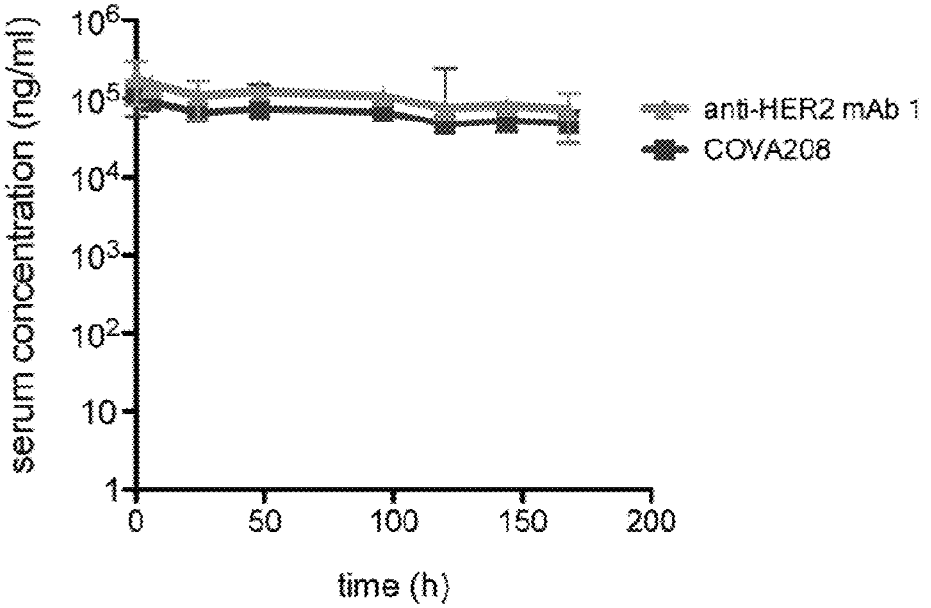

FIG. 32 Serum concentrations of COVA208 (SEQ ID NOs: 320 and 325) and the anti-HER2 antibody 1 (anti-HER2 mAb 1 (SEQ ID NOs: 320 and 321)) at different time-points after a single i.v. injection into C57131/6 mice. The six last time-points were used to calculate the terminal half-lives of 247 h (COVA208) and 187 h (anti-HER2 antibody 1). Mean serum concentrations are plotted versus time, error bars represent standard deviations (SD).

Figure 33:
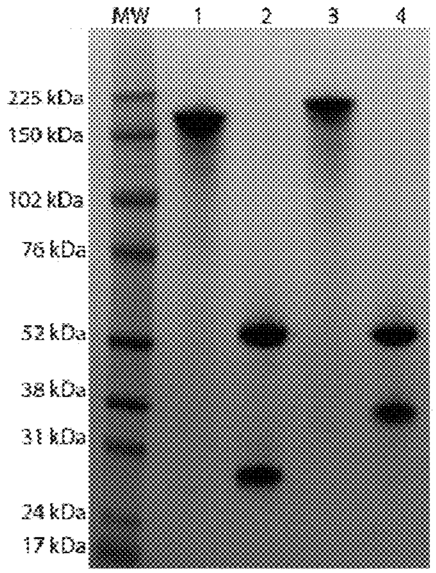
Figure 33:
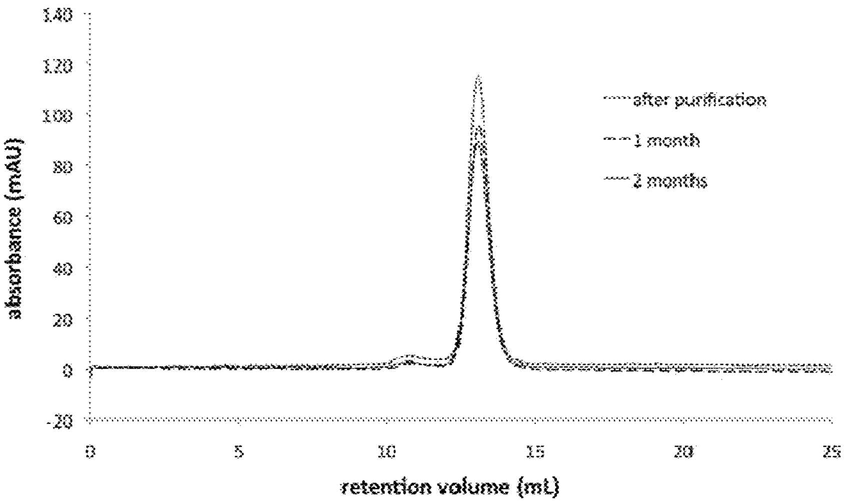

FIG. 33 SDS PAGE of COVA208 (SEQ ID NOs: 320 and 325) and anti-HER2 antibody 1 (anti-HER2 mAb 1 (SEQ ID NO: 320 and 321)) (top) and size exclusion chromatograms of COVA208 after purification and after a storage period of 1 and 2 months at 4° C. (bottom). Evidently, COVA208 did not form any aggregates.

Figure 34:
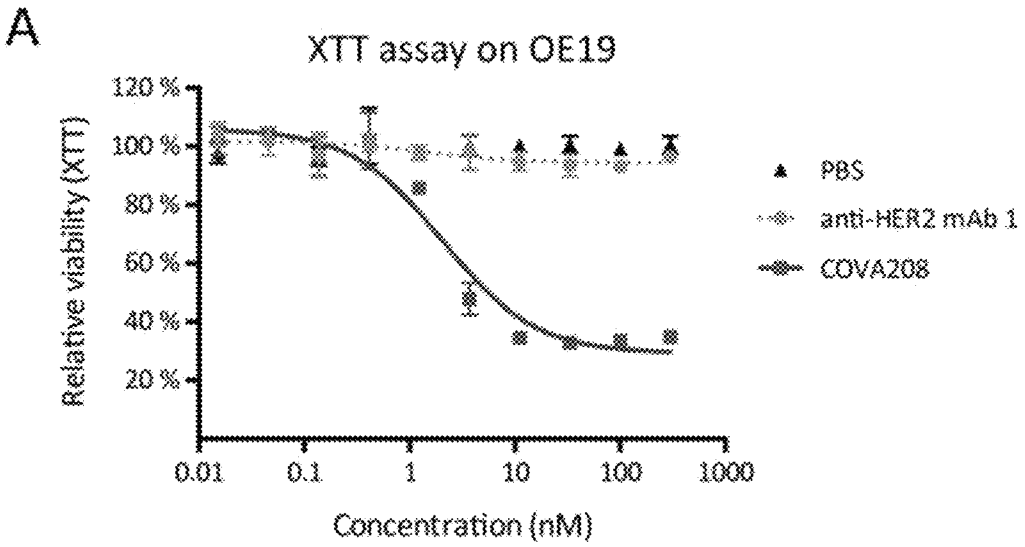
Figure 34:
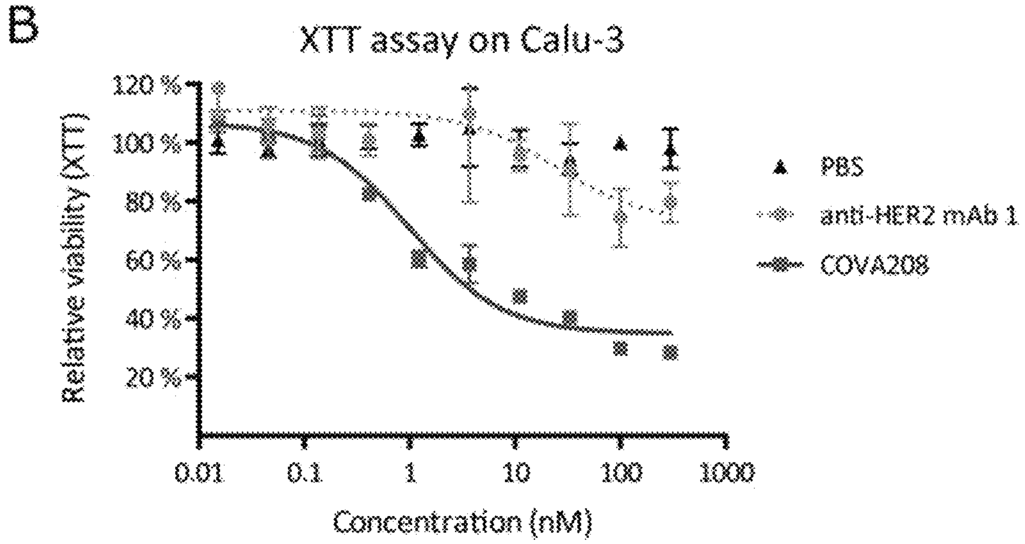
Figure 34:
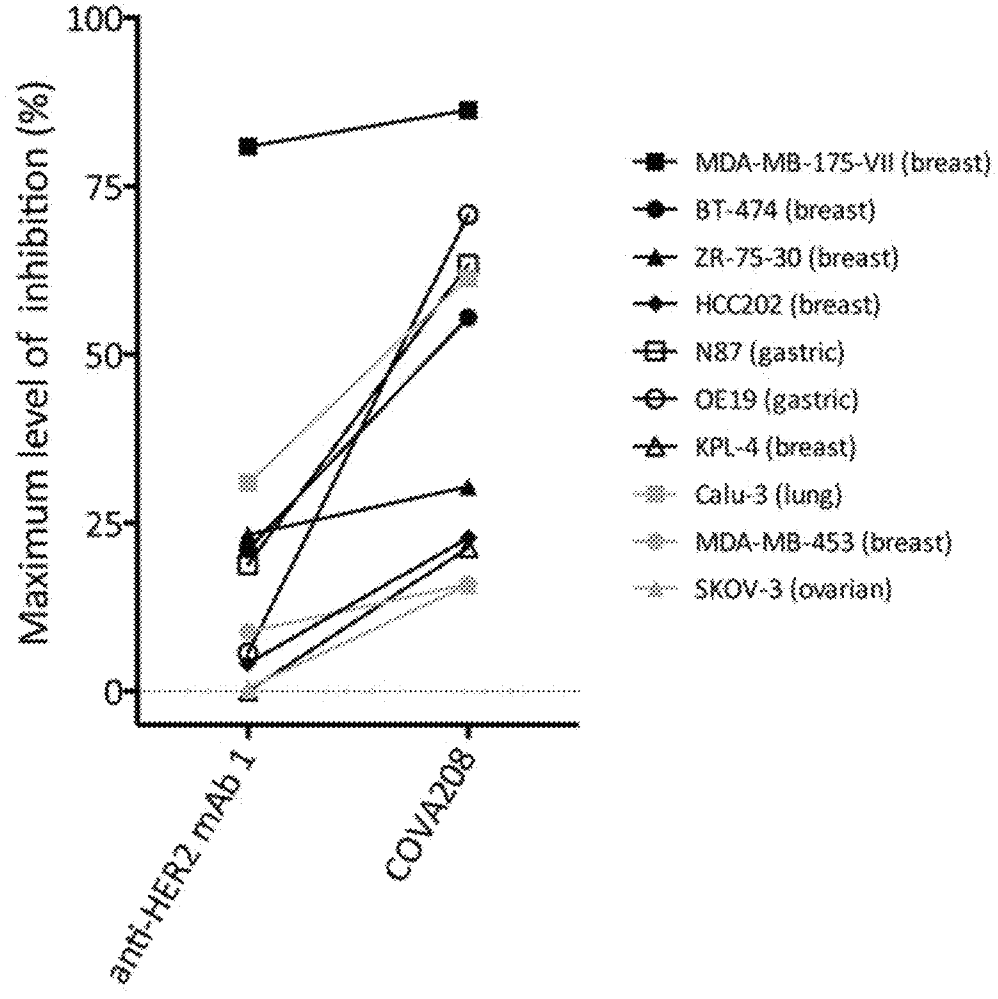

FIG. 34 In vitro proliferation assays with HER2 expressing cell lines. COVA208 (SEQ ID NOs: 320 and 325) inhibited the cell growth of 0E19 (FIG. 9A) and of Calu-3 cells (FIG. 9B) more effectively than anti-HER2 antibody 1 (anti-HER2 mAb 1 (SEQ ID NOs: 320 and 321)). FIG. 9C summarizes the results of the in vitro proliferation assays performed on 10 different cell lines, for each of which the maximal level of inhibition has been plotted. The corresponding data points for COVA208 and anti-HER2 antibody 1 were connected to facilitate the comparison between the two compounds.

COVA208 shows improved inhibition of cell growth as compared to anti-HER2 antibody 1 on all 10 cell lines.

Figure 35:
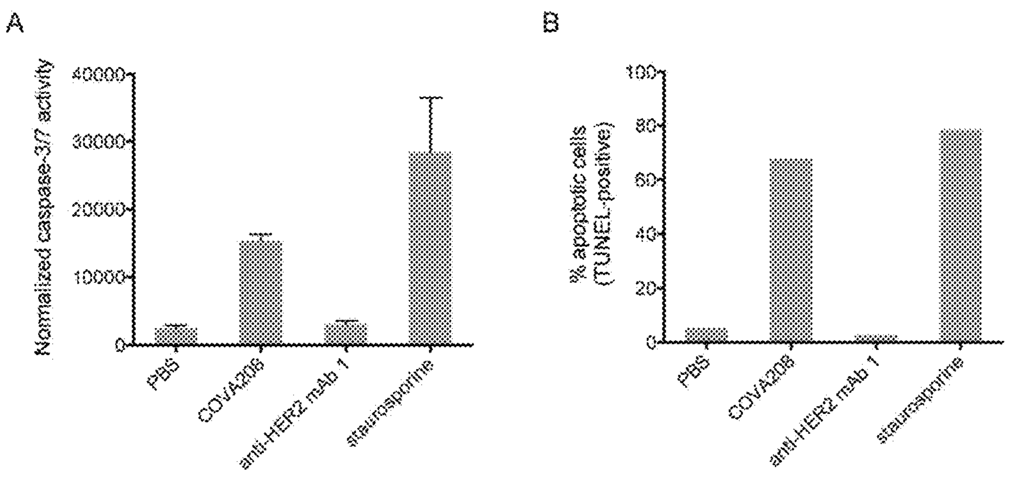

FIG. 35 COVA208 (SEQ ID NOs: 320 and 325) is capable of inducing apoptosis, as determined by caspase-3/7 activity (FIG. 35A) and by TUNEL staining (FIG. 35B). Anti-HER2 antibody 1 (anti-HER2 mAb 1 (SEQ ID NOs: 320 and 325)) did not increase caspase-3/7 activity nor the fraction of TUNEL-positive cells, indicating that the ability to induce apoptosis is unique to COVA208. Staurosporine was used as positive control. Error bars in FIG. 35A indicate standard deviation of triplicates.

Figure 36:
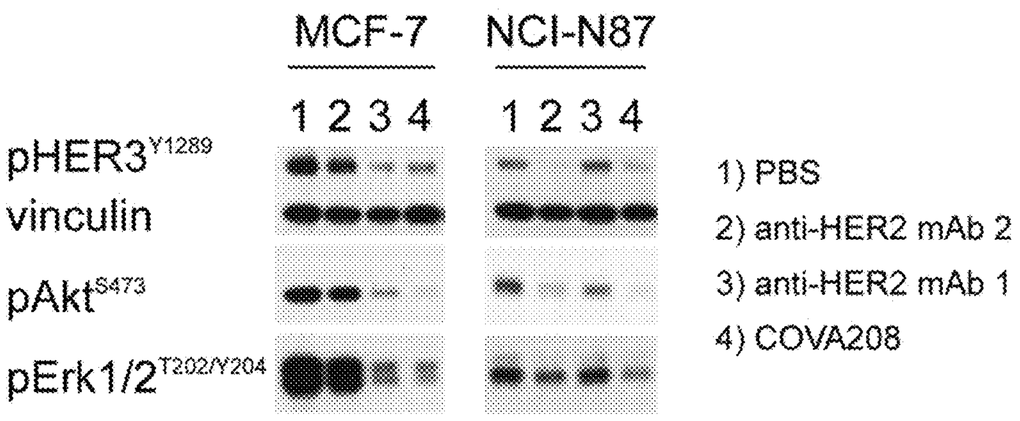

FIG. 36 COVA208 (SEQ ID NOs: 320 and 325) inhibits ligand-dependent activation of HER2 signaling on MCF-7 cells (left panel) as well as ligand-independent activation of HER2 signaling on NCI-N87 cells (right panel). Anti-HER2 antibody 1 (anti-HER2 mAb 1 (SEQ ID NOs: 320 and 321)) inhibits signaling only on MCF-7 cells, whereas anti-HER2 antibody 2 (anti-HER2 mAb 2 (SEQ ID NOs: 226 and 329)) is only active on NCI-N87 cells. Vinculin served as a loading control.

Figure 37:
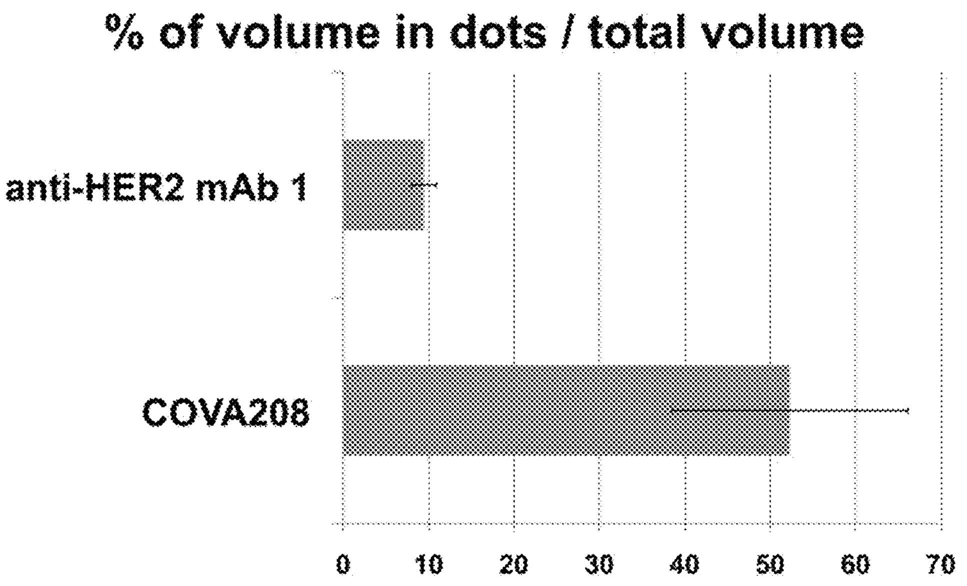

FIG. 37 COVA208 is internalized by NCI-N87 cells. After surface staining followed by 5 h incubation, 52% of COVA208 (SEQ ID NOs: 320 and 325) was found in spherical dots within the cytosol, as determined from confocal laser scanning images analyzed with Imaris software. Anti-HER2 antibody 1 (anti-HER2 mAb 1 (SEQ ID NOs: 320 and 321)) staining primarily remained membrane-associated, with only 9% of the staining localizied in cytosolic spherical dots.

Figure 38:
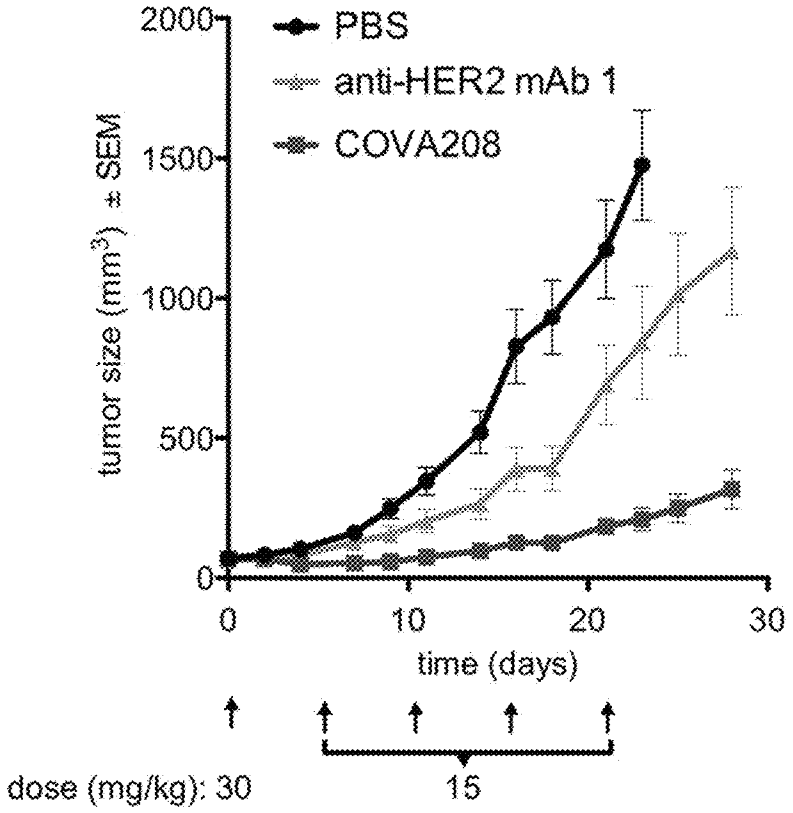

FIG. 38 depicts an animal study with a KPL-4 breast cancer xenograft mouse model. KPL-4 breast cancer cells were inoculated subcutaneously in SCID beige mice (n=8 per treatment group). When tumors reached a size of about 70 $mm^3$, animals were treated with a loading dose of 30 mg/kg COVA208 (SEQ ID NOs: 320 and 325), anti-HER2 antibody 1 (anti-HER2 mAb 1 (SEQ ID NOs: 320 and 321)) or placebo (PBS). Treatment was continued with four weekly i.p. injections (15 mg/kg) (indicated with the arrows) and size of tumors was measured with a caliper. COVA208 was found to inhibit tumor growth significantly better than the monospecific anti-HER2 antibody 1 or placebo (PBS). Mean tumor volumes of 8 mice are shown ±standard error of the mean (SEM).

Figure 39:
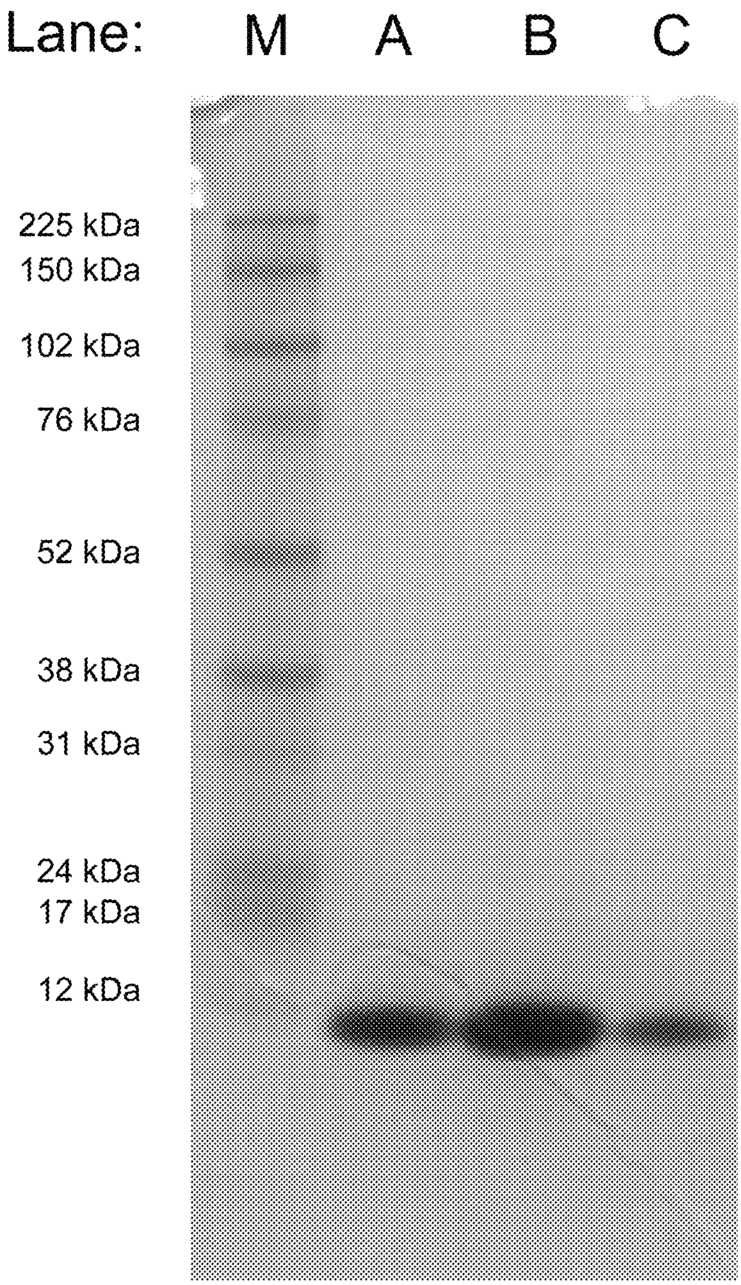

FIG. 39 shows the SDS-PAGE characterization of albumin-binding polypeptides of the invention: Lane M: molecular weight standard; Lane A: Fynomer® C1 (SEQ ID NO: 440); Lane B: Fynomer® 17H (SEQ ID NO: 441); Lane C: WT Fyn-SH3 (SEQ ID NO: 339).

Figure 40:
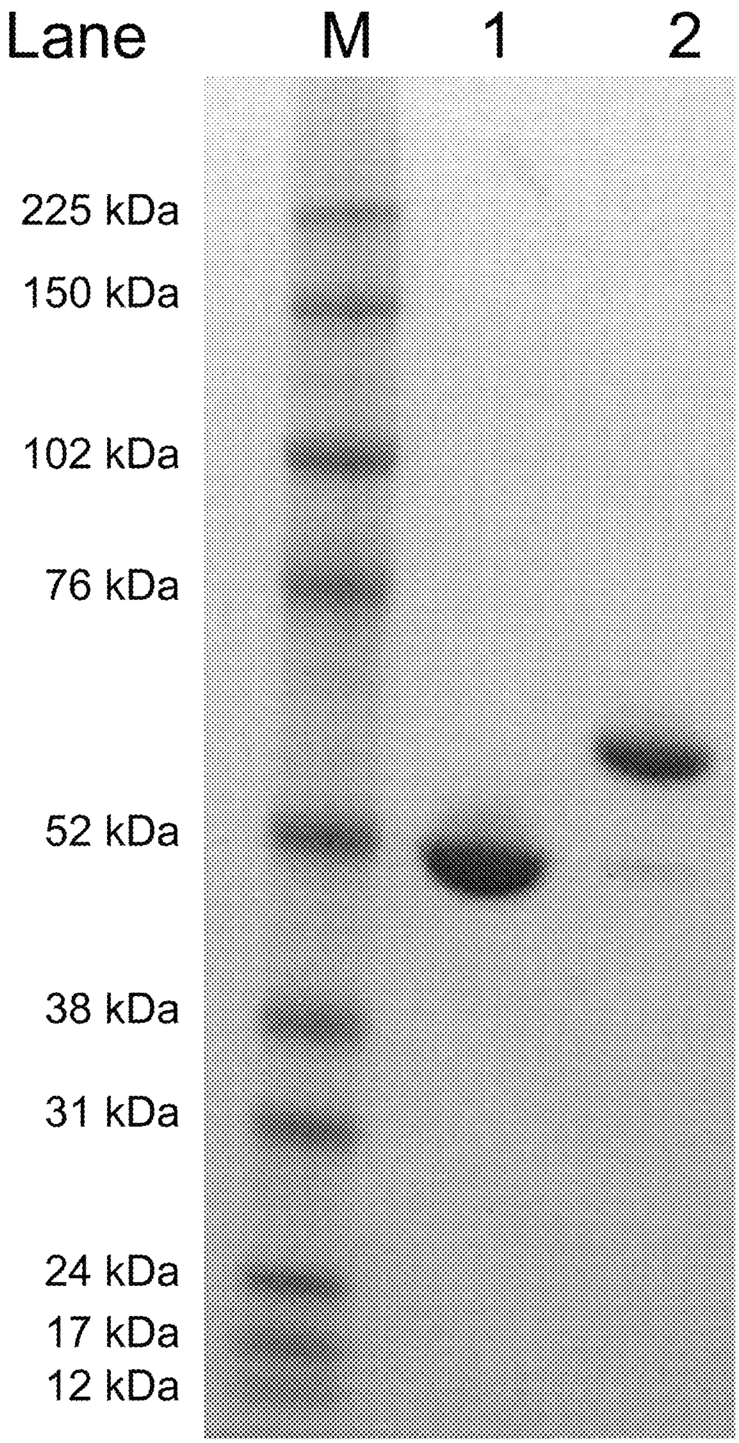

FIG. 40 shows the SDS-PAGE characterization of the unmodified BITE® polypeptide (SEQ ID NO: 378, lane 1) and the Fynomer®-BITE® fusion protein COVA406 (SEQ ID NO: 379, lane 2), consisting of the albumin binding Fynomer® 17H and the BITE® molecule. The molecular weight standard is shown in Lane M.

Figure 41:
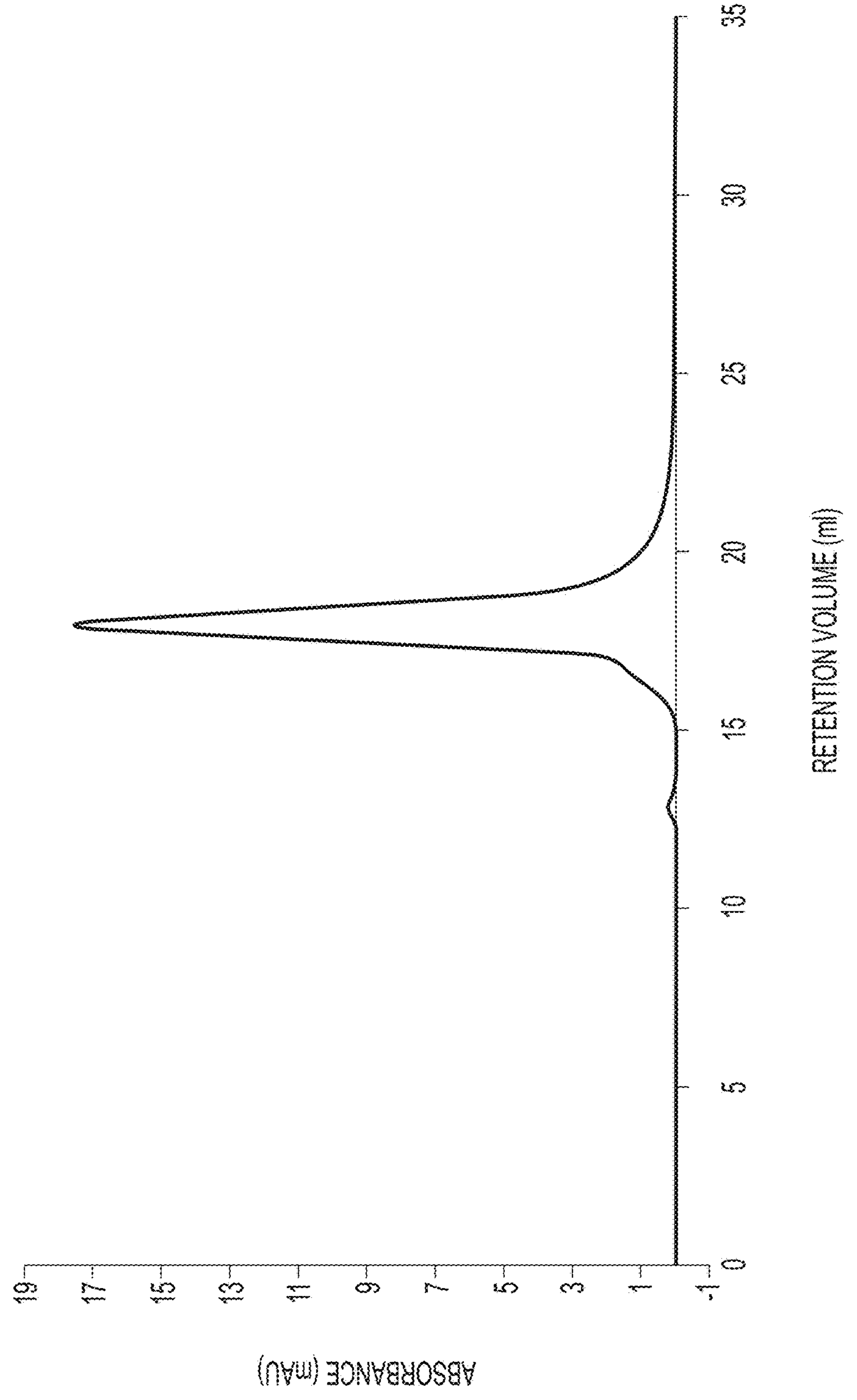

FIG. 41 shows the size exclusion chromatogram (SEC) of COVA406 (SEQ ID NO: 379).

Figure 42:
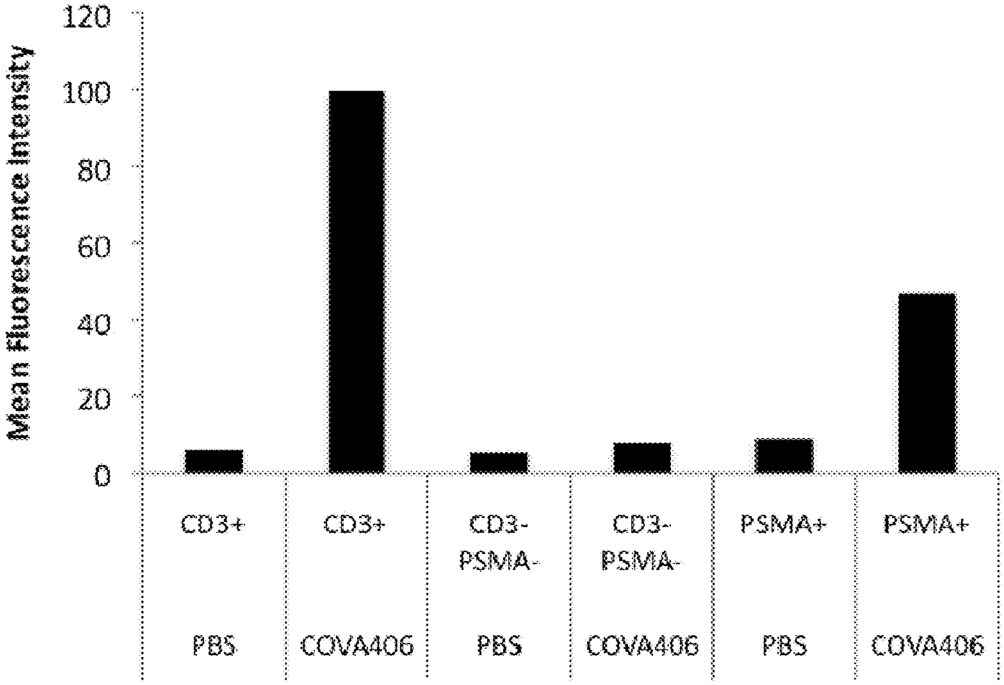

FIG. 42 depicts a FACS binding experiment with COVA406 (SEQ ID NO: 379) using cells expressing CD3 (Jurkat E6-1), cells expressing PSMA (22Rv1 cells) and an irrelevant cell line expressing neither CD3 nor PSMA (LS174T cells). Binding is expressed as mean fluorescence intensity. CD3+: CD3-positive cells; CD3−: CD3-negative cells; PSMA+: PSMA-positive cells; PSMA−: PSMA-negative cells; COVA406: COVA406 is used as binding reagent; PBS: negative control, phosphate buffered saline is added instead of COVA406. COVA406 recognizes both antigens CD3 and PSMA expressed on cells.

Figure 43:
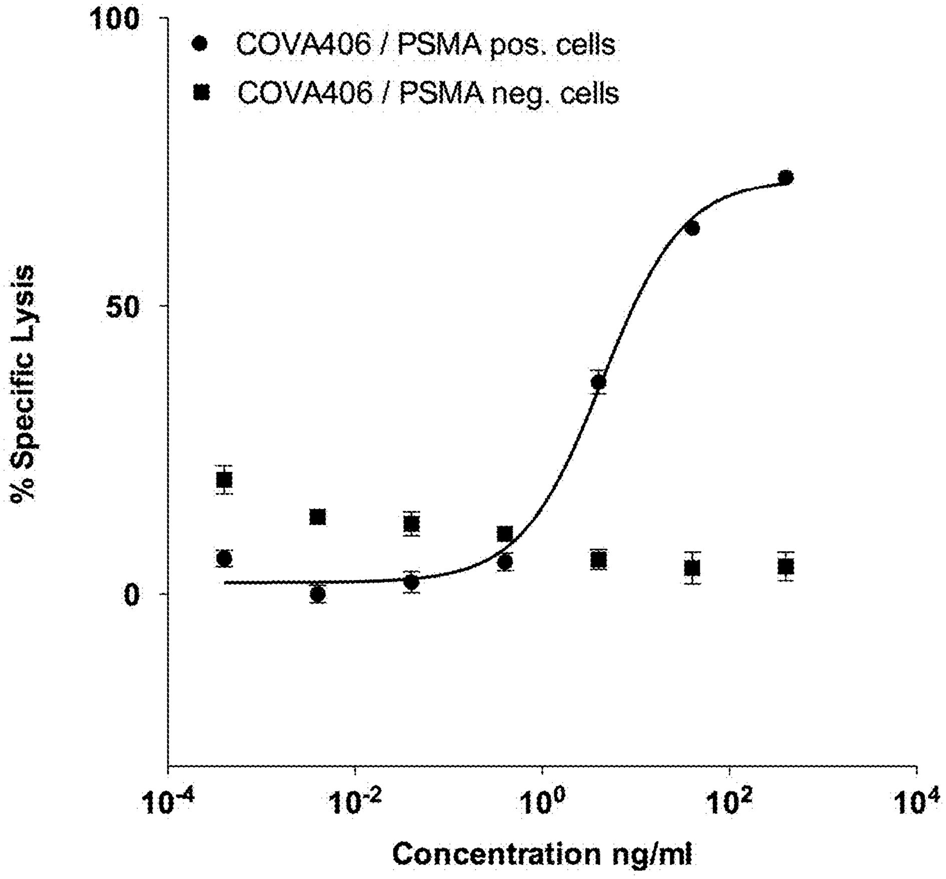

FIG. 43 depicts the analysis of redirected cell lysis of PSMA positive cells (22Rv1 cells) or PSMA negative cells (HT29 cells) by COVA406 (SEQ ID NO: 379) using human PBMCs as effector cells. The target cells 22Rv1 and HT29 were pre-labeled with Calcein AM and then incubated with human PBMCs (at effector cell to target cell ratio (E:T) of 25:1) and different concentrations of COVA406 (SEQ ID NO: 379) for 5 hours. The percentage of specific tumor cell lysis was measured by detection of calcein-release into the supernatant. Triplicates of 3 wells are shown ±SEM.

Figure 44:
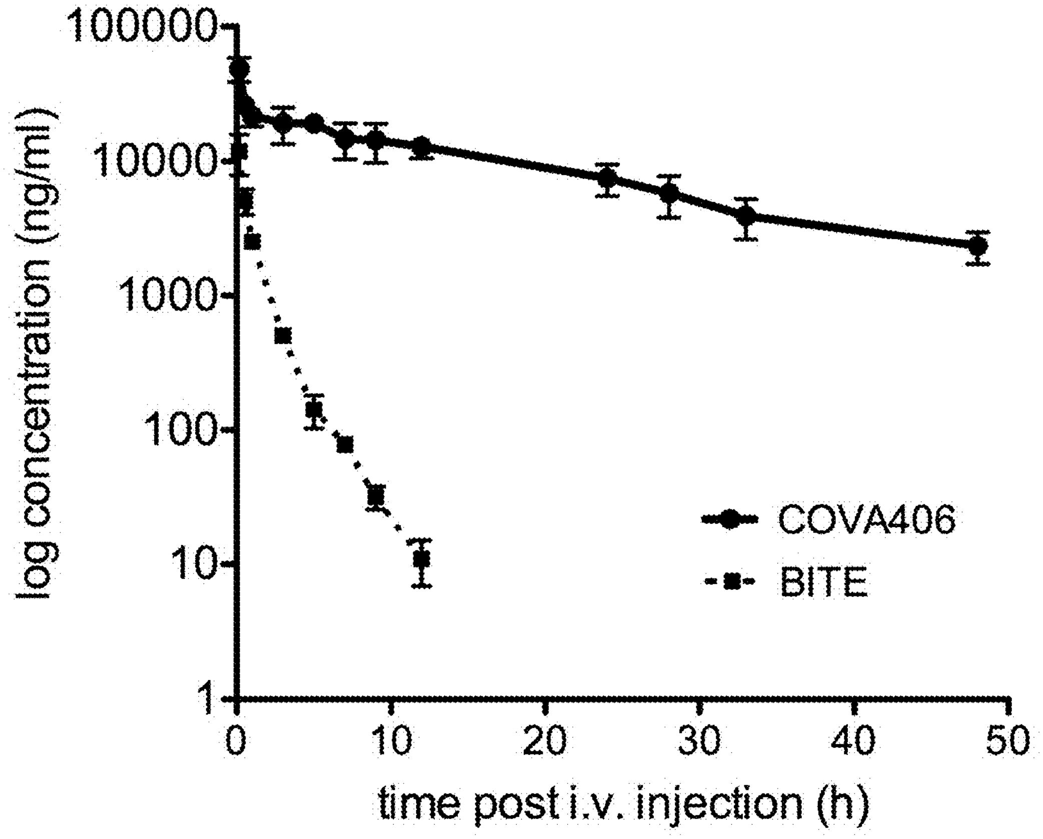

FIG. 44 shows the serum concentrations of COVA406 (SEQ ID NO: 379) and the BITE® protein (SEQ ID NO: 378) at different time-points after a single i.v. injection into C57BU6 mice. The concentration in serum was determined by ELISA. Mean values of 5 mice are shown ±SD FIG. 45 Specificity ELISA of prior art Fyn SH3 variants isolated after affinity selections. MSA=mouse serum albumin, HSA=human serum albumin, RSA=rat serum albumin, BSA=bovine serum albumin FIG. 46 shows the SDS-PAGE characterization of Fynomer®-antibody fusion proteins of the invention and control proteins. A: gel run under non-reducing conditions; B: gel run under reducing conditions. Lane M: molecular weight standard; Lane 1: anti-CD3 antibody (SEQ ID NOs 381 and 382); Lane 2: COVA420 (SEQ ID NOs 387 and 388); Lane 3: COVA446 (SEQ ID NO: 391).

Figure 47:
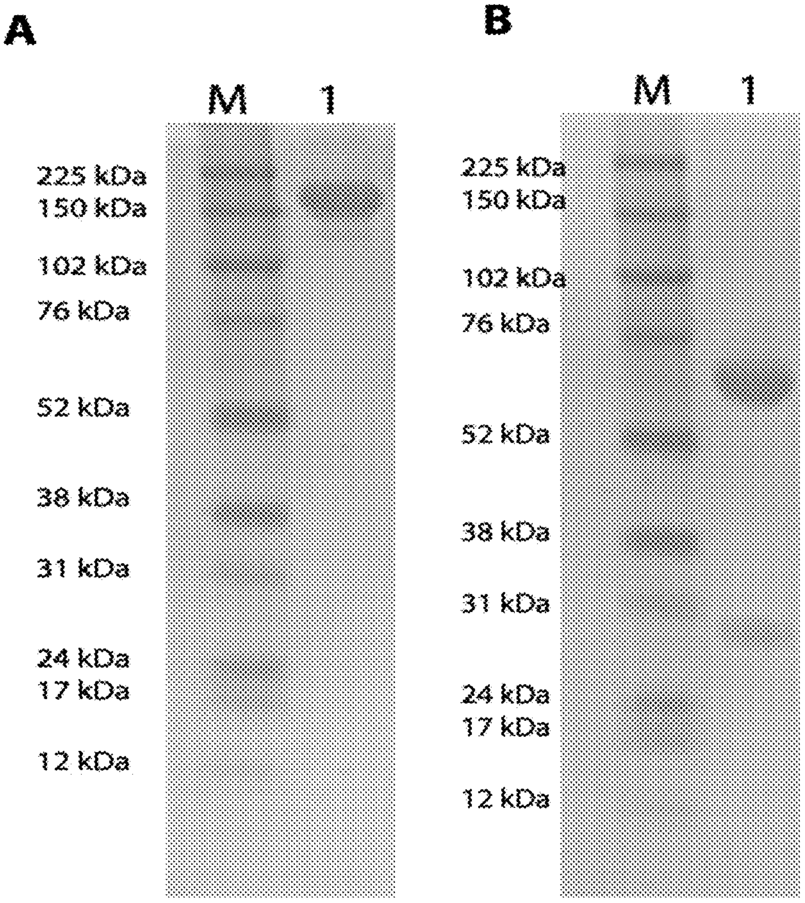

FIG. 47 shows the SDS-PAGE characterization of an Fynomer®-antibody fusion proteins of the invention. A: gel run under non-reducing conditions; B: gel run under reducing conditions. Lane M: molecular weight standard; Lane 1: COVA422 (SEQ ID NOs: 389 and 390)

Figure 48:
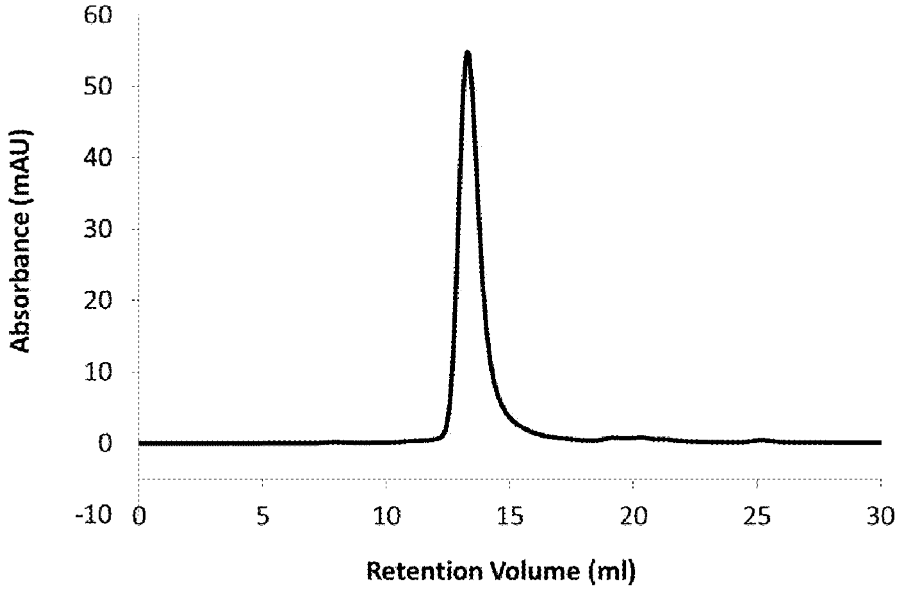
Figure 48:
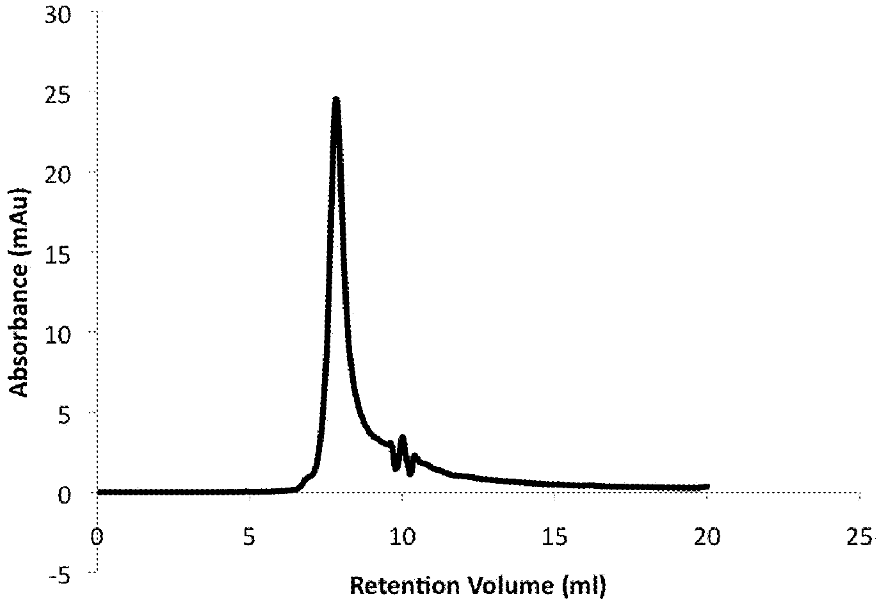
Figure 49A:
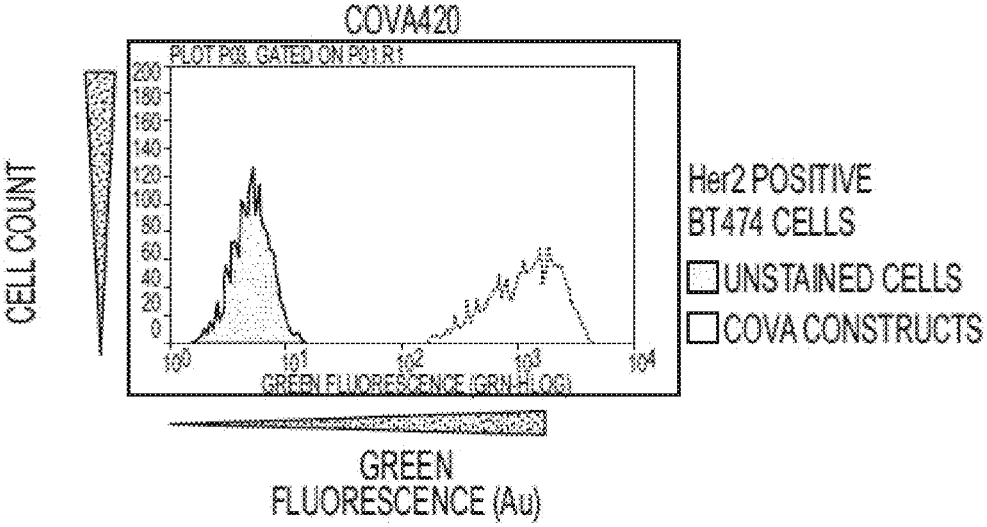
Figure 49A:
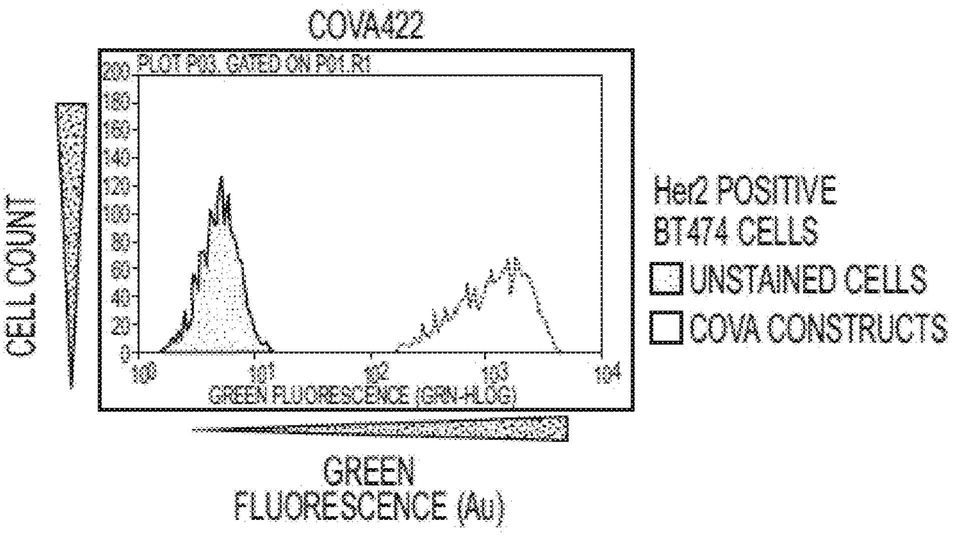
Figure 49A:
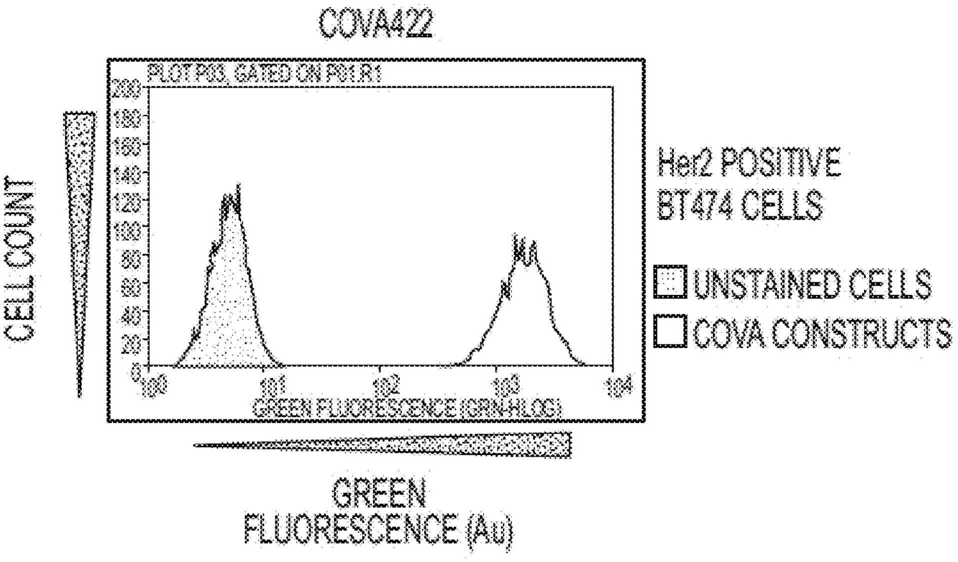

FIG. 48 shows size exclusion (SEC) profiles of Fynomer®-antibody fusion proteins. A: SEC profile of COVA420 (SEQ ID NOs 387 and 388) on FPLC system; B: SEC profile of COVA422 (SEQ ID NOs: 389 and 390) on HPLC system FIG. 49A shows the flow cytometric binding analysis of Fynomer®-antibody fusion proteins COVA420 (SEQ ID NOs: 387 and 388); COVA422 (SEQ ID NOs 389 and 390), and the bispecific scFv-control COVA446 (SEQ ID NO: 391) on HER2 positive cells. Signals are compared to the background signal obtained with the secondary detection antibody only (grey shaded histograms).

Figure 49B:
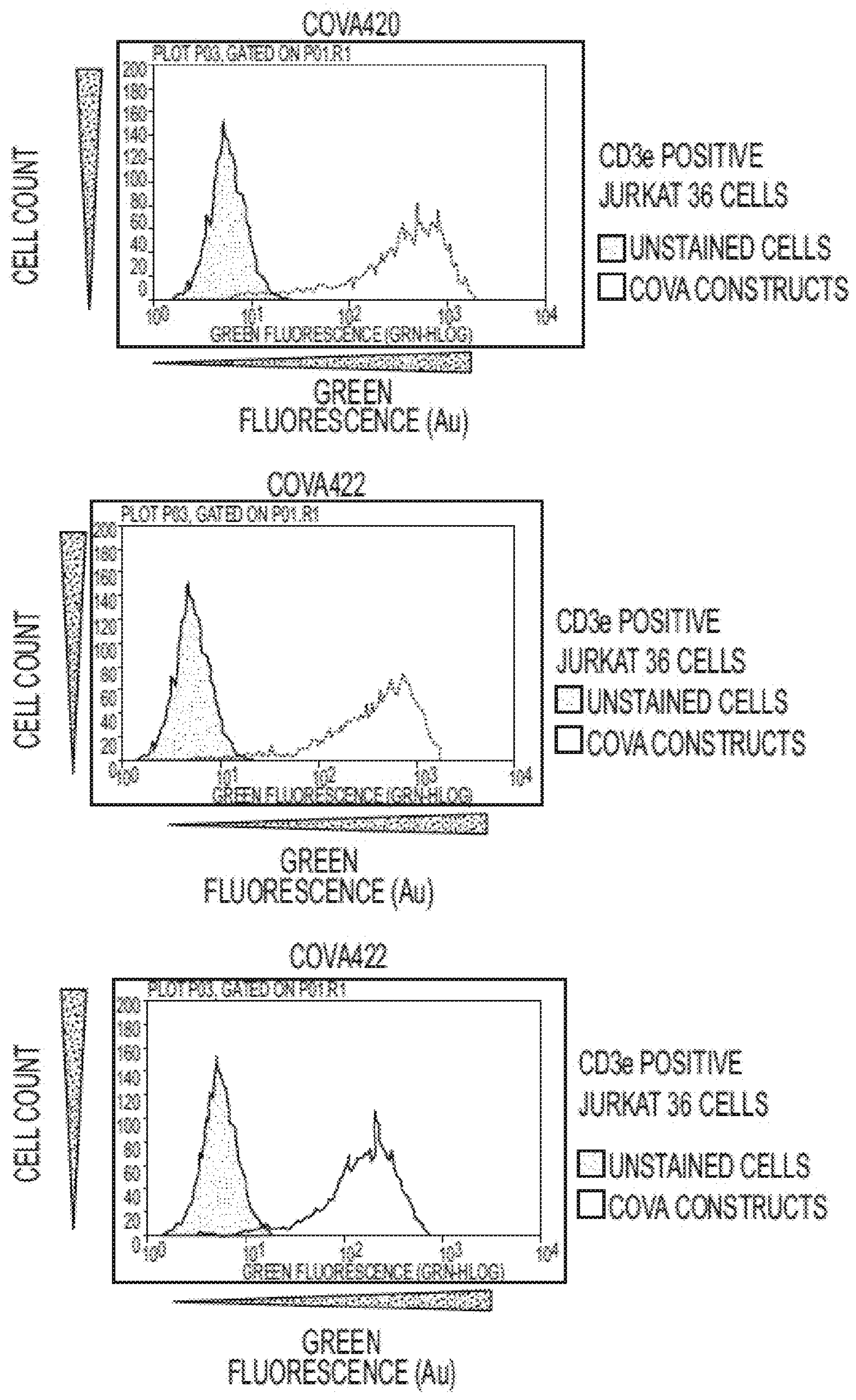

FIG. 49B shows the flow cytometric binding analysis of Fynomer®-antibody fusion proteins COVA420 (SEQ ID NOs: 387 and 388); COVA422 (SEQ ID NOs 389 and 390), and the bispecific scFv-control COVA446 (SEQ ID NO: 391) on CD3 positive cells. Signals are compared to the background signal obtained with the secondary detection antibody only (grey shaded histograms).

Figure 49C:
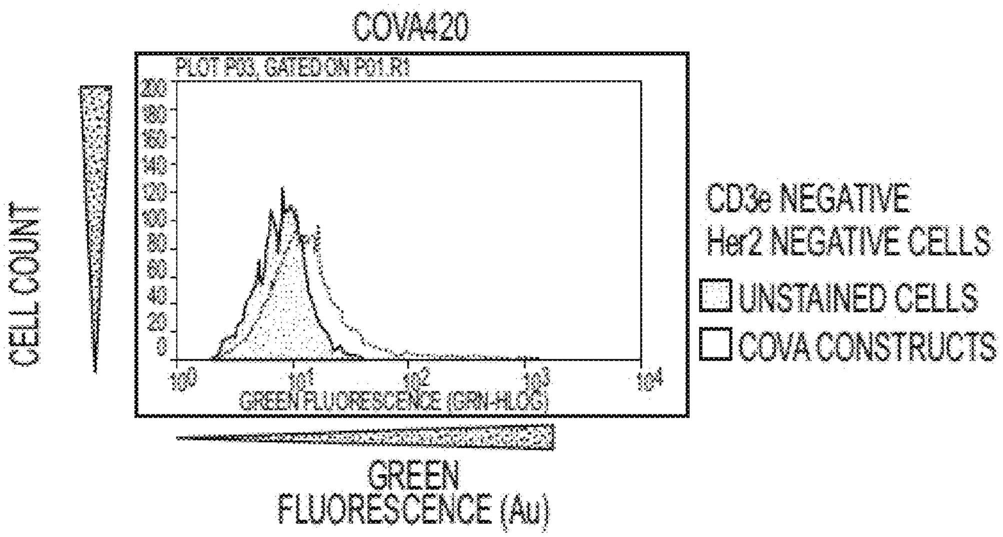
Figure 49C:
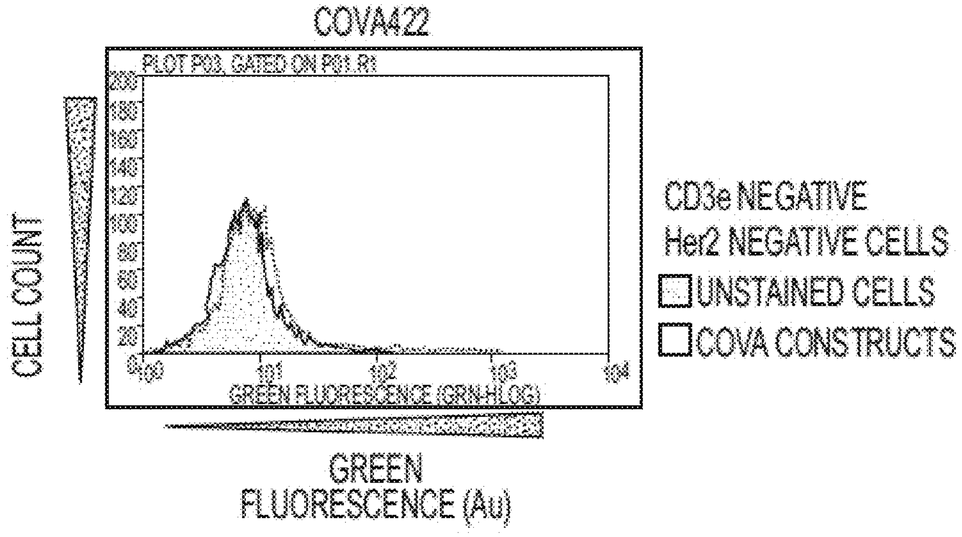
Figure 49C:
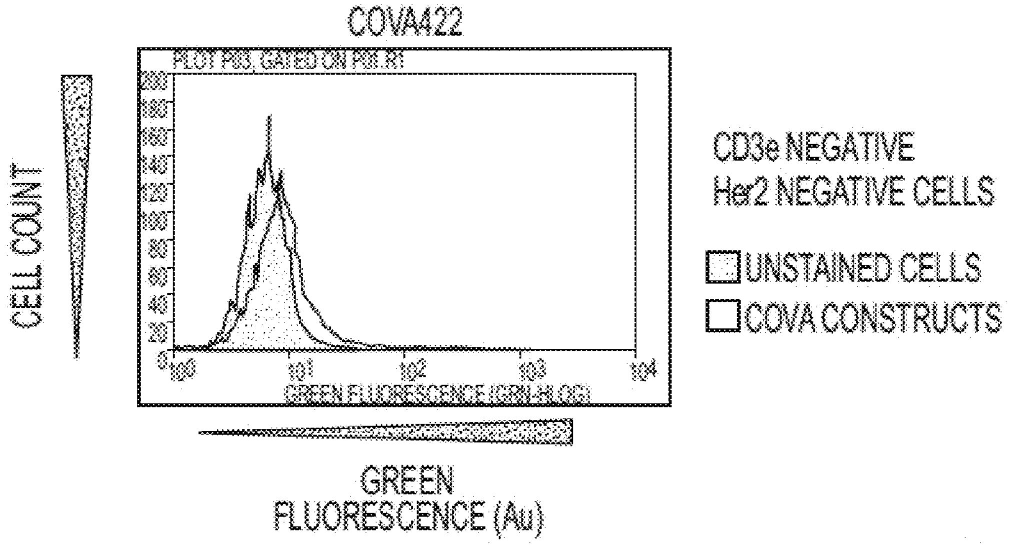

FIG. 49C shows the flow cytometric binding analysis of Fynomer®-antibody fusion proteins COVA420 (SEQ ID NOs: 387 and 388); COVA422 (SEQ ID NOs 389 and 390), and the bispecific scFv-control COVA446 (SEQ ID NO: 391) on cells that do not express HER2 nor CD3. Signals are compared to the background signal obtained with the secondary detection antibody only (grey shaded histograms).

Figure 50:
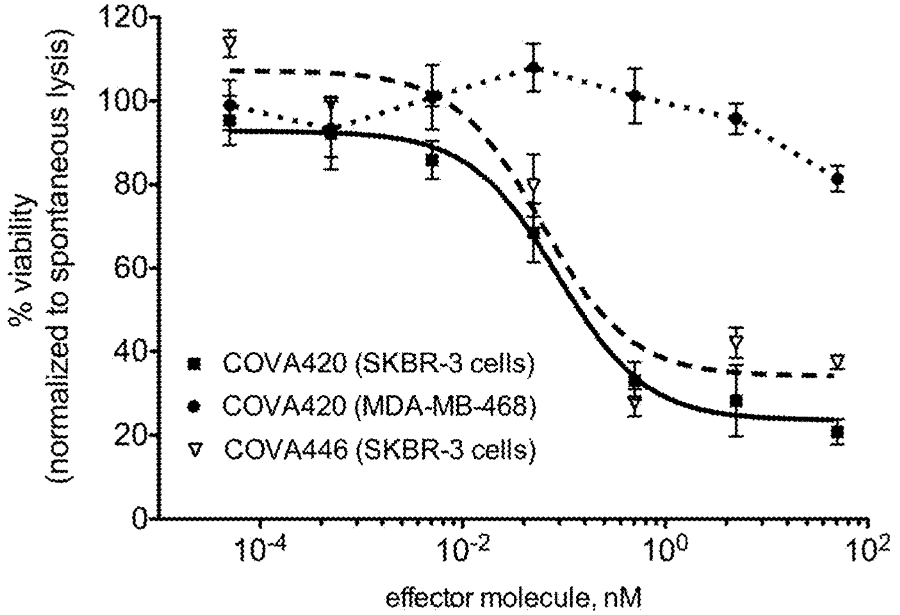

FIG. 50 shows the redirected cell kill activity of COVA420 (SEQ ID NOs: 387 and 388) and the bispecific anti-CD3×anti-HER2 control in single chain Fv format (COVA446, SEQ ID NO: 391) on HER2 positive SKBR-3 tumor cells. In addition, the absence of any kill activity of COVA420 on HER2 negative MDA-MB-468 cells is shown, demonstrating the specific kill activity towards HER2 positive cells. PBMCs were used as effector cells.

Figure 51:
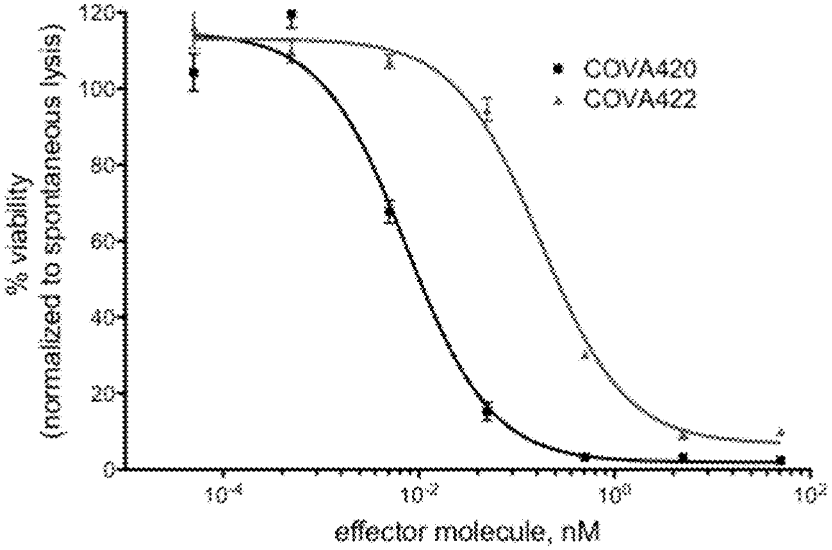

FIG. 51 shows the redirected cell kill activity of COVA420 (SEQ ID NOs: 387 and 388) and COVA422 (SEQ ID NOs 389 and 390) on HER2 positive SKOV-3 tumor cells using CD8+ enriched T-cells as effector cells.

Figure 52:
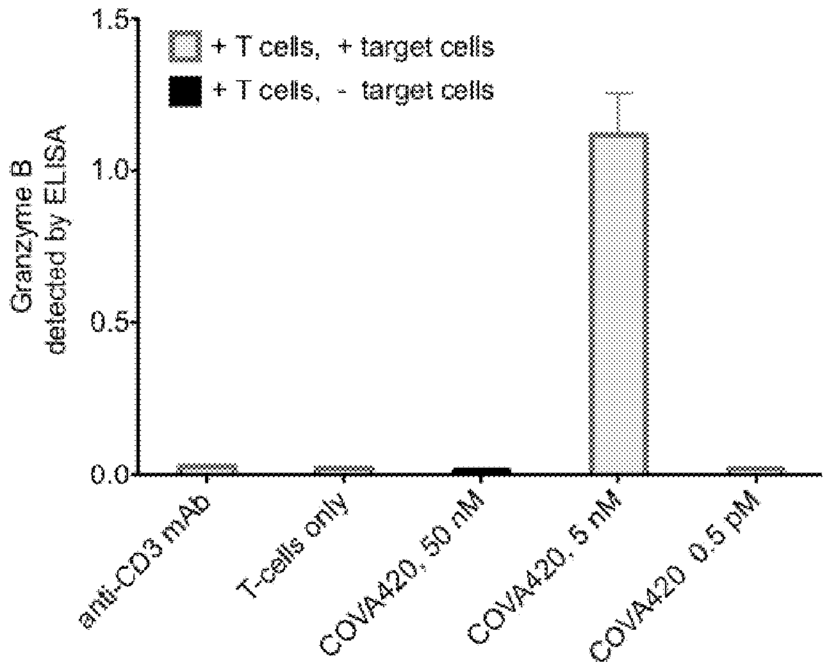

FIG. 52 depicts the release of Granzyme B into the cell culture supernatant upon incubation of indicated antibody Fynomer® fusion proteins in the presence and absence of CD8+ enriched T-cells.

Figure 53:
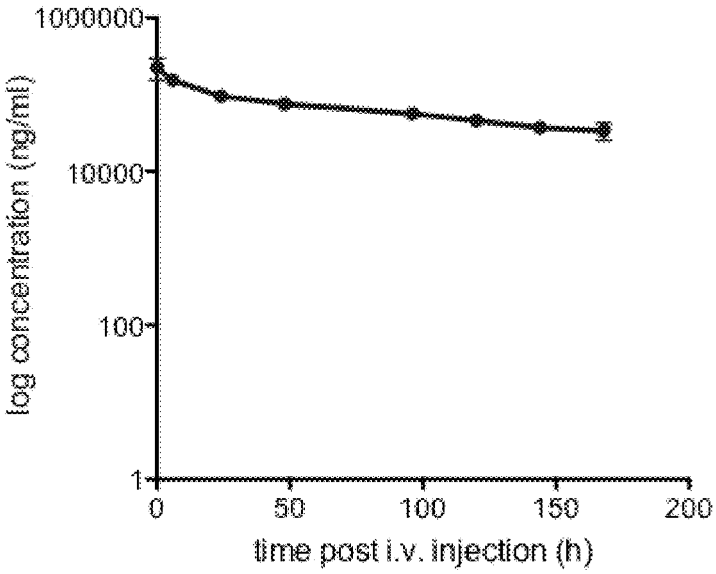

FIG. 53 shows the serum concentrations of COVA420 (SEQ ID NOs: 387 and 388), after intravenous injection in mice.

Figure 54:
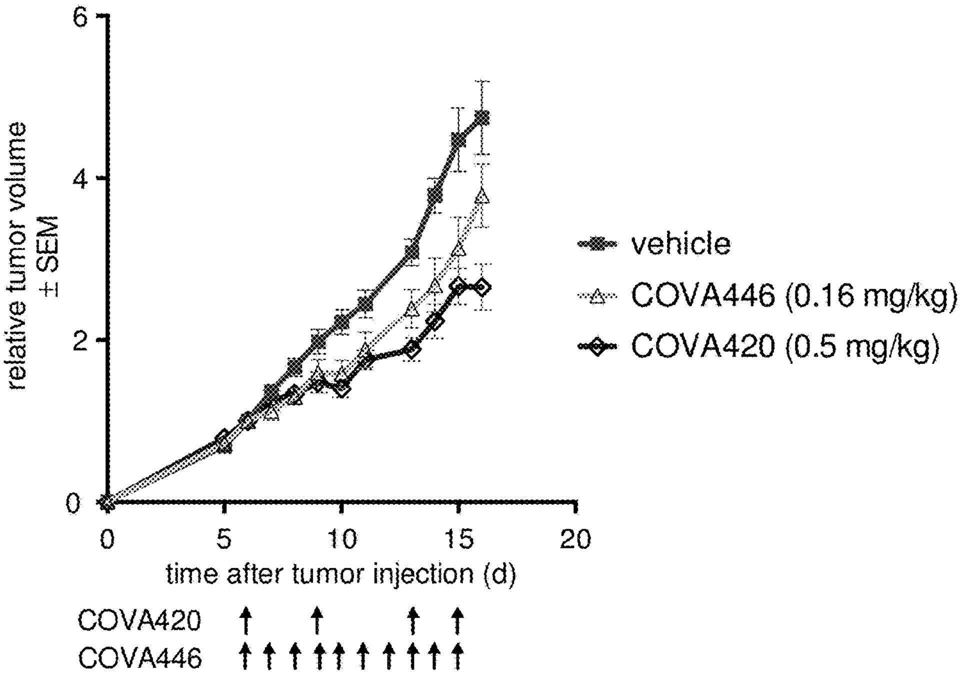

FIG. 54 shows the anti-tumor activity of COVA420 (SEQ ID NOs: 387 and 388) in an in vivo SKOV-3 xenograft model reconstituted with activated and expanded human T-cells. Tumor volumes are presented as RTV (relative tumor volume to day of therapy start). 0.5 mg/kg COVA420 and vehicle treatments were administered twice weekly (day 6, 9, 13, 15), and equimolar doses of COVA446 (SEQ ID NO: 391) (0.16 mg/kg) by daily intravenous (i.v.) bolus injections. Black arrows visualize dose intervals.

Figure 55:
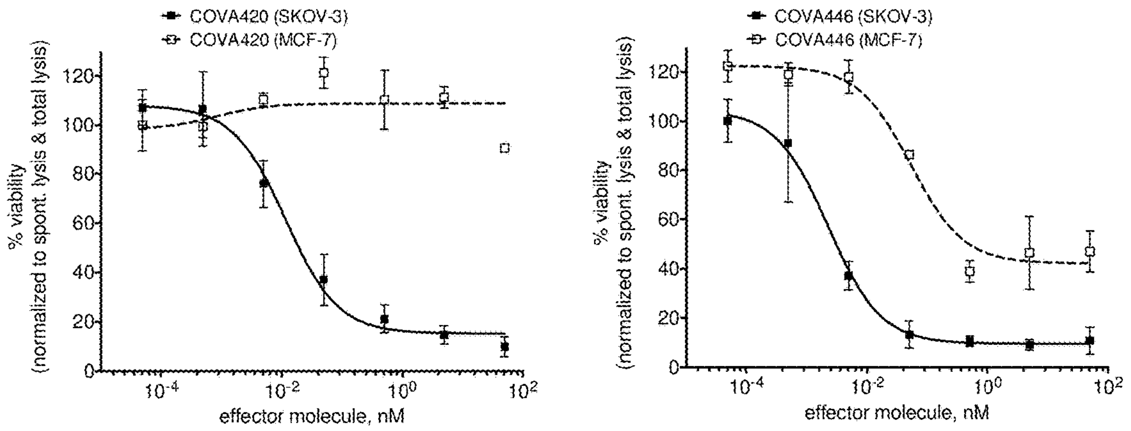

FIG. 55 shows the redirected cell kill activity of COVA420 (SEQ ID NOs 387 and 388) and the bispecific anti-CD3×anti-HER2 control in single chain Fv format (COVA446, SEQ ID NO: 391) towards SKOV-3 tumor cells expressing high level of HER2 and MCF-7 tumor cells expressing low level of HER2. CD8+ enriched T-cells were used as effector cells. The percent of remaining target cell viability is shown.

Figure 56:
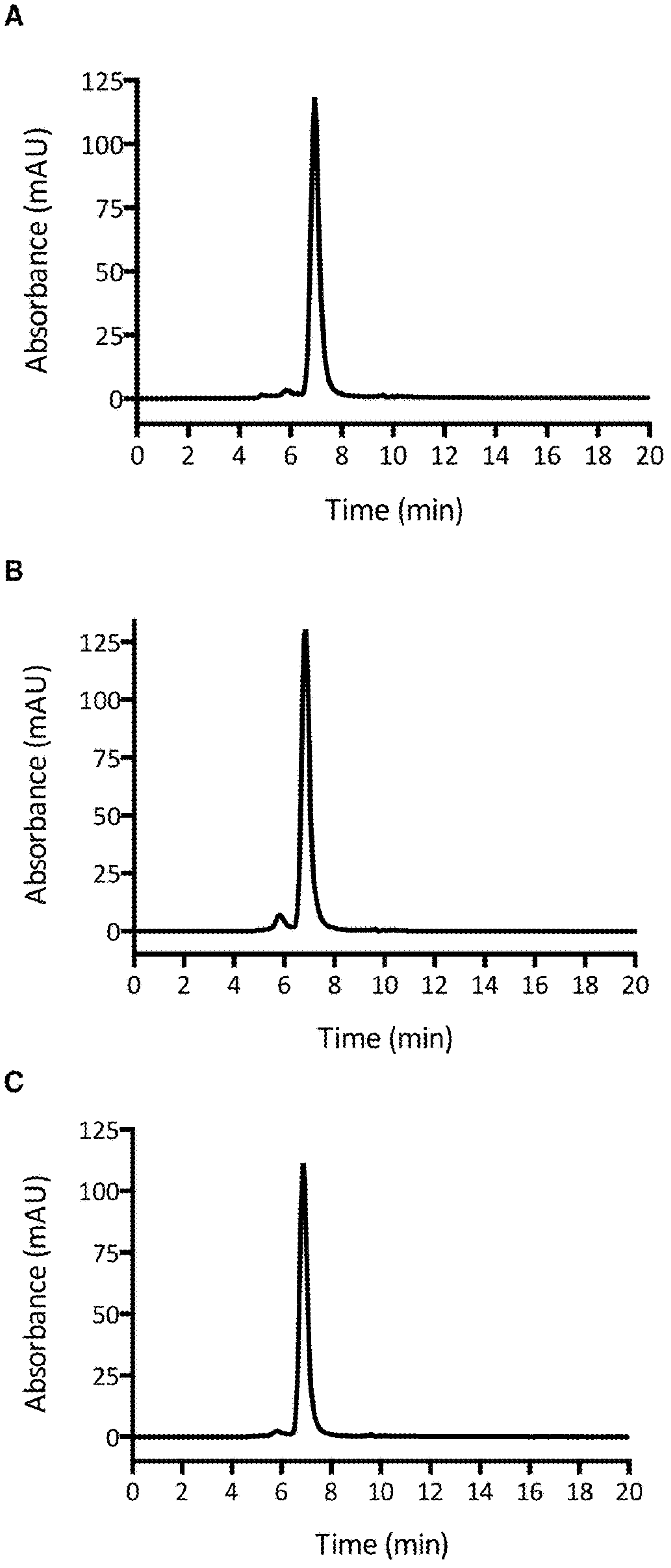
Figure 56:
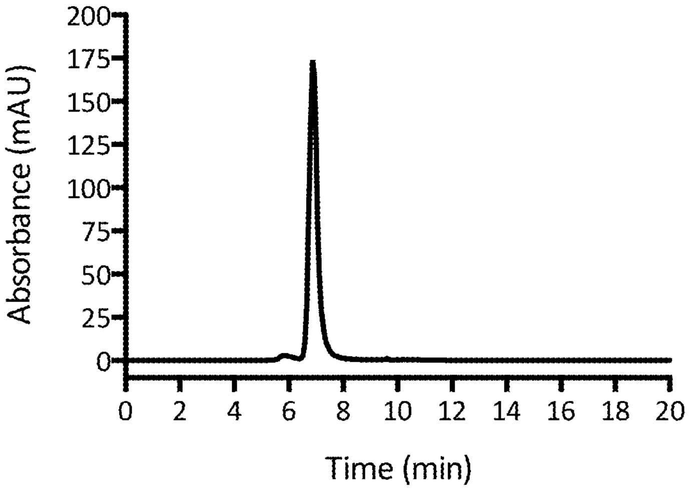
Figure 56:
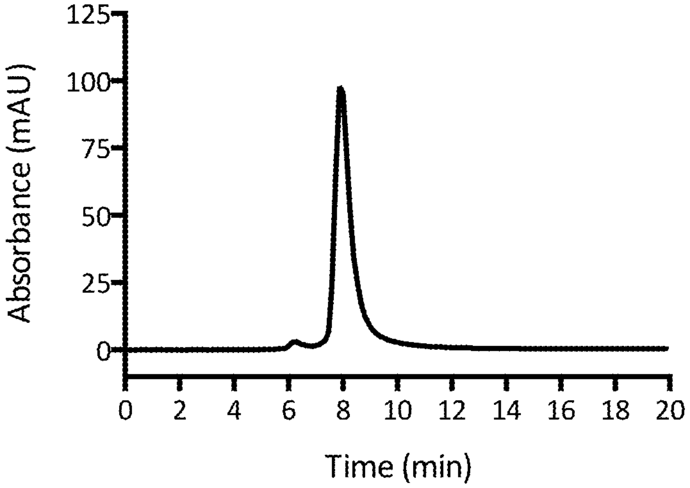

FIG. 56 shows size exclusion (SEC) profiles of Fynomer-antibody fusion proteins. A: SEC profile of COVA493 (SEQ ID NOs 393 and 395); B: SEC profile of COVA494 (SEQ ID NOs: 393 and 421); C: SEC profile of COVA497 (SEQ ID NOs: 422 and 395); D: SEC profile of COVA499 (SEQ ID NOs: 394 and 423); E: SEC profile of COVA489 (SEQ ID NOs: 394 and 395).

Figure 57:
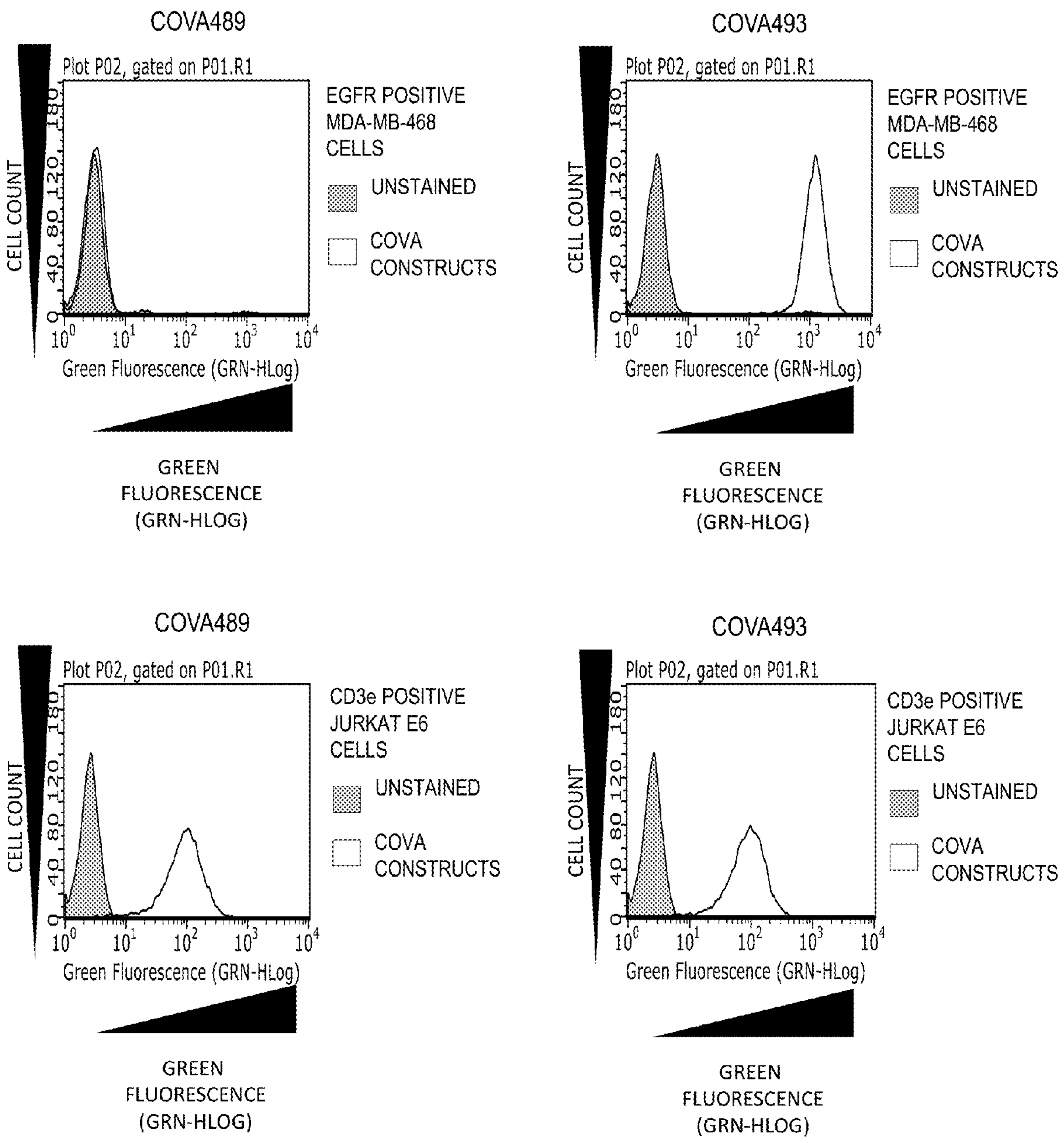
Figure 57:
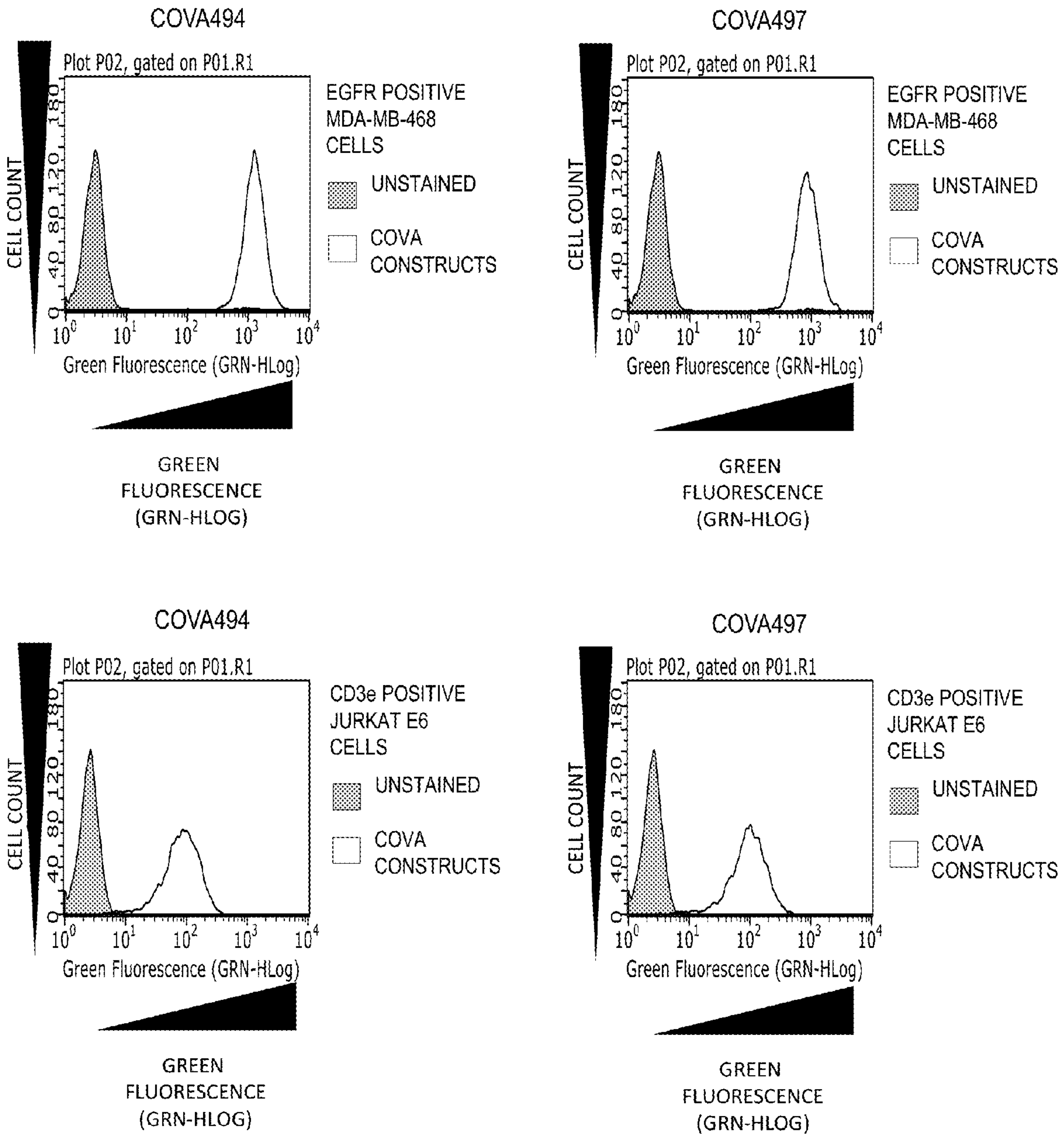
Figure 57:
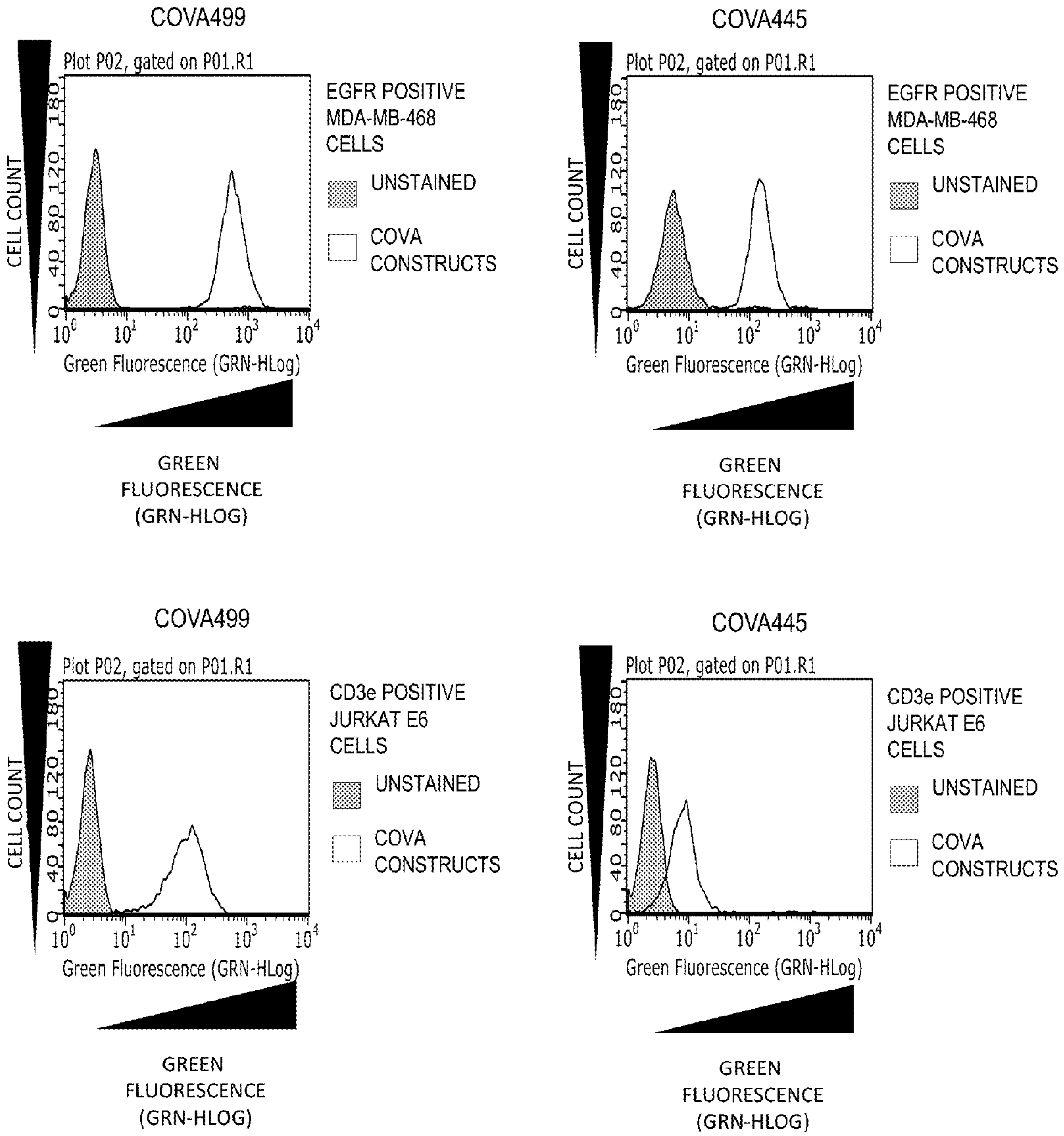

FIG. 57 shows the flow cytometric binding analysis of the anti-CD3 antibody (COVA489, SEQ ID NOs: 394 and 395), the Fynomer®-antibody fusion proteins COVA493 (SEQ ID NOs 393 and 395), COVA494 (SEQ ID NOs: 394 and 421), COVA497 (SEQ ID NOs: 422 and 395), COVA499 (SEQ ID NOs: 394 and 423) and the bispecific anti-CD3×anti-EGFR control in single chain Fv format (COVA445, SEQ ID NO: 396) on EGFR positive cells (MDA-MB-468, upper panel) and on CD3 positive cells (Jurkat E6-1. lower panel). Signals are compared to the background signal obtained with the secondary detection antibody only (grey shaded histograms).

Figure 58:
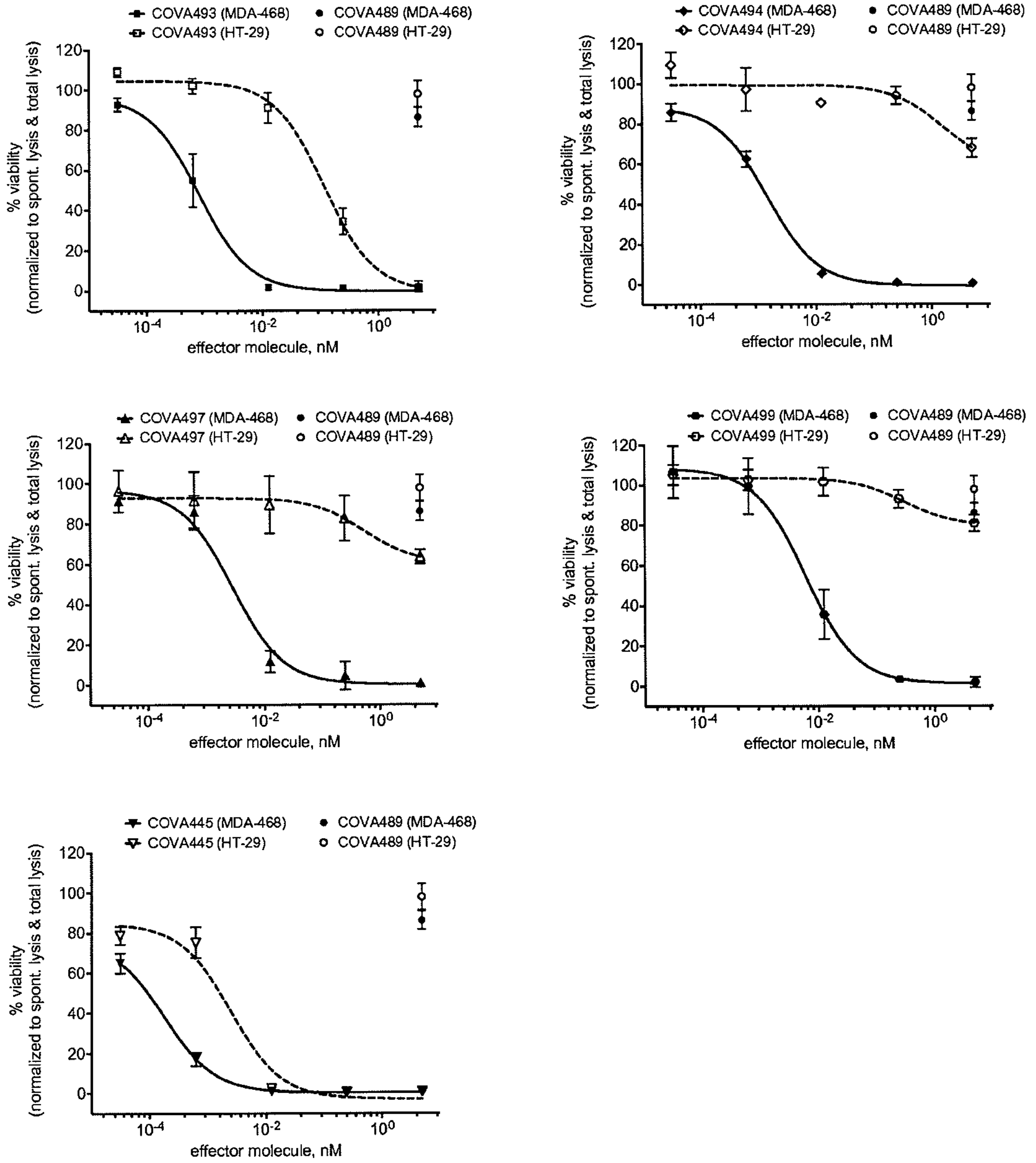

FIG. 58 shows the redirected cell kill activity of COVA493 (SEQ ID NOs 393 and 394), COVA494 (SEQ ID NOs: 394 and 421), COVA497 (SEQ ID NOs: 422 and 395), COVA499 (SEQ ID NOs: 394 and 423) and the bispecific anti-CD3×anti-EGFR control in single chain Fv format (COVA445, SEQ ID NO: 396) towards MDA-MB-468 tumor cells expressing high level of EGFR and HT-29 tumor cells expressing low level of EGFR. In addition, the absence of any kill activity of the anti-CD3 antibody (COVA489, SEQ ID NOs: 394 and 395) at the highest concentration of 5 nM is shown. CD8+ enriched T-cells were used as effector cells. The percent of remaining target cell viability is shown.

Figure 59:
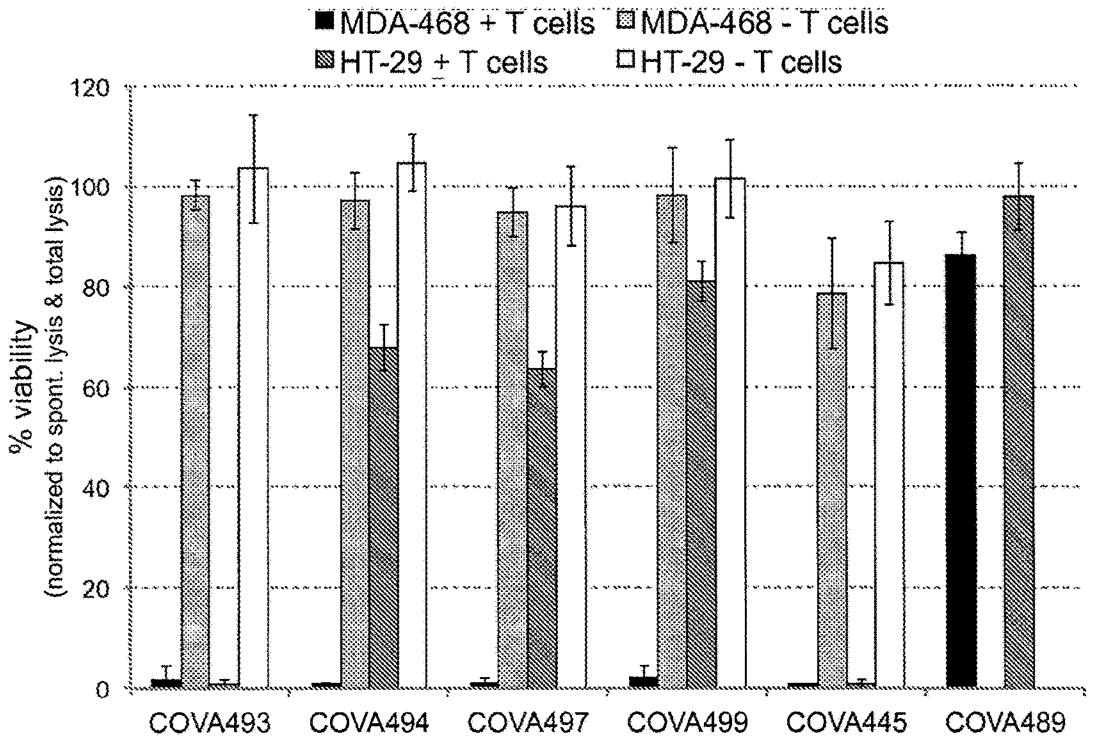

FIG. 59 shows the redirected cell kill activity of COVA493 (SEQ ID NOs 393 and 394), COVA494 (SEQ ID NOs: 394 and 421), COVA497 (SEQ ID NOs: 422 and 395), COVA499 (SEQ ID NOs: 394 and 423) and the bispecific anti-CD3×anti-EGFR control in single chain Fv format (COVA445, SEQ ID NO: 396) towards MDA-MB-468 and HT-29 tumor cells, expressing high and low level of EGFR respectively, in the presence or absence of effector T-cells. (n.d).: not determined.

Figure 60:
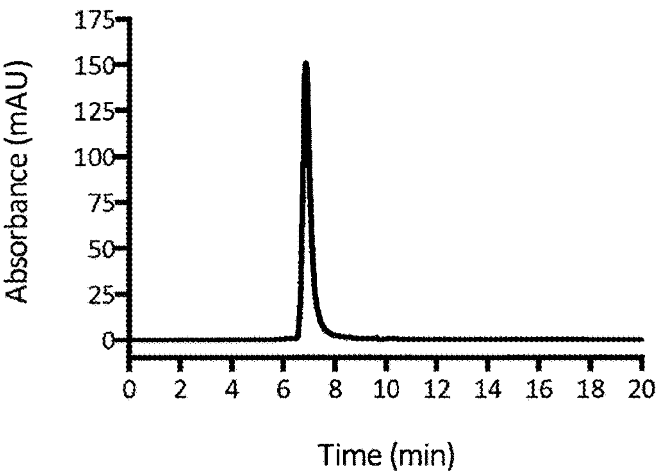
Figure 60:
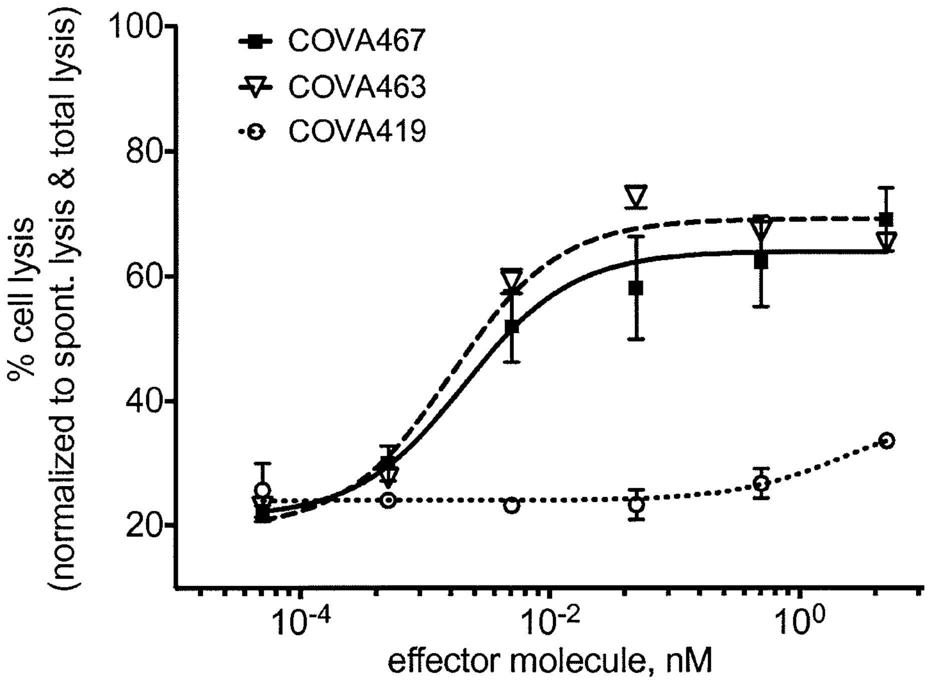

FIG. 60 (A) shows size exclusion (SEC) profiles of the Fynomer-antibody fusion protein COVA467 (SEQ ID NOs: 381 and 398) (B) shows the redirected cell kill activity of COVA467 (SEQ ID NOs: 381 and 398) and the bispecific anti-CD3×anti-CD33 control in single chain Fv format (COVA463, SEQ ID NO: 399) on CD33 positive U937 tumor cells. In addition, the absence of any kill activity of the unmodified anti-CD3 antibody (COVA419, SEQ ID NOs: 381 and 382) is shown. CD8+ enriched T-cells were used as effector cells. The percent of target cell lysis is shown.

In the following the subject-matter of the invention will be described in more detail referring to specific embodiments which are not intended to be construed as limiting to the scope of the invention.

EXAMPLES

Example 1: Anti-ED-B Fyn SH3 Derivative

Example 1.1: Expression of Fyn SH3 Mutants

Figure 1A:
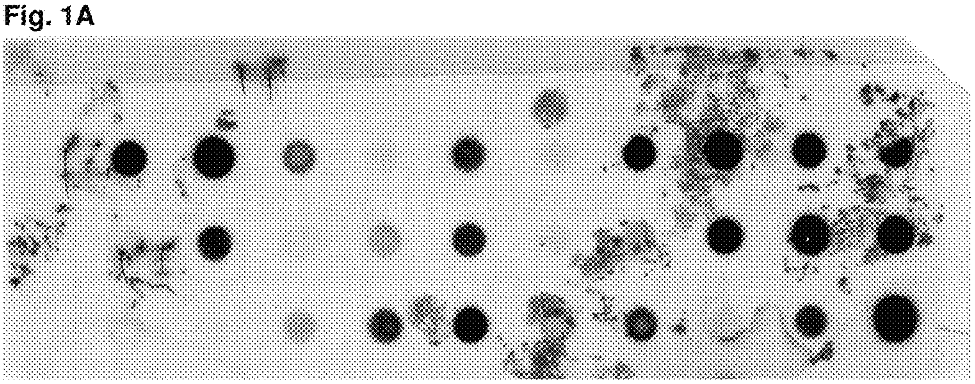
Figure 1B:
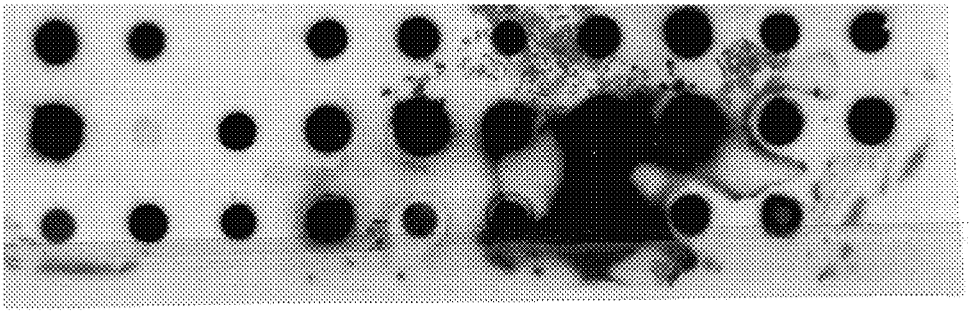
Figure 1C:
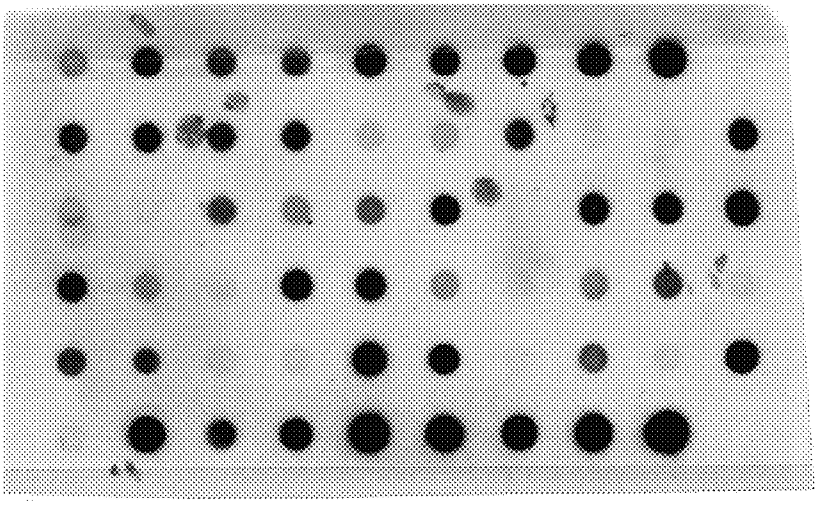

For the purpose of evaluating the expression of mutants of Fyn SH3 a dot blot analysis of three different Fyn SH3 sublibraries was performed (FIG. 1): in the first library only the RT-loop was randomized, in the second the Src loop was randomized and extended to 6 residues and in the third library the RT- and the Src loop were randomized simultaneously, the latter loop being extended from 4 to 6 residues. The percentage of expressed Fyn SH3 mutants ranged from 59-90%.

TABLE 1

| Library | Expressed mutants (%) | Number of clones tested |
|---|---|---|
| RT-Src | 59 | 29 |
| n-Src | 90 | 29 |
| RT-Src and n-Src | 62 | 58 |

Example 1.2: Phage Display Selections Against Mouse Serum Albumin

Figure 2:
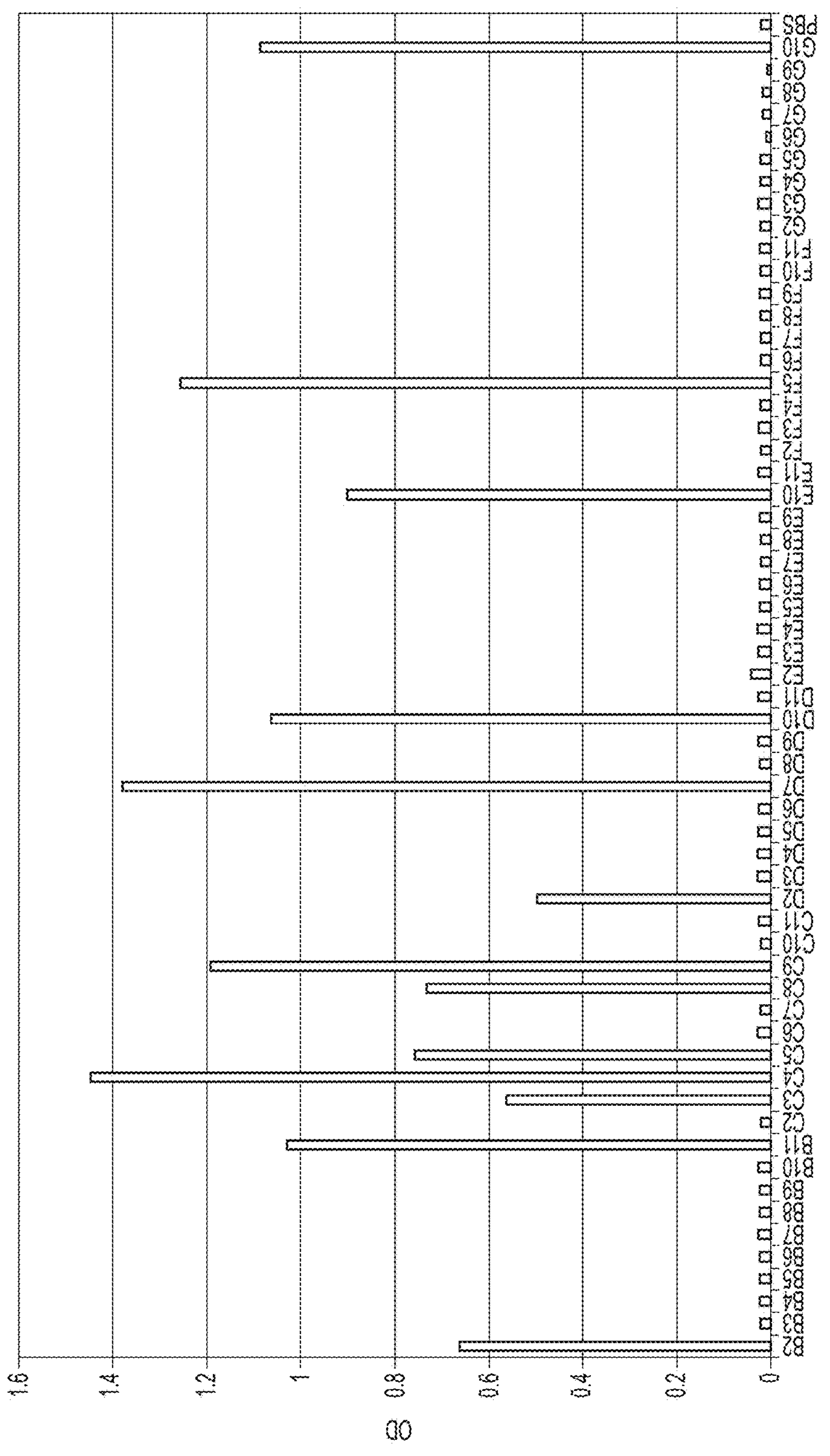

A library of $10^7$ different Fyn SH3 was created (only the RT-loop was randomized) and cloned into the phagemid vector pHEN1 (Hoogenboom et al. "Multi-subunit proteins on the surface of filamentous phage: methodologies for displaying antibody (Fab) heavy and light chains", Nucleic Acids Res, 19(15):4133-7, 1991). The library was displayed on phages and 3 rounds of panning were performed against mouse serum albumin (MSA). After the third round, screening for binding proteins was performed by monoclonal phage-ELISA; 13 positive clones were detected (FIG. 2). Sequencing of the 13 clones revealed that two different sequences were enriched, denoted G4 and C4.

Figure 3A:
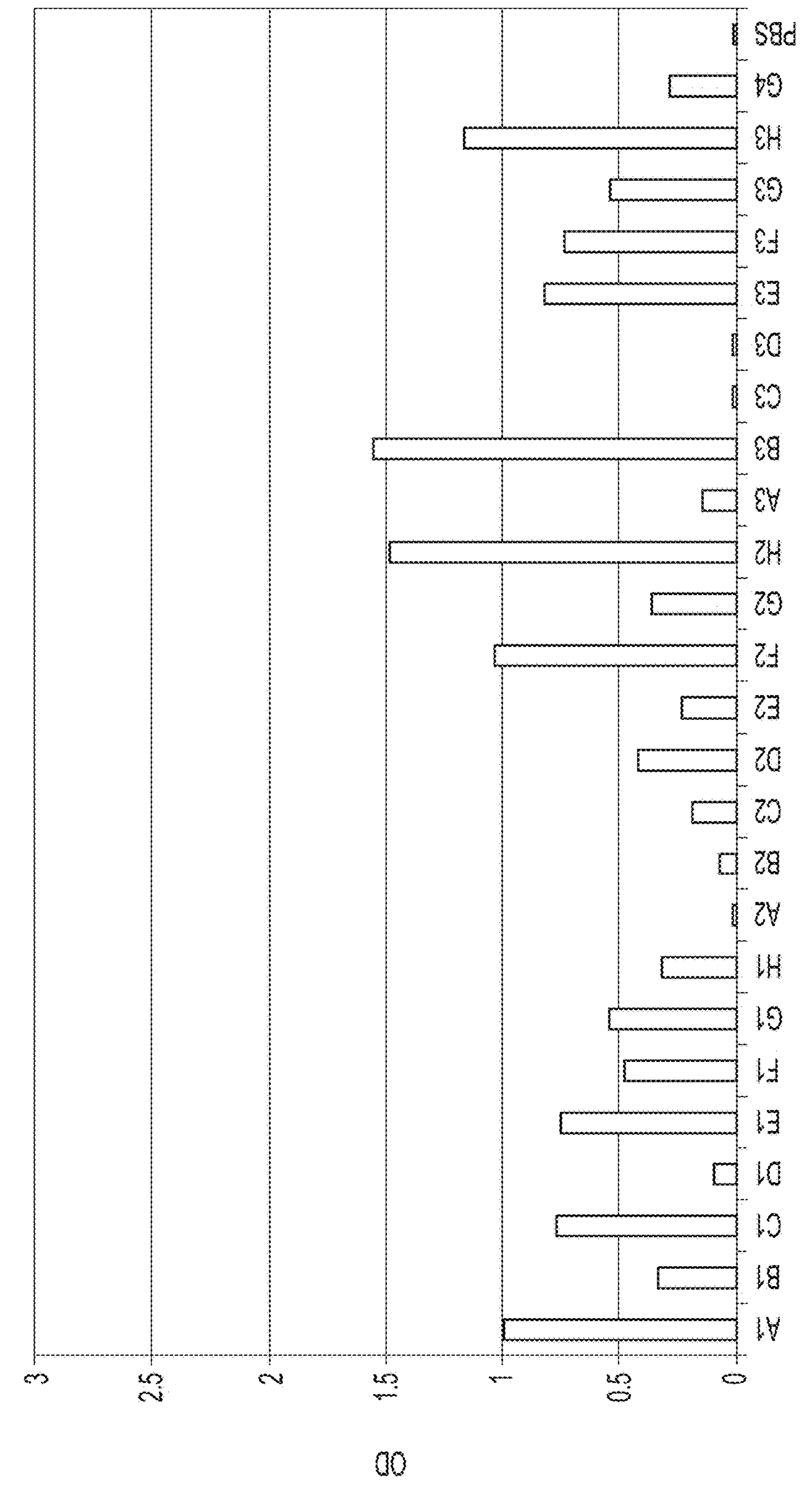
FIG. 3A illustrates monoclonal phage-ELISA (against MSA) after one round of affinity maturation selection using MaxiSorp plates (Nunc) coated with MSA (100 μg/ml overnight, 100 μl per well) for Phage ELISA of the first sub-library of G4 (randomized n-Src loop and Trp37 and Tyr50). The parental clone G4 is indicated with an arrow.
Figure 3B:
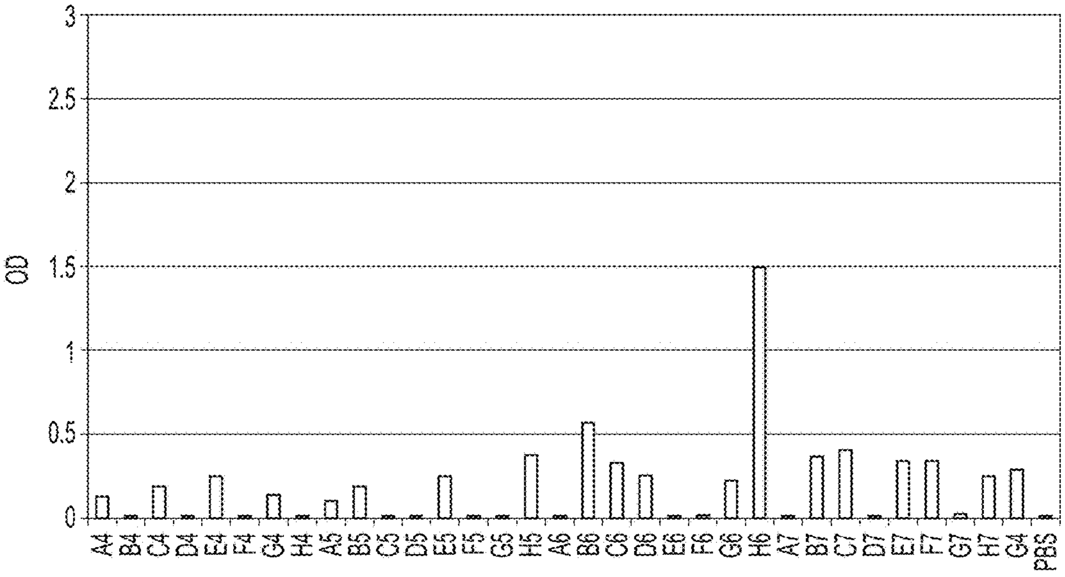
FIG. 3B illustrates monoclonal phage-ELISA (against MSA) after one round of affinity maturation selection using MaxiSorp plates (Nunc) coated with MSA (100 μg/ml overnight, 100 μl per well) for Phage ELISA of the second sub-library of G4 (randomized and extended n-Src loop). The parental clone G4 is indicated with an arrow.
Figure 3C:
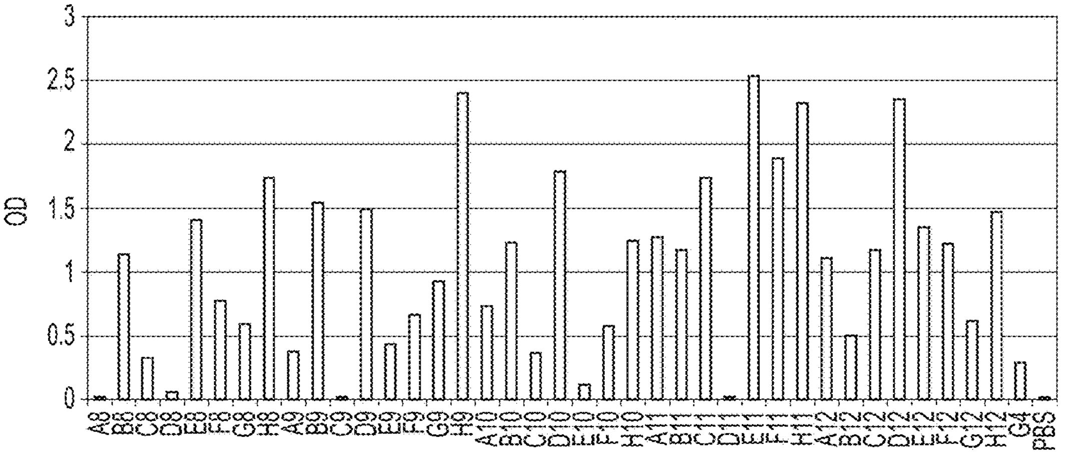
FIG. 3C illustrates monoclonal phage-ELISA (against MSA) after one round of affinity maturation selection using MaxiSorp plates (Nunc) coated with MSA (100 μg/ml overnight, 100 μl per well) for Phage ELISA of the first and second sub-library after one round of panning, performed under conditions favouring binders with a long $k_{off}$. The parental clone G4 is indicated with an arrow.

However, after subcloning and expression of G4 in the pQE-12 vector (Qiagen, expression and purification according to manufacturer's handbook under native conditions) the binding of the protein towards MSA could not be detected by ELISA (FIG. 4) due to low affinity (phage ELISA is more sensitive than the ELISA of the soluble protein). Therefore, the sequence of G4 was used for two different affinity maturation libraries (size: $10^7$ clones for each library). In the first one, the 4 residues of the n-Src loop and residues Trp37 (SEQ ID NO: 1) and Tyr50 (SEQ ID NO: 1) were randomized, in the second one the n-Src loop was extended from 4 to 6 randomized residues. After one round of panning several clones of both sublibraries gave stronger signals in Phage ELISA compared to the parental clone G4 (FIG. 3). After subcloning and expression of several clones the binding of the soluble protein was confirmed by ELISA (FIG. 4). Apparent dissociation constants were in the range of 100 nM (determined by BIAcore). Some of the clones were cross-reactive with other serum albumins (tested: human serum albumin (HSA), rat serum albumin (RSA), bovine serum albumin (BSA) and ovalbumin), whereas other clones were highly specific to MSA, indicating that it is possible to isolate high specific binding proteins (FIG. 5).

Example 1.3: Phage Display Selections Against the Extra Domain b of Fibronectin (ED-B)

ED-B was chosen as a target protein in order to demonstrate the ability to select Fyn SH3 derived binders against a pharmaceutically relevant protein. ED-B is a 91 amino acid Type III homology domain that is inserted into the fibronectin molecule by a mechanism of alternative splicing at the level of the primary transcript whenever tissue remodelling takes place (Zardi et al., "Transformed human cells produce a new fibronectin isoform by preferential alternative splicing of a previously unobserved exon." Embo J. 6(8): 2337-42, 1987). It is a good quality marker of angiogenesis that is overexpressed in a variety of solid tumors (e.g. renal cell carcinoma, colorectal carcinoma, hepatocellular carcinoma, high-grade astrocytomas, head and neck tumours, bladder cancer, etc.) but is virtually undetectable in normal adult tissue (except for the endometrium in the proliferative phase and some vessels in the ovaries). (For more details on ED-B as a target see Menrad and Menssen, "ED-B fibronectin as a target for antibody-based cancer treatments." Expert Opin. Ther. Targets 9(3): 491-500, 2005).

A library of more than 1 billion Fyn SH3 mutants was prepared and displayed on phages (simultaneous randomization of RT-Src and n-Src loops). After three rounds of panning against ED-B 3 binding clones were identified by phage ELISA. Sequencing revealed two different sequences (clones denoted B11 and D3). The dissociation constant of D3 was determined by surface plasmon resonance real-time interaction analysis using a BIAcore3000 instrument and showed a value of $8.5\times10^{-8}$ M (FIG. 6).

```
D3
                                              (SEQ ID NO: 3)
GVTLFVALYDYHAQSGADLSFHKGEKFQILKFGRGKGDWWEARSLTTGET

GYIPSNYVAPVDSIQ
```

Example 1.4: Immunogenicity

Immunogenicity of proteins is one of the major drawbacks in protein-related therapies, especially for treatments involving repetitive administrations of a drug. Due to the conservation of the Fyn SH3 sequence in mice and men the immunogenic potential of the FynSH3 wild type protein (Fyn SH3 wt) and a Fyn SH3 mutant (Fyn SH3D3, a binder against ED-B) was investigated in vivo by injecting 5 mice repeatedly with the two proteins. Mice were injected 4 times (every third day) with 20 μg of protein. One day after the $4^{th}$ injection mice were sacrificed and blood samples were taken for examining the presence or absence of murine anti-Fyn SH3 wt and anti-Fyn SH3D3 antibodies. As a positive control 4 mice were injected (equal time points of injection and equal dosages (=60 μg)) with a human antibody in the single chain Fv format (scFv). However, one mouse of the scFv group died 20 minutes after the third injection and the other 3 were about to die, so blood samples were already taken after the third injection. FIGS. 7 *a* and *b* demonstrate that there were no detectable antibodies against Fyn SH3 wt and Fyn SH3D3, whereas strong signals were observed for the control group (FIG. 7*c*).

Example 1.5: Immunohistofluorescence

In order to explore whether Fyn SH3-D3 (D3, a binder against ED-B) recognizes its target in the native conformation in the tissue, immunofluorescence on F9 teratocarcinoma sections was performed. FIG. 8 illustrates that D3 bound the tumor stroma around blood vessels (FIG. 8.*a*). The detection was performed with anti-His-Alexa488 antibody conjugate. In the negative control, no D3 protein was added (FIG. 8*b*). In order to visualize blood vessels, the same sections were co-stained with a rat anti-mouse-CD31 antibody and as a secondary antibody donkey anti-rat Alexa594 conjugate was used (FIG. 8.*c*). The negative control was done using the secondary antibody without the primary antibody (FIG. 8.*d*).

Example 1.6: Quantitative Biodistribution In Vivo

The in vivo targeting performance of Fyn SH3-D3 (a binder against ED-B) and Fyn SH3 wild type (a non-binder to ED-B) was evaluated by biodistribution experiments in mice bearing a s.c. grafted F9 murine teratocarcinoma. Since ED-B is identical in mouse and man the results of the tumor targeting studies should be predictive of the D3 performance in humans. $^{125}$I-labeled D3 and SH3 wt were injected i.v. and 24 h later, animals were sacrificed, the organs excised, weighed and radioactivity was counted. FIG. 9.*a* shows that D3 selectively accumulated in the tumor (tumor:organ ratios ranged from 3:1 to 10:1), whereas no enrichment could be observed for the Fyn SH3 wild type protein (FIG. 9.*b*).

Example 2: Anti-IL17A Fyn SH3 Derivatives

Example 2.1: Fyn SH3-Derived Polypeptides of the Invention Bind to IL-17A as Determined by Monoclonal Phage ELISA Methods DNA encoding the amino acid sequences shown in SEQ ID NOs: 4 to 119 were cloned into the phagemid vector pHEN1 as described for the FYN SH3 library in Grabulovski et al. (Grabulovski et al. (2007) JBC, 282, p. 3196-3204). Phage production was performed according to standard protocols (Viti, F. et al. (2000) Methods Enzymol. 326, 480-505). Monoclonal bacterial supernatants containing phages were used for ELISA: biotinylated IL-17A (purchased from R&D Systems, biotinylation was performed with NHS-PEO4-biotin (Pierce) according to the manufacturer's instructtions) was immobilized on streptavidin-coated wells (StreptaWells, High Bind, Roche), and after blocking with PBS, 2% milk (Rapilait, Migros, Switzerland), 20 μl of PBS, 10% milk and 80 μl of phage supernatants were applied. After incubating for 1 h and washing, bound phages were detected with anti-M13-HRP antibody conjugate (GE Healthcare). The detection of peroxidase activity was done by adding BM blue POD substrate (Roche) and the reaction was stopped by adding 1 M $H_2SO_4$. The DNA sequence of the binders was verified by DNA sequencing (BigDye Terminator v3.1 cycle sequencing kit, ABI PRISM 3130 Genetic Analyzer, Applied Biosystems).

Results

The amino acid sequences of Fyn SH3-derived IL-17A binders is presented in SEQ ID NOs: 4 to 119 as appended in the sequence listing. All SEQ ID NOs bound IL-17A in this phage ELISA experiment.

Example 2.2: Fyn SH3-Derived Polypeptides of the Invention Bind to Recombinant Human IL-17 A with High Affinities This example shows the cloning and expression of different formats of Fyn SH3-derived IL-17A-binding polypeptides, as well as the characterization of these polypeptides by size exclusion chromatography and surface plasmon resonance experiments.

a) Cloning and Expression of Fyn SH3-Derived IL-17A-Binding Polypeptides

Selected Fyn SH3-derived IL-17A-binding polypeptides (clone B1_2: SEQ ID NO: 42, clone E4: SEQ ID NO: 60 and clone 2C1: SEQ ID NO: 110) were cloned into the cytosolic expression vector pQE-12 and expressed as well as purified as described in Grabulovski et al. (Grabulovski et al. (2007) JBC, 282, p. 3196-3204).

b) Cloning and Expression of Fyn SH3-Derived IL-17A-Binding Polypeptides Fused to the Fc Part of a Human IgG1 Antibody Clones E4 and 2C1 (SEQ ID NO: 60 and SEQ ID NO: 110) were cloned and expressed as fusion proteins with the Fc part of a human IgG1 antibody (see below for procedure; SEQ ID NO: 120 and 121). Furthermore, a 2C1 dimer with a 10 amino acid linker [$(2C1)_2$-Fc] was cloned and expressed as Fc fusion protein (SEQ ID NO: 122).

The Fc part of human IgG1 was PCR-amplified using the primers fm5 (5' ATCGGGA-TCCGACAAAACTCACA-CATGCC 3', SEQ ID NO: 124) and fm6 (5' TAC-GAAGCTTT-CATTTACCCGGAGACAGGG 3', SEQ ID NO: 125) and using the commercial pFUSE-hIgG1-Fc2 (Invivogen) eukaryotic vector as template. The resulting PCR product was digested with BamHI/HindIII and ligated with the pASK-IBA2 vector (IBA-Biotagnology) previously digested with the same enzymes, yielding the new vector pAF.

The genetic information of clones E4 and 2C1 (SEQ ID NO: 60 and SEQ ID NO: 110) was PCR amplified with fm7 (5' ATATCACCATGGGGCCGGAGTGACACTCTTT-GTG-GCCCTTTATG 3', SEQ ID NO: 126) and fm8 (5' CGTAGGA-TCCCTGGATAGAGTC-AACTGGAGC 3', SEQ ID NO: 127). For the preparation of the 2C1 dimer fused to Fc, the 2C1 DNA template was used for two independent PCRs. In the first reaction the primers 47b.fo (5' AGA GCC ACC TCC GCC TGA ACC GCC TCC ACC CTG GAT AGA GTC AAC TGG AGC CAC 3', SEQ ID NO: 128) and 52. ba (5' gac taa cga gat cgc gga tcc gga gtg aca ctc ttt gtg gcc ctt tat 3', SEQ ID NO: 129) were used and in the second PCR primers 48b.ba (5' GGT GGA GGC GGT TCA GGC GGA GGT GGC TCT GGA GTG ACA CTC TTT GTG GCC CTT TAT 3', SEQ ID NO: 130) and 51. fo (5' ATC CCA AGC TTA GTG ATG GTG ATG GTG ATG CAG ATC CTC TTC TGA GAT GAG TTT TTG TTC ACC CTG GAT AGA GTC AAC TGG AGC CAC 3', SEQ ID NO: 131) were used.

The two DNA fragments were assembled by PCR, yielding a 2C1 homodimer with a 10 amino acid linker (GGGGSGGGGS, SEQ ID NO: 123) between the two domains. The resulting DNA fragment was further amplified as described for the 2C1 monomer using the primers fm7 and fm8. Obtained PCR products were then digested with NcoI/BamHI and cloned into the double-digested periplasmic expression vector pAF. Plasmids were electroporated into *E. coli* TG1 and protein expression was induced with 0.2 μg/ml anhydrotetracyclin. Bacterial cultures were grown overnight at 25° C. in a rotary shaker and Fynomer-Fc fusion proteins were purified from the periplasmic fraction in a single protein A-affinity chromatography step. SDS PAGE (Invitrogen) analysis was performed with 20 μl of protein solution.

c) Size Exclusion Chromatography (SEC)

Size Exclusion Chromatography (SEC) was performed on an ÄKTA FPLC system using a Superdex 75 column (10/300) or Superdex 75 Short Column (5/150) (GE Healthcare).

d) Affinity Measurements

Affinity measurements were performed using a BIAcore 3000 instrument (Biacore). For the interaction analysis between biotinylated IL-17A and monomeric Fyn SH3-derived IL-17A-binding polypeptides, and between biotinylated IL-17A and E4-Fc (SEQ ID NO: 120), a streptavidin SA chip (Biacore) was used with 1300 and 510 RU biotinylated IL-17A immobilized, respectively. The running buffer was PBS, 0.1% $NaN_3$ and surfactant P20 (Biacore). The interactions were measured at a flow of 20 μl/min and injection of different concentrations of Fyn SH3-derived IL-17A-binding polypeptides. For the interaction analysis between IL-17A and the 2C1-Fc fusions as well as the $(2C1)_2$-Fc fusion, a CM5 chip (Biacore) was coated with 2900 RU goat anti-human IgG Fc-specific antibody (Jackson Immunoresearch). The running buffer was HBS-EP (Biacore). The interactions were measured by injecting about 250 to 275 RU Fc fusion protein at a flow rate of 10 μl/min, followed by injection of different concentrations of IL-17A (R&D Systems) at a flow rate of 30 μl/min. All kinetic data of the interaction (separate kon/koff) were evaluated using BIA evaluation 3.2RC1 software.

e) Results

The expression yields for monomeric Fyn SH3-derived IL-17A-binding polypeptides of the invention ranged from 60 to 85 mg/liter of bacterial culture under non-optimized conditions in shake flasks. The Fc-fusion proteins were expressed with a yield of 0.2 to 0.4 mg/liter (Table 2). The Fc-fusion proteins have the sequences listed in SEQ ID NOs: 120 to 122 as appended)

TABLE 2

Expression yields after purification of bacterial culture under non-optimized conditions in shake flasks in *E. coli.*

| Clone | SEQ ID NO: | Expression yield (mg/L) |
|---|---|---|
| B1_2 | 42 | 65 |
| E4 | 60 | 85 |
| 2C1 | 110 | 60 |
| E4-Fc | 120 | 0.4 |
| 2C1-Fc | 121 | 0.3 |
| $[(2C1)_2\text{-Fc}]$ | 122 | 0.2 |

FIG. 10 shows the SDS PAGE analysis of the indicated purified proteins.

Size exclusion chromatography (SEC) profiles demonstrated that all constructs eluted mainly as single, monomeric peaks (see FIG. 11). As already observed in earlier studies for Fyn SH3-derived binding proteins (Grabulovski et al. (2007) JBC, 282, p. 3196-3204), the main peak elutes later than expected for a protein of about 8 kDa. For the Fc-fusion proteins of the invention a second purification step by size exclusion chromatography was performed after the single-step protein A-sepharose purification yielding monomeric proteins as shown for the fusion protein E4-Fc (SEQ ID NO: 120) in FIG. 11*e*. E4-Fc (SEQ ID NO: 120) was stable for at least 40 days when stored at 4° C. in PBS. The binding properties were analyzed by real-time interaction analysis on a BIAcore chip (FIG. 12) revealing the following dissociation constants ($K_D$) for selected IL-17A-binding polypeptides and fusion proteins:

TABLE 2

| Clone | SEQ ID NO: | $K_D$ |
|---|---|---|
| B1_2 | 42 | 117 nM |
| E4 | 60 | 31 nM |
| 2C1 | 110 | 5 nM |
| E4-Fc | 120 | 5 nM |
| 2C1-Fc | 121 | 305 pM |
| $[(2C1)_2\text{-Fc}]$ | 122 | 180 pM |

Example 2.3: IL-17A Inhibition Cell Assay

IL-17A induces the production of IL-6 in fibroblasts in a dose-dependent manner (Yao et al. (1995) Immunity, 3, p. 811-821). The inhibitory activities of the indicated Fyn SH3-derived IL-17A-binding polypeptides and fusion proteins were tested by stimulating human dermal fibroblasts with recombinant IL-17A in the absence or presence of various concentrations of Fyn SH3 mutants or human IL-17A receptor-Fc chimera. Cell culture supernatants were taken after 24 h of stimulation and assayed for IL-6 with ELISA. In addition, a colorimetric test was performed using the reagent XTT in order to demonstrate that the cells were viable after 24 h of incubation with IL-17A alone, or IL-17A and Fyn SH3-derived inhibitory IL-17A-binding polypeptides of the invention, or IL-17A and IL-17R-Fc chimera. Only viable and metabolic active cells are capable of reducing the tetrazolium salt XTT to orange-colored compounds of formazan (Scudiero, et al. (1988), Cancer Res. 48, p. 4827-4833).

Methods

For endotoxin removal the indicated protein solutions were filtered three times with the Acrodisc Mustang E membrane (VWR). After filtration the endotoxin levels of the protein solutions containing inhibitory Fyn SH3-derived IL-17A-binding polypeptides of the invention were less than 0.1 EU/ml, as determined by the Limulus amebocyte lysate (LAL) test (PYROGENT Single test Gel Clot LAL Assay (Lonza)).

400 μl of a cell suspension containing about $1\times10^4$ Normal Human Dermal Fibroblasts (PromoCell, NHDF-c, C12300) were distributed per well (24 well plate, Nunc or TPP) and cultured for 24 hours at 37° C. (medium: Fibroblast Growth Medium C-23010, PromoCell). The supernatant was aspirated and after mixing different concentrations of Fyn SH3 derived IL-17A-binding polypeptides of the invention or IL-17A receptor Fc chimera (RnD Systems) with IL-17A (RnD Systems) containing medium (50 ng/ml final concentration), 350 μl of the corresponding solution was added per well (mixing ratio between inhibitor solution and IL-17A-containing medium was 1:3). As a positive control PBS was mixed with the IL-17A containing medium ("no inhibitor") in a ratio of 1:3 and as a negative control PBS was mixed with medium only ("no IL-17A") in a ratio of 1:3. For the determination of the IL-17A-dependent IL-6 production, IL-17A containing medium was used (final concentrations of IL-17A: 10, 25 and 50 ng/ml) and mixed with PBS in a ratio of 3:1. After 24 hours incubation at 37° C. the supernatant was aspirated and the IL-6 concentration was determined by ELISA according to the manufacturer's instructions (IL-6 ELISA kit, R&D Systems). Immediately after the aspiration of the supernatant the XTT-containing medium was added (Cell Proliferation Kit II, Roche) and cell viability was determined according to the manufacturer's instructions.

The percentage of IL-17A inhibition was determined with the following formula:

$$\text{Inhibition}(\%) = 100 - \frac{(A450-650\ \text{nm (sample)} - A450-650\ \text{nm (neg. control)} \times 100)}{(A450-650\ \text{nm (pos. control)} - A450-650\ \text{nm(neg. control)})}$$

Results

Normal Human Dermal Fibroblasts (NHDF) were incubated with IL-17A at different concentrations. FIG. 13 (*a*) shows the IL-17A dose-dependent induction of IL-6. In a next step NHDF cells were incubated with IL-17A (50 ng/ml) and different concentrations of indicated Fyn SH3-derived IL-17A-binding polypeptides of the invention or IL-17A receptor-Fc chimera (FIG. 13(*b*)). It was observed that both clones 2C1 (SEQ ID NOD: 110) and E4 (SEQ ID NO: 60) inhibited the IL-17A induced IL-6 production with $IC_{50}$ values of about 1 nM and 6 nM, respectively. The IL-17A receptor-Fc chimera has a reported $IC_{50}$ value of 500 pM (R&D Systems). In this experiment, a value of about 1 nM was obtained. The assay depicts a representative result of three independent experiments. In order to further demonstrate that the inhibition of IL-6 production was a consequence of a specific IL-17A neutralization, the cells were incubated with the Fyn SH3 wt domain (Grabulovski et al. (2007) JBC, 282, p. 3196-3204) as a protein of irrelevant binding specificity in presence of IL-17A (FIG. 13 (*c*)). As expected, no inhibition of IL-6 production was observed, whereas clone 2C1 (SEQ ID NO: 110) was capable of inhibiting IL-17A-induced Il-6 production. In FIG. 13(*d*) the XTT assay is shown, confirming that all cells were viable after incubation with Fyn SH3-derived IL-17A-binding polypeptides of the invention (at a concentration of 750 nM) and IL-17 receptor (10 nM) for 24 hours.

Example 2.4: Stability

A crucial aspect of any biological compound intended for therapeutic applications is its stability and resistance to aggregation when stored in solution. Fyn SH3-derived IL-17A-binding polypeptides of the invention are particularly useful drug and diagnostic candidates because they have proven stable when stored at 4° C. or at −20° C. for at least 6 months in simple phosphate-buffered saline.

Methods

Protein solutions of the IL-17A-binding polypeptides of the invention were stored for 6 months at 4° C. and at −20° C. after purification. In order to analyze protein stability and aggregation state, the protein solutions were filtered (Millex GP, 0.22 μm, Millipore) and size exclusion chromatography (SEC) was performed on an ÄKTA FPLC system using a Superdex 75 Short Column (5/150) (GE Healthcare)

Results

Fyn SH3-derived IL-17A-binding polypeptide G3 (SEQ ID NO: 37) was produced with an expression yield of 123 mg/L and eluted mainly as single peak from the size exclusion chromatography column (see FIG. 14).

The stability and aggregation resistance of G3 (SEQ ID NO: 37) was assessed by storing the protein at 4° C. and −20° C. in PBS. After 6 months the status of the protein was examined by size exclusion chromatography. The measurements did not reveal any sign of aggregation or degradation. The elution profiles after 6 months of storage are shown in FIG. 15.

Example 2.5: In Vivo Half-Life

The in vivo half-life of the fusion protein of the invention E4-Fc (SEQ ID NO: 120) was determined by measuring E4-Fc (SEQ ID NO: 120) concentrations in mouse serum at different time points after a single i.v. injection by ELISA.

Methods

Cloning and expression of E4-Fc (SEQ ID NO: 120) is described in Example 2.2. 200 μl of a 3.3 μM (0.22 mg/ml) solution of E4-Fc (SEQ ID NO: 120) was injected i.v. into 5 mice (C57BL/6, Charles River). After 7 minutes, 20 minutes, 1, 2, 4, 8, 24 and 48 h about 20 μl of blood were taken from the vena saphena with the capillary Microvette CB 300 (Sarstedt). The blood samples were centrifuged for 10 min at 9500×g and the serum was stored at −20° until ELISA analysis was performed. Using an E4-Fc (SEQ ID NO: 120) dilution series with known concentrations, the E4-Fc (SEQ ID NO: 120) concentration in serum was determined by ELISA: 50 μl of biotinylated IL-17A (30 nM) (R&D Systems, biotinylated using NHS-PEO4-biotin (Pierce) according to the manufacturer's instructions) were added to streptavidin-coated wells (Reactibind, Pierce) and after blocking with PBS, 4% milk (Rapilait, Migros, Switzerland), 45 μl of PBS, 4% milk and 5 μl of serum sample were added. After incubation for 1 h and washing, bound Fc fusion proteins were detected with protein A-HRP conjugate (Sigma). Peroxidase activity was detected by addition of QuantaRed enhanced chemifluorescent HRP substrate (Pierce). Fluorescence intensity was measured after 5 to 10 min at 544 nm (excitation) and 590 nm (emission). From the concentrations of E4-Fc (SEQ ID NO: 120) determined in serum (n≥3 per time point, except last time point: n=1) at different time points and the resulting slope k of the elimination phase (plotted in a semi-logarithmic scale) the half-life of E4-Fc (SEQ ID NO: 120) was calculated using to the formula $t^{1/2}$=ln 2/−k.

Results

The half-life of fusion protein of the invention E4-Fc (SEQ ID NO: 120) as calculated from the elimination phase (beta phase, 4 last time points) was 50.6 hours (see FIG. 16).

Example 2.6: ELISA for Determining the Binding Specificity of IL-17A-Binding Polypeptides and Fusion Proteins Methods Target proteins human IL-17F (R&D systems), murine IL-17A (R&D Systems), human TNF-alpha (Thermo Scientific), human IL-6 (R&D Systems), bovine serum albumin (Sigma) and ovalbumin (Sigma) were coated on a MaxiSorp plate (Nunc) overnight (100 μl of each target at a concentration of 5 μg/ml). Wells were washed three times with PBS and after blocking with 200 μl of PBS, 4% Milk (Rapilait, Migros) and a washing step with PBS (as above), 50 μl of 2C1 (SEQ ID No: 110) at a final concentration of 50 nM were added to the wells together with 50 μl of an anti-myc antibody (9E10, produced in-house, a stock solution of OD=2 and diluted 1:250 in PBS, 2% milk). After incubation the wells were washed three times with PBS and 100 μl of anti-mouse-HRP immunoconjugate (Sigma) diluted 1:1000 in PBS, 2% milk were added to the wells. The 96-well plate was incubated for 1 h at RT and then washed three times with PBS, 0.1% Tween followed by three washes with PBS only. Colorimetric detection was done by addition of 100 μl of BM blue POD substrate (Roche) and the reaction was stopped with 60 μl 1 M $H_2SO_4$.

Results

Clone 2C1 (SEQ ID NO: 110) bound human IL-17A in a highly specific manner and did not cross-react with any of the other tested proteins as shown by ELISA (FIG. 17). A small signal above background was observed for IL-17F, but when 2C1 was probed to a IL-17F coated BIAcore chip, no detectable binding was determined (data not shown).

Example 2.7: Fyn SH3-Derived Polypeptide of the Invention Binds Specifically and with High Affinity to Human and Cynomolgus IL-17A Methods a) Specificity For the determination of the binding specificity of IL-17A-binding polypeptides of the invention, the following target proteins were used (more target proteins compared to Example 2.6):

human IL-17A (R & D Systems)
human IL-17B (Peprotech)
human IL-17C (R & D Systems)
human IL-17D (Peprotech)
human IL-17E (Peprotech)

human IL-17F (Abd Serotec)
mouse IL-17A (R & D Systems)
rat IL-17A (Akron Biotech)
canine IL-17A (R & D Systems)
cynomolgus (*macaca fascicularis*) IL-17A (produced in-house in *E. coli*, without signal peptide, with a C-terminal glycine residue followed by a hexa-his tag, refolded from inclusion bodies, SEQ ID NO: 132)
extra domain B of fibronectin (produced in-house, *E. coli*; see Carnemolla et al. (1996) Int J Cancer, 68(3), p. 397-405)
Human IL-6 (R & D Systems)
Human TNF alpha (Thermo Scientific)
Ovalbumin (Sigma)
BSA (Sigma)

The target proteins were coated on a MaxiSorp plate (Nunc) overnight (100 μl of each target at a concentration of 10 μg/ml). Wells were washed three times with PBS and after blocking with 200 μl of PBS, 4% Milk (Rapilait, Migros) for 1 hour at room temperature and a subsequent washing step with PBS (as above), 50 μl of the Fyn SH3-derived polypeptide of the invention 2C1 (SEQ ID No: 110) at a final concentration of 80 nM were added to the wells together with 50 μl of anti-myc antibody 9E10 (produced in-house, a stock solution of OD=2 and diluted 1:250 in PBS, 2% milk). After incubation the wells were washed three times with PBS and 100 μl of anti-mouse-HRP immunoconjugate (Sigma) diluted 1:1000 in PBS, 2% milk were added to the wells. The 96-well plate was incubated for 1 h at RT and then washed three times with PBS, 0.1% Tween followed by three washes with PBS only. Colorimetric detection was done by addition of 100 μl of BM blue POD substrate (Roche) and the reaction was stopped with 60 μl 1 M $H_2SO_4$.

b) Affinity Measurements to Cynomolgus IL-17A

Affinity measurements were performed using a BIAcore 3000 instrument (Biacore). For the interaction analysis between cynomolgus IL-17A and the Fyn SH3-derived polypeptide of the invention 2C1 (SEQ ID NO: 110) a CM5 chip (Biacore) was coated with 6900 RU cynomolgus IL-17A. The running buffer was HBS-EP (Biacore). The interactions were measured at a flow of 20 μl/min and injection of different concentrations of Fyn SH3-derived IL-17A-binding polypeptide of the invention 2C1 (SEQ ID NO: 110). All kinetic data of the interaction (separate kon/koff) were evaluated using BIA evaluation 3.2RC1 software.

Results

Fyn SH3-derived polypeptide of the invention 2C1 (SEQ ID NO: 110) bound human and cynomolgus IL-17A in a highly specific manner and did not cross-react with any of the other tested proteins as shown by ELISA (FIG. 18).

The affinity of monomeric Fyn SH3-derived polypeptide of the invention 2C1 (SEQ ID NO: 110) for cynomolgus IL-17A was measured with Biacore using cynomolgus IL-17A produced in *E. coli* (refolded from inclusion bodies). 2C1 was found to bind cynomolgus IL-17A with a $K_D$ of 11 nM (FIG. 19).

Example 2.8: Expression of Fyn SH3-Derived Polypeptides of the Invention Fused to an Fc Part and to a Modified Fc Part of a Human IgG1 Antibody in Mammalian Cells The Fyn SH3-derived polypeptide of the invention 2C1 (SEQ ID NO: 110) was genetically fused to the Fc part of IgG1 (2C1-Fc, SEQ ID NO: 133) and expressed in HEK EBNA cells. The Fyn SH3-derived polypeptide of the invention 2C1 (SEQ ID NO: 110) was also cloned as genetic fusion to the modified Fc part of human IgG1, comprising mutations L234A (alanine instead of leucine at amino acid position 234) and L235A and expressed in HEK EBNA cells (2C1-Fc(LALA), SEQ ID NO: 134). Furthermore, the following four variants of 2C1-Fc(LALA) fusion protein with different linker length between the Fyn SH3-derived polypeptide of the invention and the Fc part were produced:

(SEQ ID NO: 135) "2C1-m5E-Fc(LALA)"; extension of hinge region by 5 amino acids: EPKSS linker
(SEQ ID NO: 136) "2C1-m5-Fc(LALA)"; 5 amino acids extension, GGGGS linker
(SEQ ID NO: 137) "2C1-m10-Fc(LALA)"; 10 amino acids extension, $GGGGS)_2$ linker
(SEQ ID NO: 138) "2C1-m15-Fc(LALA)"; 15 amino acids extension, $(GGGGS)_3$ linker Methods Cloning of "2C1-Fc": Fyn SH3-Derived Polypeptide of the Invention 2C1 (SEQ ID NO: 110) Fused to an Fc Part of a Human IgG1 Antibody (SEQ ID NO: 133):

The gene encoding clone 2C1 (SEQ ID NO: 110) was used as a template and amplified using the primers SB3 (5' CGA ATT CGG GAG TGA CAC TCT TTG TGG CCC 3', SEQ ID NO: 139) and SB4 (5' GAA GAT CTC TGG ATA GAG TCA ACT GGA GCC 3', SEQ ID NO: 140) introducing the restriction sites EcoRI and BglII. Obtained PCR product was digested with EcoRI and BglII and cloned into the previously double-digested pFUSE-hIgG1-Fc2 vector (Invivogen). For cloning this Fc fusion into the pCEP4 vector (Invitrogen), the resulting pFUSE vector containing the gene encoding the 2C1-Fc fusion was used as template and amplified with the primers SB5 (5' CCC AAG CTT GGG ATG GGC TAC AGG ATG CAA CTC CTG TC 3', SEQ ID NO: 141) and SB6 (5' CGG GAT CCT CAT TTA CCC GGA GAC AGG GAG 3', SEQ ID NO: 142), introducing HindIII and BamHI restriction sites. After digestion with HindIII/BamHI, the insert was ligated with previously double-digested pCEP4 vector, yielding the plasmid containing the genetic information of SEQ ID NO: 133.

Cloning of "2C1-Fc(LALA)": Fyn SH3-Derived Polypeptide of the Invention 2C1 (SEQ ID NO: 110) fused to a modified Fc part of a human IgG1 antibody (L234A, L235A) (yielding SEQ ID NO: 134)

The above mentioned plasmid containing the genetic information of 2C1-Fc (SEQ ID NO: 133) was used as a template for two PCR reactions. In the first reaction, the primers SB5 and SB7 (5' ACT GAC GGT CCC CCC GCG GCT TCA GGT GCT GGG CAC 3', SEQ ID NO: 143) were used. In the second PCR the primers SB8 (5' GCC GCG GGG GGA CCG TCA GTC TTC CTC TTC CC 3', SEQ ID NO: 144) and SB6 were used. A PCR assembly with both fragments as templates was performed, the resulting PCR product was digested with BamHI and HindIII and ligated with the digested pCEP4 vector as described above.

Cloning of "2C1-m5E-Fc(LALA)" (SEQ ID NO: 135): Fyn SH3-Derived Polypeptide of the Invention 2C1 (SEQ ID NO: 107) Fused with a 5 Amino Acid Linker EPKSS to a Modified Fc Part of a Human IgG1 Antibody (L234A, L235A)

The above mentioned plasmid containing the genetic information of 2C1-Fc(LALA) (SEQ ID NO: 134) was used as a template for two PCRs. In the first reaction the primers SB5 and "Ba_2C1_R_EPKSS" (5' GCT GCT TTT CGG TTC CTG GAT AGA GTC AAC TGG AGC CAC 3', SEQ ID NO: 145) were used. In the second reaction the primers SB6 and "Ba_Hinge_F_EPKSS" (5' GAA CCG AAA AGC AGC GAC AAA ACT CAC ACA TGC CCA CCG 3', SEQ ID NO: 146) were used. A PCR assembly with both fragments as templates was performed, the resulting PCR product was digested with BamHI and HindIII and ligated with the digested pCEP4 vector as described above.

Cloning of "2C1-m5-Fc(LALA)" (SEQ ID NO: 136): Fyn SH3-Derived Polypeptide of the Invention 2C1 (SEQ ID NO: 110) Fused with a 5 Amino Acid Linker GGGGS to a Modified Fc Part of a Human IgG1 Antibody (L234A, L235A)

The above mentioned plasmid containing the genetic information of 2C1-Fc(LALA) (SEQ ID NO: 134) was used as a template for two PCRs. In the first reaction the primers SB5 and 47c.fo (5' TGA ACC GCC TCC ACC CTG GAT AGA GTC AAC TGG AGC CAC 3', SEQ ID NO: 147) were used. In the second reaction the primers SB6 and "Ba_Hinge_F_5aaGS-linker" (5' GGT GGA GGC GGT TCA GAC AAA ACT CAC ACA TGC CCA CCG 3', SEQ ID NO: 148) were used. A PCR assembly with both fragments as templates was performed, the resulting PCR product was digested with BamHI and HindIII and ligated with the digested pCEP4 vector as described above.

Cloning of "2C1-m10-Fc(LALA)" (SEQ ID NO: 137): Fyn SH3-Derived Polypeptide of the Invention 2C1 (SEQ ID NO: 110) Fused with a 10 Amino Acid Linker $(GGGGS)_2$ to a Modified Fc Part of a Human IgG1 Antibody (L234A, L235A)

The above mentioned plasmid containing the genetic information of 2C1-Fc(LALA) (SEQ ID NO: 134) was used as a template for two PCRs. In the first reaction the primers SB5 and 47b.fo (5' AGA GCC ACC TCC GCC TGA ACC GCC TCC ACC CTG GAT AGA GTC AAC TGG AGC CAC 3', SEQ ID NO: 149) were used. In the second reaction the primers SB6 and "Ba_Hinge_F_10aaGS-linker" (5' GGT GGA GGC GGT TCA GGC GGA GGT GGC TCT GAC AAA ACT CAC ACA TGC CCA CCG 3', SEQ ID NO: 150) were used. A PCR assembly with both fragments as templates was performed, the resulting PCR product was digested with BamHI and HindIII and ligated with the digested pCEP4 vector as described above.

Cloning of "2C1-m15-Fc(LALA)" (SEQ ID NO: 138): Fyn SH3-Derived Polypeptide of the Invention 2C1 (SEQ ID NO: 110) Fused with a 15 Amino Acid Linker $(GGGGS)_3$ to a Modified Fc Part of a Human IgG1 Antibody (L234A, L235A)

The above mentioned plasmid containing the genetic information of 2C1-Fc(LALA) (SEQ ID NO: 134) was used as a template for two PCRs. In the first reaction the primers SB5 and 47.fo.corr (5' TGA TCC GCC ACC GCC AGA GCC ACC TCC GCC TGA ACC GCC TCC ACC CTG GAT AGA GTC AAC TGG AGC CAC 3', SEQ ID NO: 151) were used. In the second reaction the primers SB6 and "Ba_Hinge_F_15aaGS-linker" (5' GGT GGA GGC GGT TCA GGC GGA GGT GGC TCT GGC GGT GGC GGA TCA GAC AAA ACT CAC ACA TGC CCA CCG 3', SEQ ID NO: 152) were used. A PCR assembly with both fragments as templates was performed, the resulting PCR product was digested with BamHI and HindIII and ligated with the digested pCEP4 vector as described above.

For expression of the fusion proteins, the corresponding plasmids were purified using an endotoxin free Megaprep kit (Qiagen) and used for transient transfection of HEK EBNA cells (ATCC No CRL-10852). HEK EBNA cells were seeded at 30% confluence 24 hours prior to transfection. The medium was replaced with DMEM/5% FCS/penstrep (Invitrogen) immediately prior to transfection. 60 μg of DNA was used to transfect 150 $cm^2$ of adherent cells. DNA and PEI (25 kDa from Polysciences) were mixed in a 1:3 ratio and vortexed for 10 sec. Then, the DNA/PEI mixture was incubated at RT for 10 minutes and subsequently added to the HEK EBNA cells. After 24 hours the medium was replaced with CD-CHO/HT/L-glutamine/Penstrep (Invitrogen) and incubated at 37° C. with 5% $CO_2$. The cell culture supernatant was harvested after 96 hours.

For protein purification, the cell culture supernatant was applied to a protein A-sepharose affinity column. Subsequently, the column was washed with PBS followed by protein elution using 0.1 M glycine pH 2.7. Eluted protein was then dialysed into PBS. If needed, a second purification step for removal of endotoxins with Triton-X114 was performed (Magalhães et al. (2007) J Pharm Pharmaceut Sci, 10(3), p. 388-404).

Results

The Fyn SH3-derived Fc fusions of the invention could be expressed and purified. FIG. 20 shows the SDS PAGE analysis of the Fc fusion proteins.

Example 2.9: Fyn SH3-Derived Polypeptides of the Invention are Stable in Human Serum Protein drugs should be stable in serum for a certain period of time, in order to be able to elicit pharmacodynamic effects in patients. In this example, the serum stability of 2C1-Fc (SEQ ID NO: 133) was tested.

Methods

A solution of 3 ml of human serum (Sigma) containing 10 μg/ml 2C1-Fc (SEQ ID NO: 133) was prepared and placed in an incubator at 37° C. 200 μl samples were removed at indicated time points and frozen at −20° C. until the end of the experiment. After 5 days, an ELISA was performed with the collected samples, using a 2C1-Fc sample (SEQ ID NO: 133) which has been stored at 4° C. in PBS as a control standard.

To perform the ELISA, IL-17A (R&D Systems) was coated on a MaxiSorp plate (Nunc) overnight (100 μl of 5 μg/ml). Wells were washed three times with PBS and after blocking with 200 μl of PBS, 4% Milk (Rapilait, Migros) and a washing step with PBS (as above), 100 μl of the test samples comprising 2C1-Fc (SEQ ID NO: 133) (at the indicated concentrations) diluted in PBS, 2% Milk were added. After incubation, the wells were washed three times with PBS, followed by addition of 100 μl Protein A-HRP (Sigma) diluted 1:1000 in PBS, 2% milk. The 96-well plate was incubated for 1 h at RT and then washed three times with PBS, 0.1% Tween followed by three washes with PBS only. Colorimetric detection was done by addition of 100 μl of BM blue POD substrate (Roche) and the reaction was stopped with 60 μl 1 M $H_2SO_4$.

Results

After a 5-day storage period in human serum at 37° C. 2C1-Fc (SEQ ID NO: 133) was able to bind its target IL-17A essentially as well as 2C1-Fc (SEQ ID NO: 133) which was stored in PBS at 4° C., indicating that 2C1-Fc (SEQ ID NO: 133) is stable in human serum at 37° C. (FIG. 21).

Example 2.10: Fyn SH3-Derived Polypeptides of the Invention Inhibit IL-17A In Vitro In this assay the indicated Fyn SH3-derived polypeptides of the invention were tested for their ability to inhibit IL-17A in vitro. The cell assay is similar to the cell assay described in Example 2.3 of this invention, with the main exception that IL-17A is used at a low concentration of 1 ng/ml (compared to 50 ng/ml in Example 2.3) together with TNF alpha (50 μg/ml).

Methods

Endotoxin levels of tested Fyn SH3-derived IL-17A-binding polypeptides of the invention were less than 0.1 EU/ml, as determined by the Limulus amebocyte lysate (LAL) test (PYROGENT Single test Gel Clot LAL Assay (Lonza)).

Normal human dermal fibroblasts (NHDF, PromoCell Inc., NHDF-c, C12300) are used for the IL-17A inhibition cell assay. Addition of human IL-17A (R&D Systems) in combination with human tumor necrosis factor-α (TNF-α, Thermo Fisher Scientific) to the cell culture medium induces IL-6 production by NHDF cells in a dose-dependent manner. IL-6 released into the cell culture medium (PromoCell, C-23010) is quantified in cell culture supernatant by ELISA using a commercially available ELISA kit (R&D Systems, DuoSet ELISA System kit (DY206)).

$10^4$ Normal Human Dermal Fibroblasts (PromoCell, NHDF-c, C12300) were distributed per well (24 well plate, Nunc or TPP) and cultured for 24 hours at 37° C. (medium: Fibroblast Growth Medium C-23010, PromoCell). The supernatant was aspirated and after mixing different concentrations of Fyn SH3 derived IL-17A-binding polypeptides of the invention or IL-17A receptor Fc chimera (RnD Systems) with IL-17A (RnD Systems) and TNF alpha (Thermo Scientific) containing medium (1 ng/ml final IL-17A concentration and 50 μg/ml TNF alpha), 350 μl of the corresponding solution was added per well, in triplicate (mixing ratio between inhibitor solution and cytokine-containing medium was 1:23). Control wells included incubation without Fyn SH3-derived polypeptides (PBS only), IL-17A alone, TNF-α alone and medium only. After 24 hours incubation at 37° C. the supernatant was aspirated and the ELISA absorbance (correlating to the IL-6 concentration) was determined by ELISA according to the manufacturer's instructions (IL-6 ELISA kit, R&D Systems).

Results

NHDF cells were incubated with a constant concentration of IL-17A (1 ng/ml) and TNF alpha (50 μg/ml) and with different concentrations of the commercially available IL-17A receptor-Fc chimera or with different concentrations of the following Fyn SH3-derived polypeptides of the invention:

2C1 (SEQ ID NO: 110)
2C1-Fc (SEQ ID NO:133)
2C1-Fc(LALA) (SEQ ID NO: 134)
2C1-m5E-Fc(LALA) (SEQ ID NO: 135)
2C1-m5-Fc(LALA) (SEQ ID NO: 136)
2C1-m10-Fc(LALA) (SEQ ID NO: 137)
2C1-m15-Fc(LALA) (SEQ ID NO: 138)

Table 3 shows the average of the $IC_{50}$ values obtained from several cell assays performed with the indicated Fyn SH3-derived polypeptides of the invention. The best $IC_{50}$ value (0.11 nM) was obtained with 2C1-m15-Fc(LALA) (SEQ ID NO: 138).

TABLE 3

Average $IC_{50}$ values of Fyn SH3-derived polypeptides of the invention obtained from several cell assays.

| | $IC_{50}$ value (nM) | Standard Deviation | Number of cell assays |
|---|---|---|---|
| 2C1 (SEQ ID NO: 110) | 2.31 | 0.08 | 3 |
| 2C1-Fc (SEQ ID NO: 133) | 1.13 | 0.30 | 4 |
| 2C1-Fc(LALA) (SEQ ID NO: 134) | 1.09 | 0.53 | 4 |
| 2C1-m5E-Fc(LALA) (SEQ ID NO: 135) | 0.72 | 0.30 | 4 |
| 2C1-m5-Fc(LALA) (SEQ ID NO: 136) | 1.45 | n.d. | 2 |
| 2C1-m10-Fc(LALA) (SEQ ID NO: 137) | 0.27 | 0.13 | 6 |
| 2C1-m15-Fc(LALA) (SEQ ID NO: 138) | 0.11 | 0.02 | 3 |
| IL-17A-Receptor Fc chimera (R&D Systems) | 0.61 | 0.38 | 6 |

Example 2.11: In Vivo Half-Life of 2C1-Fc(LALA) (SEQ ID NO: 134)

The in vivo half-life of the fusion protein of the invention 2C1-Fc(LALA) (SEQ ID NO: 134) was determined by measuring 2C1-Fc(LALA) (SEQ ID NO: 134) concentrations in mouse serum at different time points after a single i.v. injection.

Methods

2C1-Fc(LALA) (SEQ ID NO: 134) solution (0.2 mg/ml) was injected i.v. into 5 mice (C57BL/6, Charles River), 200 μl per mouse. After indicated time-points about 20 μl of blood were taken from the vena saphena with the capillary Microvette CB 300 (Sarstedt). The blood samples were centrifuged for 10 min at 9500×g and the serum was stored at −20° until ELISA analysis was performed. Using a 2C1-Fc(LALA) (SEQ ID NO: 134) dilution series with known concentrations, the 2C1-Fc(LALA) (SEQ ID NO: 134) concentration in serum was determined by ELISA: 50 μl of biotinylated IL-17A (30 nM) (R&D Systems, biotinylated using NHS-PEO4-biotin (Pierce) according to the manufacturer's instructions) were added to streptavidin-coated wells (Reactibind, Pierce) and after blocking with PBS, 4% milk (Rapilait, Migros, Switzerland), 45 μl of PBS, 4% milk and 5 μl of serum sample were added. After incubation for 1 h and washing, bound Fc fusion proteins were detected with protein A-HRP conjugate (Sigma). Peroxidase activity was detected by addition of QuantaRed enhanced chemifluorescent HRP substrate (Pierce). Fluorescence intensity was measured after 5 to 10 min at 544 nm (excitation) and 590 nm (emission). From the concentrations of 2C1-Fc(LALA) (SEQ ID NO: 134) determined in serum (mouse number n=5 per time point) at different time points and the resulting slope k of the elimination phase (plotted in a semi-logarithmic scale) the half-life of 2C1-Fc(LALA) (SEQ ID NO: 134) was calculated using to the formula $t^{1/2}=\ln 2/-k$.

Results

The half-life of fusion protein of the invention 2C1-Fc (LALA) (SEQ ID NO: 134) as calculated from the elimination phase (beta phase, 4 last time points) was 53 hours (see FIG. 22).

Example 2.12: Fyn SH3-Derived Polypeptides of the Invention Neutralize Human IL-17A in Vivo Human IL-17A is able to bind and stimulate the mouse IL-17 receptor, leading to an elevation and subsequent secretion of mouse KC (CXCL1) chemokine (Allan B. et al. (2007) WO2007/070750 of Eli Lilly, US). The observed KC levels 2 hours after s.c. IL-17A injection (3 μg) were between 500 and 1000 μg/ml in the serum, compared to around 100 μg/ml KC basal levels.

Methods a) In Vivo Neutralization of IL-17A Using Monomeric Fyn SH3 Derived Polypeptide of the Invention 2C1 (SEQ ID NO: 110)

Fyn SH3-derived polypeptide of the invention 2C1 (SEQ ID NO: 110) (17 μg) was co-injected (s.c.) with 3 μg of human IL-17A (R&D Systems) into C57BL/6 mice, and 2 hours after injection, blood samples were taken from the vena saphena with the capillary Microvette CB 300 (Sarstedt). The blood samples were centrifuged for 10 min at 9500×g and the serum was stored at −20° until ELISA analysis was performed. KC levels in serum were determined using the commercially available Quantikine mouse CLCL1/KC kit (R&D Systems). Control groups included mice injected with IL-17A and the Fyn SH3 wt domain (see Grabulovski et al. (2007) JBC, 282, p. 3196-3204) as a protein of irrelevant binding specificity, PBS only, IL-17A only, only Fyn SH3-derived polypeptide of the invention 2C1 (SEQ ID NO: 110) or mice given Fyn SH3 wt protein only.

b) In Vivo Neutralization Using the 2C1-Fc Fusion (SEQ ID NO: 133):

Fyn SH3-derived polypeptide of the invention 2C1-Fc (SEQ ID NO: 133) (44 μg/mouse) was injected i.v. into C57BL/6 mice. After 20-60 minutes, 3 μg/mouse of human IL-17A (R&D Systems) was injected s.c. and 2 hours after IL-17A injection, blood samples were taken from the vena saphena with the capillary Microvette CB 300 (Sarstedt). The blood samples were centrifuged for 10 min at 9500×g and the serum was stored at −20° until ELISA analysis was performed. KC levels in serum were determined using the commercially available Quantikine mouse CLCL1/KC kit (R&D Systems). Control groups included mice injected with PBS (i.v.) and IL-17A (s.c.), PBS only (i.v. and s.c.), and Fyn SH3-derived polypeptide of the invention 2C1-Fc (SEQ ID NO: 133) i.v. followed by PBS (s.c.).

Results

After s.c. injection of human IL-17A into mice the animals overexpress a chemokine called KC. Elevated KC levels in the sera of mice can be measured by ELISA. Injection of a Fyn SH3-derived polypeptide of the invention prevented the up-regulation of KC.

a)

IL-17A and monomeric Fyn SH3-derived polypeptide 2C1 (SEQ ID NO: 110) of the invention were co-injected s.c. into mice (C57BL/6). Because of the inhibitory properties of the Fyn SH3-derived polypeptide of the invention 2C1 (SEQ ID NO: 110), KC levels were not elevated in this group, they remained low, almost comparable to basal levels. In order to demonstrate that inhibition of KC production was due to specific IL-17A neutralization, mice were co-injected with IL-17A and the wild-type Fyn SH3 domain (which has no binding affinity to IL-17A); in these mice, KC levels were as high as in the group receiving IL-17A only. FIG. 23 shows the results obtained from this experiment.

b)

In this second acute inflammation experiment, the Fyn SH3-derived polypeptide of the invention 2C1-Fc (SEQ ID NO: 133) was injected i.v., followed by s.c. injection of IL-17A. As above in a), the Fyn SH3-derived polypeptide of the invention prevented the up-regulation of KC levels in the serum. FIG. 24 shows the inhibition of IL-17A by 2C1-Fc (SEQ ID NO: 133) in vivo.

Example 3: Anti-Chymase Fyn SH3 Derivatives

Example 3.1: Fyn SH3-Derived Polypeptides of the Invention Bind to Chymase as Determined by Monoclonal ELISA Using Bacterial Lysate Supernatants Containing the Fyn SH3-Derived Polypeptides of the Invention Methods:

DNA encoding the amino acid sequences shown in SEQ ID NOs: 153 to 166 were cloned into the cytosolic expression vector pQE-12 with a C-terminal myc and hexa his tag. After bacterial electroporation, bacterial lysates containing the Fyn SH3-derived polypeptides were produced as described in Bertschinger et al. (Bertschinger et al. (2007) Protein Eng Des Sel, 20(2), p. 57-68). Chymase was produced as described in Perspicace et al. (Perspicace et al. (2009) J Biomol Screen, 14(4), p. 337-349). The protein was biotinylated according to the manufacturer's instructions using EZ-link sulfo-NHS-SS-biotin (Perbio) and finally contained 3 biotin molecules per chymase molecule. For the ELISA experiment, biotinylated chymase was added to streptavidin-coated wells (StreptaWells, High Bind, Roche) at a concentration of 100 nM and after blocking with PBS, 2% milk (Rapilait, Migros, Switzerland), 40 μl of the bacterial supernatant containing the corresponding Fyn SH3-derived polypeptide were added to the wells together with 10 μl of an anti-myc antibody (9E10, at a final concentration of 10 μg/ml in PBS, 2% Milk). After incubating for 1 h and washing, detection was made with anti-mouse IgG HRP antibody conjugate (Sigma). Peroxidase activity was detected by adding BM blue POD substrate (Roche) and the reaction was stopped by adding 1M $H_2SO_4$. The DNA sequence of the binders was verified by DNA sequencing (BigDye Terminator v3.1 cycle sequencing kit, ABI PRISM 3130 Genetic Analyzer, Applied Biosystems).

Results:

The amino acid sequences of Fyn SH3-derived chymase binders (as determined by phage ELISA) is presented in SEQ ID NOs: 153 to 166 as appended in the sequence listing. SEQ ID NOs: 2 to 15 read:

```
                                        SEQ ID NO: 153
(E4)
GVTLFVALYDYNATRWTDLSFHKGEKFQILEFGPGDWWEARSLTTGETGY

IPSNYVAPVDSIQ

                                        SEQ ID NO: 154
(B5)
GVTLFVALYDYNATRWTDLSFHKGEKFQILDGDSGDWWEARSLTTGETGY

IPSNYVAPVDSIQ

                                        SEQ ID NO: 155
(A4)
GVTLFVALYDYQADRWTDLSFHKGEKFQILDASPPGDWWEARSLTTGETG

YIPSNYVAPVDSIQ

                                        SEQ ID NO: 156
(F12)
GVTLFVALYDYRAERSTDLSFHKGEKFQILDMTVPNGDWWEARSLTTGET

GYIPSNYVAPVDSIQ
```

-continued

```
                                        SEQ ID NO: 157
(G2.3)
GVTLFVALYDYNATRWTDLSFHKGEKFQILDWTTANGDWWEARSLTTGET

GYIPSNYVAPVDSIQ

                                        SEQ ID NO: 158
(D7)
GVTLFVALYDYQADRWTDLSFHKGEKFQILSFHVGDWWEARSLTTGETGY

IPSNYVAPVDSIQ

                                        SEQ ID NO: 159
(H2)
GVTLFVALYDYQADRWTDLSFHKGEKFQILRFDIGDWWEARSLTTGETGY

IPSNYVAPVDSIQ

                                        SEQ ID NO: 160
(E3)
GVTLFVALYDYQADRWTDLSFHKGEKFQILNASGPGDWWEARSLTTGETG

YIPSNYVAPVDSIQ

                                        SEQ ID NO: 161
(D2)
GVTLFVALYDYEAQTWHDLSFHKGEKFQILNSSEGEYWEARSLTTGETGL

IPSNYVAPVDSIQ

                                        SEQ ID NO: 162
(H11)
GVTLFVALYDYKAQRWTDLSFHKGEKFQILQAHQKTGDWWEARSLTTGET

GLIPSNYVAPVDSIQ

                                        SEQ ID NO: 163
(B10)
GVTLFVALYDYEALHWHQLSFHKGEKSQILNSSEGTYWEARSLTTGETGW
IPSNYVAPGDSIQ
                                        SEQ ID NO: 164
(E5)
GVTLFVALYDYKAQRWLDLSFHEGEKFQILSTDSGDWWEARSLTTGETGY

IPSNYVAPVDSIQ

                                        SEQ ID NO: 165
(C5)
GVTLFVALYDYEAPTWLHLSFHKGEKFQILNSSEGPWWEARSLTTGETGF

IPSNYVAPVDSIQ

                                        SEQ ID NO: 166
(A8)
GVTLFVALYDYEAANWFQLSFHKGEKFQILNSSEGPLWEARSLTTGETGG

IPSNYVAPVDSIQ
```

Example 3.2: Purified Fyn SH3-Derived Polypeptides of the Invention Bind Specifically to Chymase as Determined by ELISA Methods:

Fyn SH3-derived polypeptides (SEQ ID NO: 153-160) were expressed and purified as described in Grabulovski et al. (Grabulovski et al. (2007) JBC, 282, p. 3196-3204). Biotinylated chymase or biotinylated bovine serum albumin (BSA) as an irrelevant target protein (Sigma; biotinylation was performed according to the manufacturer's instructions using EZ-link sulfo-NHS-SS-biotin (Perbio)) was added to streptavidin-coated wells (StreptaWells, High Bind, Roche) at a concentration of 100 nM and after blocking with PBS, 2% milk (Rapilait, Migros, Switzerland), 50 μl of the corresponding Fyn SH3-derived polypeptide at a final concentration of 200 nM were added to the wells together with 50 μl of an anti-myc antibody (9E10, at a final concentration of 5 μg/ml in PBS, 2% Milk). After incubating for 1 h and washing, detection was made with anti-mouse IgG HRP antibody conjugate (Sigma). Peroxidase activity was detected by adding BM blue POD substrate (Roche) and the reaction was stopped by adding 1M $H_2SO_4$.

Results:

FIG. 25 shows the ELISA signals on chymase and BSA coated wells, indicating specific binding to chymase.

Example 3.3: Fyn SH3-Derived Polypeptides of the Invention are Monomeric and do not Aggregate as Determined by Size Exclusion Chromatography Methods After purification of the Fyn SH3-derived polypeptides (SEQ ID NOs: 153-160) as described in Example 3.2, size exclusion chromatography (SEC) was performed on an ÄKTA FPLC system using a Superdex 75 Column (5/150) (GE Healthcare).

Results

Size exclusion chromatography (SEC) profiles demonstrated that all selected constructs eluted mainly as single, monomeric peaks (see FIG. 26).

Example 3.4: Fyn SH3-Derived Polypeptides of the Invention Bind with High Affinity to Chymase as Determined by Surface Plasmon Resonance Experiments Methods:

Affinity measurements of selected Fyn SH3-derived polypeptides (SEQ ID NO: 153-160) were performed using a BIAcore 3000 instrument (Biacore). For the interaction analysis between biotinylated chymase and monomeric Fyn SH3-derived polypeptides, a streptavidin SA chip (Biacore) was immobilized with 1331 RU biotinylated chymase. The running buffer was PBS, 0.005% Tween 20. The interactions were measured at a flow of 30 μl/min and injections of different concentrations of Fyn SH3-derived chymase-binding polypeptides. All kinetic data of the interaction (separate kon/koff) were evaluated using BIA evaluation 3.2RC1 software Results:

The binding properties were analyzed by real-time interaction analysis on a BIAcore chip revealing the following dissociation constants (KD) and $k_{off}$ values for the Fyn SH3-derived polypeptides (Table 4):

TABLE 4

Dissociation konstants and $k_{off}$ values of Fyn SH3-derived polypeptides.

| Clone | SEQ ID NO: | $K_D$ (nM) | $k_{off}$ ($s^{-1}$) |
|---|---|---|---|
| F12 | 156 | 36.0 | $2.3 \times 10^{-3}$ |
| G2.3 | 157 | 14.0 | $8.2 \times 10^{-3}$ |
| B5 | 154 | 5.0 | $3.6 \times 10^{-3}$ |
| D7 | 158 | 15.0 | $1.1 \times 10^{-2}$ |
| E3 | 160 | 13.0 | $9.3 \times 10^{-3}$ |
| H2 | 159 | 32.0 | $2.1 \times 10^{-3}$ |
| A4 | 155 | 2.0 | $2.0 \times 10^{-3}$ |
| E4 | 153 | 0.9 | $6.6 \times 10^{-4}$ |

Example 3.5: Fyn SH3-Derived Polypeptides of the Invention Inhibit Protease Activity of Chymase The MR121 peptide fluorescence assay described below is based on the fact that MR121 forms a non-fluorescent ground state complex with tryptophan. In solution this formation occurs at millimolar concentrations of tryptophan. Here, the substrate peptide is labeled at one terminus with tryptophan and at the other terminus with the fluorophore MR121. In absence of protease activity, the substrate remains intact and the MR121 fluorescence is reduced by the high local concentration of tryptophan. If the substrate is cleaved by chymase, the MR121 fluorescence can be recorded. Therefore, the enzymatic reaction can be followed in a kinetic measurement detecting an increase of MR121 fluorescence during the reaction time. Calculating the slope in the linear range of the kinetic provides the value for the activity of the enzyme.

Methods:

The chymase fluorescent substrate kinetic assay was performed in triplicate at room temperature in 96-well microtiter plates (Costar). Each well contained 100 µl assay buffer (100 mM Hepes, pH 7.4; 0.01% Triton X-100, 80 µg/ml heparin) with 1 nM chymase, 1 OA unlabeled and 100 nM MR121 peptide (MR121-CAAPFW; Biosyntan GmbH, Berlin). Fyn SH3-derived (SEQ ID NOs: 153-160) were serially diluted in assay buffer (100 mM Hepes, pH 7.4; 0.01% Triton X-100, 80 µg/ml heparin) and added to the reaction solution as specified above. The enzymatic reaction was followed in a plate reader (Tecan Ultra, Tecan) at 612 nm excitation and 670 nm emission for 20 min in a kinetic measurement, detecting an increase of MR121 fluorescence during the reaction time. The slope in the linear range of the kinetic was calculated and $IC_{50}$ values of the Fyn SH3-derived polypeptides were calculated using a four parameter equation for curve fitting.

Results:

The titrated Fyn SH3-derived polypeptides showed dose-response curves demonstrating that they are potent inhibitors of chymase activity (see Table 5).

TABLE 5

$IC_{50}$ values for inhibition of chymase activity.

| Clone | SEQ ID NO: | $IC_{50}$ (nM) |
|---|---|---|
| F12 | 156 | 5 |
| G2.3 | 157 | 1 |
| B5 | 154 | 11 |
| D7 | 158 | 6 |
| E3 | 160 | 78 |
| H2 | 159 | 18 |
| A4 | 155 | 4 |
| E4 | 154 | 2 |

Example 3.6: Crystal Structure of Chymase and Fyn SH3-Derived Polypeptides of the Invention Reveals Blockade of the Catalytic Site of Chymase by Fyn SH3-Derived Polypeptides of the Invention Three selected Fyn SH3-derived polypeptides, B5 (SEQ ID NO: 154), A4 (SEQ ID NO: 155) and E4 (SEQ ID NO: 153) were co-crystallized with chymase.

Methods:

Prior to crystallization experiments the Fyn SH3-derived polypeptides—chymase complexes were concentrated to 15 mg/ml. Crystallization screening against an INDEX screen (Hampton Research) was performed at 21° C. either in sitting drops by vapor diffusion or in microbatch experiments. Crystals appeared within one day and grew to their final size within 3 days after setup.

In all cases, data were processed with XDS (Kabsch W. (2010) Acta Crystallogr D Biol Crystallogr. (66) p. 125-132.) and scaled with SADABS (obtained from Bruker AXS). Refinement was performed with Refmac5 (Murshudov G N, et al. (1997). Acta Crystallogr D Biol Crystallogr., (53) p. 240-255) from the CCP4 suite (The CCP4 suite: programs for protein crystallography. (1994) Acta Crystallogr D Biol Crystallogr., (50), p. 760-763) or BUSTER (Bricogne G. (1993) Acta Crystallogr D Biol Crystallogr. (49), p. 37-60. Roversi P et al. (2000), Acta Crystallogr D Biol Crystallogr., (56) p. 1316-23, Blanc E. et al. (2004), Acta Crystallogr D Biol Crystallogr. (60) p. 2210-2221) and model building done with COOT (Emsley P et al. (2004) Acta Crystallogr D Biol Crystallogr., (60), p. 2126-2132).

Results:

Three different Fyn SH3 derived polypeptides binding to chymase (B5 (SEQ ID NO: 154) A4 (SEQ ID NO: 155) and E4 (SEQ ID NO: 153)) were co-crystallized with chymase.

TABLE 6

The chymase-Fyn-SH3 derived polypeptide A4 (SEQ ID NO: 155) complex:

| | |
|---|---|
| Crystal parameters | SG19 59.630 92.792 116.256 90 90 90 |
| Resolution | 1.51 Å |
| Crystallization buffer | 0.1M Citric acid pH 3.5, 25% PEG 3'350 |
| Data collection and refinement | Data were collected on beam line X10SA (PXIII) at the Swiss Light Source (SLS) at wavelength 1.0 Å using a Pilatus pixel detector. For 101765 unique reflections to 1.51 Å resolution the merging R-factor on intensities was 6.5%. The final R-values were 18.9% (all data) and 21.5% (5% R-free). |

TABLE 7

Contacts between chymase and Fyn SH3-derived polypeptide A4 (SEQ ID NO: 155)
All atom-atom contacts <3.5 Å are tabulated.
Duplicates may occur as some residues have alternate conformations. The Fynomer numbering was chosen so that the first residue well visible in the first electron density is numbered 2. The chymase sequence is numbered serially from 1, so the catalytic serine is 182.
49 contacts found:

| CHYMASE | | FYNOMER | | DISTANCE |
|---|---|---|---|---|
| 201(SER) | OG | 13(ALA) | C | 3.45 |
| | | 13(ALA) | O | 3.31 |
| | | 14(ASP) | C | 3.06 |
| 200(ARG) | CA | 14(ASP) | O | 3.30 |
| 201(SER) | N | 14(ASP) | O | 2.90 |
| 201(SER) | OG | 14(ASP) | O | 3.33 |
| | | 15(ARG) | N | 3.19 |
| 199(GLY) | O | 15(ARG) | CA | 3.32 |
| 201(SER) | OG | 15(ARG) | C | 3.09 |
| | | 15(ARG) | O | 2.97 |
| 83(THR) | O | 15(ARG) | NH1 | 2.94 |
| 84(SER) | O | 15(ARG) | NH1 | 3.14 |
| 86(LEU) | CD1 | 15(ARG) | NH1 | 3.49 |
| 83(THR) | O | 15(ARG) | NH2 | 3.26 |
| 199(GLY) | O | 16(TRP) | N | 2.86 |
| 179(LYS) | CE | 16(TRP) | O | 3.37 |
| 199(GLY) | N | 16(TRP) | CD2 | 3.39 |
| 182(SER) | OG | 16(TRP) | NE1 | 3.32 |
| 199(GLY) | CA | 16(TRP) | CE3 | 3.42 |
| 199(GLY) | N | 16(TRP) | CE3 | 3.26 |
| 199(GLY) | C | 16(TRP) | CE3 | 3.45 |
| 199(GLY) | CA | 16(TRP) | CZ3 | 3.44 |
| 199(GLY) | N | 16(TRP) | CZ3 | 3.37 |
| 177(ALA) | O | 16(TRP) | CZ3 | 3.40 |
| | | 16(TRP) | CH2 | 3.45 |

TABLE 7-continued

Contacts between chymase and Fyn SH3-derived polypeptide A4 (SEQ ID NO: 155)
All atom-atom contacts <3.5 Å are tabulated.
Duplicates may occur as some residues have alternate conformations. The Fynomer numbering was chosen so that the first residue well visible in the first electron density is numbered 2. The chymase sequence is numbered serially from 1, so the catalytic serine is 182.
49 contacts found:

| CHYMASE | | FYNOMER | | DISTANCE |
|---|---|---|---|---|
| 77(ARG) | NH1 | 31(ASP) | OD2 | 2.82 |
| 77(ARG) | NH2 | 33(SER) | OG | 3.08 |
| | | 34(PRO) | CG | 3.50 |
| 82(ASN) | CA | 35(PRO) | O | 3.31 |
| 83(THR) | N | 35(PRO) | O | 2.84 |
| 83(THR) | OG1 | 35(PRO) | O | 3.46 |
| 81(TYR) | O | 35(PRO) | CD | 3.41 |
| 84(SER) | OG | 36(GLY) | CA | 3.48 |
| 83(THR) | OG1 | 36(GLY) | CA | 3.31 |
| | | 36(GLY) | C | 3.48 |
| 84(SER) | OG | 37(ASP) | N | 2.73 |
| | | 37(ASP) | CB | 3.42 |
| | | 37(ASP) | CG | 3.15 |
| | | 37(ASP) | OD1 | 3.43 |
| | | 37(ASP) | OD2 | 3.44 |
| 158(ARG) | NH1 | 37(ASP) | OD2 | 2.98 |
| 83(THR) | OG1 | 38(TRP) | N | 3.27 |
| | | 38(TRP) | O | 2.83 |
| 83(THR) | O | 38(TRP) | CD1 | 3.27 |
| 28(LYS) | NZ | 40(GLU) | OE2 | 2.78 |
| 22(THR) | O | 42(ARG) | NH1 | 3.31 |
| 81(TYR) | OH | 51(TYR) | CZ | 3.45 |
| 81(TYR) | CZ | 51(TYR) | OH | 3.49 |
| 81(TYR) | OH | 51(TYR) | OH | 2.59 |

It may be clearly seen that Trp16 of A4 inserts into the primary specificity pocket of chymase, which is thus inhibited.

TABLE 8

The chymase-Fyn SH3-derived polypeptide E4 (SEQ ID NO: 153) complex:

| | |
|---|---|
| Crystal parameters | SG19 58.998 59.855 89.711 90 90 90 |
| Resolution | 1.4 Å |
| Crystallization buffer | 0.1M Bis-Tris pH 5.5, 25% PEG 3'350 |
| Data collection and refinement | Data were collected on beam line X10SA (PXIII) at the Swiss Light Source (SLS) at wavelength 1.0 Å using a Pilatus pixel detector.<br>For 63158 unique reflections to 1.4 Å resolution the merging R-factor on intensities was 9.9%. The final R-values were 18.6% (all data) and 20.5% (5% R-free). |

TABLE 9

Contacts between chymase and E4 (SEQ ID NO: 153)
All atom-atom contacts <3.5 Å are tabulated. Duplicates may occur as some residues have alternate conformations. The Fynomer numbering was chosen so that the first residue well visible in the first electron density is numbered 2. The chymase sequence is numbered serially from 1, so the catalytic serine is 182 (with closest contact 3.52 Å in this structure).
In this structure the increased number of contacts occurs only because at the higher resolution it was possible to assign more alternative conformations to side chains, which are then counted twice.
75 contacts found:

| CHYMASE | | FYNOMER | | DISTANCE |
|---|---|---|---|---|
| 201(SER) | OG | 13(ALA) | C | 3.36 |
| | | 13(ALA) | O | 3.23 |

TABLE 9-continued

Contacts between chymase and E4 (SEQ ID NO: 153)
All atom-atom contacts <3.5 Å are tabulated. Duplicates may occur as some residues have alternate conformations. The Fynomer numbering was chosen so that the first residue well visible in the first electron density is numbered 2. The chymase sequence is numbered serially from 1, so the catalytic serine is 182 (with closest contact 3.52 Å in this structure).
In this structure the increased number of contacts occurs only because at the higher resolution it was possible to assign more alternative conformations to side chains, which are then counted twice.
75 contacts found:

| CHYMASE | | FYNOMER | | DISTANCE |
|---|---|---|---|---|
| | | 14(THR) | C | 3.15 |
| | | 14(THR) | O | 3.49 |
| 200(ARG) | CA | 14(THR) | O | 3.42 |
| 201(SER) | N | 14(THR) | O | 3.05 |
| 201(SER) | OG | 15(ARG) | N | 3.26 |
| | | 15(ARG) | N | 3.27 |
| 199(GLY) | O | 15(ARG) | CA | 3.24 |
| | | 15(ARG) | CA | 3.24 |
| 201(SER) | OG | 15(ARG) | C | 3.20 |
| 199(GLY) | O | 15(ARG) | C | 3.50 |
| 201(SER) | OG | 15(ARG) | C | 3.12 |
| 199(GLY) | O | 15(ARG) | C | 3.49 |
| 201(SER) | OG | 15(ARG) | O | 3.05 |
| | | 15(ARG) | O | 2.84 |
| 84(SER) | O | 15(ARG) | CZ | 3.43 |
| 83(THR) | O | 15(ARG) | NH1 | 3.33 |
| 84(SER) | O | 15(ARG) | NH1 | 2.80 |
| 84(SER) | O | 15(ARG) | NH1 | 3.04 |
| 86(LEU) | CG | 15(ARG) | NH1 | 3.35 |
| 84(SER) | O | 15(ARG) | NH1 | 2.66 |
| 84(SER) | O | 15(ARG) | NH1 | 2.85 |
| 83(THR) | O | 15(ARG) | NH2 | 3.08 |
| 84(SER) | O | 15(ARG) | NH2 | 3.35 |
| 84(SER) | O | 15(ARG) | NH2 | 3.38 |
| 159(ASP) | OD2 | 15(ARG) | NH2 | 2.71 |
| 199(GLY) | O | 16(TRP) | N | 2.83 |
| 179(LYS) | NZ | 16(TRP) | O | 2.82 |
| 179(LYS) | CE | 16(TRP) | O | 3.43 |
| 199(GLY) | N | 16(TRP) | CD2 | 3.43 |
| 178(PHE) | CD1 | 16(TRP) | CE3 | 3.44 |
| 199(GLY) | N | 16(TRP) | CE3 | 3.22 |
| 199(GLY) | CA | 16(TRP) | CE3 | 3.42 |
| 199(GLY) | N | 16(TRP) | CZ3 | 3.35 |
| 199(GLY) | CA | 16(TRP) | CZ3 | 3.44 |
| 177(ALA) | O | 16(TRP) | CZ3 | 3.44 |
| | | 16(TRP) | CH2 | 3.49 |
| 24(ASN) | ND2 | 28(GLN) | CB | 3.50 |
| 24(ASN) | OD1 | 28(GLN) | CG | 3.39 |
| 24(ASN) | ND2 | 28(GLN) | CG | 3.23 |
| | | 28(GLN) | CD | 3.40 |
| | | 28(GLN) | OE1 | 3.33 |
| 23(SER) | OG | 30(LEU) | O | 3.13 |
| 24(ASN) | N | 30(LEU) | CD2 | 3.39 |
| 24(ASN) | N | 30(LEU) | CD2 | 3.44 |
| 77(ARG) | NH1 | 31(GLU) | OE1 | 2.84 |
| | | 31(GLU) | OE2 | 3.42 |
| 77(ARG) | NH2 | 31(GLU) | OE2 | 2.96 |
| 83(THR) | N | 34(PRO) | O | 2.83 |
| 83(THR) | OG1 | 34(PRO) | O | 3.37 |
| 83(THR) | CG2 | 34(PRO) | O | 3.49 |
| 82(ASN) | CA | 34(PRO) | O | 3.32 |
| 84(SER) | OG | 36(ASP) | N | 3.48 |
| | | 36(ASP) | CB | 3.39 |
| 83(THR) | OG1 | 37(TRP) | N | 3.17 |
| | | 37(TRP) | C | 3.45 |
| 83(THR) | CB | 37(TRP) | O | 3.39 |
| 83(THR) | OG1 | 37(TRP) | O | 2.68 |
| | | 37(TRP) | CB | 3.46 |
| 84(SER) | OG | 37(TRP) | CD1 | 3.43 |
| 28(LYS) | CE | 39(GLU) | OE2 | 3.49 |
| 28(LYS) | NZ | 39(GLU) | OE2 | 2.63 |
| 24(ASN) | O | 41(ARG) | NE | 3.05 |
| 24(ASN) | O | 41(ARG) | NE | 2.63 |
| 24(ASN) | O | 41(ARG) | CZ | 3.38 |
| 24(ASN) | O | 41(ARG) | CZ | 3.29 |

TABLE 9-continued

Contacts between chymase and E4 (SEQ ID NO: 153)
All atom-atom contacts <3.5 Å are tabulated. Duplicates may occur as some residues have alternate conformations. The Fynomer numbering was chosen so that the first residue well visible in the first electron density is numbered 2. The chymase sequence is numbered serially from 1, so the catalytic serine is 182 (with closest contact 3.52 Å in this structure).
In this structure the increased number of contacts occurs only because at the higher resolution it was possible to assign more alternative conformations to side chains, which are then counted twice.
75 contacts found:

| CHYMASE | | FYNOMER | | DISTANCE |
|---|---|---|---|---|
| 24(ASN) | O | 41(ARG) | NH2 | 2.86 |
| 24(ASN) | O | 41(ARG) | NH2 | 3.09 |
| 22(THR) | OG1 | 41(ARG) | NH2 | 2.95 |
| 26(PRO) | O | 41(ARG) | NH2 | 2.59 |
| 83(THR) | CG2 | 50(TYR) | CE1 | 3.41 |
| 81(TYR) | OH | 50(TYR) | CE2 | 3.37 |
| | | 50(TYR) | CZ | 3.33 |
| | | 50(TYR) | OH | 2.69 |

TABLE 10

The chymase-Fyn SH3-derived polypeptide B5 (SEQ ID NO: 154) complex:

| | |
|---|---|
| Crystal parameters | SG19 56.937 64.124 174.987 90 90 90 |
| Resolution | 1.8 Å |
| Crystallization buffer | 0.15M DL-Malic acid pH 7.0, 20% PEG 3'350 |
| Data collection and refinement | Data were collected on beam line X10SA (PXIII) at the Swiss Light Source (SLS) at wavelength 1.0 Å using a Pilatus pixel detector. For 62210 unique reflections to 1.78 Å resolution the merging R-factor on intensities was 9.4%. The final R-values were 18.0% (all data) and 21.2% (5% R-free). |

TABLE 11

Contacts between chymase and B5 (SEQ ID NO: 154)
All atom-atom contacts <3.5 Å are tabulated. Duplicates may occur as some residues have alternate conformations. The Fynomer numbering was chosen so that the first residue well visible in the first electron density is numbered 2. The Chymase sequence is numbered serially from 1, so the catalytic serine is 182.
In this structure the increased number of contacts occurs partly because Trp16 of B5 was assigned 2 alternative conformations and partly due to slight differences in B5 Arg15.
67 contacts found:

| CHYMASE | | FYNOMER | | DISTANCE |
|---|---|---|---|---|
| 201(SER) | OG | 13(ALA) | C | 3.28 |
| | | 13(ALA) | O | 3.34 |
| | | 13(ALA) | CB | 3.33 |
| | | 14(THR) | N | 3.43 |
| | | 14(THR) | C | 3.11 |
| 200(ARG) | CA | 14(THR) | O | 3.45 |
| 201(SER) | N | 14(THR) | O | 2.96 |
| 201(SER) | OG | 14(THR) | O | 3.44 |
| | | 15(ARG) | N | 3.18 |
| 199(GLY) | O | 15(ARG) | CA | 3.14 |
| 201(SER) | OG | 15(ARG) | C | 3.26 |
| | | 15(ARG) | O | 3.17 |
| 198(TYR) | OH | 15(ARG) | NH1 | 3.43 |
| 198(TYR) | CZ | 15(ARG) | NH1 | 3.38 |
| 85(THR) | O | 15(ARG) | NH1 | 3.38 |
| 159(ASP) | OD2 | 15(ARG) | NH1 | 3.14 |
| 159(ASP) | CG | 15(ARG) | NH2 | 3.41 |
| 159(ASP) | OD2 | 15(ARG) | NH2 | 3.16 |
| 159(ASP) | OD1 | 15(ARG) | NH2 | 2.88 |

TABLE 11-continued

Contacts between chymase and B5 (SEQ ID NO: 154)
All atom-atom contacts <3.5 Å are tabulated. Duplicates may occur as some residues have alternate conformations. The Fynomer numbering was chosen so that the first residue well visible in the first electron density is numbered 2. The Chymase sequence is numbered serially from 1, so the catalytic serine is 182.
In this structure the increased number of contacts occurs partly because Trp16 of B5 was assigned 2 alternative conformations and partly due to slight differences in B5 Arg15.
67 contacts found:

| CHYMASE | | FYNOMER | | DISTANCE |
|---|---|---|---|---|
| 199(GLY) | O | 16(TRP) | N | 2.92 |
| | | 16(TRP) | N | 2.94 |
| 179(LYS) | NZ | 16(TRP) | O | 2.82 |
| | | 16(TRP) | O | 2.91 |
| 178(PHE) | CD1 | 16(TRP) | CD1 | 3.28 |
| 178(PHE) | CE1 | 16(TRP) | CD1 | 3.35 |
| 200(ARG) | O | 16(TRP) | CD1 | 3.15 |
| 199(GLY) | C | 16(TRP) | CD1 | 3.39 |
| 199(GLY) | O | 16(TRP) | CD1 | 3.37 |
| 199(GLY) | N | 16(TRP) | CD2 | 3.40 |
| | | 16(TRP) | NE1 | 3.06 |
| 199(GLY) | CA | 16(TRP) | NE1 | 3.30 |
| 199(GLY) | N | 16(TRP) | CE2 | 3.34 |
| | | 16(TRP) | CE3 | 3.19 |
| 199(GLY) | CA | 16(TRP) | CE3 | 3.36 |
| 178(PHE) | CD1 | 16(TRP) | CE3 | 3.43 |
| 177(ALA) | O | 16(TRP) | CZ3 | 3.29 |
| 199(GLY) | N | 16(TRP) | CZ3 | 3.26 |
| 199(GLY) | CA | 16(TRP) | CZ3 | 3.32 |
| 182(SER) | OG | 16(TRP) | CZ3 | 2.92 |
| 177(ALA) | O | 16(TRP) | CH2 | 3.41 |
| 182(SER) | OG | 16(TRP) | CH2 | 2.95 |
| 77(ARG) | NH1 | 31(ASP) | OD2 | 2.86 |
| 83(THR) | N | 34(SER) | O | 3.04 |
| 83(THR) | OG1 | 34(SER) | O | 3.44 |
| 83(THR) | CG2 | 34(SER) | O | 3.37 |
| 77(ARG) | NH2 | 34(SER) | CB | 3.44 |
| 77(ARG) | CZ | 34(SER) | OG | 3.36 |
| 77(ARG) | NH1 | 34(SER) | OG | 3.27 |
| 77(ARG) | NH2 | 34(SER) | OG | 2.67 |
| 83(THR) | OG1 | 35(GLY) | CA | 3.23 |
| | | 35(GLY) | C | 3.30 |
| 84(SER) | OG | 36(ASP) | N | 3.35 |
| 83(THR) | OG1 | 37(TRP) | N | 3.41 |
| | | 37(TRP) | C | 3.49 |
| 83(THR) | CB | 37(TRP) | O | 3.21 |
| 83(THR) | OG1 | 37(TRP) | O | 2.55 |
| 84(SER) | OG | 37(TRP) | CD1 | 3.48 |
| 28(LYS) | NZ | 39(GLU) | CD | 3.43 |
| | | 39(GLU) | OE2 | 2.53 |
| 25(GLY) | CA | 41(ARG) | CZ | 3.33 |
| 26(PRO) | O | 41(ARG) | NH1 | 3.25 |
| 23(SER) | O | 41(ARG) | NH2 | 3.07 |
| 25(GLY) | N | 41(ARG) | NH2 | 3.27 |
| 25(GLY) | CA | 41(ARG) | NH2 | 3.38 |
| 81(TYR) | OH | 50(TYR) | CZ | 3.40 |
| 45(HIS) | CB | 50(TYR) | OH | 3.41 |
| 81(TYR) | OH | 50(TYR) | OH | 2.71 |

From the solved structures it can be seen that the main element for the interaction between the Fyn SH3-derived polypeptides and chymase are the sequence motif Arg15-Trp16 of the Fyn SH3-derived polypeptides, which confer to tight binding into the chymase active site. It is obvious that such a binding in the active site prevents the enzyme from being active, thus explaining the potent $IC_{50}$ values which have been determined in the enzymatic assay (Example 3.5).

Other indicated amino acids of the Fyn SH3-derived polypeptides make additional surface contacts with the 24 loop of chymase.

All six complex structures are very similar. The slight differences in the Fyn SH3-derived polypeptides—chymase orientation come from both the sequence differences and crystal packing and are approximately a rigid body rotation about Trp16 in the S1 pocket of chymase. The presence of a Fyn SH3-derived polypeptide has only a minor influence on the overall conformation of chymase. The most pronounced change affects the 24 loop of chymase which seems to adapt slightly upon binding.

All resolved Fyn SH3-derived polypeptides adopt a typical SH3 domain fold.

Example 4: Anti-HER2 Fyn SH3 Derivatives

Example 4.1: Fyn SH3 Derived Polypeptides Bind to HER2

Methods

1) Phage ELISA on Recombinant HER2 Protein

DNA encoding the amino acids shown in SEQ ID NOs: 175 to 287 were cloned into the phagemid vector pHEN1 as described for the Fyn SH3 library in Grabulovski et al. (Grabulovski et al. (2007) JBC, 282, p. 3196-3204). Phage production was performed according to standard protocols (Viti, F. et al. (2000) Methods Enzymol. 326, 480-505). Monoclonal bacterial supernatants containing phages were used for ELISA: biotinylated extracellular domain of HER2 comprising amino acids 23-652 of the full-length protein (purchased from Bender Medsystems, or from R&D as fusion to human Fcγ1; biotinylation was performed with sulfo-NHS-LC-biotin (Pierce) according to the manufacturer's instructions) was immobilized on streptavidin-coated wells (StreptaWells, High Bind, Roche), and after blocking with 2% milk (Rapilait, Migros, Switzerland) in PBS, 20 μl of 10% milk in PBS and 80 μl of phage supernatants were applied. After incubation for 1 hr, unbound phage were washed off, and bound phages were detected with anti-M13-HRP antibody conjugate (GE Healthcare). The detection of peroxidase activity was done by adding BM blue POD substrate (Roche) and the reaction was stopped by adding 1 M $H_2SO_4$. The phage ELISA positive clones were tested by phage ELISA for the absence of cross reactivity to Streptavidin (StreptaWells, High Bind, Roche) and to human IgG (Sigma).

The DNA sequence of the specific binders was verified by DNA sequencing.

2) FACS Experiment on HER2 Overexpressing SKOV-3 Cells

DNA encoding the polypeptides shown in SEQ ID NOs: 167 to 174 and SEQ ID NOs: 288-318 were subcloned into the bacterial expression vector pQE12 so that the resulting constructs carried a C-terminal myc-hexahistidine tag (SEQ ID NO: 328) as described in Grabulovski et al. (Grabulovski et al. (2007) JBC, 282, p. 3196-3204). The polypeptides were expressed in the cytosol of *E. coli* bacteria, and 1.8 ml of cleared lysate was prepared per ml original culture. 100 μl cleared lysate containing the polypeptides was mixed with 100 μl cell suspension containing $1.25\times10^5$ SKOV-3 cells in PBS/1% FCS/0.2% sodium azide. After 60 min incubation on ice, cells were washed, and bound sequences were detected by 10 μg/ml anti-myc mouse antibody 9E10 (Roche), followed by anti-mouse IgG—Alexa488 conjugate (Invitrogen). The stained cells were then analyzed in a FACS analyzer. The DNA sequence of the specific binders was verified by DNA sequencing.

Results:

The amino acid sequences of Fyn SH3 derived HER2 binders is presented in SEQ ID NOs: 167 to 318 as appended in the sequence listing.

Example 4.2: Fyn SH3 Derived Polypeptides Bind to Other Epitopes on HER2 Compared to Anti-HER2 Antibodies Methods:

The DNA sequences encoding FynSH3-derived clones C12 (SEQ ID NO: 167) and G10 (SEQ ID NO: 168) were subcloned into the bacterial expression vector pQE12 so that the resulting constructs carried a C-terminal myc-hexahistidine tag (SEQ ID NO: 328), and the two constructs were expressed and purified by means of the hexahistidine tag as described in Grabulovski et al. (Grabulovski et al. (2007) JBC, 282, p. 3196-3204).

The heavy and light chains (SEQ ID NO: 320 and SEQ ID NO: 321) of the anti-HER2 antibody 1 and the anti-HER2 antibody 2 (SEQ ID NO: 326 and SEQ ID NO: 329) were transiently co-expressed in CHO cells. The antibodies were purified from the culture supernatant by affinity chromatography on a MabSelect SuRe column (GE healthcare).

$10^5$ BT-474 cells (ATCC) were pre-incubated with an excess of 1 μM anti-HER2 antibody 1, anti-HER2 antibody 2, or PBS for 60 min on ice. Subsequently, 300 nM C12 or G10 plus 20 nM mouse anti-myc antibody 9E10 (Roche) were added to the cells without washing off the blocking antibodies. After 45 min incubation, cells were washed and bound C12/9E10- and G10/9E10 complexes were detected with anti-mouse IgG—Alexa488 conjugate. The cells were analyzed by FACS. Binding of C12 and G10 to anti-HER2 antibody 1 or anti-HER2 antibody 2-blocked cell surface was compared against binding to non-blocked cells. In order to analyze the efficacy of the epitope blockade by anti-HER2 antibody 1 and 2, 25 nM biotinylated antibody (biotinylation was performed with sulfo-NHS-LC-biotin (Pierce) according to the manufacturer's instructions) was added to the pre-blocked cells, followed by detection with Streptavidin-allophycocyanin conjugate.

Results:

The results of the experiments are shown in FIG. 27. Preblocking with either of the antibodies drastically reduced binding of the corresponding biotinylated antibodies, indicating that the preblocking step efficiently and specifically blocked the epitopes of the two different antibodies (FIG. 27B).

Binding of C12 and of G10 was not affected by preblocking with anti-HER2 antibody 1 nor with anti-HER2 antibody 2, indicating that both clones bind to an epitope different to anti-HER2 antibody 1 and anti-HER2 antibody 2 (FIG. 27A).

Example 4.3: The Inventive Binding Molecules have a Stronger Antiproliferative Effect than the Combination of the Individual Binding Proteins HER2 targeting molecules with two different binding specificities were created by fusion of C12 via a glycine-serine $(Gly_4Ser)_3$ linker to the N-terminus of the light chain of anti-HER2 antibody 1 (resulting in the protein termed COVA208) or anti-HER2 antibody 2 (termed COVA210).

Methods:

Anti-HER2 antibody 1 (SEQ ID NO: 320 and SEQ ID NO: 321), anti-HER2 antibody 2 (SEQ ID NO: 326 and SEQ ID NO: 329), COVA208 (SEQ ID NO: 320 and SEQ ID NO: 325) and COVA210 (SEQ ID NO: 326, SEQ ID NO: 327) were transiently co-expressed in CHO cells and purified from the culture supernatant by affinity chromatography on a MabSelect SuRe column (GE healthcare). A bivalent monospecific format of clone C12 was created by fusion via a $(Gly_4Ser)_3$ to the C-terminus of human Fcγ1, resulting in Fc-C12 (SEQ ID NO: 319). The protein was expressed and purified as described above for anti-HER2 antibody 1, anti-HER2 antibody 2, COVA208 and COVA210.

The growth inhibitory effect of the HER2 targeting constructs was investigated in vitro on the NCI-N87 tumor cell line (purchased from ATCC). This human HER2 overexpressing gastric cell line was grown in RPMI1640 (Gibco) supplemented with 10% FBS (Gibco; heat inactivated at 56° C. for 45 min). 7000 cells in 100 μl growth medium per well were seeded into a 96-well plate. After incubation at 37° C./5% $CO_2$ for 24 h, 20 μl of the anti-HER2 constructs Fc-C12, COVA208, COVA210, anti-HER2 antibody 1 or anti-HER2 antibody 2, or combinations of the agents, were added. Each condition was performed in triplicate, and the agents were added in three-fold serial dilutions at concentrations between 300 nM and 0.015 nM. For combinations, each agent was used at the indicated concentration (e.g. 300 nM Fc-C12+300 nM anti-HER2 antibody 1). After 5 days, the viability of the treated cultures was analyzed with XTT (Roche). The XTT reagent is converted by metabolically active cells into a colored formazan product which absorbs light at 450 nm wavelength. The absorbance directly correlates with the live cell number. The % viability relative to PBS treated cells was calculated according to the formula:

$$\%\ \text{viability} = \left(\frac{OD_{experimental} - OD_{blank}}{OD_{untreated} - OD_{blank}}\right) \times 100$$

The average % viability was plotted against $\log_{10}$ (concentration), and the resulting dose-response curves were analyzed by nonlinear regression with the software Prism, using the three parameter equation:

$$\%\ \text{viability} = \text{bottom} + \frac{\text{top} - \text{bottom}}{1 + 10^{x - LogIC_{50}}}$$

Results:

The fusion of Fyn SH3 derived binder C12 to the C-terminus of human Fcγ1, Fc-C12, did not have any effect on cell viability (FIGS. 28A and 28C). When added in combination with anti-HER2 antibody 1 or anti-HER2 antibody 2, Fc-C12 did not increase or decrease the activity of these two antibodies significantly (FIGS. 28A and 28C). However, when clone C12 was fused to the N-terminus of the light chain of the anti-HER2 antibody 1 (COVA208) or anti-HER2 antibody 2 (COVA210) to generate molecules with two different binding specificities for an antigen, it increased the antiproliferative effect of the unmodified corresponding antibodies (FIGS. 28B and 28D).

In summary, these results show that the molecules COVA208 and COVA210 are superior to the combination of the individual monospecific binding proteins.

Example 4.4: The Anti-Proliferative Activity of Anti-HER2 Fynomer-Antibody Fusions is Different Depending on the Relative Orientation of the Fynomer and the Binding Site of the Antibody Several different C12—antibody fusions were tested for their ability to inhibit growth of NCI-N87 tumor cells in order to investigate the influence of the fusion site where the Fyn SH3-derived sequence is attached to the antibody.

Methods:

COVA201 (SEQ ID NO:322; SEQ ID NO:321), COVA202 (SEQ ID NO:320; SEQ ID NO:323), COVA207 (SEQ ID NO:324; SEQ ID NO:321) and COVA208 (SEQ ID NO:320; SEQ ID NO:325) are all C12-anti-HER2 antibody 1 fusions in which the clone C12 is fused to either the C-terminus of the heavy chain (COVA201), C-terminus of the light chain (COVA202), N-terminus of the heavy chain (COVA207) and N-terminus of the light chain (COVA208). Expression and purification was performed as described for COVA208 in Example 4.3. The cell growth inhibition assay was performed on NCI-N87 cells as described in Example 4.3.

Results:

The different C12-anti-HER2 antibody 1 formats were found to exhibit different activities (FIGS. 29A and 29B). COVA208 was most efficacious at inhibiting tumor cell growth and reduced the relative viability to 37%. COVA207 and COVA201 showed intermediate activity (viability: 52% and 61%, respectively) while COVA202 was less active and reduced the viability to 67%, but was still better than anti-HER2 antibody 1 (81-82% viability).

These results show that fusions of one pair of a Fyn SH3-derived sequence and an antibody have different activities, depending on the site of fusion and that the N-terminal light chain fusion of C12 to anti-HER2 antibody 1 (=COVA208) showed the strongest anti-proliferative efficacy.

Example 4.5: COVA208 Inhibits the Growth of BT-474 Cells with Higher Efficacy than Anti-HER2 Antibody 1

Methods:

The tumor cell growth inhibition of COVA208 (SEQ ID NOs: 320 and 325) was compared to anti-HER2 antibody 1 (SEQ ID NO: 320 and 321) on the human breast tumor cell line BT-474 (purchased from ATCC). This HER2 overexpressing cell line is one of the best characterized models to study the activity of HER2 targeted agents. BT-474 cells were grown in DMEM/F12 medium (Gibco) supplemented with 10% heat-inactivated FBS (Gibco) and 10 μg/ml human recombinant insulin. The assay was performed as described in Example 4.3 for NCI-N87 cells.

Results:

COVA208 showed better antiproliferative activity than the anti-HER2 antibody 1 (FIG. 30).

Example 4.6: COVA208 Inhibits NCI-N87 Tumor Growth In Vivo More Efficiently than the Anti-HER2 Antibody 1

COVA208 was investigated in vivo for tumor growth inhibition and compared to anti-HER2 antibody 1.

Methods:

$5\times10^6$ human gastric tumor cells (ATCC; CRL-5822) were implanted s.c. into athymic CD-1 Nude mice (Charles River). Tumor dimensions and body weights were recorded three times weekly. The tumor volume was calculated according to the formula volume=$(\text{width})^2\times\text{length}\times\pi/6$. When the average tumor size reached about 140 $mm^3$, which was 42 days after tumor inoculation, mice were randomized into three treatment groups comprising six mice each, and the treatment was initiated. COVA208 (SEQ ID NOs: 320 and 325) and anti-HER2 antibody 1 (SEQ ID NOs: 320 and 321) were administered i.p. once a week for four weeks (five injections in total). The first (loading) dose was 30 mg/kg, and each following (maintenance) dose was 15 mg/kg. Mice in the control group were injected with PBS.

Results:

Anti-HER2 antibody 1 treatment resulted in only weak tumor growth inhibition (FIG. 31). COVA208 showed improved tumor growth control for the duration of the treatment compared to anti-HER2 antibody 1. On day 32, the tumors in COVA208 treated mice were reduced in volume by 8% compared to the initial tumor size at the beginning of the treatment (d=0), whereas the anti-HER2 antibody 1-treated mice showed an increase in volume by 88%.

This result demonstrates that COVA208 shows significant superior efficacy in vivo compared to anti-HER2 antibody 1.

Example 4.7: COVA208 Exhibits an Antibody-Like PK Profile In Vivo

Methods:

The pharmacokinetic profile of COVA208 in C57BL/6 mice (Charles River) was investigated and compared to anti-HER2 antibody 1. Three C57BL/6 mice were injected i.v. with 200 μg COVA208 (SEQ ID NOs: 320 and 325) or anti-HER2 antibody 1 (SEQ ID NOs: 320 and 321). After 10 min, 6, 24, 48, 96, 120, 144 and 168 hours, blood was collected into EDTA coated microvettes (Sarstedt), centrifuged for 10 min at 9300 g and the serum levels of COVA208 or anti-HER2 antibody 1 were determined by ELISA. Black maxisorp microtiter plates (Nunc) were coated with 50 nM HER2 ECD (Bender MedSystems). After blocking with 4% milk (Rapilait, Migros, Switzerland) in PBS, 40 μl of PBS and 10 μl of serum at appropriate dilution were applied. After incubation for 1 hr, wells were washed with PBS, and bound COVA208 or anti-HER2 antibody 1 were detected with protein A-HRP conjugate (Sigma). The assay was developed with QuantaRed fluorogenic substrate (Pierce) and the fluorescence intensity was measured after 5 to 10 min at 544 nm (excitation) and 590 nm (emission). The serum levels of COVA208 and anti-HER2 antibody 1 were determined using a standard curve of COVA208 and anti-HER2 antibody 1 (diluted to 333-0.5 ng/ml each). From the concentrations of COVA208 and anti-HER2 antibody 1 determined in serum at different time points and the resulting slope k of the elimination phase (plotted in a semi-logarithmic scale), the half-lives were calculated using to the formula $t^{1/2}=\ln 2/-k$.

Results:

As shown in FIG. 32, the half-lives of COVA208 and the anti-HER2 antibody 1 as determined from the elimination phase (beta phase, time-points 24 h-168 h) were highly similar (247 and 187 h, respectively). These data demonstrate that COVA208 has drug-like in vivo PK properties.

Example 4.8: COVA208 is Stable and does not Aggregate

The integrity and stability of COVA208 was assessed by SDS-PAGE and by size exclusion chromatography.

Methods

Purified COVA208 (SEQ ID NOs: 320 and 325) and anti-HER2 antibody 1 (SEQ ID NOs: 320 and 321) were analyzed by SDS-PAGE. 4 μg protein were loaded either with reduced or with nonreduced disulphide bonds onto a 4-12% Bis/Tris Novex gel in 1×MOPS running buffer (Invitrogen), together with a molecular weight marker (RPN800e; GE healthcare). Protein bands were visualized by coomassie staining.

The size exclusion chromatography (SEC) profile of COVA208 was determined immediately after purification as well as after storage of the protein in PBS at 4° C. for one or two months. 100 μl COVA208 at a concentration of 1.75 mg/mL was loaded onto a Superdex 200 10/300 GL column in PBS (GE healthcare) at a flow rate of 0.5 ml/min, and the elution from the column was monitored by reading the $OD_{280}$.

Results:

The results of the SDS-PAGE and the SEC profiles of COVA208 are shown in FIG. 33. COVA208 runs in clearly defined bands at the expected molecular weight on an SDS-PAGE (top). Of particular interest is the finding that there is no native light chain detectable in COVA208 (MW around 30 kDa), indicating that there is no cleavage of the Fyn SH3-derived clone C12 from the antibody light chain.

COVA208 eluted in one main peak form the SEC column with a retention volume of 13.1 ml (bottom). Anti-HER2 antibody 1 eluted at 13.2 ml. Most importantly, no aggregates, which would elute at around 8 ml, were detectable in the COVA208 protein preparation. The SEC profile of COVA208 did not change over two months of storage at 4° C. The elution peak remained narrow, symmetrical and appeared at the same retention volume. The protein preparation remained free of aggregates after 1 and 2 months of storage. This indicates that COVA208 remains stable over extended periods of storage at 4° C. In summary, these results support that COVA208 is a stable, monodisperse molecule with optimal biophysical properties.

Example 4.9: COVA208 has Superior Growth Inhibitory Activity as Compared to Anti-HER2 Antibody 1 on a Panel of Ten HER2-Expressing Tumor Cell Lines The anti-proliferative activity of COVA208 (SEQ ID NOs: 320 and 325) was compared to anti-HER2 antibody 1 (SEQ ID NOs: 320 and 321) on different HER2 positive cell lines. XTT assays were performed essentially as described in example 4.3. The cell lines used in this experiment and the experimental conditions are given in Table 12. Dose-response curves were fitted to the three parameter equation as described in example 4.3, and the maximal growth inhibition was calculated with the formula:

$$\text{Maxiumum level of inhibition (\%)}=100\%-\text{bottom}$$

With the variable bottom derived from the nonlinear regression of the dose-response curves using the formula:

$$\%\ \text{viability} = \text{bottom} + \frac{\text{top} - \text{bottom}}{1 + 10^{x - LogIC_{50}}}$$

The results of these assays are shown in FIG. 34. FIGS. 34A and 34B show dose-response curves obtained on the 0E19 and on the Calu-3 cell lines, respectively. FIG. 34C represents the maximal growth inhibition obtained on each cell line with COVA208 and anti-HER2 antibody 1, including the results on NCI-N87 and BT-474 cell lines shown in FIGS. 28 and 30. COVA208 shows improved anti-proliferative activity as compared to anti-HER2 antibody 1 on all 10 cell lines.

Example 4.10: COVA208 Induces Apoptosis in NCI-N87 Gastric Cancer Cells

The ability of COVA208 to induce apoptosis was investigated on NCI-N87 cells by analyzing caspase 3/7 enzymatic activity and by detecting DNA fragmentation by TUNEL staining.

Methods

Caspase 3/7 assay: 45'000 NCI-N87 cells were seeded into the wells of a 96-well microtiter plate. One day later, 100 nM anti-HER2 antibody 1 (SEQ ID NOs: 320 and 321), COVA208 (SEQ ID NOs: 320 and 325) or PBS were added to the cells in triplicate. As positive control, 1 μM staurosporine was added. After two days incubation, the activity of caspase-3 and caspase-7 was determined using the fluorescence Apo-ONE® homogenous caspase-3/7 kit (Pierce).

The viability of the treated cultures was analyzed by XTT in parallel on replica plates, and the % viability relative to PBS treated samples was calculated as described in example 4.3.

Caspase 3/7 activity was divided by % viability to obtain the normalized caspase 3/7 activity.

TUNEL assay: $0.8\times10^6$ NCI-N87 cells in 2 mL were distributed in 6-well plates. On the next day, 300 nM anti-HER2 antibody 1 (SEQ ID NOs: 320 and 321), COVA208 (SEQ ID NOs: 320 and 325) or PBS were added to the cells. As positive control, 1 μM staurosporine was added. After three days incubation, cells were detached, formalin-fixed, permeabilized in 70% ice-cold ethanol and the 3'-hydroxyl DNA ends labeled with fluorescein-deoxyuridine triphosphate (FITC-dUTP), using the APO-DIRECT kit (Phoenix flow systems). Labeled cells were analyzed by FACS, and the % TUNEL-positive cells determined by gating on the FITC-dUTP positive cell population.

Results

The results of the caspase 3/7 assay are shown in FIG. 35A. COVA208 resulted in increased caspase 3/7 activity, indicating that COVA208 induced apoptosis in NCI-N87 cells. Anti-HER2 antibody 1 did not result in induced caspase 3/7 activity.

The results of the TUNEL assay are shown in FIG. 35B. COVA208 induces DNA fragmentation in the majority of cells, further supporting that it is capable of inducing apoptosis, whereas anti-HER2 antibody 1 is not.

Example 4.11: COVA208 Inhibits Ligand-Dependent and Ligand-Independent HER2-Mediated Signalling Activation of HER2 downstream signaling leads to phosphorylation of HER3, resulting in the activation of the PI3K-Akt-mTOR pathway, or to the activation of the MAPK/Erk pathway. In tumor cell lines that display sufficiently high surface density of HER2, these downstream pathways are constitutively activated in the absence of HER3 ligands (ligand-independent signaling). In addition to ligand-independent activation of HER2 downstream signalling, the downstream pathways can also be activated by HER3 ligands which promote HER2-HER3 heterodimer formation (ligand-dependent signaling).

In order to investigate the effects of COVA208 on HER2 downstream signaling, HER2-overexpressing NCI-N87 cells were treated with COVA208 (SEQ ID NOs: 320 and 325), anti-HER2 antibody 1 (SEQ ID NOs: 320 and 321), anti-HER2 antibody 2 (SEQ ID NOs: 326 and 329), or PBS, and the cell lysates were analyzed for phospho-proteins by immunoblotting.

The assay was also performed on HER2 low-expressing MCF-7 cells, in which HER2 downstream phosphorylation is triggered only after addition of the HER3 ligand heregulin-1β.

Methods

NCI-N87 cells (ATCC; CRL-5822) were distributed in 6-well culture dishes in complete medium at $1\times10^6$ cells in 3 mL per well. After overnight incubation at 37° C./5% $CO_2$, 40 μg/mL anti-HER2 agents were added and the cells were incubated at 37° C./5% $CO_2$ for 72 h. Cells were subsequently lysed on ice in cell lysis buffer containing 1% Triton-X, protease inhibitor and phosphatase inhibitor cocktails (Roche Applied Sciences).

MCF-7 cells (ATCC; HTB-22) were cultured in MEM (Gibco)+10% FBS (Gibco). Cells were distributed in 6-well culture dishes at $0.5\times10^6$ cells in 3 mL per well. After overnight incubation at 37° C./5% $CO_2$, cells were starved in medium without serum for 3 h. 40 μg/mL anti-HER2 agents were then added for 1 h during which the cells were kept at 37° C./5% $CO_2$. After 45 min, 2 nM human recombinant heregulin-1β (R&D systems) was added for 15 min. Cells were subsequently lysed on ice in cell lysis buffer containing 1% Triton-X, protease inhibitor and phosphatase inhibitor cocktails (Roche Applied Sciences).

Total cell lysates were cleared by centrifugation at 16,000×g for 10 min at 4° C. and the protein concentration in the cleared lysates was determined by Bradford assay (Bio-Rad). 10 μg of protein were separated on Novex® 4-12% Bis-Tris gels (Invitrogen) and transferred onto PVDF membrane.

Phospho-proteins were detected on PVDF membrane with antibodies against $pHER3^{Y1289}$ (Millipore), $pAkt^{S473}$ (CST) or $pErk1/2^{T202/Y204}$ (CST), followed by secondary HRP-conjugated antibodies (Jackson Immuno Research). Vinculin was detected with a vinculin-specific antibody (Millipore) and served as loading control. The immunoblots were developed with ECD prime chemiluminescent HRP substrate (GE healthcare) and exposed onto X-Ray film.

Results:

The results of this experiment are shown in FIG. 36. In MCF-7 cells, in which activation of HER2 downstream signaling requires HER3 ligands, COVA208 and anti-HER2 antibody 1 both block phosphorylation of HER3, Akt and Erk1/2 equally well, indicating that COVA208 retained the activity of its parental antibody. In contrast, anti-HER2 antibody 2 does not block ligand-induced phosphorylation of HER3, Akt or Erk1/2.

In NCI-N87 cells, where phosphorylation of HER2 downstream signaling proteins occurs independent of HER3 ligands, COVA208 efficiently blocks phosphorylation of HER3, Akt or Erk1/2, whereas anti-HER2 antibody 1 does not block phosphorylation. Anti-HER2 antibody 2 is also capable of efficiently blocking HER2 signaling under these conditions. These results indicate that COVA208 blocks ligand-dependent as well as ligand-independent HER2 downstream signalling events, in contrast to anti-HER2 antibodies 1 and 2, which block one but not the other.

Example 4.12: COVA208 is Internalized by NCI-N87 Cells

In order to investigate whether COVA208 promotes internalization of the HER2 receptor in vitro, NCI-N87 cells were cultured in the presence of COVA208 (SEQ ID NOs: 320 and 325) or with anti-HER2 antibody 1 (SEQ ID NOs: 320 and 321) followed by fixation and permeabilization of the cells and subsequent detection of the anti-HER2 agents by means of a fluorescent secondary antibody. Microscopic imaging was used to assess the sub-cellular distribution of the fluorescent signal.

Methods

NCI-N87 cells grown in Lab-Tek II $CC^2$ chamber slide wells were surface labelled on ice for 1 h with 100 nM COVA208 or anti-HER2 antibody 1. Unbound anti-HER2 agent was then washed off. As positive control, 1 μM geldanamycin (Hsp90 inhibitor) which causes rapid internalization of HER2 was added to some wells. The cells were transferred to 37° C./5% $CO_2$ for 0 h or 5 h to allow for internalization, then fixed with formalin and permeabilized with saponin. An Alexa488-labeled anti-human IgG antibody (Invitrogen) was used to detect anti-HER2 agents on permeabilized cells, and nuclei were stained with Hoechst 33342 dye. The stained cells were analyzed on a Leica TCS SP2-AOBS laser scanning confocal microscope. Optical sections (z-stacks, d=0.2 μm) were collected and three regions were analyzed. The amount of anti-HER2 agents which localized into distinct dots was quantified with the software Imaris 7.4.0 (Bitplane), using the surface tool of Imaris to detected spheroid dots, and expressing the percentage of anti-HER2 agents present in dots:

% anti-HER2 agents in dots=(volume of dots/volume of total anti-HER2 staining)×100

Results

After surface labelling and before incubation at 37° C., COVA208 and anti-HER2 antibody 1 localized to the cell membrane. After 5 hours incubation at 37° C., COVA208 was present in distinct dots within the cytosol, while the cell membrane was only very weakly stained. In contrast, the anti-HER2 antibody 1 was confined to the cell membrane after 5 h incubation at 37° C., and only very few dots in the cytosol were detected. If co-incubated with geldanamycin, anti-HER2 antibody 1 was also found in dots and the cell membrane was negative for the antibody. These results indicate that unlike anti-HER2 antibody 1, COVA208 rapidly internalizes into NCI-N87 cells.

The quantification of the % staining appearing within dots is shown in FIG. 37. The majority of COVA208 localizes into dots, whereas only a small fraction of anti-HER2 antibody 1 is found in dots.

Example 4.13: COVA208 Inhibits KPL-4 Breast Tumor Growth In Vivo More Efficiently than the Anti-HER2 Antibody 1

COVA208 was investigated in vivo in KPL-4 breast tumors for growth inhibition and compared to anti-HER2 antibody 1.

Methods:

$3\times10^6$ human KPL-4 breast tumor cells (Kurebayashi et al. (1999) Br. J. Cancer. 79; 707-717) were implanted into the mammary fat pad of female SCID beige mice (Charles River). Tumor dimensions and body weights were recorded three times weekly. The tumor volume was calculated according to the formula volume=$(\text{width})^2\times\text{length}\times\pi/6$. When the average tumor size reached 70 $mm^3$, mice were randomized into three treatment groups comprising eight mice each, and the treatment was initiated. COVA208 (SEQ ID NOs: 320 and 325), anti-HER2 antibody 1 (SEQ ID NOs: 320 and 321) or PBS were administered i.p. once a week for four weeks (five injections in total). The first (loading) dose was 30 mg/kg, and each following (maintenance) dose was 15 mg/kg.

Results:

Anti-HER2 antibody 1 treatment resulted in very weak tumor growth inhibition only (FIG. 38). COVA208 showed significantly improved tumor growth control. This result further supports that COVA208 shows significantly superior efficacy in vivo compared to anti-HER2 antibody 1.

Example 4.14: Determination of the HER2 Epitope Bound by the Fyn SH3-Derived Polypeptide C12

The epitope bound by the Fyn SH3-derived clone C12 (SEQ ID NO: 167) on HER2 was identified by an alanine scanning mutation approach and was performed at Integral Molecular Inc. (Philadelphia, USA). A shotgun mutagenesis mutation library was created as described in Paes et al (2009) J Am Chem Soc 131(20): 6952-6954. Briefly, a eukaryotic expression plasmid encoding full-length human HER2 was constructed with a C-terminal V5His epitope tag. Using the parental cDNA construct as a template, alanine scanning mutations were introduced into the extracellular domain of HER2 (amino acids 23-652 of SEQ ID NO: 337) using PCR-based mutagenesis. Residues which were already alanine in the parental construct were mutated to methionine. Mutated constructs and the parental HER2 control construct were expressed in HEK-293T cells. Twenty-four hours post-transfection, cells were washed in PBS and fixed in 4% paraformaldehyde. Cells were incubated with control anti-HER2 monoclonal antibody (MAB1129, R&D Systems) or with Fyn SH3-derived clone C12 (expressed as N-terminal Fc fusion) in PBS with $Ca^{2+}/Mg^{2+}$ (PBS++) and 10% Normal Goat Serum (NGS) for 1 hour. After two washes in PBS, cells were incubated with goat anti-human Alexa Fluor 488-conjugated secondary antibodies (Jackson, West Grove, Pa.) in PBS++ and NGS for 1 hour, followed by 2 washes in PBS. Microplates were measured by flow cytometry using the Intellicyt HTFC Screening System and quantified using Forecyt software (Intellicyt Corporation, Albuquerque, N. Mex.).

It has been found that the Fyn SH3-derived polypeptide C12 (SEQ ID NO: 167) binds to an epitope of HER2 which is located within domain I of HER2 (SEQ ID NO: 338). In more detail, five alanine scanning mutations were identified which resulted in markedly reduced binding of the binding molecules comprising the Fyn SH3-derived polypeptide C12 (SEQ ID NO: 167) while binding of the control antibody MAB1129 was retained. These mutations included T166A, R188A, P197A, S202A and R203A as compared to the sequence of SEQ ID NO: 338. In other terms, at least amino acid positions T166, R188, P197, S202 and R203 of domain I of HER2 are involved in binding between the Fyn SH3-derived polypeptide C12 and HER2.

TABLE 12

HER2 expressing cell lines used in in vitro proliferation assays described in FIG. 34 and the conditions applied in the in vitro proliferation assays.

| | | | | XTT assay conditions | |
|---|---|---|---|---|---|
| Cell line | Description | Distributor | growth medium | cells/ well seeded | incuation time with anti-HER2 agents |
| NCI-N87 | gastric carcinoma, liver metastasis | ATCC | RPMI1640 + 10% FBS | 7000 | 5 days |
| BT-474 | breast, ductal carcinoma | ATCC | DMEM/F12 + insulin + 10% FBS | 7000 | 5 days |

TABLE 12-continued

HER2 expressing cell lines used in in vitro proliferation assays described in FIG. 34 and the conditions applied in the in vitro proliferation assays.

| Cell line | Description | Distributor | growth medium | XTT assay conditions cells/well seeded | XTT assay conditions incuation time with anti-HER2 agents |
|---|---|---|---|---|---|
| KPL-4 | breast, malignant pleural effusion | Prof. Kurebayashi* | DMEM + 10% FBS | 2000 | 3 days |
| OE19 | gastric (oesophagal carcinoma) | hpa cultures | RPMI1640 + 10% FBS | 5000 | 5 days |
| Calu-3 | pleural effusion of lung adenocarcinoma | ATCC | MEM + 10% FBS | 5000 | 5 days |
| SKOV-3 | ovarian adenocarcinoma, ascites | ATCC | modified McCoy5a + 10% FBS | 2000 | 3 days |
| MDA-MB-453 | pericardial effusion of metastatic breast carc. | ATCC | DMEM + 10% FBS | 2000 | 5 days |
| HCC202 | primary ductal carcinoma | ATCC | RPMI1640 + 10% FBS | 5000 | 5 days |
| ZR-75-30 | breast, ductal carcinoma, malignant ascites | ATCC | RPMI1640 + 10% FBS | 5000 | 5 days |
| MDA-MB-175-VII | pleural effusion of ductal carcinoma | ATCC | DMEM + 10% FBS | 5000 | 5 days |

*Kurebayashi et al. (1999) Br. J. Cancer. 79; 707-717

Example 5: Anti-Human Serum Albumin Fyn SH3 Derivatives

Example 5.1: Fyn SH3 Derived Polypeptides Bind to Human Serum Albumin

Methods

1) Lysate ELISA on Human Serum Albumin Protein

Using the Fynomer® phage libraries described in Schlatter et al. (Schlatter et al. (2012) mAbs, 4(4) p. 497-50) Fyn-SH3 derived binding proteins specific to human serum albumin were isolated using human serum albumin (Sigma-Aldrich, cat. no A3782) and serum albumin from a rodent species (rat serum albumin, Sigma-Aldrich, cat. no A6414) as antigens and standard phage display as selection technology (Grabulovski D. et al., (2007) J Biol Chem 282, p. 3196-3204, Viti, F. et al. (2000) Methods Enzymol. 326, 480-505).

After naïve and affinity maturation selections, enriched Fyn SH3-derived polypeptides were screened for binding to human serum albumin and/or serum albumin from a rodent species (mouse/rat) by lysate ELISA. DNA encoding the Fyn SH3-derived binding proteins was cloned into the bacterial expression vector pQE12 (Qiagen) so that the resulting constructs carried a C-terminal myc-hexahistidine tag as described in Grabulovski et al. (Grabulovski et al. (2007) JBC, 282, p. 3196-3204). The polypeptides were expressed in the cytosol of *E. coli* bacteria in a 96-well format and 200 μl of cleared lysate per well was prepared essentially as described in Bertschinger et al. (Bertschinger et al. (2007) Protein Eng Des Sel 20(2): p. 57-68). Briefly, transformed bacterial colonies were picked from agar plates and grown in a round bottom 96-well plate (Nunc, cat. no. 163320) in 200 μl 2×YT medium containing 100 μg/ml ampicillin and 0.1% (w/v) glucose. Protein expression was induced after growth for 3 h at 37° C. and 200 r.p.m. by adding 1 mM IPTG (Applichem, Germany). Proteins were expressed overnight in a rotary shaker (200 r.p.m., 30° C.). Subsequently, the 96-well plate was centrifuged at 1800 g for 10 min and the supernatant was discarded. The bacterial pellets were resuspended in 65 μl Bugbuster containing Benzonase Nuclease (VWR, cat. No. 70750-3) and incubated at RT for 30 minutes. Afterwards, the monoclonal bacterial lysates were cleared by centrifugation (1800 g for 10 min), diluted with 170 μL PBS and filtered using a multiscreen filter plate (0.45 μm pore size; Millipore cat. No. MSHVN4510). Monoclonal bacterial lysates were used for ELISA: human serum albumin was immobilized on maxisorp F96 wells (Nunc, cat. no 439454) overnight at room temperature. Plates were then blocked with PBS, 4% (w/v) milk (Rapilait, Migros, Switzerland). Subsequently, 20 μl of PBS, 10% milk containing 25 μg/ml anti-myc antibody 9E10 and 80 μl of bacterial lysate were applied (resulting in a final anti-myc antibody concentration of 5 mg/ml). After incubating for 1 h and washing, bound Fyn SH3-derived polypeptides were detected with anti-mouse-HRP antibody conjugate (Sigma) at a final concentration of 5 μg/ml. The detection of peroxidase activity was done by adding 100 μL per well BM blue POD substrate (Roche) and the reaction was stopped by adding 50 μl 1 M $H_2SO_4$. The DNA sequence of the specific binders was verified by DNA sequencing. Cross-reactivity towards serum albumin from a rodent species was detected by monoclonal lysate ELISA using mouse serum albumin (Sigma-Aldrich, cat. no A3139) as an antigen and the protocol described above. Alternatively, cross-reactivity towards mouse and rat serum albumin was confirmed surface plasmon resonance experiments (see below).

2) Expression and Purification of Fyn SH3-Derived Polypeptides in *E. coli*

Fyn SH3-derived albumin-binding polypeptides were expressed in the cytosol of TG1 *E. coli* bacteria as well as purified as described in Grabulovski et al. (Grabulovski et al. (2007) JBC, 282, p. 3196-3204).

3) Affinity Measurements

Affinity measurements were performed using a Biacore T200 instrument (GE Healthcare). For the interaction analysis between serum albumin, derived from mouse, rat or human, and Fyn SH3-derived albumin-binding polypeptides, a Series S CM5 chip (GE Healthcare) was used with albumin proteins immobilized using the amine coupling kit (GE healthcare). Serum albumin proteins from different species (mouse, rat or human) were immobilized (2000-3000 RU) on different flow cells of the chip whereas a blank-immobilized flow cell served as a reference flow cell. The running buffer was PBS containing 0.05% Tween 20 at pH 7.4. The interactions were measured at a flow of 30 μl/min and 25° C. and different concentrations of Fyn SH3-derived albumin-binding polypeptides were injected. All kinetic data of the interaction was evaluated using Biacore T200 evaluation software.

Results

1) The amino acid sequences of ELISA positive Fyn SH3-derived polypeptides binding to human serum albumin is presented in SEQ ID NOs: 340 to 376 as appended in the sequence listing. In addition, Fyn SH3-derived polypeptides (SEQ ID NOs: 340 to 368) also showed binding to mouse serum albumin as confirmed by lysate ELISA and/or Biacore affinity measurements.

2) The expression yields of two selected Fyn SH3-derived albumin-binding polypeptides of the invention from bacterial cultures under non-optimized conditions in shake flasks is depicted in Table 13. The yield was in the same range as the expression yield of the WT Fyn-SH3 polypeptide. High protein-purity was confirmed by SDS-PAGE analysis and the gel is depicted in FIG. 39.

TABLE 13

Expression yields of Fyn SH3-derived albumin-binding polypeptides produced in TG1 *E. coli* bacteria

| Fynomer ® | SEQ ID NO. | Yield (mg/l) |
|---|---|---|
| 17H | 341 | 10 |
| C1 | 340 | 25 |
| WT Fyn-SH3 | 339 | 10 |

3) The binding properties were analyzed by real-time interaction analysis on a Biacore chip revealing the following dissociation constants ($K_D$) for selected albumin-binding polypeptides against albumin derived from either rat (RSA), mouse (MSA) or human (HSA) (depicted in Table 14).

TABLE 14

Dissociation constants of Fyn SH3-derived serum albumin-binding polypeptides to RSA, MSA and HSA.

| Fynomer ® | SEQ ID NO. | $K_D$ (nM) RSA | $K_D$ (nM) MSA | $K_D$ (nM) HSA |
|---|---|---|---|---|
| C1 | 340 | 72 | 408 | 1290 |
| 17H | 341 | 17 | 96 | 455 |

Example 5.2: Albumin-Binding Fyn SH3 Derived Polypeptides have a Prolonged Serum Half-Life in Mice Methods The pharmacokinetic profile of albumin-binding Fyn-SH3 derived polypeptides was investigated in BALB/c mice (Charles River) and compared to the WT Fyn-SH3 molecule. Fynomer® C1 (SEQ ID NO: 340), Fynomer® 17H (SEQ ID NO: 341) and WT Fyn-SH3 (SEQ ID NO: 339) were radiolabeled using Iodine-125 (Perkin Elmer cat no. NEZ033A001MC) and Chloramine T (Sigma-Aldrich cat NO 31224). The labeling reaction was carried out for two minutes at room temperature before removal of labeling reagents using PD MiniTrap G-25 columns (GE Healthcare cat.no 28-9180-07). Three BALB/c mice were injected i.v. with 13.5 μg of either radiolabeled Fynomer® C1 (SEQ ID NO: 340), Fynomer® 17H (SEQ ID NO: 341) or WT Fyn-SH3 (SEQ ID NO: 339). After 10 minutes, 2.5, 4, 6, 9, 25, 35 hours, blood was collected into EDTA coated microvettes (Sarstedt) and centrifuged for 10 min at 9300 g. Radioactivity was counted by mixing the serum with Supermix Perkin Elmer Scintillation Fluid and quantification of beta-emission of each sample with a 1450 MicroBeta Trilux scintillation counter and serum levels were calculated (results expressed as % injected dose (ID)/ml of blood). From the serum levels of Fynomer® C1, Fynomer® 17H and WT Fyn-SH3 determined in serum at different time points and the resulting slope k of the elimination phase (plotted in a semi-logarithmic scale), the half-lives were calculated using the formula $t_{1/2}=\ln 2/-k$.

Results

As depicted in Table 15, Fynomer® C1 (SEQ ID NO: 340) and Fynomer® 17H (SEQ ID NO: 341) show a significantly better terminal half-life as the WT Fyn-SH3 protein (SEQ ID NO: 339). Time-points used for half-life calculation: Fynomer® C1 and Fynomer® 17H: 2.5-35 h; WT Fyn-SH3: 2.5-25 h)

TABLE 15

Terminal half-life of Fyn SH3-derived serum albumin-binding polypeptides in mice compared to the WT Fyn-SH3 protein.

| Fynomer ® | SEQ ID NO: | $t_{1/2}$ (h) |
|---|---|---|
| C1 | 340 | 10.5 |
| 17H | 341 | 21.3 |
| WT Fyn-SH3 | 339 | 4.4 |

Example 5.3: Albumin-Binding Fyn SH3 Derived Polypeptides can Extend Serum Half-Life of BITE® Molecules Methods:

1) Expression and Purification of an Albumin Binding Fyn-SH3 Fusion Protein

The Fynomer® 17H (Seq ID NO: 341) has been genetically fused to the N-terminus of the CD3-PSMA specific BITE® (Seq ID NO: 378) via a 15 amino acid linker (linker SEQ ID NO: 377) yielding the trispecific anti-albumin/PSMA/CD3 protein COVA406 (SEQ ID NO: 379). The BITE® protein (SEQ ID NO: 378) and the fusion molecule of the invention COVA406 (SEQ ID NO: 379) carrying a C-terminal penta-his-tag were transiently transfected into FreeStyle CHO-S cells and expressed in serum-free/animal component-free media for 6 days. The proteins were purified from the supernatants by Protein L affinity chromatography (Thermo Scientific, cat. No. 89928) with an ÄKTA Purifier instrument (GE Healthcare). Concentrations were determined by absorbance measurement at 280 nm. Yields are listed in Table 16. The SDS PAGE of both proteins is shown in FIG. 40.

After purification size exclusion chromatography has been performed with COVA406 using an ÄKTA FPLC system and a Superdex G200, 30/100 GL column (GE Healthcare) (see FIG. 41).

2) FACS Binding Experiment with a BITE® Fusion Protein of the Invention

The polypeptide COVA406 (SEQ ID NO: 379, final concentration 300 nM) was mixed with 100 μl cell suspension containing either (i) $1\times10^5$ Jurkat E6-1 cells (CD3 positive cells), (ii) $1\times10^5$ 22 Rv1 prostate carcinoma cells (PSMA positive cells) or (iii) $1\times10^5$ LS174T colorectal adenocarinoma cells (PSMA and CD3 negative, ATCC cat. No. CL-188) in PBS/1% BSA/0.2% sodium azide. As a negative control, the same cells were incubated with PBS/1% BSA/0.2% sodium azide instead of COVA406 (PBS control). After 60 min incubation on ice, cells were washed, and bound protein was detected by incubation with 10 μg/ml mouse anti tetra-HIS antibody (Qiagen, cat no. 34670), followed by incubation with anti-mouse IgG—Alexa488 conjugate (Invitrogen) at a concentration of 10 ug/mL.

Finally cells were washed three times and stained cells were then analyzed on a Guava easyCyte™ (Millipore) flow cytometer.

3) Redirected T-Cell Mediated Cell Cytotoxicity Analysis

The polypeptide COVA406 (SEQ ID NO: 379) was tested in a redirected T-cell mediated cell cytotoxicity assay using a protocol adapted from Dreier et. al. (2002) Int. J. Cancer: 100, 690-697.

Human PBMCs were used as effector cells. On the day before the experiment PBMCs were isolated from fresh buffy coat preparations by Ficoll Plaque plus (GE Healthcare) and density gradient centrifugation using standard procedures. Isolated PBMCs were then incubated over night at a cell concentration of $4\times10^6$ cells/ml in 10% FCS, RPMI and 37° C., 5% $CO_2$.

For the cell kill experiment PBMCs were centrifuged and resuspended in 10% FCS, RPMI at a cell concentration of $2.5\times10^7$ cells/ml.

Target cells were labeled with Calcein AM by incubating cells at a final Calcein AM concentration of 10 μM for 30 min at 37° C., 5% $CO_2$. Subsequently excess dye was removed by washing cells twice with approx. 15 mL Medium. Finally target cell number was adjusted to $1*10^6$ cells/ml. Target tumor cells were either 22Rv1 cells (PSMA positive, ATCC cat. No. CRL-2505) or HT29 colon carcinoma cells (PSMA negative, DSMZ cat. No. ACC-299).

Effector molecules were diluted in 10% FCS, RPMI to a maximum concentration of 1200 ng/mL. A dilution series of 1/10 dilutions was prepared.

Finally target cell suspension, effector cell suspension and the different concentrations of the polypeptide COVA406 (SEQ ID NO: 379) were then mixed in equal amounts. A total of 50000 target cells were added per well and the effector to target cell ratio was 25/1, The final maximal concentration of effector molecules was 400 ng/μl. Cell lysis was measured after 5 hours incubation at 37° C. and 5% $CO_2$. After incubation, the cell suspension was centrifuged and cell lysis was quantified by detection of Calcein AM fluorescence in the supernatant using a fluorescence reader.

The amount of redirected cell lysis was normalized to the maximum lysis control (cells lysed by the addition of 1% Triton X-100) and spontaneous lysis (target cells incubated with PMBCs in the absence of effector molecules). Percentage of cell lysis was calculated according to the following formula:

% lysis=(((fluorescence sample)−(fluorescence spontaneous lysis control))/((fluorescence maximum lysis control)−(fluorescence spontaneous lysis control)))×100

All measurements were done in triplicates. Specific cell lysis was plotted versus the concentration of COVA406 and evaluated using Prism 5 (GraphPad Software) by fitting a sigmoidal dose-response.

4) Comparison of the Pharmacokinetic Profiles of COVA406 and the BITE® Molecule

The pharmacokinetic profile of COVA406 in C57BL/6 mice (Charles River) was investigated and compared to the parental BITE® molecule. Five C57BL/6 mice were injected i.v. each with 48 μg COVA406 (SEQ ID NO: 379) or BITE® (SEQ ID NO: 378). After 10 and 30 min, 1, 3, 5, 7, 9, 12, 24, 28, 33 and 48 hours, blood was collected into EDTA coated microvettes (Sarstedt), centrifuged for 10 min at 9300 g and the serum levels of COVA406 or BITE® were determined by ELISA. Briefly, black maxisorp microtiter plates (Nunc) were coated with 10 μg/ml of a peptide derived from CD3 (Sequence: QDGNEEMGGITQTPYKVSISGTTVILT; SEQ ID NO: 380) (expressed as Fc-fusion) and incubated over night at 4° C. After blocking with 4% milk (Rapilait, Migros, Switzerland) in PBS, serum samples at appropriate dilutions were applied, resulting in a final buffer concentration of 2% mouse serum (Sigma) and 4% milk. After incubation for 1 hr, wells were washed with PBS, and bound COVA406 or BITE® were detected with Penta-His-biotin (Qiagen) followed by Streptavidin-HRP conjugate (Sigma). The assay was developed with QuantaRed fluorogenic substrate (Pierce). The reaction was stopped after 3 min incubation and the fluorescence intensity was measured at 544 nm (excitation) and 590 nm (emission). The serum levels of COVA406 and BITE® were determined using a standard curve of COVA406 and BITE® (diluted to 333-0.5 ng/ml each). From the concentrations of COVA406 and BITE® determined in serum at different time points and the resulting slope k of the elimination phase (plotted in a semi-logarithmic scale), the half-lives were calculated using the formula $t_{1/2}=\ln 2/-k$. Timepoints used for half-life calculation: COVA406: 1-48 h; BITE®: 1-12 h.

Result:

COVA406 (SEQ ID NO: 379) expressed with a similar yield as the BITE® molecule (SEQ ID NO: 378) (Table 16).

TABLE 16

Purification yields of the BITE ® and Fyn-SH3 derived albumin-binding polypeptide fusions produced in transiently transfected CHO—S cells.

| | SEQ ID NO: | Yield (mg/l) |
|---|---|---|
| BITE ® | 378 | 8.1 |
| COVA406 | 379 | 5.0 |

The size exclusion chromatography (SEC) profile after purification demonstrated that COVA406 eluted as a single, monomeric peak showing that the fusion protein has excellent biophysical properties (FIG. 41). Specific binding to PSMA-positive cells (22Rv1 cells) and CD3-positive cells (Jurkat E6-1, CD3 positive) was validated in a FACS experiment. Mean fluorescence intensities (MFI) of the stainings are depicted in FIG. 42. Redirected T-cell mediated cell cytotoxicity was validated in a Calcein release assay using PBMCs as effector cells. Specific redirected cell-lysis of PSMA-positive cells with COVA406 ($EC_{50}$=4.35 ng/ml) is shown in FIG. 43. Cells with no PSMA expression (HT29 cells) were not lysed under the same conditions, showing that COVA406 is able to kill specifically PSMA positive cells. An improved pharmacokinetic profile of COVA406 (SEQ ID NO: 380) compared to the BITE® protein (SEQ ID NO: 379) was observed in mice. FIG. 44 shows the serum concentrations (ng/ml) and terminal elimination phase of COVA406 and the parental BITE®. COVA406 shows a significantly better half-life (14.3 hours) compared to the BITE® (1.5 hours). This example shows that serum albumin binding proteins of the invention are able to prolong the in vivo half-life of otherwise short-lived molecules, in particular of BITE® molecules.

Example 5.4: Prior Art Fynomers which Bind to Serum Albumin

For Material and Methods, see Publications EP2054432 and “Grabulovski, Dragan: The SH3 domain of fyn kinase as a scaffold for the generation of new binding proteins. ETH Dissertation Nr 17216 (May 2007). http://dx.doi.org/10.3929/ethz-a-005407897”.

Figure 45:
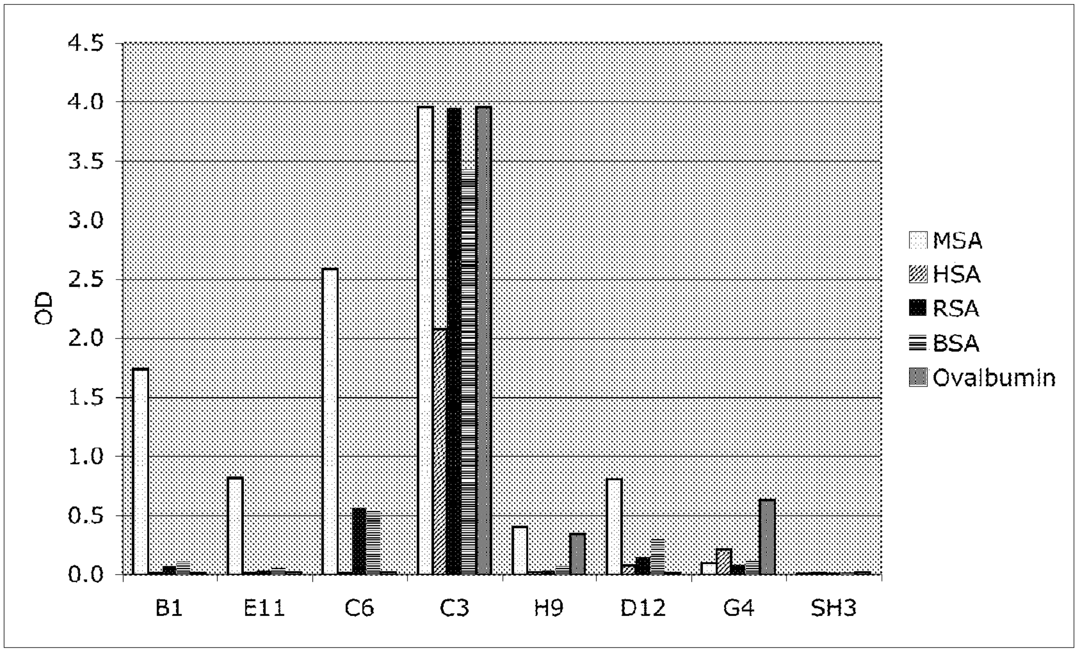
Figure 46:
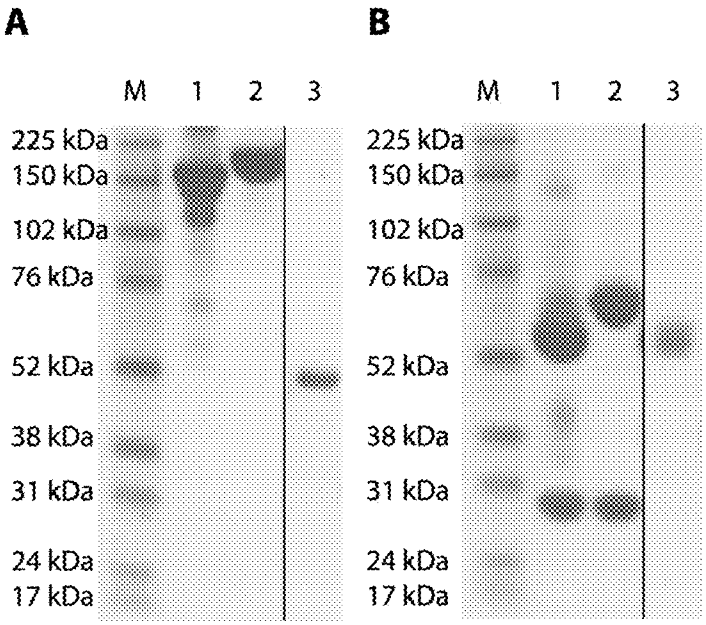

FIG. 45 shows specificity ELISA of Fyn SH3 variants isolated after affinity selections. None of the Fynomers® binds to HSA or HSA/rodent serum albumin, except for C3. However, C3 cross-reacts also with the non-related ovalbumin (hen egg white albumin). Therefore, C3 is considered as an unspecific binding protein.

Example 6: Anti-Human Anti-Her2/EGFR/CD33 Fyn SH3 Derivatives

Example 6.1: Redirected T-Cell Mediated Cell Cytotoxicity Analysis Towards HER2 Positive Tumor Cells

Example 6.1.1. —Expression and Purification of Anti-CD3 Antibody Anti-HER2 Fynomer® Fusion Proteins The HER2 binding Fynomer® C12 (Seq ID NO: 383) has been genetically fused to the anti CD3 binding antibody (SEQ ID NOs: 381 and 382) via a 15 amino acid linker (SEQ ID NO: 386) yielding the bispecific antibody Fynomer® fusion proteins of the present invention. In COVA420 the Fynomer® C12 was fused to the N-terminus of the heavy chain of the anti CD3 antibody (SEQ ID NOs: 381 and 382). In COVA422 the Fynomer® C12 was fused to the C-terminus of the heavy chain of the anti CD3 antibody (SEQ ID NO: 381 and 382).

The anti-CD3 antibody (SEQ ID NO: 381 and 382), COVA420 (SEQ ID NO: 387 and 388), COVA422 (SEQ ID NO: 389 and 390) and the anti-CD3×anti-HER2 scFv control (SEQ ID NO: 391) (carrying a hexa-his tag), were transiently transfected into FreeStyle CHO-S cells and expressed in serum-free/animal component-free media for 6 days. The anti-CD3 antibody and the bispecific proteins of the invention were purified from the supernatants by Protein A affinity chromatography (GE-Healthcare cat no 89928) with an ÄKTA Purifier instrument (GE Healthcare). Purification of the anti-CD3×anti-HER2 scFv control (COVA446, SEQ ID NO: 391) was achieved by immobilized metal ion affinity chromatography via a HIStrap Excel column (GE Healthcare). Concentrations were determined by absorbance measurement at 280 nm. Yields are listed in Table 17.

Results

Antibody Fynomer® fusion proteins of the invention and the control antibodies could be expressed and purified in a single step. A purity of >95% could be demonstrated by SDS-PAGE analysis as shown in FIGS. 46 and 47. Table 17 summarizes the expression yield after transient transfection into CHO cells and protein expression for 6 days at 37° C.

TABLE 17

| Protein | SEQ ID NO: | Yield (mg/l) |
|---|---|---|
| Anti-CD3 antibody (COVA419) | 381, 382 | 46 |
| COVA420 | 387, 388 | 59 |
| COVA422 | 389, 390 | 21 |
| Anti-CD3 × HER2 scFv control (COVA446) | 391 | 17 |

After purification size exclusion chromatography has been performed using an ÄKTA FPLC system and a Superdex G200, 30/100 GL column (GE Healthcare) or an Agilent HPLC 12/60 system and a Bio SEC5, 5 mm; 300 Å; 4.6×300 mm column. The bispecific proteins of the invention eluted as a single monomeric peak demonstrating that the antibody Fynomer® fusion proteins of the present invention have very favourable biophysical properties (FIG. 48).

Example 6.1.2—FACS Experiment with Anti-HER2 Fynomer® Anti-CD3 Antibody Fusion Proteins of the Current Invention The proteins COVA420 (SEQ ID NO: 386 and 387), COVA422 (SEQ ID NO: 388 and 390) and COVA446 (SEQ ID NO: 391) were incubated at a concentration of 100 nM in a total volume of 100 μl containing either (i) $1\times10^5$ Jurkat E6-1 cells (CD3 positive cells), (ii) $1\times10^5$ BT474 HER2 positive breast cancer cells, (iii) $1\times10^5$ HER2 or CD3 negative MDA MB 468 cells in PBS/1% BSA/0.2% sodium azide. As a negative control, the same cells were incubated with PBS/1% BSA/0.2% sodium azide only instead of proteins (PBS control).

After 60 min incubation on ice, cells were washed twice with 150 uL PBS-1% BSA buffer and bound antibodies were detected by adding 5 ug/mL goat anti human-Alexa 488 conjugate (Invitrogen) for 40 min in the dark. For the bispecific scFv control COVA446 (SEQ ID NO: 391), carrying a hexa his tag, binding was detected by the addition of 5 ug/ml mouse anti HIS tag antibody (Fisher Scientific) and incubation at 4° C. for 40 min followed by an additional wash step followed by an incubation with 5 ug/mL goat anti mouse Alexa 488 conjugate (Invitrogen) again for 40 min at 4° C.

Finally cells were washed three times, resuspended in 100 μl PBS-1% BSA, and stained cells were then analyzed on a Guava easyCyte™ flow cytometer (Millipore).

Results

Binding properties of Fynomer®-antibody fusion proteins were evaluated via flow cytometry. (COVA420 (SEQ ID NO: 387 and 388), COVA422 (SEQ ID NO: 389 and 390) and the bispecific scFv control (COVA446, SEQ ID NO: 391) specifically bound to HER2 expressing BT474 cells (panel A) and CD3 expressing Jurkat E6 cells (panel B) as shown in FIG. 49. No non-specific binding was observed on cell lines that did not express either CD3 or HER2 (panel C).

Example 6.1.3—Redirected T-Cell Mediated Cell Cytotoxicity Analysis Towards Cells Expressing HER2

Polypeptides COVA420 (SEQ ID NO: 387 and 388), and the bispecific scFv control (SEQ ID NO: 381) were tested in a redirected T-cell mediated cell cytotoxicity assay using a protocol adapted from Jäger et al (2009) Cancer Research, 69 (10):4270-6.

In brief, human PBMCs were used as effector cells. On the day before the experiment PBMCs were isolated from fresh buffy coat preparations obtained from Blutspende Zürich by Ficoll Plaque plus (GE Healthcare) and density gradient centrifugation using standard procedures. Isolated PBMCs were then incubated over night at a cell concentration of $4\times10^6$ cells/ml in 10% FCS, RPMI and 37° C., 5% $CO_2$. The isolated PBMCs could then serve as effector cells in redirected cell cytotoxicity assays.

Also on the night before the experiment an appropriate amount of target cells were detached by Accutase treatment and target cells were seeded in 96 well plates at cell densities ranging from 3000-5000 cells per well in 100 uL complete cell culture medium supplemented with 10% FCS. Assay plates were incubated over night at 37° C. and 5% CO2.

Target tumor cells used were SKBR-3 (ATCC cat no HTB-30™) and MDA-MB-468 (ATCC cat no: HTB-132™).

Prior to the cell kill experiment an appropriate amount of PBMCs was centrifuged and resuspended in 10% FCS, RPMI. Depending on the number of target cells used the cell concentration was adjusted ranging from 1.5 to $2.5\times10^6$ cells/mL and cells stored at room temperature until further use.

Redirected T-cell mediated cell cytotoxicity was additionally monitored using enriched CD8+ T-cells as effector cells and SKOV-3 (ATCC cat no HTB-77™) as target tumor cells. For these assays, isolated PBMCs were further purified to obtain enriched CD8+ T-cells. CD8+ T cells were isolated using the Dynbead® Untouched™ Human CD8 T-cell kit (Life Technologies cat no: 11348D) according to manufacturers recommendation.

After purification cells were then resuspended in 10% FCS, RPMI at a concentration ranging from $6\times10^5$ to $1\times10^7$ per ml.

On the day of the experiment effector molecules were diluted in 10% FCS, RPMI to a maximum concentration of 150 nM and a dilution series of 1/10 dilutions was prepared. Finally, consumed medium was removed from the assay plates and substituted with 50 ul of fresh medium per well. Then appropriate amounts of effector molecules and effector cells were added. The final effector cell to target cell ratio was 25/1 for PBMC assays and 10/1 for assays in which CD8+ T-cells served as effector cells. The final maximum concentration of effector molecule was 50 nM. The final assay volume was 150 uL per well.

The assay plates were incubated between 24 h and 72 h at 37° C., 5% CO2. Then, cell culture supernatants were removed and stored at −80° C. for subsequent assays (granzyme release assay, see Example 6.1.4 below). Prior to the addition of developing solution each well was washed with PBS twice. Cell viability was evaluated using XTT-reagent (Sigma cat no: X4626) according to manufactures recommendation. A 100% lysis control was included by treating the target cells with 1% Triton-X100 (Sigma), and the value for spontaneous lysis was obtained by treating the target cells with effector cells only ("spont lysis"). Absorbance at 450 nm was measured between 2.5 and 4 h after addition of XTT substrate. All measurements were done in triplicates.

Percent cell viability was calculated using the following formula:

% viability=(value−100% lysis)/(spont lysis−100% lysis)*100

% cell viability was then plotted against the effector molecule concentration and data were evaluated using Prism 5 (GraphPad Software) by fitting a sigmoidal dose-response.

Results

It could be demonstrated that a dose dependent cytotoxicity of COVA420 (SEQ ID NO: 387 and 388) on HER2 expressing SKBR-3 cells could be observed (FIG. 50). In this representative assay, COVA420 (SEQ ID NO: 387 and 388) had an $EC_{50}$ value of 87 pM.

Importantly, the cytotoxic effects were antigen dependent since no cytotoxicity was observed on HER2 negative MDA-MB-468 as shown in FIG. 50.

Under the same assay conditions an $EC_{50}$ value of 60 pM was obtained for the bispecific anti-HER2×anti-CD3 scFv-scFv control molecule (SEQ ID NO: 391). It was surprisingly found that bivalent and full length IgG based Fynomer-antibody fusion proteins show potencies in a redirected kill assay that are in the same range as currently used scFv-scFv proteins, but which do not suffer from the drawbacks of suboptimal biophysical properties and short in vivo half-life.

Table 18 summarizes the $EC_{50}$ values obtained for the proteins tested:

TABLE 18

| Protein | SEQ ID NO. | $EC_{50}$ (pM) PBMCs |
|---|---|---|
| COVA420 | 387, 388 | 87 |
| scFv-scFv control (COVA446) | 391 | 60 |

In order to demonstrate that the Fynomer-antibody fusion proteins of the invention exert the killing activity through the engagement of T-cells (and not through ADCC mediated activity), redirected cell kill experiments using CD8+ enriched T-cells that cannot mediate cell killing through ADCC were performed.

FIG. 51 shows that cell killing could be confirmed using CD8+ enriched T-cells as effector cells. Here, COVA420 (SEQ ID NO: 387 and 388) showed an $EC_{50}$ value of 8 pM and the $EC_{50}$ value of COVA422 (SEQ ID NO: 389 and 390) was 175 pM These results confirm the potent (sub-nM) killing activity of COVA420 (SEQ ID NO: 387 and 388) and COVA22 (SEQ ID NO: 389 and 390).

Example 6.1.4—Analysis of Granzyme B Release in the Presence and Absence of Target Cells The release of Granzyme B into the cell culture medium upon incubation of COVA420 (SEQ ID NO: 387 and 388) and the anti-CD3 antibody (SEQ ID NO: 381 and 382) as a control in the presence and absence of antigen positive target cells and CD8+ enriched T-cells was evaluated. Release of Granzyme B is a main indicator of T-cell mediated cytotoxic activity induced by BiTE® like agents as described by Haas A. et. al. Immunobiology, 2009, 214 (6): 441-53.

Samples were incubated as described above for evaluating the cytotoxic activity of Fynomer®-antibody fusion proteins. At the end of the incubation period the cell culture supernatants were collected and the concentration of Granzyme B was evaluated by using a Granzyme B ELISA kit (R&D Systems) according to manufacturers recommendation.

Results:

FIG. 52 depicts the expression level of Granzyme B after 3 days of incubation of COVA420 (SEQ ID NO: 387 and 388) in the presence of $CD8^+$ T-Cells and in the presence and absence of antigen positive target cells at the indicated concentrations. No unspecific release of Granzyme B could be detected if T-cells were only incubated with 50 nM COVA420 (SEQ ID NOs: 387 and 388) in the absence of target cells. A pronounced increase in Granzyme B expression was observed when target cells COVA420 (SEQ ID No: 387 and 388) and T-cells were present. No substantial Granzyme B expression could be detected when COVA420 (SEQ ID No: 387 and 388) was used at concentrations in which no cytotoxic effect was detectable which indicates a correlation between cytotoxic activity and Granzyme B release (0.5 pM). The control anti-CD3 antibody (SEQ ID NO: 381 and 382) (50 nM) did not trigger Granzyme B release in the presence of tumor target and effector cells, as expected.

Example 6.1.5—Pharmacokinetic Analysis

The pharmacokinetic profile of COVA420 (SEQ ID NO: 387 and 388) in C57BL/6 mice (Charles River) was investigated. Five C57BL/6 mice were injected i.v. with 200 μg COVA420 (SEQ ID NO: 387 and 388). After 10 min, 6, 24, 48, 96, 120, 144 and 168 hours, blood was collected into EDTA coated microvettes (Sarstedt), centrifuged for 10 min at 9300 g and the serum levels of COVA420 (SEQ ID NO: 387 and 388) was determined by ELISA. Black maxisorp microtiter plates (Nunc) were coated with 50 nM HER2 ECD (Bender MedSystems). After blocking with 2% BSA (Sigma) in PBS, 40 μl of PBS and 10 μl of serum at appropriate dilution were applied. After incubation for 1 hr, wells were washed with PBS, and bound COVA420 (SEQ ID NO: 387 and 388) was detected with anti-hIgG-HRP (Jackson ImmunoResearch). The assay was developed with QuantaRed fluorogenic substrate (Pierce) and the fluorescence intensity was measured after 5 min at 544 nm (excitation) and 590 nm (emission). The serum levels of COVA420 (SEQ ID NO: 387 and 388) were determined using a standard curve of COVA420 (SEQ ID NO: 387 and 388) (diluted to 333-0.5 ng/ml). From the concentrations determined in serum at different time points and the resulting slope k of the elimination phase (plotted in a semi-logarithmic scale), the half-life was calculated using to the formula $t_{1/2}$=ln 2/−k.

Results:

FIG. 53 shows the serum concentrations of COVA420 (SEQ ID NO: 387 and 388) after an iv bolus injection in mice. The half-life value for COVA420 (SEQ ID NO: 387 and 388) as determined from the elimination phase (beta phase, time-points 24 h-168 h) was 140 hours. This finding demonstrates that COVA420 (SEQ ID NO: 387 and 388) has IgG-like in vivo PK properties, as the half-life was comparable to the half-lives obtained for other human antibodies in mice (eg. adalimumab: 102-193 hours, Humira® Drug Approval Package (Drug Approval Package, Humira®, FDA Application No.: 125057s0110, Pharmacology Review, Jan. 18, 2008).

Example 6.1.6—In Vivo Efficacy of COVA420 in HER2-Overexpressing SKOV-3 Tumor Bearing Mice Reconstituted with Human T-Cells The anti-tumor activity of COVA420 was investigated in irradiated NOD.CB17 Prkdc mice bearing a HER2-expressing human SKOV-3 tumor xenograft.

Methods:

$3\times10^6$ SKOV-3 (ATCC cat no HTB-77™) cells were injected subcutaneously (s.c.) into 2 Gy-irradiated NOD.CB17 Prkdc mice (Charles River). When tumors reached an average size of ca. 50 $mm^3$, animals were treated with a single intravenous (i.v.) bolus injection of anti-asialo GM1 rabbit antibody (WAKO, Germany) one day before human T-cell injection. In vitro activated and expanded (22 days) human T-cells (Miltenyi Biotech, Germany) isolated from a buffy coat of a single healthy donor, were injected ($1.6\times10^7$ per mouse) into the peritoneal cavity. Three days after T-cell injection, mice were randomized and received 0.5 mg/kg COVA420 (SEQ ID NO: 387 and 388; n=8), vehicle (PBS; n=7) treatments twice per week (days 6, 9, 13, 15) or daily equimolar doses (=0.16 mg/kg) of COVA446 (SEQ ID NO: 391; n=8) by i.v. bolus injection into the lateral tail vein for a total of 15 days. Treatment efficacy was assessed by tumor growth inhibition. Tumor size was measured by external caliper measurements and volume calculated using the standard hemi-ellipsoid formula: volume=$(\text{width})^2\times\text{length}\times0.5$. Relative tumor volumes (RTV) to day 6 (initiation of therapy) are presented as mean±SEM.

Statistical analysis was performed using GraphPad Prism 6 software, version 6a. Statistical significance of anti-tumor efficacy was calculated by using an unpaired, nonparametric t-test (Mann-Whitney). Anti-tumor efficacy of COVA420 vs vehicle treatment on day 16 was further evaluated as tumor volume inhibition relative to the vehicle control, expressed as treatment-to-control ratio (T/C): T/C (%)=RTV (day 16)/RTV (day 6) (Wu (2010), Journal of Biopharmaceutical Statistics, 20:5, 954-964).

Results:

COVA420 significantly reduces SKOV-3 tumor growth by actively recruiting T-cells to the tumor (FIG. 54). COVA420 treatment resulted in a significant growth inhibition as compared to the vehicle control on day 16, after 4 doses of 0.5 mg/kg COVA420 (P=0.0059). COVA420 treatment was also significantly more efficacious as compared to the daily injected 0.16 mg/kg COVA446 control (P=0.04). T/C ratio on the same day equals to 55% growth inhibition of COVA420 and 79% of COVA446 as compared to the vehicle treatment. The results demonstrate that COVA420 is pharmacologically active and exerts its anti-tumor activity by efficiently recruiting human T-cells to the tumor resulting in inhibited tumor growth as compared to the vehicle-treated control.

Example 6.1.7—Analysis of Redirected T-Cell Mediated Cell Cytotoxicity Selectively Towards Tumor Cells Expressing High Levels of HER2

Polypeptides COVA420 (SEQ ID NOs: 387 and 388) and the bispecific scFv control COVA446 (SEQ ID NO: 391) were tested in a redirected T-cell mediated cell cytotoxicity assay using a protocol adapted from Jäger et al (2009) Cancer Research, 69 (10):4270-6.

In brief, human PBMCs were isolated from fresh buffy coat the day before and CD8+ T-cells were isolated on the day of the experiment as described in example 6.1.3.

On the night before the experiment an appropriate number of target cells were detached by Accutase treatment and target cells were seeded in 96 well plates at a cell density of 5000 cells per well in 150 μl appropriate growth medium supplemented with 10% FCS. Assay plates were incubated over night at 37° C. and 5% $CO_2$. Target tumor cells used were SKOV-3 (ATCC® HTB-77™) expressing high level of HER2 (approx. $1.7\times10^6$ HER2 molecules/cell) and MCF-7 (ATCC® HTB-22™) expressing low level of HER2 (approx. $1\times10^4$ HER2 molecules/cell). HER2 surface expression was quantified using Qifikit (Dako K0078) according to the manufacturers recommendation. Briefly, cells were stained with a saturating concentration of anti-HER2 antibody (R&D MAB1129) or isotype matched control IgG, followed by anti-mouse-FITC secondary antibody, and flow cytometric analysis. At the same time, beads coated with different well-defined quantities of mouse monoclonal antibody molecules were stained with the secondary antibody, analysed and a standard curve was plotted as a reference for molecules/cell.

On the day of the experiment, effector molecules were diluted in 10% FCS, RPMI to a maximum concentration of 150 nM and a dilution series of 1/10 dilutions was prepared. An appropriate amount of T-cells was centrifuged and resuspended in 10% FCS, RPMI. The cell concentration was adjusted to, $1\times10^6$ cells/mL.

Finally, consumed medium was removed from the assay plates and substituted with 50 μl of fresh 10% FCS, RPMI per well. Then 50 μl of effector molecules and 50 μl of effector T-cells were added. The final effector cell to target cell ratio was 10:1. The final maximum concentration of effector molecule was 50 nM. The final assay volume was 150 μl per well.

The assay plates were incubated for 60 h at 37° C., 5% $CO_2$. Then, cell culture supernatants were removed and each well was washed once with PBS. Cell viability was evaluated using XTT-reagent (Sigma X4626) according to the manufacturer's recommendation. A 100% lysis control was included by treating the target cells with 1% Triton-X100 (Sigma), and the value for spontaneous lysis was obtained by incubating the target cells with effector cells only ("spont lysis"). Absorbance at 450 nm was measured 2 h after addition of XTT substrate. All measurements were done in triplicates.

Percent cell viability was calculated using the following formula:

% viability=(value−100% lysis)/(spont lysis−100% lysis)*100

% cell viability was then plotted against the effector molecule concentration and data were evaluated using Prism 5 (GraphPad Software) by fitting a sigmoidal dose-response.

Results

Dose dependent redirected T-cell cytotoxicity of COVA420 towards SKOV-3 target cells expressing high level of HER2 could be observed (FIG. 55). Table 19 summarizes the $EC_{50}$ values obtained for the proteins tested.

Furthermore, dose dependent redirected T-cell cytotoxicity of the bispecific anti-CD3×anti-HER2 scFv control molecule COVA446 towards MCF-7 target cells expressing low level of HER2 could be observed. In this representative assay, COVA446 had an $EC_{50}$ value of 53 pM. Surprisingly, COVA420 did not exhibit significant redirected T-cell cytotoxicity towards MCF-7 target cells expressing low level of HER2 (Table 3).

TABLE 19

| Protein | SEQ ID NO. | SKOV-3 $EC_{50}$ (pM) | MCF-7 $EC_{50}$ (pM) | Factor difference |
|---|---|---|---|---|
| COVA420 | 387, 388 | 11.6 | n.d. | >4310 |
| anti-CD3 × EGFR scFv control (COVA446) | 391 | 2.3 | 53 | 23 |

Example 6.2: Redirected T-Cell Mediated Cell Cytotoxicity Analysis Towards EGFR Positive Tumor Cells Example 6.2.1. —Expression and Purification of Anti-CD3 Antibody Anti-EGFR Fynomer Fusion Proteins DNA encoding the polypeptides shown in SEQ ID NOs: 392 and 410 to 420 were cloned into the bacterial expression vector pQE12 so that the resulting constructs carried a C-terminal myc-hexahistidine tag as described in Grabulovski et al. (Grabulovski et al. (2007) JBC, 282, p. 3196-3204). The polypeptides were expressed in the cytosol of *E. coli* bacteria in 200 μl scale cultures. Cleared lysate containing the polypeptides was diluted 5:1 in PBS/1% FCS/0.2% sodium azide buffer containing 10 μg/ml anti-myc mouse antibody 9E10 (Roche) and added to $1\times10^5$ MDA-MB-468 cells (ATCC® HTB-132™). After 60 min incubation on ice, cells were washed, and bound sequences were detected by anti-mouse IgG—Alexa488 conjugate (Invitrogen). The stained cells were then analyzed in a FACS analyzer. The DNA sequence of the specific binders was verified by DNA sequencing. The amino acid sequences of Fyn SH3 derived EGFR binders is presented in SEQ ID NOs: 392 and 410 to 420 as appended in the sequence listing.

The EGFR binding Fynomer ER7L2D6 (SEQ ID NO: 392) has been genetically fused to the N-terminus of the heavy chain (SEQ ID NO: 394) of a CD3 binding antibody (COVA489, SEQ ID NOs: 394 and 395) via a 15 amino acid linker (SEQ ID NO: 386) yielding the bispecific antibody Fynomer fusion protein COVA493 (SEQ ID NOs: 393 and 394). In addition, ER7L2D6 (SEQ ID NO: 381) was fused to the N-terminus of the antibody light chain resulting in the bispecific antibody Fynomer fusion protein COVA494 (SEQ OD NOs: 394 and 421).

The EGFR binding Fynomer ER9L3D7 (SEQ ID NO: 410) has been genetically fused to the N-terminus of the antibody heavy chain (SEQ ID NO: 394) of an anti-CD3 binding antibody (COVA489, SEQ ID NOs: 394 and 395) via a 15 amino acid linker (SEQ ID NO: 386) yielding the bispecific antibody Fynomer fusion protein COVA497 (SEQ ID NOs: 422 and 395). In addition, ER9L3D7 (SEQ ID NO: 381) was fused to the C-terminus of the antibody light chain (SEQ ID NOs: 395) resulting in the bispecific antibody Fynomer fusion protein COVA499 (SEQ OD NOs: 394 and 423).

The anti-CD3 antibody COVA489, the bispecific proteins COVA493, COVA494, COVA497, COVA499 and the anti-CD3×anti-EGFR scFv control COVA445 (SEQ ID NO: 396) (carrying a hexa-his tag), were transiently transfected into FreeStyle CHO-S cells and expressed in serum-free/animal component-free media for 6 days. The anti-CD3 antibody and the bispecific proteins of the invention were purified from the supernatants by Protein A affinity chromatography (GE-Healthcare cat no 89928) with an ÄKTA Purifier instrument (GE Healthcare). Purification of the anti-CD3×anti-EGFR scFv control (COVA445, SEQ ID NO: 396) was achieved by immobilized metal ion affinity chromatography via a HIStrap Excel column (GE Healthcare). Concentrations were determined by absorbance measurement at 280 nm. Yields are listed in Table 20.

After purification, analytical size exclusion chromatography was performed using a silica-based SEC-5 column (Agilent; 5 mm; 300 Å) on an Agilent HPLC 12/60 system.

Results

Antibody Fynomer fusion proteins of the invention and the control antibodies could be expressed and purified in a single step. Table 1 summarizes the purification yield after transient transfection into CHO cells and protein expression for 6 days at 37° C.

TABLE 20

Expression yields.

| Protein | SEQ ID NO: | Yield (mg/l) |
|---|---|---|
| Anti-CD3 antibody (COVA489) | 394, 395 | 66 |
| COVA493 | 393, 395 | 40 |
| COVA494 | 394, 421 | 39 |
| COVA497 | 422, 395 | 35 |
| COVA499 | 394, 423 | 74 |
| Anti-CD3 × EGFR scFv control (COVA445) | 396 | 34 |

The bispecific proteins of the invention eluted as a single monomeric peak from the size exclusion column, demonstrating that the antibody Fynomer fusion proteins of the present invention have very favorable biophysical properties (FIG. 56). The bispecific constructs of the invention expressed at least as good as the unmodified anti-CD3 antibody and did not aggregate after purification as shown by SEC analysis.

Example 6.2.2—FACS Assay Experiment with Anti-EGFR Fynomer® Anti-CD3 Antibody Fusion Proteins of the Current Invention COVA489, COVA493, COVA494, COVA497, COVA499 and COVA445 were incubated either (i) at 30 nM concentration in a total volume of 100 μl with $1\times10^5$ Jurkat E6-1 cells (CD3 positive cells; ATCC® TIB-152™), or (ii) at 100 nM concentration in a total volume of 100 μl with $1\times10^5$ EGFR-overexpressing MDA-MB-468 breast cancer cells (ATCC® HTB-132™) in PBS/1% BSA/0.2% sodium azide. As a negative control, the same cells were incubated with PBS/1% BSA/0.2% sodium azide only instead of proteins (PBS control).

After 45 min incubation on ice, cells were washed twice with 150 μL PBS-1% BSA buffer and bound antibodies were detected by adding 4 ug/mL goat anti-human-Alexa 488 conjugate (Invitrogen) for 40 min at 4° C. For the bispecific scFv control COVA445 carrying a hexa his tag, binding was detected by concomitant incubation of COVA445 with a mouse anti HIS tag antibody (Fisher Scientific) at a molar ratio of 1:4 (anti-HIS tag antibody: COVA445), followed by additional wash steps, followed by incubation with 4 ug/mL goat anti-mouse-Alexa 488 conjugate (Invitrogen) for 40 min at 4° C. Finally cells were washed three times, resuspended in 1000 PBS-1% BSA, and stained cells were then analyzed on a Guava easyCyte™ flow cytometer (Millipore).

Results

All constructs bound to Jurkat E6-1 cells which express human CD3, and all Fynomer-antibody fusions as well as the anti-CD3×anti-EGFR scFv control COVA445 bound to MDA-MB-468 (FIG. 57). No specific binding was observed for the anti-CD3 antibody COVA489 on MDA-MB-468, as expected.

Example 6.2.3—Analysis of Redirected T-Cell Mediated Cell Cytotoxicity Selectively Towards Tumor Cells Expressing High Levels of EGFR Polypeptides COVA493, COVA494, COVA497, COVA499, the bispecific scFv control COVA445 and the anti-CD3 antibody (COVA489, SEQ ID Nos: 394 and 395) were tested in a redirected T-cell mediated cell cytotoxicity assay using a protocol adapted from Jäger et al (2009) Cancer Research, 69 (10):4270-6.

In brief, on the night before the experiment an appropriate number of target cells were detached by Accutase treatment and target cells were seeded in 96 well plates at a cell density of 3000-5000 cells per well in 150 μl appropriate growth medium supplemented with 10% FCS. Assay plates were incubated over night at 37° C. and 5% $CO_2$. Target tumor cells used were MDA-MB-468 (ATCC® HTB-132™) expressing high level of EGFR (approx. $1.5\times10^6$ EGFR molecules/cell) and HT-29 (ATCC® HTB-38™) expressing low level of EGFR (approx. $5\times10^4$ EGFR molecules/cell). EGFR surface expression was quantified as described in Example 6.1.7 but using a saturating concentration of anti-EGFR antibody (Millipore MABF120).

On the day of the experiment, effector molecules were diluted in 10% FCS, RPMI to a maximum concentration of 15 nM and a dilution series of 1/20 dilutions was prepared. Human CD8+ enriched T-cells were used as effector cells. CD8+ enriched T-cells were isolated from fresh buffy coat preparations obtained from Blutspende Bern using the MACSxpress human CD8+ isolation kit (Miltenyi 130-098-194) together with the MACSxpress Separator (Milteny 130-098-309) and Red blood cell lysis solution (Milteny 130-094-183) as recommended by the manufacturer.

An appropriate amount of T-cells was centrifuged and resuspended in 10% FCS, RPMI. The cell concentration was adjusted to, $1\times10^6$ cells/mL.

Finally, consumed medium was removed from the assay plates and substituted with 50 μl of fresh 10% FCS, RPMI per well. Then 50 μl of effector molecules and 50 μl of effector T-cells were added. The final effector cell to target cell ratio was 10:1. The final maximum concentration of effector molecule was 5 nM. The final assay volume was 150 μl per well.

In order to demonstrate that the Fynomer-antibody fusion proteins of the invention exert the killing activity through the engagement of T-cells, target cells were incubated with COVA493, COVA494, COVA497, COVA499 and COVA445 at a concentration of 5 nM also in the absence of T-cells.

The assay plates were incubated for 64 h at 37° C., 5% $CO_2$. Then, cell culture supernatants were removed and each well was washed once with PBS. Cell viability was evaluated using XTT-reagent (Sigma X4626) according to the manufacturer's recommendation. A 100% lysis control was included by treating the target cells with 1% Triton-X100 (Sigma), and the value for spontaneous lysis was obtained by incubating the target cells with effector cells only ("spont lysis"). Absorbance at 450 nm was measured 5 h after addition of XTT substrate. All measurements were done in triplicates.

Percent cell viability was calculated using the following formula:

% viability=(value−100% lysis)/(spont lysis−100% lysis)*100

% cell viability was then plotted against the effector molecule concentration and data were evaluated using Prism 5 (GraphPad Software) by fitting a sigmoidal dose-response.

Results

Dose dependent redirected T-cell cytotoxicity of COVA493, COVA494, COVA497 and COVA499 towards MDA-MB-468 target cells expressing high level of EGFR could be observed (FIG. 58. Table 21 summarizes the $EC_{50}$ values obtained for the proteins tested.

Furthermore, dose dependent redirected T-cell cytotoxicity of COVA493 and the bispecific anti-CD3×anti-EGFR scFv control molecule towards HT-29 target cells expressing low level of EGFR could be observed. In this representative assay, COVA493 had an $EC_{50}$ value of 117.3 pM, and COVA445 had an $EC_{50}$ value of 2.5 pM. Surprisingly, COVA494, COVA497 and COVA499 did not exhibit significant redirected T-cell cytotoxicity towards HT-29 target cells expressing low level of EGFR even at the highest concentration of 5 nM (Table 5).

The cytotoxic effects were dependent on the presence of the anti-EGFR Fynomer since no cytotoxicity was observed with the anti-CD3 antibody (COVA489, SEQ ID NOs: 384 and 385, measured at the highest concentration of 5 nM).

TABLE 21

EC50 values for T-cell mediated cytotoxicity.

| Protein | SEQ ID NO. | MDA-MB-468 $EC_{50}$ (pM) | HT-29 $EC_{50}$ (pM) | Factor difference |
|---|---|---|---|---|
| COVA493 | 393, 395 | 0.2 | 117.3 | 580 |
| COVA494 | 394, 421 | 1.4 | n.a. | >3500 |
| COVA497 | 422, 395 | 2.8 | n.a. | >1750 |
| COVA499 | 394, 423 | 6 | n.a. | >830 |
| anti-CD3 × EGFR scFv control (COVA445) | 396 | 0.2 | 2.5 | 12.5 |

(n.a. not applicable)

The cytotoxic effects were dependent on the presence of effector T-cells (FIG. 59), since no cytotoxicity was observed when target cells were incubated with COVA493, COVA494, COVA497, COVA499 and the bispecific anti-CD3×anti-EGFR scFv control molecule (COVA445).

Example 6.3: Redirected T-Cell Mediated Cell Cytotoxicity Analysis Towards CD33 Positive Tumor Cells

Example 6.3.1. —Expression and Purification of Anti-CD3 Antibody Anti-CD33 Fynomer Fusion Proteins DNA encoding the amino acids shown in SEQ ID NOs: 397 and 400 to 409 were cloned into the bacterial expression vector pQE12 so that the resulting constructs carried a C-terminal myc-hexahistidine tag as described in Grabulovski et al. (Grabulovski et al. (2007) JBC, 282, p. 3196-3204). The polypeptides were expressed in the cytosol of *E. coli* bacteria in 200 µl scale cultures. Monoclonal cleared lysates were used for ELISA: human recombinant CD33 (purchased from R&D as fusion to human Fcγ1) was immobilized on MaxiSorp wells (Nunc), and after blocking with 4% milk (Rapilait, Migros, Switzerland) in PBS, 12.5 µl of 10% milk in PBS containing 50 µg/ml mouse anti-myc mouse antibody 9E10 (Roche) and 50 µl of cleared lysate were applied. After incubation for 1 hr, unbound Fynomers were washed off, and bound Fynomers were detected with anti-mouse IgG-HRP antibody conjugate (Sigma). The detection of peroxidase activity was done by adding BM blue POD substrate (Roche) and the reaction was stopped by adding 1 M $H_2SO_4$. The ELISA positive clones were tested by an identical ELISA for the absence of cross reactivity to human IgG (Sigma) and to uncoated MaxiSorp wells. Furthermore, DNA encoding the polypeptides shown in SEQ ID NOs: 397 and 400 to 409 were purified from the bacterial lysates using immobilized metal affinity chromatography columns as described in Grabulovski et al. (Grabulovski et al. (2007) JBC, 282, p. 3196-3204). 93 nM purified Fynomer were incubated with $1\times10^5$ U937 cells (ATCC CRL-1593.2™) in 100 µl PBS/1% FCS/0.2% sodium azide containing 23 nM mouse anti-myc antibody 9E10. After 60 min incubation on ice, cells were washed, and bound sequences were detected by anti-mouse IgG—Alexa488 conjugate (Invitrogen). The stained cells were then analyzed in a FACS analyzer. The DNA sequence of the specific binders was verified by DNA sequencing. The amino acid sequences of Fyn SH3 derived CD33 binders are presented in SEQ ID NOs: 397 and 400 to 409 as appended in the sequence listing.

The CD33 binding Fynomer EE1L1B3 (Seq ID NO: 397) has been genetically fused to the C-terminus of the light chain (SEQ ID NO: 382) of an anti-CD3 binding antibody (SEQ ID NOs: 381 and 382) via a 15 amino acid linker (SEQ ID NO: 386) yielding the bispecific antibody Fynomer antibody fusion protein COVA467 (SEQ ID NOs: 381 and 175) of the present invention. COVA467 and the anti-CD3×anti-CD33 scFv control COVA463 (SEQ ID NO: 399) described in patent application WO 2010/037835 were expressed and purified as described in Example 6.1.1. COVA467 expressed as good as the unmodified anti-CD3 antibody (yields: 56 mg/l for COVA467 vs. 46 mg/l for the parental anti-CD3 antibody COVA419) and did not aggregate after purification as shown by SEC analysis FIG. 60 A.

Example 6.3.2—Analysis of Redirected T-Cell Mediated Cell Cytotoxicity Towards Tumor Cells Expressing CD33

Polypeptides COVA467 (SEQ ID NOs: 381 and 398), and the bispecific scFv control COVA463 (SEQ ID NO: 399) were tested in a redirected T-cell mediated cell cytotoxicity assay using a protocol adapted from Jäger et al (2009) Cancer Research, 69 (10):4270-6.

In brief, U937 (ATCC cat no: CRL-1593.2™) target cells were seeded in round bottom 96 well plates at a cell density of 10000 cells per well in 50 µL RPMI medium supplemented with 10% FCS. Effector molecules were diluted in 10% FCS, RPMI to a maximum concentration of 15 nM and a dilution series of 1/10 dilutions was prepared. Human CD8+ enriched T-cells were used as effector cells. CD8+ enriched T-cells were isolated as described in Example 6.1.3 and adjusted to a concentration of to $2\times10^6$ cells/mL. Then 50 µl of effector molecules at the indicated concentrations and 50 µl of effector T-cells were added. The final effector cell to target cell ratio was 10:1. The final assay volume was 150 µl per well.

The assay plates were incubated for 24 h at 37° C., 5% $CO_2$. Cell lysis was evaluated using CytoTox-Fluor™ cytotoxicity assay (Promega G9260) according to manufactures recommendation. A 100% lysis control was included by treating the target cells with 2% Saponin (Sigma) at 0 h incubation. Spontaneous lysis was measured by incubating the target cells with effector T-cells only ("spont lysis").

After 24 h incubation, assay plates were spun down at 400×g for 10 min and 100 µl of supernatant was transferred into black 96 well plates. CytoTox-Fluor™ reagent and assay buffer was thawed at room temperature and 60 µl of reagent were diluted in 30 ml assay buffer. Subsequently 50 µl of this mixture was added to each well of assay plate supernatant. Plates were incubated for 2 h at 37° C. and fluorescence was recorded at 485 nm excitation/520 nm emission. All measurements were done in triplicates.

Percent cell viability was calculated using the following formula:

$$\%\ \text{cell lysis}=(\text{value}-\text{spont lysis})/(100\%\ \text{lysis}-\text{spont lysis})*100$$

% cell lysis was then plotted against the effector molecule concentration and data were evaluated using Prism 5 (GraphPad Software) by fitting a sigmoidal dose-response.

Results

It could be demonstrated that a dose dependent cytotoxicity of COVA467 (SEQ ID NOs: 381 and 398) on CD33 expressing U937 cells could be observed (FIG. 60 B). In this representative assay, COVA467 (SEQ ID NOs: 381 and 398) had an $EC_{50}$ value of 2.1 pM. Importantly, the cytotoxic effects were dependent on the presence of the anti-CD33 Fynomer since no cytotoxicity was observed with the anti-CD3 antibody (COVA419, SEQ ID NOs: 381 and 382).

Under the same assay conditions an $EC_{50}$ value of 1.6 pM was obtained for the bispecific anti-CD33×anti-CD3 scFv-scFv control molecule (SEQ ID NO: 399). It was surprisingly found that bivalent and full length IgG based Fynomer-antibody fusion proteins show potencies in a redirected kill assay that are in the same range as currently used scFv-scFv proteins, but which do not suffer from the drawbacks of suboptimal biophysical properties and short in vivo half-life.

Table 22 summarizes the $EC_{50}$ values obtained for the proteins tested:

TABLE 22

| Fynomer | SEQ ID NO. | $EC_{50}$ (pM) |
|---|---|---|
| COVA467 | 381, 398 | 2.1 |
| scFv-scFv control (COVA463) | 399 | 1.6 |

Example 7: Anti-BACE2 Serum Albumin Fyn SH3 Derivatives

Example 7.1: BACE2-Specific Fynomers

Methods:

BACE2 is a membrane-bound aspartic protease (UniProt Q95YZ0). BACE2-specific Fynomers were obtained and characterized as described in Banner et al (Banner et al (2013) Acta Cryst D69, pp. 1124-1137). Briefly, starting from a phage library with two randomized loops (RT and Src) and different loop lengths, three rounds of panning and phage amplification were performed using streptavidin-immobilized biotinylated BACE2 (biotinylation procedure is a methodology well known in the art). Phage clones were screened by phage ELISA and their loop sequences were analyzed. Clones were selected and used as templates for one round of affinity maturation with specifically designed sub-libraries. The Fynomer sequences were cloned into bacterial expression vector (pQE12) with a C-terminal 6×His tag. The Fynomers were expressed, small-scale purified and screened by ELISA and Biacore as described in Banner et al (2013) Acta Cryst D69, pp. 1124-1137.

Results:

Fynomers binding to BACE2 were isolated using standard phage-display techniques. The KD for BACE2 binding of nine Fynomers ranged from 6 to 380 nM (Table 23).

TABLE 23

$K_D$ values of BACE2 binding Fynomers

| Fynomer | $K_D$ [nM] |
|---|---|
| 1B-G10 | 260 |
| 2B-D2 | 47 |
| 1B-H10 | 45 |
| 1B-B11 | 70 |
| 1B-E11 | 380 |
| 2B-E9 | 22 |
| 2B-H11 | 6 |
| 2B-B12 | 9 |
| 1B-E10 | 200 |

Example 7.2: The BACE2 Binding Fynomers were Also Able to Inhibit BACE2 Activity Methods BACE2 activity assay was performed as described in Banner et al (2013) Acta Cryst D69, pp. 1124-1137. Briefly, to determine the IC50 of the inhibiting Fynomers, a BACE2 FRET assay was performed using a fluorescent substrate (WSEVNLDAEFRC-MR121) in triplicate at room temperature in a final volume of 50 ml in 384-well microtitre plates. All reagents were diluted in the assay buffer: 100 mM sodium acetate, 20 mM EDTA, 0.05% BSA pH 4.5. The anti-BACE-2 Fynomers were serially diluted and 20 ml of these dilutions was mixed for 10 min with 20 ml human recombinant BACE-2 (final concentration 62.5 nM). After addition of 10 ml of the substrate (final concentration 300 nM), the plates were shaken for 2 min. The enzymatic reaction was followed in a plate vision reader (PerkinElmer; excitation wavelength 630 nm; emission wavelength 695 nm) for 30 min in a kinetic measurement detecting an increase of MR121 fluorescence during the reaction time. The slope in the linear range of the kinetics was calculated and the IC50 was determined using a four-parameter equation for curve fitting Results:

The IC50 values of the seven inhibitory Fynomers are summarized in Table 24.

TABLE 24

$IC_{50}$ values of BACE2 inhibitory Fynomers

| Fynomer | IC50 [nM] |
|---|---|
| 1B-G10 (SEQ ID NO: 424) | 1325 |
| 2B-D2 (SEQ ID NO: 425) | 87 |
| 1B-H10 (SEQ ID NO: 426) | 51 |
| 1B-B11 (SEQ ID NO: 427) | 302 |
| 2B-E9 (SEQ ID NO: 428) | 879 |
| 2B-H11 (SEQ ID NO: 429) | 174 |
| 2B-B12 (SEQ ID NO: 430) | 35 |

Also described herein are the following items.

1. A recombinant binding protein, comprising at least one derivative of the Src homology 3 domain (SH3) of the FYN kinase, wherein
   (a) at least one amino acid in or positioned up to two amino acids adjacent to the src loop and/or
   (b) at least one amino acid in or positioned up to two amino acids adjacent to the RT loop,
   is substituted, deleted or added, wherein the SH3 domain derivative has an amino acid sequence having at least 70, preferably at least 80, more preferably at least 90 and most preferred at least 95% sequence identity to the amino acid sequence of SEQ ID NO: 1,
   preferably with the proviso that the recombinant binding protein does not comprise the amino acid sequence of SEQ ID NO: 2,
   and preferably with the proviso that the recombinant protein is not a natural SH3 domain containing protein existing in nature.
2. The binding protein according to item 1, wherein said SH3 domain derivative has at least 85, preferably at least 90, more preferably at least 95, most preferably at least 98 to 100% identity to the Src homology 3 domain (SH3) of the FYN kinase outside the src and RT loops.
3. The binding protein according to item 1 or 2, wherein
   (a) at least one amino acid in the src loop and
   (b) at least one amino acid in the RT loop,
   is substituted, deleted or added.

4. The binding protein according to any one of items 1 to 3, comprising at least two derivatives of the SH3 domain, preferably a bivalent binding protein.
5. The binding protein according to any one of items 1 to 4, comprising one or preferably two altered residues in positions 37 and/or 50 of the SH3 domain derivative, preferably two hydrophobic altered residues, more preferably Trp37 and/or Tyr50, Trp37 and Tyr50 being most preferred.
6. The binding protein according to any one of items 1 to 5 having a specific binding affinity to a target of $10^{-7}$ to $10^{-12}$ M, preferably $10^{-8}$ to $10^{-12}$ M, preferably a therapeutically and/or diagnostically relevant target, more preferably an amino acid-based target comprising a PxxP motif.
7. The binding protein according to any one of items 1 to 6 having a specific binding affinity of $10^{-7}$ to $10^{-12}$ M, preferably $10^{-8}$ to $10^{-12}$ M, to the extracellular domain of oncofetal fibronectin (ED-B).
8. The binding protein according to item 7 having one or more, preferably two, altered, preferably hydrophobic, residues in positions 37 and/or 50 of the SH3 domain derivative, more preferably Trp37 and/or Tyr50, and most preferred Trp37 and Tyr50.
9. The binding protein according to any one of items 1 to 8, comprising the amino acid sequence of SEQ ID NO: 3.
10. The binding protein according to any one of items 1 to 9, wherein said binding protein has binding specificity for a protein or a small organic compound.
11. A fusion protein comprising a binding protein according to any one of items 1 to 10 fused to a pharmaceutically and/or diagnostically active component.
12. The fusion protein according to item 11, wherein said component is a cytokine, preferably a cytokine selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta.
13. The fusion protein according to item 11, wherein said component is a toxic compound, preferably a small organic compound or a polypeptide, preferably a toxic compound selected from the group consisting of calicheamicin, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and recombinant gelonin.
14. The fusion protein according to item 11, wherein said component is a chemokine, preferably a chemokine selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, Eotaxin, Eotaxin-2, 1-309, MPIF-1, 6Ckine, CTACK, MEC, Lymphotactin and Fractalkine.
15. The fusion protein according to item 11, wherein said component is a fluorescent dye, preferably a component selected from Alexa Fluor or Cy dyes.
16. The fusion protein according to item 11, wherein said component is a photosensitizer, preferably bis(triethanolamine)Sn(IV) chlorine$_6$ (SnChe$_6$).
17. The fusion protein according to item 11, wherein said component is a pro-coagulant factor, preferably tissue factor.
18. The fusion protein according to item 11, wherein said component is an enzyme for pro-drug activation, preferably an enzyme selected from the group consisting of carboxy-peptidases, glucuronidases and glucosidases.
19. The fusion protein according to item 11, wherein said component is a radionuclide either from the group of gamma-emitting isotopes, preferably $^{99m}$Tc, $^{123}$I, $^{111}$In, or from the group of positron emitters, preferably $^{18}$F, $^{64}$Cu, $^{68}$Ga, $^{86}$Y, $^{124}$I, or from the group of beta-emitter, preferably $^{131}$I, $^{90}$Y, $^{177}$Lu, $^{67}$Cu, or from the group of alpha-emitter, preferably $^{213}$Bi, $^{211}$At.
20. The fusion protein according to item 11, wherein said component is a functional Fc domain, preferably a human functional Fc domain.
21. The fusion protein according to any one of items 11 to 20, further comprising a component modulating serum half-life, preferably a component selected from the group consisting of polyethylene glycol (PEG), immunoglobulin and albumin-binding peptides.
22. The fusion protein according to any one of items 11 to 21, comprising the binding protein according to item 7, 8 or 9.
23. A polynucleotide coding for a binding protein or fusion protein according to any one of items 1 to 22.
24. A vector comprising a polynucleotide according to item 23.
25. A host cell comprising a polynucleotide according to item 23 and/or a vector according to item 24.
26. Use of a binding or fusion protein according to any one of items 1 to 14, 16 to 18 and 20 to 22 for preparing a medicament.
27. Use of a binding protein according to item 7, 8 or 9 and/or a fusion protein according to item 22 for preparing a medicament for the treatment of cancer.
28. Use of a binding or fusion protein according to any one of items 1 to 10, 15, 19, 21 and 22 for preparing a diagnostic means.
29. Use of a binding protein according to item 7, 8 or 9 and/or a fusion protein according to item 22 for preparing a diagnostic means for the diagnosis of cancer.
30. A pharmaceutical composition comprising a binding or fusion protein according to any one of items 1 to 14, 16 to 18 and 20 to 22 and optionally a pharmaceutically acceptable excipient.
31. A diagnostic composition comprising a binding or fusion protein according to any one of items 1 to 11, 15, 19, 21 and 22 and optionally a pharmaceutically acceptable excipient.

The invention claimed is:

1. A method for selecting from a library comprising recombinant derivatives of the SH3 domain of the Fyn kinase of SEQ ID NO: 1 one or more of said derivatives having a specific binding affinity to a protein or peptide, said method comprising the steps of (a) contacting the library comprising derivatives of the SH3 domain of the Fyn kinase of SEQ ID NO: 1 with the protein or peptide under conditions and for a time sufficient to permit the derivatives and the protein or peptide to interact; and (b) selecting from the library one or more derivatives of the SH3 domain of the Fyn kinase of SEQ ID NO: 1 having a specific binding affinity to the protein or peptide, wherein the protein or peptide is not a natural SH3 binding ligand, and wherein each of the derivatives of the SH3 domain of the Fyn kinase of SEQ ID NO: 1 has an amino acid sequence complying with the following requirements:

(i) it has at least 80% sequence identity to the amino acid sequence of SEQ ID NO: 1, and (ii) it has at least 90% identity to the amino acid of SEQ ID NO: 1 outside the src and RT loops;

(iii, a) at least one amino acid in or positioned up to two amino acids adjacent to the RT loop of SEQ ID NO: 1 is substituted, deleted or added, or (iii, b) at least one amino acid in or positioned up to two amino acids adjacent to the src loop of SEQ ID NO: 1 is substituted, deleted or added;

wherein the src loop is located at amino acid positions 31 to 34 of SEQ ID NO: 1, and the RT loop is located at amino acid positions 12 to 17 of SEQ ID NO: 1.

2. The method of claim 1, wherein step (b) comprises (b') isolating from the library of (a) one or more derivatives having a binding affinity to the protein or peptide; and (b") selecting from the isolated one or more derivatives one or more derivatives having a specific binding affinity to the protein or peptide.

3. The method of claim 2, wherein step (b') comprises three rounds of panning against the protein or peptide.

4. The method of claim 3, wherein selecting in step (b") comprises determining the specific binding affinity by phage ELISA.

5. The method of claim 2, wherein selecting in step (b") comprises determining the specific binding affinity by phage ELISA.

6. The method of claim 1, wherein the method further comprises (c) determining the dissociation constant of the selected one or more derivatives to the protein or peptide.

7. The method of claim 6, wherein the dissociation constant is determined by surface plasmon resonance real-time interaction analysis.

* * * * *

SEQUENCE LISTING

```
<160> NUMBER OF SEQ ID NOS: 430

<210> SEQ ID NO 1
<211> LENGTH: 63
<212> TYPE: PRT
```

```
<213> ORGANISM: Homo sapiens

<400> SEQUENCE: 1

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 2
<211> LENGTH: 63
<212> TYPE: PRT
<213> ORGANISM: Artificial Sequence
<220> FEATURE:
<223> OTHER INFORMATION: Fyn SH3 variant R96I of Lee et al.

<400> SEQUENCE: 2

Gly Val Thr Leu Phe Val Ala Leu Tyr Asp Tyr Glu Ala Ile Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 3
<211> LENGTH: 65
<212> TYPE: PRT
<213> ORGANISM: Artificial Sequence
<220> FEATURE:
<223> OTHER INFORMATION: Variant of SH3 domain of Fyn kinase with high
      affinity to ED-B domain of fibronectin

<400> SEQUENCE: 3

Gly Val Thr Leu Phe Val Ala Leu Tyr Asp Tyr His Ala Gln Ser Gly
1               5                   10                  15

Ala Asp Leu Ser Phe His Lys Gly Glu Lys Phe Gln Ile Leu Lys Phe
            20                  25                  30

Gly Arg Gly Lys Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 4
<211> LENGTH: 65
<212> TYPE: PRT
<213> ORGANISM: Artificial Sequence
<220> FEATURE:
<223> OTHER INFORMATION: IL-17A binder F2

<400> SEQUENCE: 4

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Gln Gln
            20                  25                  30
```

Asn Glu Leu Thr Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 5
<211> LENGTH: 65
<212> TYPE: PRT
<213> ORGANISM: Artificial Sequence
<220> FEATURE:
<223> OTHER INFORMATION: IL-17A binder B3_1

<400> SEQUENCE: 5

Gly Val Thr Leu Phe Val Ala Leu Tyr Asp Tyr Ala Ala Phe Trp Pro
1 5 10 15

Gly Asp Leu Ser Phe His Lys Gly Glu Lys Phe Gln Ile Leu Lys Asn
20 25 30

Arg Ala Ile Thr Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 6
<211> LENGTH: 65
<212> TYPE: PRT
<213> ORGANISM: Artificial Sequence
<220> FEATURE:
<223> OTHER INFORMATION: IL-17A binder C2_1

<400> SEQUENCE: 6

Gly Val Thr Leu Phe Val Ala Leu Tyr Asp Tyr Leu Thr Arg Trp Lys
1 5 10 15

Pro Asp Leu Ser Phe His Lys Gly Glu Lys Phe Gln Ile Leu Arg Lys
20 25 30

Ile Phe Asp Tyr Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 7
<211> LENGTH: 65
<212> TYPE: PRT
<213> ORGANISM: Artificial Sequence
<220> FEATURE:
<223> OTHER INFORMATION: IL-17A binder A2

<400> SEQUENCE: 7

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu Tyr Gln
20 25 30

Pro His Ala Leu Gly Asp Trp Trp Glu Ala Arg Ser Leu Thr Thr Gly
35 40 45

```
Glu Thr Gly Tyr Ile Pro Ser Asn Tyr Val Ala Pro Val Asp Ser Ile
    50                  55                  60

Gln
65


<210> SEQ ID NO 8
<211> LENGTH: 65
<212> TYPE: PRT
<213> ORGANISM: Artificial Sequence
<220> FEATURE:
<223> OTHER INFORMATION: IL-17A binder A5_1

<400> SEQUENCE: 8

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Pro
            20                  25                  30

His Leu Met Phe Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 9
<211> LENGTH: 65
<212> TYPE: PRT
<213> ORGANISM: Artificial Sequence
<220> FEATURE:
<223> OTHER INFORMATION: IL-17A binder D2_1

<400> SEQUENCE: 9

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Asp Thr
            20                  25                  30

Leu Pro Gly Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 10
<211> LENGTH: 65
<212> TYPE: PRT
<213> ORGANISM: Artificial Sequence
<220> FEATURE:
<223> OTHER INFORMATION: IL-17A binder E1_1

<400> SEQUENCE: 10

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Trp Asp
            20                  25                  30

Asp Arg Pro Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
```

65

<210> SEQ ID NO 11
<211> LENGTH: 65
<212> TYPE: PRT
<213> ORGANISM: Artificial Sequence
<220> FEATURE:
<223> OTHER INFORMATION: IL-17A binder G2_1

<400> SEQUENCE: 11

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu Thr Ser
20 25 30

Asp Leu Arg Met Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 12
<211> LENGTH: 65
<212> TYPE: PRT
<213> ORGANISM: Artificial Sequence
<220> FEATURE:
<223> OTHER INFORMATION: IL-17A binder G4_1

<400> SEQUENCE: 12

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu Pro Asp
20 25 30

Gln Leu Pro Pro Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 13
<211> LENGTH: 65
<212> TYPE: PRT
<213> ORGANISM: Artificial Sequence
<220> FEATURE:
<223> OTHER INFORMATION: IL-17A binder H5

<400> SEQUENCE: 13

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu Phe Ser
20 25 30

Ser Tyr Thr Gln Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 14

```
<211> LENGTH: 65
<212> TYPE: PRT
<213> ORGANISM: Artificial Sequence
<220> FEATURE:
<223> OTHER INFORMATION: IL-17A binder B1_1

<400> SEQUENCE: 14

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Ala
            20                  25                  30

Ala Glu Pro Phe Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 15
<211> LENGTH: 65
<212> TYPE: PRT
<213> ORGANISM: Artificial Sequence
<220> FEATURE:
<223> OTHER INFORMATION: IL-17A binder B6

<400> SEQUENCE: 15

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Asn Met
            20                  25                  30

Pro Gln Asp Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 16
<211> LENGTH: 65
<212> TYPE: PRT
<213> ORGANISM: Artificial Sequence
<220> FEATURE:
<223> OTHER INFORMATION: IL-17A binder E6_1

<400> SEQUENCE: 16

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Glu Ser
            20                  25                  30

Asp Arg Asn Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 17
<211> LENGTH: 65
<212> TYPE: PRT
<213> ORGANISM: Artificial Sequence
<220> FEATURE:
```

-continued

<223> OTHER INFORMATION: IL-17A binder A7_1

<400> SEQUENCE: 17

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu Ser Asp
20 25 30

Thr Asp Arg Thr Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 18
<211> LENGTH: 65
<212> TYPE: PRT
<213> ORGANISM: Artificial Sequence
<220> FEATURE:
<223> OTHER INFORMATION: IL-17A binder C1_1

<400> SEQUENCE: 18

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu His Ser
20 25 30

Pro Thr Gln Pro Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 19
<211> LENGTH: 65
<212> TYPE: PRT
<213> ORGANISM: Artificial Sequence
<220> FEATURE:
<223> OTHER INFORMATION: IL-17A binder C4_1

<400> SEQUENCE: 19

Gly Val Thr Leu Phe Val Ala Leu Tyr Asp Tyr Val Ala Phe Trp Pro
1 5 10 15

Gly Asp Leu Ser Phe His Lys Gly Glu Lys Phe Gln Ile Leu Thr Ile
20 25 30

Pro Asn Asp Ala Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 20
<211> LENGTH: 65
<212> TYPE: PRT
<213> ORGANISM: Artificial Sequence
<220> FEATURE:
<223> OTHER INFORMATION: IL-17A binder E2_1

<400> SEQUENCE: 20

```
Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Pro Phe
            20                  25                  30

Gln Asp Ser Val Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 21
<211> LENGTH: 65
<212> TYPE: PRT
<213> ORGANISM: Artificial Sequence
<220> FEATURE:
<223> OTHER INFORMATION: IL-17A binder E5

<400> SEQUENCE: 21

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Thr Pro
            20                  25                  30

Gln Leu Pro Val Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 22
<211> LENGTH: 65
<212> TYPE: PRT
<213> ORGANISM: Artificial Sequence
<220> FEATURE:
<223> OTHER INFORMATION: IL-17A binder E7

<400> SEQUENCE: 22

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Ala
            20                  25                  30

His Gln Leu Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 23
<211> LENGTH: 65
<212> TYPE: PRT
<213> ORGANISM: Artificial Sequence
<220> FEATURE:
<223> OTHER INFORMATION: IL-17A binder H4

<400> SEQUENCE: 23

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser His
```

```
            20                  25                  30

Asp Gln Met Phe Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 24
<211> LENGTH: 65
<212> TYPE: PRT
<213> ORGANISM: Artificial Sequence
<220> FEATURE:
<223> OTHER INFORMATION: IL-17A binder F1_1

<400> SEQUENCE: 24

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu His Trp
            20                  25                  30

Gly Gly His Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 25
<211> LENGTH: 65
<212> TYPE: PRT
<213> ORGANISM: Artificial Sequence
<220> FEATURE:
<223> OTHER INFORMATION: IL-17A binder B3_2

<400> SEQUENCE: 25

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu His Thr
            20                  25                  30

Leu Pro Thr Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 26
<211> LENGTH: 65
<212> TYPE: PRT
<213> ORGANISM: Artificial Sequence
<220> FEATURE:
<223> OTHER INFORMATION: IL-17A binder B4_1

<400> SEQUENCE: 26

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Gly
            20                  25                  30

Pro Gln Tyr Ala Gly Asp Trp Trp Glu Ala Arg Ser Leu Thr Thr Gly
        35                  40                  45
```

```
Glu Thr Gly Tyr Ile Pro Ser Asn Tyr Val Ala Pro Val Asp Ser Ile
    50                  55                  60

Gln
65


<210> SEQ ID NO 27
<211> LENGTH: 65
<212> TYPE: PRT
<213> ORGANISM: Artificial Sequence
<220> FEATURE:
<223> OTHER INFORMATION: IL-17A binder C2_2

<400> SEQUENCE: 27

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Pro His
            20                  25                  30

Lys Met Asn Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 28
<211> LENGTH: 65
<212> TYPE: PRT
<213> ORGANISM: Artificial Sequence
<220> FEATURE:
<223> OTHER INFORMATION: IL-17A binder D2_2

<400> SEQUENCE: 28

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Arg Pro
            20                  25                  30

Thr Ile Pro Pro Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 29
<211> LENGTH: 65
<212> TYPE: PRT
<213> ORGANISM: Artificial Sequence
<220> FEATURE:
<223> OTHER INFORMATION: IL-17A binder D3_1

<400> SEQUENCE: 29

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Val Ser
            20                  25                  30

Asn Gln Thr Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60
```

Gln
65

<210> SEQ ID NO 30
<211> LENGTH: 65
<212> TYPE: PRT
<213> ORGANISM: Artificial Sequence
<220> FEATURE:
<223> OTHER INFORMATION: IL-17A binder G4_2

<400> SEQUENCE: 30

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 31
<211> LENGTH: 65
<212> TYPE: PRT
<213> ORGANISM: Artificial Sequence
<220> FEATURE:
<223> OTHER INFORMATION: IL-17A binder B2_1

<400> SEQUENCE: 31

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Pro
            20                  25                  30

Gln Pro Ile Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 32
<211> LENGTH: 65
<212> TYPE: PRT
<213> ORGANISM: Artificial Sequence
<220> FEATURE:
<223> OTHER INFORMATION: IL-17A binder A1_1

<400> SEQUENCE: 32

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Ser
            20                  25                  30

Pro Lys Tyr Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 33
<211> LENGTH: 65
<212> TYPE: PRT
<213> ORGANISM: Artificial Sequence
<220> FEATURE:
<223> OTHER INFORMATION: IL-17A binder B5_1

<400> SEQUENCE: 33

```
Gly Val Thr Leu Phe Val Ala Leu Tyr Asp Tyr Gln Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 34
<211> LENGTH: 65
<212> TYPE: PRT
<213> ORGANISM: Artificial Sequence
<220> FEATURE:
<223> OTHER INFORMATION: IL-17A binder B8

<400> SEQUENCE: 34

```
Gly Val Thr Leu Phe Val Ala Leu Tyr Asp Tyr Ser Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 35
<211> LENGTH: 65
<212> TYPE: PRT
<213> ORGANISM: Artificial Sequence
<220> FEATURE:
<223> OTHER INFORMATION: IL-17A binder C4_2

<400> SEQUENCE: 35

```
Glu Val Thr Leu Phe Val Ala Leu Tyr Asp Tyr Thr Ala Phe Trp Pro
1               5                   10                  15

Gly Asp Leu Ser Phe His Lys Gly Glu Lys Phe Gln Ile Leu Pro His
            20                  25                  30

Lys Met Asn Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 36
<211> LENGTH: 65
<212> TYPE: PRT
<213> ORGANISM: Artificial Sequence

```
<220> FEATURE:
<223> OTHER INFORMATION: IL-17A binder F3_1

<400> SEQUENCE: 36

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 37
<211> LENGTH: 65
<212> TYPE: PRT
<213> ORGANISM: Artificial Sequence
<220> FEATURE:
<223> OTHER INFORMATION: IL-17A binder G3

<400> SEQUENCE: 37

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu His Thr
            20                  25                  30

Leu Pro Thr Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 38
<211> LENGTH: 63
<212> TYPE: PRT
<213> ORGANISM: Artificial Sequence
<220> FEATURE:
<223> OTHER INFORMATION: IL-17A binder D3_2

<400> SEQUENCE: 38

Gly Val Thr Leu Phe Val Ala Leu Tyr Asp Tyr Trp Ser Pro Trp Pro
1               5                   10                  15

Ala Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 39
<211> LENGTH: 63
<212> TYPE: PRT
<213> ORGANISM: Artificial Sequence
<220> FEATURE:
<223> OTHER INFORMATION: IL-17A binder D5

<400> SEQUENCE: 39

Gly Val Thr Leu Phe Val Ala Leu Tyr Asp Tyr His Ser Pro Phe Thr
1               5                   10                  15
```

```
Phe Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 40
<211> LENGTH: 63
<212> TYPE: PRT
<213> ORGANISM: Artificial Sequence
<220> FEATURE:
<223> OTHER INFORMATION: IL-17A binder D2_3

<400> SEQUENCE: 40

Gly Val Thr Leu Phe Val Ala Leu Tyr Asp Tyr Gln Ala Phe Trp Pro
1               5                   10                  15

Glu Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 41
<211> LENGTH: 63
<212> TYPE: PRT
<213> ORGANISM: Artificial Sequence
<220> FEATURE:
<223> OTHER INFORMATION: IL-17A binder A3_1

<400> SEQUENCE: 41

Gly Val Thr Leu Phe Val Ala Leu Tyr Asp Tyr Gln Ala Phe Trp Pro
1               5                   10                  15

Gly Asp Leu Ser Phe His Lys Gly Glu Lys Phe Gln Ile Leu Gln Pro
            20                  25                  30

His Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 42
<211> LENGTH: 63
<212> TYPE: PRT
<213> ORGANISM: Artificial Sequence
<220> FEATURE:
<223> OTHER INFORMATION: IL-17A binder B1_2

<400> SEQUENCE: 42

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 43
<211> LENGTH: 63
```

<212> TYPE: PRT
<213> ORGANISM: Artificial Sequence
<220> FEATURE:
<223> OTHER INFORMATION: IL-17A binder D3_3

<400> SEQUENCE: 43

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Glu Pro
            20                  25                  30

Thr Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 44
<211> LENGTH: 63
<212> TYPE: PRT
<213> ORGANISM: Artificial Sequence
<220> FEATURE:
<223> OTHER INFORMATION: IL-17A binder E2_2

<400> SEQUENCE: 44

```
Gly Val Thr Leu Phe Val Ala Leu Tyr Asp Tyr Thr Ala Phe Trp Pro
1               5                   10                  15

Gly Asp Leu Ser Phe His Lys Gly Glu Lys Phe Gln Ile Leu Thr Val
            20                  25                  30

Tyr Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 45
<211> LENGTH: 63
<212> TYPE: PRT
<213> ORGANISM: Artificial Sequence
<220> FEATURE:
<223> OTHER INFORMATION: IL-17A binder F4

<400> SEQUENCE: 45

```
Gly Val Thr Leu Phe Val Ala Leu Tyr Asp Tyr Thr Ala Phe Trp Pro
1               5                   10                  15

Gly Asp Leu Ser Phe His Lys Gly Glu Lys Phe Gln Ile Leu Ser Asp
            20                  25                  30

Phe Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 46
<211> LENGTH: 63
<212> TYPE: PRT
<213> ORGANISM: Artificial Sequence
<220> FEATURE:
<223> OTHER INFORMATION: IL-17A binder A6_1

<400> SEQUENCE: 46

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Thr Pro
            20                  25                  30
```

```
Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 47
<211> LENGTH: 63
<212> TYPE: PRT
<213> ORGANISM: Artificial Sequence
<220> FEATURE:
<223> OTHER INFORMATION: IL-17A binder B10

<400> SEQUENCE: 47

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Gln Phe
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 48
<211> LENGTH: 63
<212> TYPE: PRT
<213> ORGANISM: Artificial Sequence
<220> FEATURE:
<223> OTHER INFORMATION: IL-17A binder B12

<400> SEQUENCE: 48

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Ala Tyr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 49
<211> LENGTH: 63
<212> TYPE: PRT
<213> ORGANISM: Artificial Sequence
<220> FEATURE:
<223> OTHER INFORMATION: IL-17A binder C5_1

<400> SEQUENCE: 49

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Tyr Ile
            20                  25                  30

Ser Asp Gly Asp Trp Trp Lys Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 50
<211> LENGTH: 63
<212> TYPE: PRT
<213> ORGANISM: Artificial Sequence
<220> FEATURE:
<223> OTHER INFORMATION: IL-17A binder D12
```

<400> SEQUENCE: 50

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Gln Tyr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 51
<211> LENGTH: 63
<212> TYPE: PRT
<213> ORGANISM: Artificial Sequence
<220> FEATURE:
<223> OTHER INFORMATION: IL-17A binder D2_4

<400> SEQUENCE: 51

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Lys Tyr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 52
<211> LENGTH: 63
<212> TYPE: PRT
<213> ORGANISM: Artificial Sequence
<220> FEATURE:
<223> OTHER INFORMATION: IL-17A binder B2_2

<400> SEQUENCE: 52

Gly Val Thr Leu Phe Val Ala Leu Tyr Asp Tyr Leu Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 53
<211> LENGTH: 63
<212> TYPE: PRT
<213> ORGANISM: Artificial Sequence
<220> FEATURE:
<223> OTHER INFORMATION: IL-17A binder D2_5

<400> SEQUENCE: 53

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln 50 55 60

<210> SEQ ID NO 54
<211> LENGTH: 63
<212> TYPE: PRT
<213> ORGANISM: Artificial Sequence
<220> FEATURE:
<223> OTHER INFORMATION: IL-17A binder D7_1

<400> SEQUENCE: 54

Gly Val Thr Leu Phe Val Ala Leu Tyr Asp Tyr Ile Ala Phe Trp Pro
1 5 10 15

Gly Asp Leu Ser Phe His Lys Gly Glu Lys Phe Gln Ile Leu Arg Thr
20 25 30

Ser Asp Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 55
<211> LENGTH: 63
<212> TYPE: PRT
<213> ORGANISM: Artificial Sequence
<220> FEATURE:
<223> OTHER INFORMATION: IL-17A binder C11

<400> SEQUENCE: 55

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Ile Ala Arg Ser Leu Thr Thr Gly Glu Gln
35 40 45

Gly Tyr Ile Pro Ser Asn Tyr Val Ala Pro Val Asp Ser Ile Gln
50 55 60

<210> SEQ ID NO 56
<211> LENGTH: 63
<212> TYPE: PRT
<213> ORGANISM: Artificial Sequence
<220> FEATURE:
<223> OTHER INFORMATION: IL-17A binder A1_2

<400> SEQUENCE: 56

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Ile Ala Arg Ser Leu Thr Thr Gly Glu Ser
35 40 45

Gly Tyr Ile Pro Ser Asn Tyr Val Ala Pro Val Asp Ser Ile Gln
50 55 60

<210> SEQ ID NO 57
<211> LENGTH: 63
<212> TYPE: PRT
<213> ORGANISM: Artificial Sequence
<220> FEATURE:
<223> OTHER INFORMATION: IL-17A binder B7_1

<400> SEQUENCE: 57

Gly Val Thr Leu Phe Val Ala Leu Tyr Asp Tyr Lys Ala Phe Trp Pro

```
1               5                   10                  15

Gly Asp Leu Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60


<210> SEQ ID NO 58
<211> LENGTH: 63
<212> TYPE: PRT
<213> ORGANISM: Artificial Sequence
<220> FEATURE:
<223> OTHER INFORMATION: IL-17A binder B5_2

<400> SEQUENCE: 58

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60


<210> SEQ ID NO 59
<211> LENGTH: 63
<212> TYPE: PRT
<213> ORGANISM: Artificial Sequence
<220> FEATURE:
<223> OTHER INFORMATION: IL-17A binder H11_1

<400> SEQUENCE: 59

Gly Val Thr Leu Phe Val Ala Leu Tyr Asp Tyr Lys Ala Phe Trp Pro
1               5                   10                  15

Gly Asp Val Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60


<210> SEQ ID NO 60
<211> LENGTH: 63
<212> TYPE: PRT
<213> ORGANISM: Artificial Sequence
<220> FEATURE:
<223> OTHER INFORMATION: IL-17A binder E4

<400> SEQUENCE: 60

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 61
```

<211> LENGTH: 63
<212> TYPE: PRT
<213> ORGANISM: Artificial Sequence
<220> FEATURE:
<223> OTHER INFORMATION: IL-17A binder F3_2

<400> SEQUENCE: 61

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Glu Ala Arg Ser Leu Thr Thr Gly Glu Glu
35 40 45

Gly Tyr Ile Pro Ser Asn Tyr Val Ala Pro Val Asp Ser Ile Gln
50 55 60

<210> SEQ ID NO 62
<211> LENGTH: 63
<212> TYPE: PRT
<213> ORGANISM: Artificial Sequence
<220> FEATURE:
<223> OTHER INFORMATION: IL-17A binder A3_2

<400> SEQUENCE: 62

Gly Val Thr Leu Phe Val Ala Leu Tyr Asp Tyr Lys Ala Phe Trp Pro
1 5 10 15

Gly Asp Ile Ser Phe His Lys Gly Glu Lys Phe Gln Ile Leu Arg Thr
20 25 30

Ser Asp Gly Glu Trp Trp Met Ala Arg Ser Leu Thr Thr Gly Glu Val
35 40 45

Gly Tyr Ile Pro Ser Asn Tyr Val Ala Pro Val Asp Ser Ile Gln
50 55 60

<210> SEQ ID NO 63
<211> LENGTH: 63
<212> TYPE: PRT
<213> ORGANISM: Artificial Sequence
<220> FEATURE:
<223> OTHER INFORMATION: IL-17A binder A5_2

<400> SEQUENCE: 63

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Asp Trp Trp Val Ala Arg Ser Leu Thr Thr Gly Glu Asp
35 40 45

Gly Tyr Ile Pro Ser Asn Tyr Val Ala Pro Val Asp Ser Ile Gln
50 55 60

<210> SEQ ID NO 64
<211> LENGTH: 63
<212> TYPE: PRT
<213> ORGANISM: Artificial Sequence
<220> FEATURE:
<223> OTHER INFORMATION: IL-17A binder A8

<400> SEQUENCE: 64

Gly Val Thr Leu Phe Val Ala Leu Tyr Asp Tyr Lys Ala Phe Trp Pro
1 5 10 15

Gly Asp Ile Ser Phe His Lys Gly Glu Lys Phe Gln Ile Leu Arg Thr
20 25 30

```
Ser Asp Gly Asp Trp Trp Tyr Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60


<210> SEQ ID NO 65
<211> LENGTH: 63
<212> TYPE: PRT
<213> ORGANISM: Artificial Sequence
<220> FEATURE:
<223> OTHER INFORMATION: IL-17A binder H10

<400> SEQUENCE: 65

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60


<210> SEQ ID NO 66
<211> LENGTH: 63
<212> TYPE: PRT
<213> ORGANISM: Artificial Sequence
<220> FEATURE:
<223> OTHER INFORMATION: IL-17A binder A9

<400> SEQUENCE: 66

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Phe Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60


<210> SEQ ID NO 67
<211> LENGTH: 63
<212> TYPE: PRT
<213> ORGANISM: Artificial Sequence
<220> FEATURE:
<223> OTHER INFORMATION: IL-17A binder B2_3

<400> SEQUENCE: 67

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Phe Ala Arg Ser Leu Thr Thr Gly Gly Asp
        35                  40                  45

Gly Tyr Ile Pro Ser Asn Tyr Val Ala Pro Val Asp Ser Ile Gln
    50                  55                  60


<210> SEQ ID NO 68
<211> LENGTH: 63
<212> TYPE: PRT
<213> ORGANISM: Artificial Sequence
<220> FEATURE:
```

<223> OTHER INFORMATION: IL-17A binder A7_2

<400> SEQUENCE: 68

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Phe Ala Arg Ser Leu Thr Thr Gly Glu Gly
35 40 45

Gly Tyr Ile Pro Ser Asn Tyr Val Ala Pro Val Asp Ser Ile Gln
50 55 60

<210> SEQ ID NO 69
<211> LENGTH: 63
<212> TYPE: PRT
<213> ORGANISM: Artificial Sequence
<220> FEATURE:
<223> OTHER INFORMATION: IL-17A binder C2_3

<400> SEQUENCE: 69

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Phe Ala Arg Ser Leu Thr Thr Gly Glu Asp
35 40 45

Gly Tyr Ile Pro Ser Asn Tyr Val Ala Pro Val Asp Ser Ile Gln
50 55 60

<210> SEQ ID NO 70
<211> LENGTH: 63
<212> TYPE: PRT
<213> ORGANISM: Artificial Sequence
<220> FEATURE:
<223> OTHER INFORMATION: IL-17A binder A3_3

<400> SEQUENCE: 70

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Val Ala Arg Ser Leu Thr Thr Gly Glu Ala
35 40 45

Gly Tyr Ile Pro Ser Asn Tyr Val Ala Pro Val Asp Ser Ile Gln
50 55 60

<210> SEQ ID NO 71
<211> LENGTH: 63
<212> TYPE: PRT
<213> ORGANISM: Artificial Sequence
<220> FEATURE:
<223> OTHER INFORMATION: IL-17A binder C1_2

<400> SEQUENCE: 71

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Leu Ala Arg Ser Leu Thr Thr Gly Glu Ala
35 40 45

Gly Tyr Ile Pro Ser Asn Tyr Val Ala Pro Val Asp Ser Ile Gln
    50                  55                  60

<210> SEQ ID NO 72
<211> LENGTH: 63
<212> TYPE: PRT
<213> ORGANISM: Artificial Sequence
<220> FEATURE:
<223> OTHER INFORMATION: IL-17A binder E9

<400> SEQUENCE: 72

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Phe Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60

<210> SEQ ID NO 73
<211> LENGTH: 63
<212> TYPE: PRT
<213> ORGANISM: Artificial Sequence
<220> FEATURE:
<223> OTHER INFORMATION: IL-17A binder D1

<400> SEQUENCE: 73

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ser Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 74
<211> LENGTH: 63
<212> TYPE: PRT
<213> ORGANISM: Artificial Sequence
<220> FEATURE:
<223> OTHER INFORMATION: IL-17A binder B3_3

<400> SEQUENCE: 74

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 75
<211> LENGTH: 63
<212> TYPE: PRT
<213> ORGANISM: Artificial Sequence
<220> FEATURE:
<223> OTHER INFORMATION: IL-17A binder A12

<400> SEQUENCE: 75

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Thr Leu
            20                  25                  30

Ser Asp Gly Glu Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 76
<211> LENGTH: 63
<212> TYPE: PRT
<213> ORGANISM: Artificial Sequence
<220> FEATURE:
<223> OTHER INFORMATION: IL-17A binder H3

<400> SEQUENCE: 76

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Leu Glu
            20                  25                  30

Ser Asp Gly Ser Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 77
<211> LENGTH: 63
<212> TYPE: PRT
<213> ORGANISM: Artificial Sequence
<220> FEATURE:
<223> OTHER INFORMATION: IL-17A binder H9

<400> SEQUENCE: 77

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Gln Val
            20                  25                  30

Ser Asp Gly Glu Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 78
<211> LENGTH: 63
<212> TYPE: PRT
<213> ORGANISM: Artificial Sequence
<220> FEATURE:
<223> OTHER INFORMATION: IL-17A binder F1_2

<400> SEQUENCE: 78

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Lys
        35                  40                  45

Gly Tyr Ile Pro Ser Asn Tyr Val Ala Pro Val Asp Ser Ile Gln
    50                  55                  60
```

<210> SEQ ID NO 79
<211> LENGTH: 63
<212> TYPE: PRT
<213> ORGANISM: Artificial Sequence
<220> FEATURE:
<223> OTHER INFORMATION: IL-17A binder F10

<400> SEQUENCE: 79

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 80
<211> LENGTH: 63
<212> TYPE: PRT
<213> ORGANISM: Artificial Sequence
<220> FEATURE:
<223> OTHER INFORMATION: IL-17A binder C5_2

<400> SEQUENCE: 80

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Tyr
        35                  40                  45

Gly Tyr Ile Pro Ser Asn Tyr Val Ala Pro Val Asp Ser Ile Gln
    50                  55                  60
```

<210> SEQ ID NO 81
<211> LENGTH: 63
<212> TYPE: PRT
<213> ORGANISM: Artificial Sequence
<220> FEATURE:
<223> OTHER INFORMATION: IL-17A binder D7_2

<400> SEQUENCE: 81

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Tyr
        35                  40                  45

Gly Tyr Ile Pro Ser Asn Tyr Val Ala Pro Val Asp Ser Ile Gln
    50                  55                  60
```

<210> SEQ ID NO 82
<211> LENGTH: 63
<212> TYPE: PRT
<213> ORGANISM: Artificial Sequence
<220> FEATURE:
<223> OTHER INFORMATION: IL-17A binder C2_4

<400> SEQUENCE: 82

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
```

```
            20                  25                  30

Ser Asp Gly Asp Trp Trp Glu Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60


<210> SEQ ID NO 83
<211> LENGTH: 63
<212> TYPE: PRT
<213> ORGANISM: Artificial Sequence
<220> FEATURE:
<223> OTHER INFORMATION: IL-17A binder E3_1

<400> SEQUENCE: 83

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Ala Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 84
<211> LENGTH: 63
<212> TYPE: PRT
<213> ORGANISM: Artificial Sequence
<220> FEATURE:
<223> OTHER INFORMATION: IL-17A binder A11

<400> SEQUENCE: 84

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 85
<211> LENGTH: 63
<212> TYPE: PRT
<213> ORGANISM: Artificial Sequence
<220> FEATURE:
<223> OTHER INFORMATION: IL-17A binder B4_2

<400> SEQUENCE: 85

Gly Val Thr Leu Phe Val Ala Leu Tyr Asp Tyr Lys Ala Phe Trp Pro
1               5                   10                  15

Gly Asp Val Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Tyr
        35                  40                  45

Gly Tyr Ile Pro Ser Asn Tyr Val Ala Pro Val Asp Ser Ile Gln
    50                  55                  60


<210> SEQ ID NO 86
<211> LENGTH: 63
<212> TYPE: PRT
<213> ORGANISM: Artificial Sequence
```

<220> FEATURE:
<223> OTHER INFORMATION: IL-17A binder D10

<400> SEQUENCE: 86

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Ser Ala Arg Ser Leu Thr Thr Gly Glu Val
35 40 45

Gly Tyr Ile Pro Ser Asn Tyr Val Ala Pro Val Asp Ser Ile Gln
50 55 60

<210> SEQ ID NO 87
<211> LENGTH: 63
<212> TYPE: PRT
<213> ORGANISM: Artificial Sequence
<220> FEATURE:
<223> OTHER INFORMATION: IL-17A binder E6_2

<400> SEQUENCE: 87

Gly Val Thr Leu Phe Val Ala Leu Tyr Asp Tyr Lys Ala Phe Trp Pro
1 5 10 15

Gly Asp Ile Ser Phe His Lys Gly Glu Lys Phe Gln Ile Leu Arg Thr
20 25 30

Ser Asp Gly Leu Trp Trp Phe Ala Arg Ser Leu Thr Thr Gly Glu Asp
35 40 45

Gly Tyr Ile Pro Ser Asn Tyr Val Ala Pro Val Asp Ser Ile Gln
50 55 60

<210> SEQ ID NO 88
<211> LENGTH: 63
<212> TYPE: PRT
<213> ORGANISM: Artificial Sequence
<220> FEATURE:
<223> OTHER INFORMATION: IL-17A binder H11_2

<400> SEQUENCE: 88

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Glu Trp Trp Glu Ala Arg Ser Leu Thr Thr Gly Glu Glu
35 40 45

Gly Tyr Ile Pro Ser Asn Tyr Val Ala Pro Val Asp Ser Ile Gln
50 55 60

<210> SEQ ID NO 89
<211> LENGTH: 63
<212> TYPE: PRT
<213> ORGANISM: Artificial Sequence
<220> FEATURE:
<223> OTHER INFORMATION: IL-17A binder A5_3

<400> SEQUENCE: 89

Gly Val Thr Leu Phe Val Ala Leu Tyr Asp Tyr Lys Ala Phe Trp Pro
1 5 10 15

Gly Asp Leu Ser Phe His Lys Gly Glu Lys Phe Gln Ile Leu Arg Thr
20 25 30

Ser Asp Gly Asn Trp Trp Glu Ala Arg Ser Leu Thr Thr Gly Glu Ala
35 40 45

```
Gly Tyr Ile Pro Ser Asn Tyr Val Ala Pro Val Asp Ser Ile Gln
    50                  55                  60


<210> SEQ ID NO 90
<211> LENGTH: 63
<212> TYPE: PRT
<213> ORGANISM: Artificial Sequence
<220> FEATURE:
<223> OTHER INFORMATION: IL-17A binder F12

<400> SEQUENCE: 90

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Asp Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60


<210> SEQ ID NO 91
<211> LENGTH: 63
<212> TYPE: PRT
<213> ORGANISM: Artificial Sequence
<220> FEATURE:
<223> OTHER INFORMATION: IL-17A binder B7_2

<400> SEQUENCE: 91

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Val Ala Arg Ser Leu Thr Thr Gly Glu Asp
        35                  40                  45

Gly Tyr Ile Pro Ser Asn Tyr Val Ala Pro Val Asp Ser Ile Gln
    50                  55                  60


<210> SEQ ID NO 92
<211> LENGTH: 63
<212> TYPE: PRT
<213> ORGANISM: Artificial Sequence
<220> FEATURE:
<223> OTHER INFORMATION: IL-17A binder G2_2

<400> SEQUENCE: 92

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Gly
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 93
<211> LENGTH: 63
<212> TYPE: PRT
<213> ORGANISM: Artificial Sequence
<220> FEATURE:
<223> OTHER INFORMATION: IL-17A binder C5_3

<400> SEQUENCE: 93
```

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Tyr Trp Trp Glu Ala Arg Ser Leu Thr Thr Gly Glu Asn
        35                  40                  45

Gly Tyr Ile Pro Ser Asn Tyr Val Ala Pro Val Asp Ser Ile Gln
    50                  55                  60


<210> SEQ ID NO 94
<211> LENGTH: 63
<212> TYPE: PRT
<213> ORGANISM: Artificial Sequence
<220> FEATURE:
<223> OTHER INFORMATION: IL-17A binder G11

<400> SEQUENCE: 94

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Thr Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 95
<211> LENGTH: 63
<212> TYPE: PRT
<213> ORGANISM: Artificial Sequence
<220> FEATURE:
<223> OTHER INFORMATION: IL-17A binder F5

<400> SEQUENCE: 95

Gly Val Thr Leu Phe Val Ala Leu Tyr Asp Tyr Lys Ala Phe Trp Pro
1               5                   10                  15

Gly Asp Met Ser Phe His Lys Gly Glu Lys Phe Gln Ile Leu Arg Thr
            20                  25                  30

Ser Asp Gly Ile Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 96
<211> LENGTH: 63
<212> TYPE: PRT
<213> ORGANISM: Artificial Sequence
<220> FEATURE:
<223> OTHER INFORMATION: IL-17A binder D3_4

<400> SEQUENCE: 96

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Gln Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 97
<211> LENGTH: 63
<212> TYPE: PRT
<213> ORGANISM: Artificial Sequence
<220> FEATURE:
<223> OTHER INFORMATION: IL-17A binder F9

<400> SEQUENCE: 97

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Ala Trp Trp Met Ala Arg Ser Leu Thr Thr Gly Glu Asn
        35                  40                  45

Gly Tyr Ile Pro Ser Asn Tyr Val Ala Pro Val Asp Ser Ile Gln
    50                  55                  60
```

<210> SEQ ID NO 98
<211> LENGTH: 63
<212> TYPE: PRT
<213> ORGANISM: Artificial Sequence
<220> FEATURE:
<223> OTHER INFORMATION: IL-17A binder F1_3

<400> SEQUENCE: 98

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Tyr Ala Arg Ser Leu Thr Thr Gly Glu Lys
        35                  40                  45

Gly Tyr Ile Pro Ser Asn Tyr Val Ala Pro Val Asp Ser Ile Gln
    50                  55                  60
```

<210> SEQ ID NO 99
<211> LENGTH: 63
<212> TYPE: PRT
<213> ORGANISM: Artificial Sequence
<220> FEATURE:
<223> OTHER INFORMATION: IL-17A binder A4

<400> SEQUENCE: 99

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Glu Gly
            20                  25                  30

Ser Trp Gly Glu Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 100
<211> LENGTH: 63
<212> TYPE: PRT
<213> ORGANISM: Artificial Sequence
<220> FEATURE:
<223> OTHER INFORMATION: IL-17A binder G5

<400> SEQUENCE: 100

```
Gly Val Thr Leu Phe Val Ala Leu Tyr Asp Tyr Lys Ala Phe Trp Pro
1               5                   10                  15
```

```
Gly Asp Leu Ser Phe His Lys Gly Glu Lys Phe Ala Ile Thr Arg Thr
            20                  25                  30

Ser Asp Gly Asp Trp Trp Glu Ala Val Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 101
<211> LENGTH: 63
<212> TYPE: PRT
<213> ORGANISM: Artificial Sequence
<220> FEATURE:
<223> OTHER INFORMATION: IL-17A binder A6_2

<400> SEQUENCE: 101

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Lys Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 102
<211> LENGTH: 63
<212> TYPE: PRT
<213> ORGANISM: Artificial Sequence
<220> FEATURE:
<223> OTHER INFORMATION: IL-17A binder D2_6

<400> SEQUENCE: 102

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Thr Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 103
<211> LENGTH: 63
<212> TYPE: PRT
<213> ORGANISM: Artificial Sequence
<220> FEATURE:
<223> OTHER INFORMATION: IL-17A binder G4_3

<400> SEQUENCE: 103

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Leu Ile Thr Arg Thr
            20                  25                  30

Ser Asp Gly Glu Trp Trp Val Ala Val Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 104
<211> LENGTH: 63
<212> TYPE: PRT
```

<213> ORGANISM: Artificial Sequence
<220> FEATURE:
<223> OTHER INFORMATION: IL-17A binder E3_2

<400> SEQUENCE: 104

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Glu Ile Val Arg Thr
            20                  25                  30

Ser Asp Gly Glu Trp Trp Val Ala Phe Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 105
<211> LENGTH: 63
<212> TYPE: PRT
<213> ORGANISM: Artificial Sequence
<220> FEATURE:
<223> OTHER INFORMATION: IL-17A binder B4_3

<400> SEQUENCE: 105

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Leu Ile Leu Arg Thr
            20                  25                  30

Ser Asp Gly Glu Trp Trp Val Ala Gln Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 106
<211> LENGTH: 63
<212> TYPE: PRT
<213> ORGANISM: Artificial Sequence
<220> FEATURE:
<223> OTHER INFORMATION: IL-17A binder C4_3

<400> SEQUENCE: 106

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe His Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 107
<211> LENGTH: 63
<212> TYPE: PRT
<213> ORGANISM: Artificial Sequence
<220> FEATURE:
<223> OTHER INFORMATION: IL-17A binder C9

<400> SEQUENCE: 107

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Phe Ile Leu Arg Thr
            20                  25                  30

Ser Asp Gly Glu Trp Trp Val Ala Gln Ser Leu Thr Thr Gly Glu Glu
```

-continued

```
        35                  40                  45

Gly Tyr Ile Pro Ser Asn Tyr Val Ala Pro Val Asp Ser Ile Gln
    50                  55                  60


<210> SEQ ID NO 108
<211> LENGTH: 63
<212> TYPE: PRT
<213> ORGANISM: Artificial Sequence
<220> FEATURE:
<223> OTHER INFORMATION: IL-17A binder E1_2

<400> SEQUENCE: 108

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ile Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 109
<211> LENGTH: 63
<212> TYPE: PRT
<213> ORGANISM: Artificial Sequence
<220> FEATURE:
<223> OTHER INFORMATION: IL-17A binder H2

<400> SEQUENCE: 109

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Arg Ile Lys Arg Thr
            20                  25                  30

Ser Asp Gly Glu Trp Trp Val Ala Val Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 110
<211> LENGTH: 63
<212> TYPE: PRT
<213> ORGANISM: Artificial Sequence
<220> FEATURE:
<223> OTHER INFORMATION: IL-17A binder 2C1

<400> SEQUENCE: 110

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 111
<211> LENGTH: 63
<212> TYPE: PRT
<213> ORGANISM: Artificial Sequence
<220> FEATURE:
<223> OTHER INFORMATION: IL-17A binder 1E2
```

<400> SEQUENCE: 111

Gly Val Thr Leu Phe Val Ala Leu Tyr Asp Tyr Arg Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 112
<211> LENGTH: 63
<212> TYPE: PRT
<213> ORGANISM: Artificial Sequence
<220> FEATURE:
<223> OTHER INFORMATION: IL-17A binder 1E9

<400> SEQUENCE: 112

Gly Val Thr Leu Phe Val Ala Leu Tyr Asp Tyr Lys Ala Ile Trp Pro
1               5                   10                  15

Thr Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 113
<211> LENGTH: 63
<212> TYPE: PRT
<213> ORGANISM: Artificial Sequence
<220> FEATURE:
<223> OTHER INFORMATION: IL-17A binder 1F3

<400> SEQUENCE: 113

Gly Val Thr Leu Phe Val Ala Leu Tyr Asp Tyr Lys Ala Phe Gly Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 114
<211> LENGTH: 63
<212> TYPE: PRT
<213> ORGANISM: Artificial Sequence
<220> FEATURE:
<223> OTHER INFORMATION: IL-17A binder 2A6

<400> SEQUENCE: 114

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu His Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 115
<211> LENGTH: 63
<212> TYPE: PRT
<213> ORGANISM: Artificial Sequence
<220> FEATURE:
<223> OTHER INFORMATION: IL-17A binder 34D3

<400> SEQUENCE: 115

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Arg Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 116
<211> LENGTH: 63
<212> TYPE: PRT
<213> ORGANISM: Artificial Sequence
<220> FEATURE:
<223> OTHER INFORMATION: IL-17A binder COMB3

<400> SEQUENCE: 116

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 117
<211> LENGTH: 63
<212> TYPE: PRT
<213> ORGANISM: Artificial Sequence
<220> FEATURE:
<223> OTHER INFORMATION: IL-17A binder COMB4

<400> SEQUENCE: 117

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60
```

<210> SEQ ID NO 118
<211> LENGTH: 63
<212> TYPE: PRT
<213> ORGANISM: Artificial Sequence
<220> FEATURE:
<223> OTHER INFORMATION: IL-17A binder COMB5

<400> SEQUENCE: 118

```
Gly Val Thr Leu Phe Val Ala Leu Tyr Asp Tyr Lys Ala Phe Trp Pro
1               5                   10                  15
```

```
Gly Asp Ile Ser Phe His Lys Gly Glu Lys Phe Gln Ile Leu His Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 119
<211> LENGTH: 63
<212> TYPE: PRT
<213> ORGANISM: Artificial Sequence
<220> FEATURE:
<223> OTHER INFORMATION: IL-17A binder COMB6

<400> SEQUENCE: 119

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Lys Ser Leu Thr Thr Gly Glu Glu
        35                  40                  45

Gly Tyr Ile Pro Ser Asn Tyr Val Ala Pro Val Asp Ser Ile Gln
    50                  55                  60


<210> SEQ ID NO 120
<211> LENGTH: 292
<212> TYPE: PRT
<213> ORGANISM: Artificial Sequence
<220> FEATURE:
<223> OTHER INFORMATION: Fusion protein E4-Fc

<400> SEQUENCE: 120

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln Arg
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
```

```
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290


<210> SEQ ID NO 121
<211> LENGTH: 292
<212> TYPE: PRT
<213> ORGANISM: Artificial Sequence
<220> FEATURE:
<223> OTHER INFORMATION: Fusion protein 2C1-Fc

<400> SEQUENCE: 121

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Arg
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
```

```
            260                 265                 270

Met His Glu Ala Leu His Asn His Tyr Thr Gln Lys Ser Leu Ser Leu
        275                 280                 285

Ser Pro Gly Lys
    290


<210> SEQ ID NO 122
<211> LENGTH: 365
<212> TYPE: PRT
<213> ORGANISM: Artificial Sequence
<220> FEATURE:
<223> OTHER INFORMATION: Fusion protein (2C1)_2-Fc

<400> SEQUENCE: 122

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Val Thr Leu Phe Val Ala
65                  70                  75                  80

Leu Tyr Asp Tyr Lys Ala Phe Trp Pro Gly Asp Ile Ser Phe His Lys
                85                  90                  95

Gly Glu Lys Phe Gln Ile Leu Arg Thr Ser Asp Gly Glu Trp Trp Ile
            100                 105                 110

Ala Arg Ser Leu Thr Thr Gly Glu Glu Gly Tyr Ile Pro Ser Asn Tyr
        115                 120                 125

Val Ala Pro Val Asp Ser Ile Gln Arg Ser Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Glu Glu Met Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
```

```
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365


<210> SEQ ID NO 123
<211> LENGTH: 10
<212> TYPE: PRT
<213> ORGANISM: Artificial Sequence
<220> FEATURE:
<223> OTHER INFORMATION: Amino acid linker

<400> SEQUENCE: 123

Gly Gly Gly Gly Ser Gly Gly Gly Gly Ser
1               5                   10


<210> SEQ ID NO 124
<211> LENGTH: 29
<212> TYPE: DNA
<213> ORGANISM: Artificial Sequence
<220> FEATURE:
<223> OTHER INFORMATION: PCR primer fm5

<400> SEQUENCE: 124

atcgggatcc gacaaaactc acacatgcc                                        29


<210> SEQ ID NO 125
<211> LENGTH: 30
<212> TYPE: DNA
<213> ORGANISM: Artificial Sequence
<220> FEATURE:
<223> OTHER INFORMATION: PCR primer fm6

<400> SEQUENCE: 125

tacgaagctt tcatttaccc ggagacaggg                                       30


<210> SEQ ID NO 126
<211> LENGTH: 44
<212> TYPE: DNA
<213> ORGANISM: Artificial Sequence
<220> FEATURE:
<223> OTHER INFORMATION: PCR primer fm7

<400> SEQUENCE: 126

atatcaccat ggggccggag tgacactctt tgtggccctt tatg                       44


<210> SEQ ID NO 127
<211> LENGTH: 31
<212> TYPE: DNA
<213> ORGANISM: Artificial Sequence
<220> FEATURE:
<223> OTHER INFORMATION: PCR primer fm8

<400> SEQUENCE: 127

cgtaggatcc ctggatagag tcaactggag c                                     31


<210> SEQ ID NO 128
<211> LENGTH: 54
<212> TYPE: DNA
<213> ORGANISM: Artificial Sequence
<220> FEATURE:
<223> OTHER INFORMATION: PCR primer 47b.fo

<400> SEQUENCE: 128
```

agagccacct ccgcctgaac cgcctccacc ctggatagag tcaactggag ccac 54

<210> SEQ ID NO 129
<211> LENGTH: 48
<212> TYPE: DNA
<213> ORGANISM: Artificial Sequence
<220> FEATURE:
<223> OTHER INFORMATION: PCR primer 52. ba

<400> SEQUENCE: 129
gactaacgag atcgcggatc cggagtgaca ctctttgtgg ccctttat 48

<210> SEQ ID NO 130
<211> LENGTH: 57
<212> TYPE: DNA
<213> ORGANISM: Artificial Sequence
<220> FEATURE:
<223> OTHER INFORMATION: PCR primer 48b.ba

<400> SEQUENCE: 130
ggtggaggcg gttcaggcgg aggtggctct ggagtgacac tctttgtggc cctttat 57

<210> SEQ ID NO 131
<211> LENGTH: 87
<212> TYPE: DNA
<213> ORGANISM: Artificial Sequence
<220> FEATURE:
<223> OTHER INFORMATION: PCR primer 51. fo

<400> SEQUENCE: 131
atcccaagct tagtgatggt gatggtgatg cagatcctct tctgagatga gtttttgttc 60
accctggata gagtcaactg gagccac 87

<210> SEQ ID NO 132
<211> LENGTH: 145
<212> TYPE: PRT
<213> ORGANISM: Macaca fascicularis

<400> SEQUENCE: 132

```
Gly Ser Ile Val Lys Ala Gly Ile Ala Ile Pro Arg Asn Ser Gly Cys
1               5                   10                  15

Pro Asn Ser Glu Asp Lys Asn Phe Pro Arg Thr Val Met Val Asn Leu
            20                  25                  30

Asn Ile His Asn Arg Asn Thr Ser Thr Asn Pro Lys Arg Ser Ser Asp
        35                  40                  45

Tyr Tyr Asn Arg Ser Thr Ser Pro Trp Asn Leu His Arg Asn Glu Asp
    50                  55                  60

Pro Glu Arg Tyr Pro Ser Val Ile Trp Glu Ala Lys Cys Arg His Leu
65                  70                  75                  80

Gly Cys Val Lys Ala Asp Gly Asn Val Asp Tyr His Met Asn Ser Val
                85                  90                  95

Pro Ile Gln Gln Glu Ile Leu Val Leu Arg Arg Glu Pro Arg His Cys
            100                 105                 110

Pro Asn Ser Phe Arg Leu Glu Lys Ile Leu Val Ser Val Gly Cys Thr
        115                 120                 125

Cys Val Thr Pro Ile Val His His Val Ala Gly His His His His His
    130                 135                 140

His
145
```

<210> SEQ ID NO 133
<211> LENGTH: 292
<212> TYPE: PRT
<213> ORGANISM: Homo sapiens

<400> SEQUENCE: 133

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Arg
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290
```

<210> SEQ ID NO 134
<211> LENGTH: 292
<212> TYPE: PRT
<213> ORGANISM: Artificial sequence
<220> FEATURE:
<223> OTHER INFORMATION: 2C1-Fc(LALA)

<400> SEQUENCE: 134

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30
```

Ser Asp Gly Glu Trp Trp Ile Ala Arg Ser Leu Thr Thr Gly Glu Glu
35 40 45

Gly Tyr Ile Pro Ser Asn Tyr Val Ala Pro Val Asp Ser Ile Gln Arg
50 55 60

Ser Asp Lys Thr His Thr Cys Pro Pro Cys Pro Ala Pro Glu Ala Ala
65 70 75 80

Gly Gly Pro Ser Val Phe Leu Phe Pro Pro Lys Pro Lys Asp Thr Leu
85 90 95

Met Ile Ser Arg Thr Pro Glu Val Thr Cys Val Val Val Asp Val Ser
100 105 110

His Glu Asp Pro Glu Val Lys Phe Asn Trp Tyr Val Asp Gly Val Glu
115 120 125

Val His Asn Ala Lys Thr Lys Pro Arg Glu Glu Gln Tyr Asn Ser Thr
130 135 140

Tyr Arg Val Val Ser Val Leu Thr Val Leu His Gln Asp Trp Leu Asn
145 150 155 160

Gly Lys Glu Tyr Lys Cys Lys Val Ser Asn Lys Ala Leu Pro Ala Pro
165 170 175

Ile Glu Lys Thr Ile Ser Lys Ala Lys Gly Gln Pro Arg Glu Pro Gln
180 185 190

Val Tyr Thr Leu Pro Pro Ser Arg Glu Glu Met Thr Lys Asn Gln Val
195 200 205

Ser Leu Thr Cys Leu Val Lys Gly Phe Tyr Pro Ser Asp Ile Ala Val
210 215 220

Glu Trp Glu Ser Asn Gly Gln Pro Glu Asn Asn Tyr Lys Thr Thr Pro
225 230 235 240

Pro Val Leu Asp Ser Asp Gly Ser Phe Phe Leu Tyr Ser Lys Leu Thr
245 250 255

Val Asp Lys Ser Arg Trp Gln Gln Gly Asn Val Phe Ser Cys Ser Val
260 265 270

Met His Glu Ala Leu His Asn His Tyr Thr Gln Lys Ser Leu Ser Leu
275 280 285

Ser Pro Gly Lys
290

<210> SEQ ID NO 135
<211> LENGTH: 295
<212> TYPE: PRT
<213> ORGANISM: Artificial sequence
<220> FEATURE:
<223> OTHER INFORMATION: 2C1-m5E-Fc(LALA)

<400> SEQUENCE: 135

Gly Val Thr Leu Phe Val Ala Leu Tyr Asp Tyr Lys Ala Phe Trp Pro
1 5 10 15

Gly Asp Ile Ser Phe His Lys Gly Glu Lys Phe Gln Ile Leu Arg Thr
20 25 30

Ser Asp Gly Glu Trp Trp Ile Ala Arg Ser Leu Thr Thr Gly Glu Glu
35 40 45

Gly Tyr Ile Pro Ser Asn Tyr Val Ala Pro Val Asp Ser Ile Gln Glu
50 55 60

Pro Lys Ser Ser Asp Lys Thr His Thr Cys Pro Pro Cys Pro Ala Pro
65 70 75 80

Glu Ala Ala Gly Gly Pro Ser Val Phe Leu Phe Pro Pro Lys Pro Lys
85 90 95

```
Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295


<210> SEQ ID NO 136
<211> LENGTH: 295
<212> TYPE: PRT
<213> ORGANISM: Artificial sequence
<220> FEATURE:
<223> OTHER INFORMATION: 2C1-m5-Fc(LALA)

<400> SEQUENCE: 136

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Asp Lys Thr His Thr Cys Pro Pro Cys Pro Ala Pro
65                  70                  75                  80

Glu Ala Ala Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160
```

```
Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295


<210> SEQ ID NO 137
<211> LENGTH: 300
<212> TYPE: PRT
<213> ORGANISM: Artificial sequence
<220> FEATURE:
<223> OTHER INFORMATION: 2C1-m10-Fc(LALA)

<400> SEQUENCE: 137

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Asp Lys Thr His Thr Cys Pro
65                  70                  75                  80

Pro Cys Pro Ala Pro Glu Ala Ala Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220
```

Phe Tyr Pro Ser Asp Ile Ala Val Glu Trp Glu Ser Asn Gly Gln Pro
225 230 235 240

Glu Asn Asn Tyr Lys Thr Thr Pro Pro Val Leu Asp Ser Asp Gly Ser
245 250 255

Phe Phe Leu Tyr Ser Lys Leu Thr Val Asp Lys Ser Arg Trp Gln Gln
260 265 270

Gly Asn Val Phe Ser Cys Ser Val Met His Glu Ala Leu His Asn His
275 280 285

Tyr Thr Gln Lys Ser Leu Ser Leu Ser Pro Gly Lys
290 295 300

<210> SEQ ID NO 138
<211> LENGTH: 305
<212> TYPE: PRT
<213> ORGANISM: Artificial sequence
<220> FEATURE:
<223> OTHER INFORMATION: 2C1-m15-Fc(LALA)

<400> SEQUENCE: 138

Gly Val Thr Leu Phe Val Ala Leu Tyr Asp Tyr Lys Ala Phe Trp Pro
1 5 10 15

Gly Asp Ile Ser Phe His Lys Gly Glu Lys Phe Gln Ile Leu Arg Thr
20 25 30

Ser Asp Gly Glu Trp Trp Ile Ala Arg Ser Leu Thr Thr Gly Glu Glu
35 40 45

Gly Tyr Ile Pro Ser Asn Tyr Val Ala Pro Val Asp Ser Ile Gln Gly
50 55 60

Gly Gly Gly Ser Gly Gly Gly Gly Ser Gly Gly Gly Gly Ser Asp Lys
65 70 75 80

Thr His Thr Cys Pro Pro Cys Pro Ala Pro Glu Ala Ala Gly Gly Pro
85 90 95

Ser Val Phe Leu Phe Pro Pro Lys Pro Lys Asp Thr Leu Met Ile Ser
100 105 110

Arg Thr Pro Glu Val Thr Cys Val Val Val Asp Val Ser His Glu Asp
115 120 125

Pro Glu Val Lys Phe Asn Trp Tyr Val Asp Gly Val Glu Val His Asn
130 135 140

Ala Lys Thr Lys Pro Arg Glu Glu Gln Tyr Asn Ser Thr Tyr Arg Val
145 150 155 160

Val Ser Val Leu Thr Val Leu His Gln Asp Trp Leu Asn Gly Lys Glu
165 170 175

Tyr Lys Cys Lys Val Ser Asn Lys Ala Leu Pro Ala Pro Ile Glu Lys
180 185 190

Thr Ile Ser Lys Ala Lys Gly Gln Pro Arg Glu Pro Gln Val Tyr Thr
195 200 205

Leu Pro Pro Ser Arg Glu Glu Met Thr Lys Asn Gln Val Ser Leu Thr
210 215 220

Cys Leu Val Lys Gly Phe Tyr Pro Ser Asp Ile Ala Val Glu Trp Glu
225 230 235 240

Ser Asn Gly Gln Pro Glu Asn Asn Tyr Lys Thr Thr Pro Pro Val Leu
245 250 255

Asp Ser Asp Gly Ser Phe Phe Leu Tyr Ser Lys Leu Thr Val Asp Lys
260 265 270

Ser Arg Trp Gln Gln Gly Asn Val Phe Ser Cys Ser Val Met His Glu
275 280 285

Ala Leu His Asn His Tyr Thr Gln Lys Ser Leu Ser Leu Ser Pro Gly
    290                 295                 300

Lys
305

<210> SEQ ID NO 139
<211> LENGTH: 30
<212> TYPE: DNA
<213> ORGANISM: Artificial sequence
<220> FEATURE:
<223> OTHER INFORMATION: Primer SB3

<400> SEQUENCE: 139
cgaattcggg agtgacactc tttgtggccc 30

<210> SEQ ID NO 140
<211> LENGTH: 30
<212> TYPE: DNA
<213> ORGANISM: Artificial sequence
<220> FEATURE:
<223> OTHER INFORMATION: Primer SB4

<400> SEQUENCE: 140
gaagatctct ggatagagtc aactggagcc 30

<210> SEQ ID NO 141
<211> LENGTH: 38
<212> TYPE: DNA
<213> ORGANISM: Artificial sequence
<220> FEATURE:
<223> OTHER INFORMATION: Primer SB5

<400> SEQUENCE: 141
cccaagcttg ggatgggcta caggatgcaa ctcctgtc 38

<210> SEQ ID NO 142
<211> LENGTH: 30
<212> TYPE: DNA
<213> ORGANISM: Artificial sequence
<220> FEATURE:
<223> OTHER INFORMATION: Primer SB6

<400> SEQUENCE: 142
cgggatcctc atttacccgg agacagggag 30

<210> SEQ ID NO 143
<211> LENGTH: 36
<212> TYPE: DNA
<213> ORGANISM: Artificial sequence
<220> FEATURE:
<223> OTHER INFORMATION: Primer SB7

<400> SEQUENCE: 143
actgacggtc cccccgcggc ttcaggtgct gggcac 36

<210> SEQ ID NO 144
<211> LENGTH: 32
<212> TYPE: DNA
<213> ORGANISM: Artificial sequence
<220> FEATURE:
<223> OTHER INFORMATION: Primer SB8

<400> SEQUENCE: 144
gccgcggggg gaccgtcagt cttcctcttc cc 32

<210> SEQ ID NO 145
<211> LENGTH: 39
<212> TYPE: DNA
<213> ORGANISM: Artificial sequence
<220> FEATURE:
<223> OTHER INFORMATION: Primer Ba_2C1_R_EPKSS

<400> SEQUENCE: 145
gctgcttttc ggttcctgga tagagtcaac tggagccac 39

<210> SEQ ID NO 146
<211> LENGTH: 39
<212> TYPE: DNA
<213> ORGANISM: Artificial sequence
<220> FEATURE:
<223> OTHER INFORMATION: Primer Ba_Hinge_F_EPKSS

<400> SEQUENCE: 146
gaaccgaaaa gcagcgacaa aactcacaca tgcccaccg 39

<210> SEQ ID NO 147
<211> LENGTH: 39
<212> TYPE: DNA
<213> ORGANISM: Artificial sequence
<220> FEATURE:
<223> OTHER INFORMATION: Primer 47c.fo

<400> SEQUENCE: 147
tgaaccgcct ccaccctgga tagagtcaac tggagccac 39

<210> SEQ ID NO 148
<211> LENGTH: 39
<212> TYPE: DNA
<213> ORGANISM: Artificial sequence
<220> FEATURE:
<223> OTHER INFORMATION: Primer Ba_Hinge_F_5aaGS-linker

<400> SEQUENCE: 148
ggtggaggcg gttcagacaa aactcacaca tgcccaccg 39

<210> SEQ ID NO 149
<211> LENGTH: 54
<212> TYPE: DNA
<213> ORGANISM: Artificial sequence
<220> FEATURE:
<223> OTHER INFORMATION: Primer 47b.fo

<400> SEQUENCE: 149
agagccacct ccgcctgaac cgcctccacc ctggatagag tcaactggag ccac 54

<210> SEQ ID NO 150
<211> LENGTH: 54
<212> TYPE: DNA
<213> ORGANISM: Artificial sequence
<220> FEATURE:
<223> OTHER INFORMATION: Primer Ba_Hinge_F_10aaGS-linker

<400> SEQUENCE: 150
ggtggaggcg gttcaggcgg aggtggctct gacaaaactc acacatgccc accg 54

<210> SEQ ID NO 151
<211> LENGTH: 69
<212> TYPE: DNA
<213> ORGANISM: Artificial sequence
<220> FEATURE:
<223> OTHER INFORMATION: Primer 47.fo.corr

<400> SEQUENCE: 151
tgatccgcca ccgccagagc cacctccgcc tgaaccgcct ccaccctgga tagagtcaac 60
tggagccac 69

<210> SEQ ID NO 152
<211> LENGTH: 69
<212> TYPE: DNA
<213> ORGANISM: Artificial sequence
<220> FEATURE:
<223> OTHER INFORMATION: Primer Ba_Hinge_F_15aaGS-linker

<400> SEQUENCE: 152
ggtggaggcg gttcaggcgg aggtggctct ggcggtggcg gatcagacaa aactcacaca 60
tgcccaccg 69

<210> SEQ ID NO 153
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 153

Gly Val Thr Leu Phe Val Ala Leu Tyr Asp Tyr Asn Ala Thr Arg Trp
1 5 10 15

Thr Asp Leu Ser Phe His Lys Gly Glu Lys Phe Gln Ile Leu Glu Phe
20 25 30

Gly Pro Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 154
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 154

Gly Val Thr Leu Phe Val Ala Leu Tyr Asp Tyr Asn Ala Thr Arg Trp
1 5 10 15

Thr Asp Leu Ser Phe His Lys Gly Glu Lys Phe Gln Ile Leu Asp Gly
20 25 30

Asp Ser Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 155
<211> LENGTH: 64
<212> TYPE: PRT
<213> ORGANISM: Artificial sequence
<220> FEATURE:
<223> OTHER INFORMATION: SH3 domain of the Fyn Kinase

<400> SEQUENCE: 155

Gly Val Thr Leu Phe Val Ala Leu Tyr Asp Tyr Gln Ala Asp Arg Trp
1 5 10 15

Thr Asp Leu Ser Phe His Lys Gly Glu Lys Phe Gln Ile Leu Asp Ala 20 25 30

Ser Pro Pro Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 156
<211> LENGTH: 65
<212> TYPE: PRT
<213> ORGANISM: Artificial sequence
<220> FEATURE:
<223> OTHER INFORMATION: SH3 domain of the Fyn Kinase

<400> SEQUENCE: 156

Gly Val Thr Leu Phe Val Ala Leu Tyr Asp Tyr Arg Ala Glu Arg Ser
1 5 10 15

Thr Asp Leu Ser Phe His Lys Gly Glu Lys Phe Gln Ile Leu Asp Met
20 25 30

Thr Val Pro Asn Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 157
<211> LENGTH: 65
<212> TYPE: PRT
<213> ORGANISM: Artificial sequence
<220> FEATURE:
<223> OTHER INFORMATION: SH3 domain of the Fyn Kinase

<400> SEQUENCE: 157

Gly Val Thr Leu Phe Val Ala Leu Tyr Asp Tyr Asn Ala Thr Arg Trp
1 5 10 15

Thr Asp Leu Ser Phe His Lys Gly Glu Lys Phe Gln Ile Leu Asp Trp
20 25 30

Thr Thr Ala Asn Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 158
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 158

Gly Val Thr Leu Phe Val Ala Leu Tyr Asp Tyr Gln Ala Asp Arg Trp
1 5 10 15

Thr Asp Leu Ser Phe His Lys Gly Glu Lys Phe Gln Ile Leu Ser Phe
20 25 30

His Val Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 159
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 159

Gly Val Thr Leu Phe Val Ala Leu Tyr Asp Tyr Gln Ala Asp Arg Trp
1 5 10 15

Thr Asp Leu Ser Phe His Lys Gly Glu Lys Phe Gln Ile Leu Arg Phe
20 25 30

Asp Ile Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 160
<211> LENGTH: 64
<212> TYPE: PRT
<213> ORGANISM: Artificial sequence
<220> FEATURE:
<223> OTHER INFORMATION: SH3 domain of the Fyn Kinase

<400> SEQUENCE: 160

Gly Val Thr Leu Phe Val Ala Leu Tyr Asp Tyr Gln Ala Asp Arg Trp
1 5 10 15

Thr Asp Leu Ser Phe His Lys Gly Glu Lys Phe Gln Ile Leu Asn Ala
20 25 30

Ser Gly Pro Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 161
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 161

Gly Val Thr Leu Phe Val Ala Leu Tyr Asp Tyr Glu Ala Gln Thr Trp
1 5 10 15

His Asp Leu Ser Phe His Lys Gly Glu Lys Phe Gln Ile Leu Asn Ser
20 25 30

Ser Glu Gly Glu Tyr Trp Glu Ala Arg Ser Leu Thr Thr Gly Glu Thr
35 40 45

Gly Leu Ile Pro Ser Asn Tyr Val Ala Pro Val Asp Ser Ile Gln
50 55 60

<210> SEQ ID NO 162
<211> LENGTH: 65
<212> TYPE: PRT
<213> ORGANISM: Artificial sequence
<220> FEATURE:
<223> OTHER INFORMATION: SH3 domain of the Fyn Kinase

<400> SEQUENCE: 162

Gly Val Thr Leu Phe Val Ala Leu Tyr Asp Tyr Lys Ala Gln Arg Trp
1 5 10 15

```
Thr Asp Leu Ser Phe His Lys Gly Glu Lys Phe Gln Ile Leu Gln Ala
            20                  25                  30

His Gln Lys Thr Gly Asp Trp Trp Glu Ala Arg Ser Leu Thr Thr Gly
        35                  40                  45

Glu Thr Gly Leu Ile Pro Ser Asn Tyr Val Ala Pro Val Asp Ser Ile
    50                  55                  60

Gln
65
```

<210> SEQ ID NO 163
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 163

```
Gly Val Thr Leu Phe Val Ala Leu Tyr Asp Tyr Glu Ala Leu His Trp
1               5                   10                  15

His Gln Leu Ser Phe His Lys Gly Glu Lys Ser Gln Ile Leu Asn Ser
            20                  25                  30

Ser Glu Gly Thr Tyr Trp Glu Ala Arg Ser Leu Thr Thr Gly Glu Thr
        35                  40                  45

Gly Trp Ile Pro Ser Asn Tyr Val Ala Pro Gly Asp Ser Ile Gln
    50                  55                  60
```

<210> SEQ ID NO 164
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 164

```
Gly Val Thr Leu Phe Val Ala Leu Tyr Asp Tyr Lys Ala Gln Arg Trp
1               5                   10                  15

Leu Asp Leu Ser Phe His Glu Gly Glu Lys Phe Gln Ile Leu Ser Thr
            20                  25                  30

Asp Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 165
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 165

```
Gly Val Thr Leu Phe Val Ala Leu Tyr Asp Tyr Glu Ala Pro Thr Trp
1               5                   10                  15

Leu His Leu Ser Phe His Lys Gly Glu Lys Phe Gln Ile Leu Asn Ser
            20                  25                  30

Ser Glu Gly Pro Trp Trp Glu Ala Arg Ser Leu Thr Thr Gly Glu Thr
        35                  40                  45

Gly Phe Ile Pro Ser Asn Tyr Val Ala Pro Val Asp Ser Ile Gln
    50                  55                  60
```

<210> SEQ ID NO 166
<211> LENGTH: 63
<212> TYPE: PRT
<213> ORGANISM: Artificial sequence
<220> FEATURE:
<223> OTHER INFORMATION: SH3 domain of the Fyn Kinase

<400> SEQUENCE: 166

```
Gly Val Thr Leu Phe Val Ala Leu Tyr Asp Tyr Glu Ala Ala Asn Trp
1               5                   10                  15

Phe Gln Leu Ser Phe His Lys Gly Glu Lys Phe Gln Ile Leu Asn Ser
            20                  25                  30

Ser Glu Gly Pro Leu Trp Glu Ala Arg Ser Leu Thr Thr Gly Glu Thr
        35                  40                  45

Gly Gly Ile Pro Ser Asn Tyr Val Ala Pro Val Asp Ser Ile Gln
    50                  55                  60
```

<210> SEQ ID NO 167
<211> LENGTH: 63
<212> TYPE: PRT
<213> ORGANISM: Artificial sequence
<220> FEATURE:
<223> OTHER INFORMATION: Fynomer #1 C12

<400> SEQUENCE: 167

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 168
<211> LENGTH: 67
<212> TYPE: PRT
<213> ORGANISM: Artificial sequence
<220> FEATURE:
<223> OTHER INFORMATION: Fynomer #1 G10

<400> SEQUENCE: 168

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Lys Arg Trp Arg Gly Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 169
<211> LENGTH: 67
<212> TYPE: PRT
<213> ORGANISM: Artificial sequence
<220> FEATURE:
<223> OTHER INFORMATION: Fynomer #3

<400> SEQUENCE: 169

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Thr Arg Trp Ala Gln Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65


<210> SEQ ID NO 170
<211> LENGTH: 64
<212> TYPE: PRT
<213> ORGANISM: Artificial sequence
<220> FEATURE:
<223> OTHER INFORMATION: Fynomer #4

<400> SEQUENCE: 170

Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Ser Pro
            20                  25                  30

Lys Asp Thr Gly Tyr Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 171
<211> LENGTH: 66
<212> TYPE: PRT
<213> ORGANISM: Artificial sequence
<220> FEATURE:
<223> OTHER INFORMATION: Fynomer #5

<400> SEQUENCE: 171

Gly Val Thr Leu Phe Val Ala Leu Tyr Asp Tyr Glu Ala Arg Glu Phe
1               5                   10                  15

Met Gly Gly Gln Asp Leu Ser Phe His Lys Gly Glu Lys Phe Gln Ile
            20                  25                  30

Leu Thr Met Trp Lys Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 172
<211> LENGTH: 67
<212> TYPE: PRT
<213> ORGANISM: Artificial sequence
<220> FEATURE:
<223> OTHER INFORMATION: Fynomer #6

<400> SEQUENCE: 172

Gly Val Thr Leu Phe Val Ala Leu Tyr Asp Tyr Glu Ala Arg Pro Tyr
1               5                   10                  15

Leu Gly Gly Gln Asp Leu Ser Phe His Lys Gly Glu Lys Phe Gln Ile
            20                  25                  30

Leu His Ala Ser Met Leu Gly Asp Trp Trp Glu Ala Arg Ser Leu Thr
```

```
        35                  40                  45

Thr Gly Glu Thr Gly Tyr Ile Pro Ser Asn Tyr Val Ala Pro Val Asp
    50                  55                  60

Ser Ile Gln
65


<210> SEQ ID NO 173
<211> LENGTH: 63
<212> TYPE: PRT
<213> ORGANISM: Artificial sequence
<220> FEATURE:
<223> OTHER INFORMATION: Fynomer #7

<400> SEQUENCE: 173

Gly Val Thr Leu Phe Val Ala Leu Tyr Asp Tyr Thr Ser Tyr Asn Gln
1               5                   10                  15

His Asp Leu Ser Phe His Lys Gly Glu Lys Phe Gln Ile Leu Gly Asp
            20                  25                  30

Asn Ile Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 174
<211> LENGTH: 67
<212> TYPE: PRT
<213> ORGANISM: Artificial sequence
<220> FEATURE:
<223> OTHER INFORMATION: Fynomer #8

<400> SEQUENCE: 174

Gly Val Thr Leu Phe Val Ala Leu Tyr Asp Tyr Glu Ala Arg Leu Ser
1               5                   10                  15

Ser His Pro His Val Leu Ser Phe His Lys Gly Glu Lys Phe Gln Ile
            20                  25                  30

Leu Asn Arg Val Ser Ile Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65


<210> SEQ ID NO 175
<211> LENGTH: 67
<212> TYPE: PRT
<213> ORGANISM: Artificial sequence
<220> FEATURE:
<223> OTHER INFORMATION: Fynomer #9

<400> SEQUENCE: 175

Gly Val Thr Leu Phe Val Ala Leu Tyr Asp Tyr Glu Ala Arg Pro Tyr
1               5                   10                  15

Leu Gly Gly Gln Asp Leu Ser Phe His Lys Gly Glu Lys Phe Gln Ile
            20                  25                  30

Leu Asn His Pro Pro Thr Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 176
<211> LENGTH: 65
<212> TYPE: PRT
<213> ORGANISM: Artificial sequence
<220> FEATURE:
<223> OTHER INFORMATION: Fynomer #10

<400> SEQUENCE: 176

```
Gly Val Thr Leu Phe Val Ala Leu Tyr Asp Tyr Glu Ala Tyr Asp Leu
1               5                   10                  15

Ser Arg Pro Asp Leu Ser Phe His Lys Gly Glu Lys Phe Gln Ile Leu
            20                  25                  30

Asn Ser Ser Glu Gly Thr Trp Trp Glu Ala Arg Ser Leu Thr Thr Gly
        35                  40                  45

Glu Thr Gly Phe Ile Pro Ser Asn Tyr Val Ala Pro Val Asp Ser Ile
    50                  55                  60

Gln
65
```

<210> SEQ ID NO 177
<211> LENGTH: 67
<212> TYPE: PRT
<213> ORGANISM: Artificial sequence
<220> FEATURE:
<223> OTHER INFORMATION: Fynomer #11

<400> SEQUENCE: 177

```
Gly Val Thr Leu Phe Val Ala Leu Tyr Asp Tyr Glu Ala Arg Met Pro
1               5                   10                  15

Lys Val Ser Asp Leu Ser Phe His Lys Gly Glu Lys Phe Gln Ile Leu
            20                  25                  30

Gln Glu Pro Gln Ser Lys Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 178
<211> LENGTH: 67
<212> TYPE: PRT
<213> ORGANISM: Artificial sequence
<220> FEATURE:
<223> OTHER INFORMATION: Fynomer #12

<400> SEQUENCE: 178

```
Gly Val Thr Leu Phe Val Ala Leu Tyr Asp Tyr Glu Ala Arg Pro Gly
1               5                   10                  15

Arg His Ser Ser Asp Leu Ser Phe His Lys Gly Glu Lys Phe Gln Ile
            20                  25                  30

Leu His Gln Ser Asn Val Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 179
<211> LENGTH: 64

<212> TYPE: PRT
<213> ORGANISM: Artificial sequence
<220> FEATURE:
<223> OTHER INFORMATION: Fynomer #13

<400> SEQUENCE: 179

Gly Val Thr Leu Phe Val Ala Leu Tyr Asp Tyr Gln Thr Thr Arg Pro
1 5 10 15

His Asp Leu Ser Phe His Lys Gly Glu Lys Phe Gln Ile Leu Gly Arg
20 25 30

Thr Gln Ile Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 180
<211> LENGTH: 63
<212> TYPE: PRT
<213> ORGANISM: Artificial sequence
<220> FEATURE:
<223> OTHER INFORMATION: Fynomer #14

<400> SEQUENCE: 180

Gly Val Thr Leu Phe Val Ala Leu Tyr Asp Tyr Gln Thr Asn Asn Ser
1 5 10 15

Arg Asp Leu Ser Phe His Lys Gly Glu Lys Phe Gln Ile Leu Gly Asn
20 25 30

Thr Gln Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 181
<211> LENGTH: 63
<212> TYPE: PRT
<213> ORGANISM: Artificial sequence
<220> FEATURE:
<223> OTHER INFORMATION: Fynomer #15

<400> SEQUENCE: 181

Gly Val Thr Leu Phe Val Ala Leu Tyr Asp Tyr Tyr Ser Tyr Asn Thr
1 5 10 15

His Asp Leu Ser Phe His Lys Gly Glu Lys Phe Gln Ile Leu Ser Arg
20 25 30

Ala Asn Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 182
<211> LENGTH: 63
<212> TYPE: PRT
<213> ORGANISM: Artificial sequence
<220> FEATURE:
<223> OTHER INFORMATION: Fynomer #16

<400> SEQUENCE: 182

Gly Val Thr Leu Phe Val Ala Leu Tyr Asp Tyr Tyr Ser Tyr Asn Asn
1 5 10 15

His Asp Leu Ser Phe His Lys Gly Glu Lys Phe Gln Ile Leu Gln Glu
20 25 30

```
Leu Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 183
<211> LENGTH: 63
<212> TYPE: PRT
<213> ORGANISM: Artificial sequence
<220> FEATURE:
<223> OTHER INFORMATION: Fynomer #17

<400> SEQUENCE: 183

Gly Val Thr Leu Phe Val Ala Leu Tyr Asp Tyr Arg Ser Tyr Asn Thr
1               5                   10                  15

Arg Asp Leu Ser Phe His Lys Gly Glu Lys Phe Gln Ile Leu Thr Lys
            20                  25                  30

Ser Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 184
<211> LENGTH: 65
<212> TYPE: PRT
<213> ORGANISM: Artificial sequence
<220> FEATURE:
<223> OTHER INFORMATION: Fynomer #18

<400> SEQUENCE: 184

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Lys Ala
            20                  25                  30

His Ser Leu Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 185
<211> LENGTH: 65
<212> TYPE: PRT
<213> ORGANISM: Artificial sequence
<220> FEATURE:
<223> OTHER INFORMATION: Fynomer #19

<400> SEQUENCE: 185

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Glu
            20                  25                  30

Gln Asp Leu Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 186
<211> LENGTH: 63
<212> TYPE: PRT
<213> ORGANISM: Artificial sequence
<220> FEATURE:
<223> OTHER INFORMATION: Fynomer #20

<400> SEQUENCE: 186

```
Gly Val Thr Leu Phe Val Ala Leu Tyr Asp Tyr Thr Ser Tyr Asn Lys
1               5                   10                  15

Leu Asp Leu Ser Phe His Lys Gly Glu Lys Phe Gln Ile Leu Arg Thr
            20                  25                  30

Asp Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 187
<211> LENGTH: 63
<212> TYPE: PRT
<213> ORGANISM: Artificial sequence
<220> FEATURE:
<223> OTHER INFORMATION: Fynomer #21

<400> SEQUENCE: 187

```
Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Gly Pro
            20                  25                  30

Lys Leu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 188
<211> LENGTH: 63
<212> TYPE: PRT
<213> ORGANISM: Artificial sequence
<220> FEATURE:
<223> OTHER INFORMATION: Fynomer #22

<400> SEQUENCE: 188

```
Gly Val Thr Leu Phe Val Ala Leu Tyr Asp Tyr Thr Ser Tyr Asn Asn
1               5                   10                  15

His Asp Leu Ser Phe His Lys Gly Glu Lys Phe Gln Ile Leu Asn Gln
            20                  25                  30

His Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 189
<211> LENGTH: 63
<212> TYPE: PRT
<213> ORGANISM: Artificial sequence
<220> FEATURE:
<223> OTHER INFORMATION: Fynomer #23

<400> SEQUENCE: 189

```
Gly Val Thr Leu Phe Val Ala Leu Tyr Asp Tyr Thr Ser Tyr Asn Leu
1               5                   10                  15

Arg Asp Leu Ser Phe His Lys Gly Glu Lys Phe Gln Ile Leu Asn Ser
```

```
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 190
<211> LENGTH: 65
<212> TYPE: PRT
<213> ORGANISM: Artificial sequence
<220> FEATURE:
<223> OTHER INFORMATION: Fynomer #24

<400> SEQUENCE: 190

Gly Val Thr Leu Phe Val Ala Leu Tyr Asp Tyr Thr Ser Tyr Asn Pro
1               5                   10                  15

Arg Asp Leu Ser Phe His Lys Gly Glu Lys Phe Gln Ile Leu Gly Ala
            20                  25                  30

Thr Asp Ala Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 191
<211> LENGTH: 63
<212> TYPE: PRT
<213> ORGANISM: Artificial sequence
<220> FEATURE:
<223> OTHER INFORMATION: Fynomer #25

<400> SEQUENCE: 191

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Glu
            20                  25                  30

Leu Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 192
<211> LENGTH: 63
<212> TYPE: PRT
<213> ORGANISM: Artificial sequence
<220> FEATURE:
<223> OTHER INFORMATION: Fynomer #26

<400> SEQUENCE: 192

Gly Val Thr Leu Phe Val Ala Leu Tyr Asp Tyr Thr Ser Tyr Asn Ser
1               5                   10                  15

Ser Asp Leu Ser Phe His Lys Gly Glu Lys Phe Gln Ile Leu Arg Glu
            20                  25                  30

Ala Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 193
```

<211> LENGTH: 67
<212> TYPE: PRT
<213> ORGANISM: Artificial sequence
<220> FEATURE:
<223> OTHER INFORMATION: Fynomer #27

<400> SEQUENCE: 193

```
Gly Val Thr Leu Phe Val Ala Leu Tyr Asp Tyr Glu Ala Arg Arg Asp
1               5                   10                  15

His Ser Pro His Asp Leu Ser Phe His Lys Gly Glu Lys Phe Gln Ile
            20                  25                  30

Leu Asn Leu Tyr Gln Val Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 194
<211> LENGTH: 66
<212> TYPE: PRT
<213> ORGANISM: Artificial sequence
<220> FEATURE:
<223> OTHER INFORMATION: Fynomer #28

<400> SEQUENCE: 194

```
Gly Val Thr Leu Phe Val Ala Leu Tyr Asp Tyr Glu Ala Arg Glu Ala
1               5                   10                  15

Leu Gly Gly Gln Asp Leu Ser Phe His Lys Gly Glu Lys Phe Gln Ile
            20                  25                  30

Leu Ser Pro Gln Thr Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65
```

<210> SEQ ID NO 195
<211> LENGTH: 64
<212> TYPE: PRT
<213> ORGANISM: Artificial sequence
<220> FEATURE:
<223> OTHER INFORMATION: Fynomer #29

<400> SEQUENCE: 195

```
Gly Val Thr Leu Phe Val Ala Leu Tyr Asp Tyr Tyr Ser Val His Pro
1               5                   10                  15

Gly Asp Leu Ser Phe His Lys Gly Glu Lys Phe Gln Ile Leu Ser Asn
            20                  25                  30

Tyr Gln Val Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 196
<211> LENGTH: 63
<212> TYPE: PRT
<213> ORGANISM: Artificial sequence
<220> FEATURE:
<223> OTHER INFORMATION: Fynomer #30

<400> SEQUENCE: 196

```
Gly Val Thr Leu Phe Val Ala Leu Tyr Asp Tyr Tyr Ser Tyr Asn Ser
1               5                   10                  15

Arg Asp Leu Ser Phe His Lys Gly Glu Lys Phe Gln Ile Leu Ala Gln
            20                  25                  30

His Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 197
<211> LENGTH: 63
<212> TYPE: PRT
<213> ORGANISM: Artificial sequence
<220> FEATURE:
<223> OTHER INFORMATION: Fynomer #31

<400> SEQUENCE: 197

Gly Val Thr Leu Phe Val Ala Leu Tyr Asp Tyr Thr Ser Tyr Asn Met
1               5                   10                  15

Arg Asp Leu Ser Phe His Lys Gly Glu Lys Phe Gln Ile Leu Gly Arg
            20                  25                  30

Gly Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 198
<211> LENGTH: 65
<212> TYPE: PRT
<213> ORGANISM: Artificial sequence
<220> FEATURE:
<223> OTHER INFORMATION: Fynomer #32

<400> SEQUENCE: 198

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gly Arg
            20                  25                  30

Pro Arg Asp Val Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 199
<211> LENGTH: 63
<212> TYPE: PRT
<213> ORGANISM: Artificial sequence
<220> FEATURE:
<223> OTHER INFORMATION: Fynomer #33

<400> SEQUENCE: 199

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu His Thr
            20                  25                  30

Thr Lys Gly Asp Trp Trp Glu Ala Arg Ser Leu Thr Thr Gly Glu Thr
        35                  40                  45
```

Gly Tyr Ile Pro Ser Asn Tyr Val Ala Pro Val Asp Ser Ile Gln
    50                  55                  60

<210> SEQ ID NO 200
<211> LENGTH: 65
<212> TYPE: PRT
<213> ORGANISM: Artificial sequence
<220> FEATURE:
<223> OTHER INFORMATION: Fynomer #34

<400> SEQUENCE: 200

Gly Val Thr Leu Phe Val Ala Leu Tyr Asp Tyr Thr Ser Tyr Asn Thr
1               5                   10                  15

Thr Asp Leu Ser Phe His Lys Gly Glu Lys Phe Gln Ile Leu His Trp
            20                  25                  30

Asn Gly Gly Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 201
<211> LENGTH: 63
<212> TYPE: PRT
<213> ORGANISM: Artificial sequence
<220> FEATURE:
<223> OTHER INFORMATION: Fynomer #35

<400> SEQUENCE: 201

Gly Val Thr Leu Phe Val Ala Leu Tyr Asp Tyr Thr Ser Tyr Asn Thr
1               5                   10                  15

Thr Asp Leu Ser Phe His Lys Gly Glu Lys Phe Gln Ile Leu Asn Asn
            20                  25                  30

Thr Thr Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 202
<211> LENGTH: 65
<212> TYPE: PRT
<213> ORGANISM: Artificial sequence
<220> FEATURE:
<223> OTHER INFORMATION: Fynomer #36

<400> SEQUENCE: 202

Gly Val Thr Leu Phe Val Ala Leu Tyr Asp Tyr Trp Ser Tyr Asn Ser
1               5                   10                  15

Arg Asp Leu Ser Phe His Lys Gly Glu Lys Phe Gln Ile Leu Asn Pro
            20                  25                  30

Glu Glu Thr Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 203
<211> LENGTH: 65
<212> TYPE: PRT

<213> ORGANISM: Artificial sequence
<220> FEATURE:
<223> OTHER INFORMATION: Fynomer #37

<400> SEQUENCE: 203

Gly Val Thr Leu Phe Val Ala Leu Tyr Asp Tyr Thr Ser Tyr Asn Pro
1 5 10 15

Arg Asp Leu Ser Phe His Lys Gly Glu Lys Phe Gln Ile Leu Asn Pro
20 25 30

Arg Gln Arg Ile Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 204
<211> LENGTH: 63
<212> TYPE: PRT
<213> ORGANISM: Artificial sequence
<220> FEATURE:
<223> OTHER INFORMATION: Fynomer #38

<400> SEQUENCE: 204

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Asn Arg
20 25 30

Pro Met Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 205
<211> LENGTH: 65
<212> TYPE: PRT
<213> ORGANISM: Artificial sequence
<220> FEATURE:
<223> OTHER INFORMATION: Fynomer #39

<400> SEQUENCE: 205

Gly Val Thr Leu Phe Val Ala Leu Tyr Asp Tyr Thr Ser Tyr Asn Gln
1 5 10 15

His Asp Leu Ser Phe His Lys Gly Glu Lys Phe Gln Ile Leu Pro Thr
20 25 30

Thr Asp Thr Ala Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 206
<211> LENGTH: 63
<212> TYPE: PRT
<213> ORGANISM: Artificial sequence
<220> FEATURE:
<223> OTHER INFORMATION: Fynomer #40

<400> SEQUENCE: 206

Gly Val Thr Leu Phe Val Ala Leu Tyr Asp Tyr Thr Ser Tyr Asn Thr 1 5 10 15

Met Asp Leu Ser Phe His Lys Gly Glu Lys Phe Gln Ile Leu Arg Glu
20 25 30

Thr Thr Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 207
<211> LENGTH: 63
<212> TYPE: PRT
<213> ORGANISM: Artificial sequence
<220> FEATURE:
<223> OTHER INFORMATION: Fynomer #41

<400> SEQUENCE: 207

Gly Val Thr Leu Phe Val Ala Leu Tyr Asp Tyr Thr Ser Tyr Asn Thr
1 5 10 15

His Asp Leu Ser Phe His Lys Gly Glu Lys Phe Gln Ile Leu Arg Gln
20 25 30

Asn Asn Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 208
<211> LENGTH: 63
<212> TYPE: PRT
<213> ORGANISM: Artificial sequence
<220> FEATURE:
<223> OTHER INFORMATION: Fynomer #42

<400> SEQUENCE: 208

Gly Val Thr Leu Phe Val Ala Leu Tyr Asp Tyr Thr Ser Tyr Asn Ser
1 5 10 15

Thr Asp Leu Ser Phe His Lys Gly Glu Lys Phe Gln Ile Leu Ser Ala
20 25 30

Pro Gln Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 209
<211> LENGTH: 63
<212> TYPE: PRT
<213> ORGANISM: Artificial sequence
<220> FEATURE:
<223> OTHER INFORMATION: Fynomer #43

<400> SEQUENCE: 209

Gly Val Thr Leu Phe Val Ala Leu Tyr Asp Tyr Thr Ser Tyr Asn Ala
1 5 10 15

Arg Asp Leu Ser Phe His Lys Gly Glu Lys Phe Gln Ile Leu Ser Ala
20 25 30

Pro Thr Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 210

<211> LENGTH: 65
<212> TYPE: PRT
<213> ORGANISM: Artificial sequence
<220> FEATURE:
<223> OTHER INFORMATION: Fynomer #44

<400> SEQUENCE: 210

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Asp
            20                  25                  30

Ala Thr Leu Glu Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 211
<211> LENGTH: 65
<212> TYPE: PRT
<213> ORGANISM: Artificial sequence
<220> FEATURE:
<223> OTHER INFORMATION: Fynomer #45

<400> SEQUENCE: 211

```
Gly Val Thr Leu Phe Val Ala Leu Tyr Asp Tyr Thr Ser Tyr Asn Lys
1               5                   10                  15

Arg Asp Leu Ser Phe His Lys Gly Glu Lys Phe Gln Ile Leu Ser Glu
            20                  25                  30

Thr Ser Pro Glu Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 212
<211> LENGTH: 65
<212> TYPE: PRT
<213> ORGANISM: Artificial sequence
<220> FEATURE:
<223> OTHER INFORMATION: Fynomer #46

<400> SEQUENCE: 212

```
Gly Val Thr Leu Phe Val Ala Leu Tyr Asp Tyr Val Ser Tyr Asn Thr
1               5                   10                  15

Thr Asp Leu Ser Phe His Lys Gly Glu Lys Phe Gln Ile Leu Ser His
            20                  25                  30

Thr Thr Ser Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 213
<211> LENGTH: 63
<212> TYPE: PRT
<213> ORGANISM: Artificial sequence
<220> FEATURE:

<223> OTHER INFORMATION: Fynomer #47

<400> SEQUENCE: 213

Gly Val Thr Leu Phe Val Ala Leu Tyr Asp Tyr Thr Ser Tyr Asn Thr
1 5 10 15

Thr Asp Leu Ser Phe His Lys Gly Glu Lys Phe Gln Ile Leu Ser Met
20 25 30

Ala Val Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 214
<211> LENGTH: 65
<212> TYPE: PRT
<213> ORGANISM: Artificial sequence
<220> FEATURE:
<223> OTHER INFORMATION: Fynomer #48

<400> SEQUENCE: 214

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Ser Asn
20 25 30

Gly Pro Asp Pro Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 215
<211> LENGTH: 63
<212> TYPE: PRT
<213> ORGANISM: Artificial sequence
<220> FEATURE:
<223> OTHER INFORMATION: Fynomer #49

<400> SEQUENCE: 215

Gly Val Thr Leu Phe Val Ala Leu Tyr Asp Tyr Thr Ser Tyr Asn Thr
1 5 10 15

Thr Asp Leu Ser Phe His Lys Gly Glu Lys Phe Gln Ile Leu Ser Asn
20 25 30

Pro Pro Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 216
<211> LENGTH: 65
<212> TYPE: PRT
<213> ORGANISM: Artificial sequence
<220> FEATURE:
<223> OTHER INFORMATION: Fynomer #50

<400> SEQUENCE: 216

Gly Val Thr Leu Phe Val Ala Leu Tyr Asp Tyr Asn Ser Tyr Asn Lys
1 5 10 15

Arg Asp Leu Ser Phe His Lys Gly Glu Lys Phe Gln Ile Leu Ser Gln
20 25 30

```
Ala Ala Glu Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 217
<211> LENGTH: 63
<212> TYPE: PRT
<213> ORGANISM: Artificial sequence
<220> FEATURE:
<223> OTHER INFORMATION: Fynomer #51

<400> SEQUENCE: 217

```
Gly Val Thr Leu Phe Val Ala Leu Tyr Asp Tyr Thr Ser Tyr Asn Thr
1               5                   10                  15

Lys Asp Leu Ser Phe His Lys Gly Glu Lys Phe Gln Ile Leu Ser Gln
            20                  25                  30

Ser Gly Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 218
<211> LENGTH: 65
<212> TYPE: PRT
<213> ORGANISM: Artificial sequence
<220> FEATURE:
<223> OTHER INFORMATION: Fynomer #52

<400> SEQUENCE: 218

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Tyr
            20                  25                  30

Pro Arg Thr Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 219
<211> LENGTH: 65
<212> TYPE: PRT
<213> ORGANISM: Artificial sequence
<220> FEATURE:
<223> OTHER INFORMATION: Fynomer #53

<400> SEQUENCE: 219

```
Gly Val Thr Leu Phe Val Ala Leu Tyr Asp Tyr Thr Ser Tyr Asn Glu
1               5                   10                  15

Arg Asp Leu Ser Phe His Lys Gly Glu Lys Phe Gln Ile Leu Thr Lys
            20                  25                  30

Thr Pro Arg Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
```

65

<210> SEQ ID NO 220
<211> LENGTH: 65
<212> TYPE: PRT
<213> ORGANISM: Artificial sequence
<220> FEATURE:
<223> OTHER INFORMATION: Fynomer #54

<400> SEQUENCE: 220

Gly Val Thr Leu Phe Val Ala Leu Tyr Asp Tyr Val Ser Tyr Asn Thr
1 5 10 15

Asn Asp Leu Ser Phe His Lys Gly Glu Lys Phe Gln Ile Leu Asp Ser
20 25 30

Gln Glu Pro Asn Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 221
<211> LENGTH: 65
<212> TYPE: PRT
<213> ORGANISM: Artificial sequence
<220> FEATURE:
<223> OTHER INFORMATION: Fynomer #55

<400> SEQUENCE: 221

Gly Val Thr Leu Phe Val Ala Leu Tyr Asp Tyr Thr Ser Tyr Asn Gln
1 5 10 15

His Asp Leu Ser Phe His Lys Gly Glu Lys Phe Gln Ile Leu Gly Gln
20 25 30

Tyr Pro Lys Thr Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 222
<211> LENGTH: 65
<212> TYPE: PRT
<213> ORGANISM: Artificial sequence
<220> FEATURE:
<223> OTHER INFORMATION: Fynomer #56

<400> SEQUENCE: 222

Gly Val Thr Leu Phe Val Ala Leu Tyr Asp Tyr Thr Ser Tyr Asn Asn
1 5 10 15

Thr Asp Leu Ser Phe His Lys Gly Glu Lys Phe Gln Ile Leu Lys Gln
20 25 30

Gln Ala Gly Asp Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 223

<211> LENGTH: 65
<212> TYPE: PRT
<213> ORGANISM: Artificial sequence
<220> FEATURE:
<223> OTHER INFORMATION: Fynomer #57

<400> SEQUENCE: 223

```
Gly Val Thr Leu Phe Val Ala Leu Tyr Asp Tyr Thr Ser Tyr Asn Asn
1               5                   10                  15

Thr Asp Leu Ser Phe His Lys Gly Glu Lys Phe Gln Ile Leu Asn Ala
            20                  25                  30

His Gln Ser Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 224
<211> LENGTH: 65
<212> TYPE: PRT
<213> ORGANISM: Artificial sequence
<220> FEATURE:
<223> OTHER INFORMATION: Fynomer #58

<400> SEQUENCE: 224

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Pro
            20                  25                  30

Gln Ser Arg Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 225
<211> LENGTH: 65
<212> TYPE: PRT
<213> ORGANISM: Artificial sequence
<220> FEATURE:
<223> OTHER INFORMATION: Fynomer #59

<400> SEQUENCE: 225

```
Gly Val Thr Leu Phe Val Ala Leu Tyr Asp Tyr Thr Ser Tyr Asn Ser
1               5                   10                  15

His Asp Leu Ser Phe His Lys Gly Glu Lys Phe Gln Ile Leu Pro Gly
            20                  25                  30

Gln Ser Met Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 226
<211> LENGTH: 65
<212> TYPE: PRT
<213> ORGANISM: Artificial sequence
<220> FEATURE:

<223> OTHER INFORMATION: Fynomer #60

<400> SEQUENCE: 226

Gly Val Thr Leu Phe Val Ala Leu Tyr Asp Tyr Thr Ser Tyr Asn Ala
1               5                   10                  15

His Asp Leu Ser Phe His Lys Gly Glu Lys Phe Gln Ile Leu Pro Arg
            20                  25                  30

Gln Asp Thr Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 227
<211> LENGTH: 63
<212> TYPE: PRT
<213> ORGANISM: Artificial sequence
<220> FEATURE:
<223> OTHER INFORMATION: Fynomer #61

<400> SEQUENCE: 227

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gln Ala
            20                  25                  30

Leu Gly Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 228
<211> LENGTH: 65
<212> TYPE: PRT
<213> ORGANISM: Artificial sequence
<220> FEATURE:
<223> OTHER INFORMATION: Fynomer #62

<400> SEQUENCE: 228

Gly Val Thr Leu Phe Val Ala Leu Tyr Asp Tyr Thr Ser Tyr Asn Glu
1               5                   10                  15

Phe Asp Leu Ser Phe His Lys Gly Glu Lys Phe Gln Ile Leu Gln Gly
            20                  25                  30

Thr Gln Leu Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 229
<211> LENGTH: 63
<212> TYPE: PRT
<213> ORGANISM: Artificial sequence
<220> FEATURE:
<223> OTHER INFORMATION: Fynomer #63

<400> SEQUENCE: 229

Gly Val Thr Leu Phe Val Ala Leu Tyr Asp Tyr Thr Ser Tyr Asn Asp
1               5                   10                  15

```
Arg Asp Leu Ser Phe His Lys Gly Glu Lys Phe Gln Ile Leu Gln His
            20                  25                  30

Lys Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 230
<211> LENGTH: 63
<212> TYPE: PRT
<213> ORGANISM: Artificial sequence
<220> FEATURE:
<223> OTHER INFORMATION: Fynomer #64

<400> SEQUENCE: 230

Gly Val Thr Leu Phe Val Ala Leu Tyr Asp Tyr Tyr Ser Tyr Asn Asn
1               5                   10                  15

Thr Asp Leu Ser Phe His Lys Gly Glu Lys Phe Gln Ile Leu Gln Lys
            20                  25                  30

Arg Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 231
<211> LENGTH: 63
<212> TYPE: PRT
<213> ORGANISM: Artificial sequence
<220> FEATURE:
<223> OTHER INFORMATION: Fynomer #65

<400> SEQUENCE: 231

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Lys
            20                  25                  30

Ser Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 232
<211> LENGTH: 65
<212> TYPE: PRT
<213> ORGANISM: Artificial sequence
<220> FEATURE:
<223> OTHER INFORMATION: Fynomer #66

<400> SEQUENCE: 232

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gln Pro
            20                  25                  30

Asn Ser Ala Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

-continued

<210> SEQ ID NO 233
<211> LENGTH: 63
<212> TYPE: PRT
<213> ORGANISM: Artificial sequence
<220> FEATURE:
<223> OTHER INFORMATION: Fynomer #67

<400> SEQUENCE: 233

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gln Pro
            20                  25                  30

Gln Val Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 234
<211> LENGTH: 63
<212> TYPE: PRT
<213> ORGANISM: Artificial sequence
<220> FEATURE:
<223> OTHER INFORMATION: Fynomer #68

<400> SEQUENCE: 234

```
Gly Val Thr Leu Phe Val Ala Leu Tyr Asp Tyr Tyr Ser Tyr Asn Lys
1               5                   10                  15

Thr Asp Leu Ser Phe His Lys Gly Glu Lys Phe Gln Ile Leu Gln Gln
            20                  25                  30

His Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 235
<211> LENGTH: 64
<212> TYPE: PRT
<213> ORGANISM: Artificial sequence
<220> FEATURE:
<223> OTHER INFORMATION: Fynomer #69

<400> SEQUENCE: 235

```
Gly Val Thr Leu Phe Val Ala Leu Tyr Asp Tyr Thr Ser Tyr Asn Leu
1               5                   10                  15

Arg Asp Leu Ser Phe His Lys Gly Glu Lys Phe Gln Ile Leu Gln Gln
            20                  25                  30

Asn Leu Asp Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 236
<211> LENGTH: 63
<212> TYPE: PRT
<213> ORGANISM: Artificial sequence
<220> FEATURE:
<223> OTHER INFORMATION: Fynomer #70

<400> SEQUENCE: 236

```
Gly Val Thr Leu Phe Val Ala Leu Tyr Asp Tyr Thr Ser Tyr Asn Leu
1               5                   10                  15

Arg Asp Leu Ser Phe His Lys Gly Glu Lys Phe Gln Ile Leu Gln Ser
```

```
            20                  25                  30

His Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 237
<211> LENGTH: 64
<212> TYPE: PRT
<213> ORGANISM: Artificial sequence
<220> FEATURE:
<223> OTHER INFORMATION: Fynomer #71

<400> SEQUENCE: 237

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Ser
            20                  25                  30

Arg Ala Ser Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 238
<211> LENGTH: 64
<212> TYPE: PRT
<213> ORGANISM: Artificial sequence
<220> FEATURE:
<223> OTHER INFORMATION: Fynomer #72

<400> SEQUENCE: 238

Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Gln Thr
            20                  25                  30

Ser Leu Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 239
<211> LENGTH: 64
<212> TYPE: PRT
<213> ORGANISM: Artificial sequence
<220> FEATURE:
<223> OTHER INFORMATION: Fynomer #73

<400> SEQUENCE: 239

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Thr
            20                  25                  30

Thr Ala Met Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 240
<211> LENGTH: 65
<212> TYPE: PRT
<213> ORGANISM: Artificial sequence
```

<220> FEATURE:
<223> OTHER INFORMATION: Fynomer #74

<400> SEQUENCE: 240

Gly Val Thr Leu Phe Val Ala Leu Tyr Asp Tyr Thr Ser Tyr Asn Arg
1 5 10 15

Arg Asp Leu Ser Phe His Lys Gly Glu Lys Phe Gln Ile Leu Gln Val
20 25 30

Asn Pro Met Asp Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 241
<211> LENGTH: 64
<212> TYPE: PRT
<213> ORGANISM: Artificial sequence
<220> FEATURE:
<223> OTHER INFORMATION: Fynomer #75

<400> SEQUENCE: 241

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Gln
20 25 30

Gln Arg Gly Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 242
<211> LENGTH: 65
<212> TYPE: PRT
<213> ORGANISM: Artificial sequence
<220> FEATURE:
<223> OTHER INFORMATION: Fynomer #76

<400> SEQUENCE: 242

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Val
20 25 30

Pro Gln Asp Asp Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 243
<211> LENGTH: 64
<212> TYPE: PRT
<213> ORGANISM: Artificial sequence
<220> FEATURE:
<223> OTHER INFORMATION: Fynomer #77

<400> SEQUENCE: 243

Gly Val Thr Leu Phe Val Ala Leu Tyr Asp Tyr Thr Ser Tyr Asn Pro
1 5 10 15

```
Asn Asp Leu Ser Phe His Lys Gly Glu Lys Phe Gln Ile Leu Ser Gln
            20                  25                  30

Gln Asp Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 244
<211> LENGTH: 65
<212> TYPE: PRT
<213> ORGANISM: Artificial sequence
<220> FEATURE:
<223> OTHER INFORMATION: Fynomer #78

<400> SEQUENCE: 244

Gly Val Thr Leu Phe Val Ala Leu Tyr Asp Tyr Thr Ser Tyr Asn Arg
1               5                   10                  15

Arg Asp Leu Ser Phe His Lys Gly Glu Lys Phe Gln Ile Leu Ser Ser
            20                  25                  30

Asn Arg Ala Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 245
<211> LENGTH: 65
<212> TYPE: PRT
<213> ORGANISM: Artificial sequence
<220> FEATURE:
<223> OTHER INFORMATION: Fynomer #79

<400> SEQUENCE: 245

Gly Val Thr Leu Phe Val Ala Leu Tyr Asp Tyr Thr Ser Tyr Asn Asn
1               5                   10                  15

Arg Asp Leu Ser Phe His Lys Gly Glu Lys Phe Gln Ile Leu Thr Pro
            20                  25                  30

Asp Ser Arg Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 246
<211> LENGTH: 64
<212> TYPE: PRT
<213> ORGANISM: Artificial sequence
<220> FEATURE:
<223> OTHER INFORMATION: Fynomer #80

<400> SEQUENCE: 246

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Thr Pro
            20                  25                  30

Pro Gln His Gly Asp Trp Trp Glu Ala Arg Ser Leu Thr Thr Gly Glu
        35                  40                  45
```

```
Thr Gly Tyr Ile Pro Ser Asn Tyr Val Ala Pro Val Asp Ser Ile Gln
    50                  55                  60


<210> SEQ ID NO 247
<211> LENGTH: 65
<212> TYPE: PRT
<213> ORGANISM: Artificial sequence
<220> FEATURE:
<223> OTHER INFORMATION: Fynomer #081

<400> SEQUENCE: 247

Gly Val Thr Leu Phe Val Ala Leu Tyr Asp Tyr Thr Ser Tyr Asn Asn
1               5                   10                  15

Thr Asp Leu Ser Phe His Lys Gly Glu Lys Phe Gln Ile Leu Thr Gln
            20                  25                  30

Asp Pro Leu His Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 248
<211> LENGTH: 63
<212> TYPE: PRT
<213> ORGANISM: Artificial sequence
<220> FEATURE:
<223> OTHER INFORMATION: Fynomer #82

<400> SEQUENCE: 248

Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Thr Gln
            20                  25                  30

Lys Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 249
<211> LENGTH: 65
<212> TYPE: PRT
<213> ORGANISM: Artificial sequence
<220> FEATURE:
<223> OTHER INFORMATION: Fynomer #83

<400> SEQUENCE: 249

Gly Val Thr Leu Phe Val Ala Leu Tyr Asp Tyr Ser Ser Tyr Asn Thr
1               5                   10                  15

Thr Asp Leu Ser Phe His Lys Gly Glu Lys Phe Gln Ile Leu Thr Gln
            20                  25                  30

Pro Pro Leu Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 250
<211> LENGTH: 65
<212> TYPE: PRT
```

<213> ORGANISM: Artificial sequence
<220> FEATURE:
<223> OTHER INFORMATION: Fynomer #84

<400> SEQUENCE: 250

```
Gly Val Thr Leu Phe Val Ala Leu Tyr Asp Tyr Thr Ser Tyr Asn Thr
1               5                   10                  15

Gln Asp Leu Ser Phe His Lys Gly Glu Lys Phe Gln Ile Leu Asp Ser
            20                  25                  30

Glu Thr Gly Lys Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 251
<211> LENGTH: 65
<212> TYPE: PRT
<213> ORGANISM: Artificial sequence
<220> FEATURE:
<223> OTHER INFORMATION: Fynomer #85

<400> SEQUENCE: 251

```
Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Arg Lys
            20                  25                  30

Pro Lys Tyr Asn Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 252
<211> LENGTH: 63
<212> TYPE: PRT
<213> ORGANISM: Artificial sequence
<220> FEATURE:
<223> OTHER INFORMATION: Fynomer #86

<400> SEQUENCE: 252

```
Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Ser Glu
            20                  25                  30

Pro Leu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 253
<211> LENGTH: 64
<212> TYPE: PRT
<213> ORGANISM: Artificial sequence
<220> FEATURE:
<223> OTHER INFORMATION: Fynomer #87

<400> SEQUENCE: 253

```
Gly Val Thr Leu Phe Val Ala Leu Tyr Asp Tyr Thr Ser Tyr Asn Gln
```

```
1               5                   10                  15

Arg Asp Leu Ser Phe His Lys Gly Glu Lys Phe Gln Ile Leu Val His
            20                  25                  30

Asp Pro Ala Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 254
<211> LENGTH: 62
<212> TYPE: PRT
<213> ORGANISM: Artificial sequence
<220> FEATURE:
<223> OTHER INFORMATION: Fynomer #88

<400> SEQUENCE: 254

Gly Val Thr Leu Phe Val Ala Leu Tyr Asp Tyr Val Ser Trp Asn Thr
1               5                   10                  15

Leu Asp Leu Ser Phe His Lys Gly Glu Lys Phe Gln Ile Leu Arg Met
            20                  25                  30

Pro Gly Asp Trp Trp Glu Ala Arg Ser Leu Thr Thr Gly Glu Thr Gly
        35                  40                  45

Tyr Ile Pro Ser Asn Tyr Val Ala Pro Val Asp Ser Ile Gln
    50                  55                  60


<210> SEQ ID NO 255
<211> LENGTH: 64
<212> TYPE: PRT
<213> ORGANISM: Artificial sequence
<220> FEATURE:
<223> OTHER INFORMATION: Fynomer #89

<400> SEQUENCE: 255

Gly Val Thr Leu Phe Val Ala Leu Tyr Asp Tyr Glu Ala Arg Leu Tyr
1               5                   10                  15

Ser Leu Asp Leu Ser Phe His Lys Gly Glu Lys Phe Gln Ile Leu Asn
            20                  25                  30

Arg Arg Trp Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 256
<211> LENGTH: 64
<212> TYPE: PRT
<213> ORGANISM: Artificial sequence
<220> FEATURE:
<223> OTHER INFORMATION: Fynomer #90

<400> SEQUENCE: 256

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Ala Pro
            20                  25                  30

Pro Asn Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 257
```

<211> LENGTH: 64
<212> TYPE: PRT
<213> ORGANISM: Artificial sequence
<220> FEATURE:
<223> OTHER INFORMATION: Fynomer #91

<400> SEQUENCE: 257

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Ala Arg
            20                  25                  30

Met Pro Pro Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 258
<211> LENGTH: 66
<212> TYPE: PRT
<213> ORGANISM: Artificial sequence
<220> FEATURE:
<223> OTHER INFORMATION: Fynomer #92

<400> SEQUENCE: 258

Gly Val Thr Leu Phe Val Ala Leu Tyr Asp Tyr Glu Ala Arg Phe Arg
1               5                   10                  15

Arg Asn Tyr Ser Asp Leu Ser Phe His Lys Gly Glu Lys Phe Gln Ile
            20                  25                  30

Leu Ser Ala Gln Gln Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65

<210> SEQ ID NO 259
<211> LENGTH: 65
<212> TYPE: PRT
<213> ORGANISM: Artificial sequence
<220> FEATURE:
<223> OTHER INFORMATION: Fynomer #93

<400> SEQUENCE: 259

Gly Val Thr Leu Phe Val Ala Leu Tyr Asp Tyr Asp Arg Arg Tyr Gly
1               5                   10                  15

Ala Asp Leu Ser Phe His Lys Gly Glu Lys Phe Gln Ile Leu Arg Asp
            20                  25                  30

Glu Ala Val Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 260
<211> LENGTH: 65
<212> TYPE: PRT
<213> ORGANISM: Artificial sequence
<220> FEATURE:
<223> OTHER INFORMATION: Fynomer #94

<400> SEQUENCE: 260

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu His Asp
20 25 30

Pro Pro Ser Asn Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 261
<211> LENGTH: 64
<212> TYPE: PRT
<213> ORGANISM: Artificial sequence
<220> FEATURE:
<223> OTHER INFORMATION: Fynomer #95

<400> SEQUENCE: 261

Gly Val Thr Leu Phe Val Ala Leu Tyr Asp Tyr Glu Ala Arg Tyr Ala
1 5 10 15

Pro Ala Asp Leu Ser Phe His Lys Gly Glu Lys Phe Gln Ile Leu Asn
20 25 30

His Asp Arg Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 262
<211> LENGTH: 65
<212> TYPE: PRT
<213> ORGANISM: Artificial sequence
<220> FEATURE:
<223> OTHER INFORMATION: Fynomer #96

<400> SEQUENCE: 262

Gly Val Thr Leu Phe Val Ala Leu Tyr Asp Tyr Thr Ser Ser Tyr Pro
1 5 10 15

Gly Asp Leu Ser Phe His Lys Gly Glu Lys Phe Gln Ile Leu Ser Asn
20 25 30

Asp Pro Val His Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 263
<211> LENGTH: 65
<212> TYPE: PRT
<213> ORGANISM: Artificial sequence
<220> FEATURE:
<223> OTHER INFORMATION: Fynomer #97

<400> SEQUENCE: 263

Gly Val Thr Leu Phe Val Ala Leu Tyr Asp Tyr Gln Thr Trp Thr Pro
1 5 10 15

Gly Asp Leu Ser Phe His Lys Gly Glu Lys Phe Gln Ile Leu Thr Gln
20 25 30

-continued

```
Asp Glu Gln Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 264
<211> LENGTH: 65
<212> TYPE: PRT
<213> ORGANISM: Artificial sequence
<220> FEATURE:
<223> OTHER INFORMATION: Fynomer #98

<400> SEQUENCE: 264

Gly Val Thr Leu Phe Val Ala Leu Tyr Asp Tyr Phe Thr Asn Thr Pro
1               5                   10                  15

Gly Asp Leu Ser Phe His Lys Gly Glu Lys Phe Gln Ile Leu Asn Thr
            20                  25                  30

Ser Tyr Leu Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 265
<211> LENGTH: 63
<212> TYPE: PRT
<213> ORGANISM: Artificial sequence
<220> FEATURE:
<223> OTHER INFORMATION: Fynomer #99

<400> SEQUENCE: 265

Gly Val Thr Leu Phe Val Ala Leu Tyr Asp Tyr Lys Thr His Asn Pro
1               5                   10                  15

Gly Asp Leu Ser Phe His Lys Gly Glu Lys Phe Gln Ile Leu Gln Gly
            20                  25                  30

Arg Val Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 266
<211> LENGTH: 65
<212> TYPE: PRT
<213> ORGANISM: Artificial sequence
<220> FEATURE:
<223> OTHER INFORMATION: Fynomer #100

<400> SEQUENCE: 266

Gly Val Thr Leu Phe Val Ala Leu Tyr Asp Tyr Gln Thr Tyr Thr Pro
1               5                   10                  15

Gly Asp Leu Ser Phe His Lys Gly Glu Lys Phe Gln Ile Leu Ser Lys
            20                  25                  30

Pro Pro Gln Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
```

65

<210> SEQ ID NO 267
<211> LENGTH: 65
<212> TYPE: PRT
<213> ORGANISM: Artificial sequence
<220> FEATURE:
<223> OTHER INFORMATION: Fynomer #101

<400> SEQUENCE: 267

```
Gly Val Thr Leu Phe Val Ala Leu Tyr Asp Tyr Glu Ala Arg Tyr Gln
1               5                   10                  15

Asp Leu Glu Asp Leu Ser Phe His Lys Gly Glu Lys Phe Gln Ile Leu
            20                  25                  30

Asn Gly Arg Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 268
<211> LENGTH: 63
<212> TYPE: PRT
<213> ORGANISM: Artificial sequence
<220> FEATURE:
<223> OTHER INFORMATION: Fynomer #102

<400> SEQUENCE: 268

```
Gly Val Thr Leu Phe Val Ala Leu Tyr Asp Tyr Asp Arg His Tyr Thr
1               5                   10                  15

Phe Asp Leu Ser Phe His Lys Gly Glu Lys Phe Gln Ile Leu Gln Asn
            20                  25                  30

Lys Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 269
<211> LENGTH: 63
<212> TYPE: PRT
<213> ORGANISM: Artificial sequence
<220> FEATURE:
<223> OTHER INFORMATION: Fynomer #103

<400> SEQUENCE: 269

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Asp
            20                  25                  30

Ser Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 270
<211> LENGTH: 65
<212> TYPE: PRT
<213> ORGANISM: Artificial sequence
<220> FEATURE:
<223> OTHER INFORMATION: Fynomer #104

<400> SEQUENCE: 270

Gly Val Thr Leu Phe Val Ala Leu Tyr Asp Tyr Glu Ala Arg Asp Arg
1 5 10 15

Pro Thr Asp Leu Ser Phe His Lys Gly Glu Lys Phe Gln Ile Leu Gly
20 25 30

Asp Glu Gln Ile Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 271
<211> LENGTH: 64
<212> TYPE: PRT
<213> ORGANISM: Artificial sequence
<220> FEATURE:
<223> OTHER INFORMATION: Fynomer #105

<400> SEQUENCE: 271

Gly Val Thr Leu Phe Val Ala Leu Tyr Asp Tyr Thr Thr Tyr Arg Lys
1 5 10 15

Gly Asp Leu Ser Phe His Lys Gly Glu Lys Phe Gln Ile Leu Asn Arg
20 25 30

Val Ser Ile Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 272
<211> LENGTH: 64
<212> TYPE: PRT
<213> ORGANISM: Artificial sequence
<220> FEATURE:
<223> OTHER INFORMATION: Fynomer #106

<400> SEQUENCE: 272

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Asn Arg
20 25 30

Val Ser Ile Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 273
<211> LENGTH: 63
<212> TYPE: PRT
<213> ORGANISM: Artificial sequence
<220> FEATURE:
<223> OTHER INFORMATION: Fynomer #107

<400> SEQUENCE: 273

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Gly Asp
20 25 30

Asn Ile Gly Asp Trp Trp Glu Ala Arg Ser Leu Thr Thr Gly Glu Thr
35 40 45

```
Gly Tyr Ile Pro Ser Asn Tyr Val Ala Pro Val Asp Ser Ile Gln
    50                  55                  60


<210> SEQ ID NO 274
<211> LENGTH: 63
<212> TYPE: PRT
<213> ORGANISM: Artificial sequence
<220> FEATURE:
<223> OTHER INFORMATION: Fynomer #108

<400> SEQUENCE: 274

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Ser
            20                  25                  30

Ser Asp Gly Thr Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 275
<211> LENGTH: 64
<212> TYPE: PRT
<213> ORGANISM: Artificial sequence
<220> FEATURE:
<223> OTHER INFORMATION: Fynomer #109

<400> SEQUENCE: 275

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Trp Ser
            20                  25                  30

Asp Ala Leu Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 276
<211> LENGTH: 63
<212> TYPE: PRT
<213> ORGANISM: Artificial sequence
<220> FEATURE:
<223> OTHER INFORMATION: Fynomer #110

<400> SEQUENCE: 276

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Met Ala
            20                  25                  30

Trp Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 277
<211> LENGTH: 65
<212> TYPE: PRT
<213> ORGANISM: Artificial sequence
<220> FEATURE:
<223> OTHER INFORMATION: Fynomer #111

<400> SEQUENCE: 277
```

Gly Val Thr Leu Phe Val Ala Leu Tyr Asp Tyr Glu Ala Arg Glu Gly
1 5 10 15

Gly Asn Asp Leu Ser Phe His Lys Gly Glu Lys Phe Gln Ile Leu Asn
20 25 30

Arg Val Ser Ile Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 278
<211> LENGTH: 66
<212> TYPE: PRT
<213> ORGANISM: Artificial sequence
<220> FEATURE:
<223> OTHER INFORMATION: Fynomer #112

<400> SEQUENCE: 278

Gly Val Thr Leu Phe Val Ala Leu Tyr Asp Tyr Glu Ala His Asp Gln
1 5 10 15

His Arg Pro Asp Leu Ser Phe His Lys Gly Glu Lys Phe Gln Ile Leu
20 25 30

Asn Arg Val Ser Ile Gly Asp Trp Trp Glu Ala Arg Ser Leu Thr Thr
35 40 45

Gly Glu Thr Gly Tyr Ile Pro Ser Asn Tyr Val Ala Pro Val Asp Ser
50 55 60

Ile Gln
65

<210> SEQ ID NO 279
<211> LENGTH: 66
<212> TYPE: PRT
<213> ORGANISM: Artificial sequence
<220> FEATURE:
<223> OTHER INFORMATION: Fynomer #113

<400> SEQUENCE: 279

Gly Val Thr Leu Phe Val Ala Leu Tyr Asp Tyr Glu Ala Arg Leu Ser
1 5 10 15

Ser His Pro His Val Leu Ser Phe His Lys Gly Glu Lys Phe Gln Ile
20 25 30

Leu Asn Ser Ser Ala Gly Asp Trp Trp Glu Ala Arg Ser Leu Thr Thr
35 40 45

Gly Glu Thr Gly Tyr Ile Pro Ser Asn Tyr Val Ala Pro Val Asp Ser
50 55 60

Ile Gln
65

<210> SEQ ID NO 280
<211> LENGTH: 64
<212> TYPE: PRT
<213> ORGANISM: Artificial sequence
<220> FEATURE:
<223> OTHER INFORMATION: Fynomer #114

<400> SEQUENCE: 280

Gly Val Thr Leu Phe Val Ala Leu Tyr Asp Tyr Thr Ser Tyr Asn Ser
1 5 10 15

```
Arg Asp Leu Ser Phe His Lys Gly Glu Lys Phe Gln Ile Leu Leu Met
            20                  25                  30

His Pro Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 281
<211> LENGTH: 64
<212> TYPE: PRT
<213> ORGANISM: Artificial sequence
<220> FEATURE:
<223> OTHER INFORMATION: Fynomer #115

<400> SEQUENCE: 281

Gly Val Thr Leu Phe Val Ala Leu Tyr Asp Tyr Glu Ala Arg His Ala
1               5                   10                  15

Pro Val Asp Leu Ser Phe His Lys Gly Glu Lys Phe Gln Ile Leu Gly
            20                  25                  30

Asp Asn Ile Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 282
<211> LENGTH: 64
<212> TYPE: PRT
<213> ORGANISM: Artificial sequence
<220> FEATURE:
<223> OTHER INFORMATION: Fynomer #116

<400> SEQUENCE: 282

Gly Val Thr Leu Phe Val Ala Leu Tyr Asp Tyr Glu Ala Arg Thr Lys
1               5                   10                  15

His Phe Asp Leu Ser Phe His Lys Gly Glu Lys Phe Gln Ile Leu Ser
            20                  25                  30

Gln Pro His Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 283
<211> LENGTH: 64
<212> TYPE: PRT
<213> ORGANISM: Artificial sequence
<220> FEATURE:
<223> OTHER INFORMATION: Fynomer #117

<400> SEQUENCE: 283

Gly Val Thr Leu Phe Val Ala Leu Tyr Asp Tyr Glu Ala Arg His Glu
1               5                   10                  15

Asn Phe Asp Leu Ser Phe His Lys Gly Glu Lys Phe Gln Ile Leu Asn
            20                  25                  30

Arg Gly Ala Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 284
<211> LENGTH: 65
<212> TYPE: PRT
```

<213> ORGANISM: Artificial sequence
<220> FEATURE:
<223> OTHER INFORMATION: Fynomer #118

<400> SEQUENCE: 284

```
Gly Val Thr Leu Phe Val Ala Leu Tyr Asp Tyr Glu Ala Arg Pro Asp
1               5                   10                  15

Ser His Asp Leu Ser Phe His Lys Gly Glu Lys Phe Gln Ile Leu Asn
            20                  25                  30

Arg Val Ser Ile Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 285
<211> LENGTH: 63
<212> TYPE: PRT
<213> ORGANISM: Artificial sequence
<220> FEATURE:
<223> OTHER INFORMATION: Fynomer #119

<400> SEQUENCE: 285

```
Gly Val Thr Leu Phe Val Ala Leu Tyr Asp Tyr Glu Ala Arg Arg Thr
1               5                   10                  15

His Asp Leu Ser Phe His Lys Gly Glu Lys Phe Gln Ile Leu Ser Gln
            20                  25                  30

Pro His Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 286
<211> LENGTH: 65
<212> TYPE: PRT
<213> ORGANISM: Artificial sequence
<220> FEATURE:
<223> OTHER INFORMATION: Fynomer #120

<400> SEQUENCE: 286

```
Gly Val Thr Leu Phe Val Ala Leu Tyr Asp Tyr Glu Ala Arg Pro Met
1               5                   10                  15

Ser Ser Asp Leu Ser Phe His Lys Gly Glu Lys Phe Gln Ile Leu Asn
            20                  25                  30

Arg Val Ser Ile Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 287
<211> LENGTH: 63
<212> TYPE: PRT
<213> ORGANISM: Artificial sequence
<220> FEATURE:
<223> OTHER INFORMATION: Fynomer #121

<400> SEQUENCE: 287

```
Gly Val Thr Leu Phe Val Ala Leu Tyr Asp Tyr Thr Ser Tyr Asn Thr
```

```
1               5                   10                  15

Arg Asp Leu Ser Phe His Lys Gly Glu Lys Phe Gln Ile Leu Arg Phe
            20                  25                  30

Asn Pro Gly Asp Trp Trp Glu Ala Arg Ser Leu Thr Thr Gly Glu Thr
        35                  40                  45

Gly Tyr Ile Pro Ser Ser Tyr Val Ala Pro Val Asp Ser Ile Gln
    50                  55                  60


<210> SEQ ID NO 288
<211> LENGTH: 63
<212> TYPE: PRT
<213> ORGANISM: Artificial sequence
<220> FEATURE:
<223> OTHER INFORMATION: Fynomer #122

<400> SEQUENCE: 288

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Phe Pro
            20                  25                  30

Asp Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 289
<211> LENGTH: 63
<212> TYPE: PRT
<213> ORGANISM: Artificial sequence
<220> FEATURE:
<223> OTHER INFORMATION: Fynomer #123

<400> SEQUENCE: 289

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Gln
            20                  25                  30

Pro His Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 290
<211> LENGTH: 63
<212> TYPE: PRT
<213> ORGANISM: Artificial sequence
<220> FEATURE:
<223> OTHER INFORMATION: Fynomer #124

<400> SEQUENCE: 290

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gly Lys
            20                  25                  30

Gly Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 291
```

<211> LENGTH: 63
<212> TYPE: PRT
<213> ORGANISM: Artificial sequence
<220> FEATURE:
<223> OTHER INFORMATION: Fynomer #125

<400> SEQUENCE: 291

Gly Val Thr Leu Phe Val Ala Leu Tyr Asp Tyr Thr Ser Tyr Asn Ser
1 5 10 15

Arg Asp Leu Ser Phe His Lys Gly Glu Lys Phe Gln Ile Leu Ser Asp
20 25 30

Gln His Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 292
<211> LENGTH: 63
<212> TYPE: PRT
<213> ORGANISM: Artificial sequence
<220> FEATURE:
<223> OTHER INFORMATION: Fynomer #126

<400> SEQUENCE: 292

Gly Val Thr Leu Phe Val Ala Leu Tyr Asp Tyr Thr Ser Tyr Asn Asp
1 5 10 15

Arg Asp Leu Ser Phe His Lys Gly Glu Lys Phe Gln Ile Leu Ser Ala
20 25 30

Pro Gln Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 293
<211> LENGTH: 63
<212> TYPE: PRT
<213> ORGANISM: Artificial sequence
<220> FEATURE:
<223> OTHER INFORMATION: Fynomer #127

<400> SEQUENCE: 293

Gly Val Thr Leu Phe Val Ala Leu Tyr Asp Tyr Thr Ser Tyr Asn Asp
1 5 10 15

Arg Asp Leu Ser Phe His Lys Gly Glu Lys Phe Gln Ile Leu Glu Tyr
20 25 30

Thr Thr Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 294
<211> LENGTH: 65
<212> TYPE: PRT
<213> ORGANISM: Artificial sequence
<220> FEATURE:
<223> OTHER INFORMATION: Fynomer #128

<400> SEQUENCE: 294

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Thr Thr
20 25 30

Glu Ala Thr Asp Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile
50 55 60

Gln
65

<210> SEQ ID NO 295
<211> LENGTH: 63
<212> TYPE: PRT
<213> ORGANISM: Artificial sequence
<220> FEATURE:
<223> OTHER INFORMATION: Fynomer #129

<400> SEQUENCE: 295

Gly Val Thr Leu Phe Val Ala Leu Tyr Asp Tyr Thr Ser Tyr Asn Ser
1 5 10 15

Arg Asp Leu Ser Phe His Lys Gly Glu Lys Phe Gln Ile Leu Gln Asn
20 25 30

Ser Gln Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 296
<211> LENGTH: 63
<212> TYPE: PRT
<213> ORGANISM: Artificial sequence
<220> FEATURE:
<223> OTHER INFORMATION: Fynomer #130

<400> SEQUENCE: 296

Gly Val Thr Leu Phe Val Ala Leu Tyr Asp Tyr Thr Ser Tyr Asn Ser
1 5 10 15

Arg Asp Leu Ser Phe His Lys Gly Glu Lys Phe Gln Ile Leu Gly Asn
20 25 30

Thr Gln Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 297
<211> LENGTH: 63
<212> TYPE: PRT
<213> ORGANISM: Artificial sequence
<220> FEATURE:
<223> OTHER INFORMATION: Fynomer #131

<400> SEQUENCE: 297

Gly Val Thr Leu Phe Val Ala Leu Tyr Asp Tyr Thr Ser Tyr Asn Ala
1 5 10 15

Gln Asp Leu Ser Phe His Lys Gly Glu Lys Phe Gln Ile Leu Gly Ala
20 25 30

Arg Tyr Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 298
<211> LENGTH: 63

<212> TYPE: PRT
<213> ORGANISM: Artificial sequence
<220> FEATURE:
<223> OTHER INFORMATION: Fynomer #132

<400> SEQUENCE: 298

```
Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Gly His
            20                  25                  30

His Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 299
<211> LENGTH: 63
<212> TYPE: PRT
<213> ORGANISM: Artificial sequence
<220> FEATURE:
<223> OTHER INFORMATION: Fynomer #133

<400> SEQUENCE: 299

```
Gly Val Thr Leu Phe Val Ala Leu Tyr Asp Tyr Thr Ser Tyr Asn Met
1               5                   10                  15

Arg Asp Leu Ser Phe His Lys Gly Glu Lys Phe Gln Ile Leu Asn Asn
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 300
<211> LENGTH: 65
<212> TYPE: PRT
<213> ORGANISM: Artificial sequence
<220> FEATURE:
<223> OTHER INFORMATION: Fynomer #134

<400> SEQUENCE: 300

```
Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Ser Lys
            20                  25                  30

Asp Ser Ala Leu Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 301
<211> LENGTH: 63
<212> TYPE: PRT
<213> ORGANISM: Artificial sequence
<220> FEATURE:
<223> OTHER INFORMATION: Fynomer #135

<400> SEQUENCE: 301

```
Gly Val Thr Leu Phe Val Ala Leu Tyr Asp Tyr Thr Ser Tyr Asn Ser
1               5                   10                  15
```

```
Arg Asp Leu Ser Phe His Lys Gly Glu Lys Phe Gln Ile Leu Asn Arg
            20                  25                  30

Gly Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 302
<211> LENGTH: 63
<212> TYPE: PRT
<213> ORGANISM: Artificial sequence
<220> FEATURE:
<223> OTHER INFORMATION: Fynomer #136

<400> SEQUENCE: 302

Gly Val Thr Leu Phe Val Ala Leu Tyr Asp Tyr Thr Ser Tyr Asn Thr
1               5                   10                  15

His Asp Leu Ser Phe His Lys Gly Glu Lys Phe Gln Ile Leu Lys Met
            20                  25                  30

Gln Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 303
<211> LENGTH: 63
<212> TYPE: PRT
<213> ORGANISM: Artificial sequence
<220> FEATURE:
<223> OTHER INFORMATION: Fynomer #137

<400> SEQUENCE: 303

Gly Val Thr Leu Phe Val Ala Leu Tyr Asp Tyr Thr Ser Tyr Asn Arg
1               5                   10                  15

Arg Asp Leu Ser Phe His Lys Gly Glu Lys Phe Gln Ile Leu Glu Thr
            20                  25                  30

Gln Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 304
<211> LENGTH: 63
<212> TYPE: PRT
<213> ORGANISM: Artificial sequence
<220> FEATURE:
<223> OTHER INFORMATION: Fynomer #138

<400> SEQUENCE: 304

Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Gly Ser
            20                  25                  30

Thr Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 305
<211> LENGTH: 67
<212> TYPE: PRT
```

<213> ORGANISM: Artificial sequence
<220> FEATURE:
<223> OTHER INFORMATION: Fynomer #139

<400> SEQUENCE: 305

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Arg Ser Trp Pro Glu Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 306
<211> LENGTH: 67
<212> TYPE: PRT
<213> ORGANISM: Artificial sequence
<220> FEATURE:
<223> OTHER INFORMATION: Fynomer #140

<400> SEQUENCE: 306

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Lys Thr Trp Glu Gly Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 307
<211> LENGTH: 67
<212> TYPE: PRT
<213> ORGANISM: Artificial sequence
<220> FEATURE:
<223> OTHER INFORMATION: Fynomer #141

<400> SEQUENCE: 307

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Gln Ala Trp Gln Glu Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 308
<211> LENGTH: 63
<212> TYPE: PRT
<213> ORGANISM: Artificial sequence
<220> FEATURE:
<223> OTHER INFORMATION: Fynomer #142

<400> SEQUENCE: 308

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Met
20 25 30

Glu Asp Gly Val Trp Trp Ala Ala Arg Ser Leu Thr Thr Gly Glu Ile
35 40 45

Gly Tyr Ile Pro Ser Asn Tyr Val Ala Pro Val Asp Ser Ile Gln
50 55 60

<210> SEQ ID NO 309
<211> LENGTH: 63
<212> TYPE: PRT
<213> ORGANISM: Artificial sequence
<220> FEATURE:
<223> OTHER INFORMATION: Fynomer #143

<400> SEQUENCE: 309

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Met
20 25 30

Glu Asp Gly Val Trp Trp Arg Ala Arg Ser Leu Thr Thr Gly Glu Ile
35 40 45

Gly Leu Ile Pro Ser Asn Tyr Val Ala Pro Val Asp Ser Ile Gln
50 55 60

<210> SEQ ID NO 310
<211> LENGTH: 63
<212> TYPE: PRT
<213> ORGANISM: Artificial sequence
<220> FEATURE:
<223> OTHER INFORMATION: Fynomer #144

<400> SEQUENCE: 310

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Met
20 25 30

Glu Asp Gly Val Trp Trp Thr Ala Arg Ser Leu Thr Thr Gly Glu Val
35 40 45

Gly Phe Ile Pro Ser Asn Tyr Val Ala Pro Val Asp Ser Ile Gln
50 55 60

<210> SEQ ID NO 311
<211> LENGTH: 63
<212> TYPE: PRT
<213> ORGANISM: Artificial sequence
<220> FEATURE:
<223> OTHER INFORMATION: Fynomer #145

<400> SEQUENCE: 311

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Met
20 25 30

Glu Asp Gly Ile Trp Trp Gln Ala Arg Ser Leu Thr Thr Gly Glu Thr
35 40 45

Gly Phe Ile Pro Ser Asn Tyr Val Ala Pro Val Asp Ser Ile Gln
50 55 60

<210> SEQ ID NO 312
<211> LENGTH: 65
<212> TYPE: PRT
<213> ORGANISM: Artificial sequence
<220> FEATURE:
<223> OTHER INFORMATION: Fynomer #146

<400> SEQUENCE: 312

```
Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Pro Pro
            20                  25                  30

Tyr Pro Thr Gly Gly Tyr Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 313
<211> LENGTH: 64
<212> TYPE: PRT
<213> ORGANISM: Artificial sequence
<220> FEATURE:
<223> OTHER INFORMATION: Fynomer #147

<400> SEQUENCE: 313

```
Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Gln Val
            20                  25                  30

Leu Asp Asn Gly Tyr Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 314
<211> LENGTH: 65
<212> TYPE: PRT
<213> ORGANISM: Artificial sequence
<220> FEATURE:
<223> OTHER INFORMATION: Fynomer #148

<400> SEQUENCE: 314

```
Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Thr Ala
            20                  25                  30

Leu Pro Asp Arg Gly Tyr Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 315
<211> LENGTH: 63
<212> TYPE: PRT
<213> ORGANISM: Artificial sequence
<220> FEATURE:

```
<223> OTHER INFORMATION: Fynomer #149

<400> SEQUENCE: 315

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Asp
            20                  25                  30

Asp Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 316
<211> LENGTH: 65
<212> TYPE: PRT
<213> ORGANISM: Artificial sequence
<220> FEATURE:
<223> OTHER INFORMATION: Fynomer #150

<400> SEQUENCE: 316

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Phe
            20                  25                  30

Gln Ser Ala Gly Gly Val Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 317
<211> LENGTH: 63
<212> TYPE: PRT
<213> ORGANISM: Artificial sequence
<220> FEATURE:
<223> OTHER INFORMATION: Fynomer #151

<400> SEQUENCE: 317

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ala Arg
            20                  25                  30

Asp Asn Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 318
<211> LENGTH: 66
<212> TYPE: PRT
<213> ORGANISM: Artificial sequence
<220> FEATURE:
<223> OTHER INFORMATION: Fynomer #152

<400> SEQUENCE: 318

Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30
```

Leu Trp Asn Thr Gly Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65

<210> SEQ ID NO 319
<211> LENGTH: 305
<212> TYPE: PRT
<213> ORGANISM: Artificial sequence
<220> FEATURE:
<223> OTHER INFORMATION: Fc fusion of Fynomer C12 (Fynomer #1; SEQ ID NO:1)

<400> SEQUENCE: 319

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Gly Val Thr Leu Phe Val Ala Leu Tyr Asp Tyr Thr Ser Tyr
                245                 250                 255

Asn Thr Arg Asp Leu Ser Phe His Lys Gly Glu Lys Phe Gln Ile Leu
            260                 265                 270

Arg Met Glu Asp Gly Val Trp Trp Glu Ala Arg Ser Leu Thr Thr Gly
        275                 280                 285

Glu Thr Gly Tyr Ile Pro Ser Asn Tyr Val Ala Pro Val Asp Ser Ile
    290                 295                 300

Gln
305

<210> SEQ ID NO 320
<211> LENGTH: 449
<212> TYPE: PRT
<213> ORGANISM: Artificial sequence
<220> FEATURE:
<223> OTHER INFORMATION: anti HER2 antibody 1, heavy chain

<400> SEQUENCE: 320

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 321
<211> LENGTH: 214
<212> TYPE: PRT
<213> ORGANISM: Artificial sequence
<220> FEATURE:
<223> OTHER INFORMATION: anti HER2 antibody 1, light chain

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 322
<211> LENGTH: 527
<212> TYPE: PRT
<213> ORGANISM: Artificial sequence
<220> FEATURE:
<223> OTHER INFORMATION: C-terminal heavy chain fusion protein of
      Fynomer C12 (Fynomer #1; SEQ ID NO:1) with anti HER2 antibody 1,
      heavy chain (SEQ ID NO:154)
```

<400> SEQUENCE: 322

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys

-continued

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gly Val Thr Leu Phe Val Ala Leu Tyr Asp Tyr Thr Ser Tyr Asn Thr
465                 470                 475                 480

Arg Asp Leu Ser Phe His Lys Gly Glu Lys Phe Gln Ile Leu Arg Met
                485                 490                 495

Glu Asp Gly Val Trp Trp Glu Ala Arg Ser Leu Thr Thr Gly Glu Thr
            500                 505                 510

Gly Tyr Ile Pro Ser Asn Tyr Val Ala Pro Val Asp Ser Ile Gln
        515                 520                 525


<210> SEQ ID NO 323
<211> LENGTH: 292
<212> TYPE: PRT
<213> ORGANISM: Artificial sequence
<220> FEATURE:
<223> OTHER INFORMATION: C-terminal light chain fusion protein of
      Fynomer C12 (Fynomer #1; SEQ ID NO:1) with anti HER2 antibody 1,
      light chain (SEQ ID NO:155)

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gly Val Thr Leu Phe Val Ala Leu Tyr Asp Tyr
225                 230                 235                 240
```

```
Thr Ser Tyr Asn Thr Arg Asp Leu Ser Phe His Lys Gly Glu Lys Phe
                245                 250                 255

Gln Ile Leu Arg Met Glu Asp Gly Val Trp Trp Glu Ala Arg Ser Leu
            260                 265                 270

Thr Thr Gly Glu Thr Gly Tyr Ile Pro Ser Asn Tyr Val Ala Pro Val
        275                 280                 285

Asp Ser Ile Gln
    290


<210> SEQ ID NO 324
<211> LENGTH: 527
<212> TYPE: PRT
<213> ORGANISM: Artificial sequence
<220> FEATURE:
<223> OTHER INFORMATION: N-terminal heavy chain fusion of Fynomer C12
      (Fynomer #1; SEQ ID NO:1) with anti HER2 antibody 1, heavy chain
      (SEQ ID NO:154)

<400> SEQUENCE: 324

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Gly Gly Gly Ser Glu Val
65                  70                  75                  80

Gln Leu Val Glu Ser Gly Gly Gly Leu Val Gln Pro Gly Gly Ser Leu
                85                  90                  95

Arg Leu Ser Cys Ala Ala Ser Gly Phe Thr Phe Thr Asp Tyr Thr Met
            100                 105                 110

Asp Trp Val Arg Gln Ala Pro Gly Lys Gly Leu Glu Trp Val Ala Asp
        115                 120                 125

Val Asn Pro Asn Ser Gly Gly Ser Ile Tyr Asn Gln Arg Phe Lys Gly
    130                 135                 140

Arg Phe Thr Leu Ser Val Asp Arg Ser Lys Asn Thr Leu Tyr Leu Gln
145                 150                 155                 160

Met Asn Ser Leu Arg Ala Glu Asp Thr Ala Val Tyr Tyr Cys Ala Arg
                165                 170                 175

Asn Leu Gly Pro Ser Phe Tyr Phe Asp Tyr Trp Gly Gln Gly Thr Leu
            180                 185                 190

Val Thr Val Ser Ser Ala Ser Thr Lys Gly Pro Ser Val Phe Pro Leu
        195                 200                 205

Ala Pro Ser Ser Lys Ser Thr Ser Gly Gly Thr Ala Ala Leu Gly Cys
    210                 215                 220

Leu Val Lys Asp Tyr Phe Pro Glu Pro Val Thr Val Ser Trp Asn Ser
225                 230                 235                 240

Gly Ala Leu Thr Ser Gly Val His Thr Phe Pro Ala Val Leu Gln Ser
                245                 250                 255

Ser Gly Leu Tyr Ser Leu Ser Ser Val Val Thr Val Pro Ser Ser Ser
            260                 265                 270

Leu Gly Thr Gln Thr Tyr Ile Cys Asn Val Asn His Lys Pro Ser Asn
        275                 280                 285
```

```
Thr Lys Val Asp Lys Lys Val Glu Pro Lys Ser Cys Asp Lys Thr His
    290                 295                 300

Thr Cys Pro Pro Cys Pro Ala Pro Glu Leu Leu Gly Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Glu Glu Met Thr Lys Asn Gln Val Ser Leu Thr Cys Leu
        435                 440                 445

Val Lys Gly Phe Tyr Pro Ser Asp Ile Ala Val Glu Trp Glu Ser Asn
    450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
            500                 505                 510

His Asn His Tyr Thr Gln Lys Ser Leu Ser Leu Ser Pro Gly Lys
        515                 520                 525
```

<210> SEQ ID NO 325
<211> LENGTH: 292
<212> TYPE: PRT
<213> ORGANISM: Artificial sequence
<220> FEATURE:
<223> OTHER INFORMATION: N-terminal light chain fusion protein of Fynomer C12 (Fynomer #1; SEQ ID NO:1) with anti HER2 antibody 1, light chain (SEQ ID NO:155)

<400> SEQUENCE: 325

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Gly Gly Gly Ser Asp Ile
65                  70                  75                  80

Gln Met Thr Gln Ser Pro Ser Ser Leu Ser Ala Ser Val Gly Asp Arg
                85                  90                  95

Val Thr Ile Thr Cys Lys Ala Ser Gln Asp Val Ser Ile Gly Val Ala
            100                 105                 110

Trp Tyr Gln Gln Lys Pro Gly Lys Ala Pro Lys Leu Leu Ile Tyr Ser
```

```
        115                 120                 125

Ala Ser Tyr Arg Tyr Thr Gly Val Pro Ser Arg Phe Ser Gly Ser Gly
    130                 135                 140

Ser Gly Thr Asp Phe Thr Leu Thr Ile Ser Ser Leu Gln Pro Glu Asp
145                 150                 155                 160

Phe Ala Thr Tyr Tyr Cys Gln Gln Tyr Tyr Ile Tyr Pro Tyr Thr Phe
                165                 170                 175

Gly Gln Gly Thr Lys Val Glu Ile Lys Arg Thr Val Ala Ala Pro Ser
            180                 185                 190

Val Phe Ile Phe Pro Pro Ser Asp Glu Gln Leu Lys Ser Gly Thr Ala
        195                 200                 205

Ser Val Val Cys Leu Leu Asn Asn Phe Tyr Pro Arg Glu Ala Lys Val
    210                 215                 220

Gln Trp Lys Val Asp Asn Ala Leu Gln Ser Gly Asn Ser Gln Glu Ser
225                 230                 235                 240

Val Thr Glu Gln Asp Ser Lys Asp Ser Thr Tyr Ser Leu Ser Ser Thr
                245                 250                 255

Leu Thr Leu Ser Lys Ala Asp Tyr Glu Lys His Lys Val Tyr Ala Cys
            260                 265                 270

Glu Val Thr His Gln Gly Leu Ser Ser Pro Val Thr Lys Ser Phe Asn
        275                 280                 285

Arg Gly Glu Cys
    290


<210> SEQ ID NO 326
<211> LENGTH: 450
<212> TYPE: PRT
<213> ORGANISM: Artificial sequence
<220> FEATURE:
<223> OTHER INFORMATION: anti HER2 antibody 2, heavy chain

<400> SEQUENCE: 326

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 327
<211> LENGTH: 292
<212> TYPE: PRT
<213> ORGANISM: Artificial sequence
<220> FEATURE:
<223> OTHER INFORMATION: N-terminal light chain fusion protein of Fynomer C12 (Fynomer #1; SEQ ID NO:1) with anti HER2 antibody 2, light chain (SEQ ID NO:163)

<400> SEQUENCE: 327

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Gly Gly Ser Asp Ile
65                  70                  75                  80
```

```
Gln Met Thr Gln Ser Pro Ser Ser Leu Ser Ala Ser Val Gly Asp Arg
                85                  90                  95

Val Thr Ile Thr Cys Arg Ala Ser Gln Asp Val Asn Thr Ala Val Ala
            100                 105                 110

Trp Tyr Gln Gln Lys Pro Gly Lys Ala Pro Lys Leu Leu Ile Tyr Ser
        115                 120                 125

Ala Ser Phe Leu Tyr Ser Gly Val Pro Ser Arg Phe Ser Gly Ser Arg
    130                 135                 140

Ser Gly Thr Asp Phe Thr Leu Thr Ile Ser Ser Leu Gln Pro Glu Asp
145                 150                 155                 160

Phe Ala Thr Tyr Tyr Cys Gln Gln His Tyr Thr Thr Pro Pro Thr Phe
                165                 170                 175

Gly Gln Gly Thr Lys Val Glu Ile Lys Arg Thr Val Ala Ala Pro Ser
            180                 185                 190

Val Phe Ile Phe Pro Pro Ser Asp Glu Gln Leu Lys Ser Gly Thr Ala
        195                 200                 205

Ser Val Val Cys Leu Leu Asn Asn Phe Tyr Pro Arg Glu Ala Lys Val
    210                 215                 220

Gln Trp Lys Val Asp Asn Ala Leu Gln Ser Gly Asn Ser Gln Glu Ser
225                 230                 235                 240

Val Thr Glu Gln Asp Ser Lys Asp Ser Thr Tyr Ser Leu Ser Ser Thr
                245                 250                 255

Leu Thr Leu Ser Lys Ala Asp Tyr Glu Lys His Lys Val Tyr Ala Cys
            260                 265                 270

Glu Val Thr His Gln Gly Leu Ser Ser Pro Val Thr Lys Ser Phe Asn
        275                 280                 285

Arg Gly Glu Cys
    290


<210> SEQ ID NO 328
<211> LENGTH: 17
<212> TYPE: PRT
<213> ORGANISM: Artificial sequence
<220> FEATURE:
<223> OTHER INFORMATION: myc-hexahistidine tag (SEQ ID NO: 162)

<400> SEQUENCE: 328

Gly Glu Gln Lys Leu Ile Ser Glu Glu Asp Leu His His His His His
1               5                   10                  15

His


<210> SEQ ID NO 329
<211> LENGTH: 214
<212> TYPE: PRT
<213> ORGANISM: Artificial sequence
<220> FEATURE:
<223> OTHER INFORMATION: anti HER2 antibody 2, light chain

<400> SEQUENCE: 329

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 330
<211> LENGTH: 63
<212> TYPE: PRT
<213> ORGANISM: Artificial sequence
<220> FEATURE:
<223> OTHER INFORMATION: wildt-type SH3 domain of the Fyn kinase (Fyn SH3)

<400> SEQUENCE: 330

```
Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 331
<211> LENGTH: 1362
<212> TYPE: DNA
<213> ORGANISM: Artificial sequence
<220> FEATURE:
<223> OTHER INFORMATION: Anti-HER2 antibody 1 (heavy chain) (coding for amino acids shown in SEQ ID NO: 154)

<400> SEQUENCE: 331

```
gaggtgcagc tggtcgaatc tggtgggggc ctggtgcagc ctgggggctc cctgagactg      60

tcctgtgccg catccggttt tacatttacc gactacacaa tggattgggt gcgacaggca     120

cccgggaagg gtctggagtg ggtggctgac gtgaacccta attccggcgg aagcatctac     180

aaccagaggt tcaagggccg gtttactctg tctgtggaca ggagtaaaaa caccctgtat     240

ctgcagatga attccctgag agccgaagat acagctgtct actattgcgc tcgcaatctg     300

ggtccatcat tctactttga ctattggggg cagggaactc tggtgactgt ctcatccgct     360

agcacaaagg gccctagtgt gtttcctctg gctccctctt ccaaatccac ttctggtggc     420
```

-continued

```
actgctgctc tgggatgcct ggtgaaggat tactttcctg aacctgtgac tgtctcatgg    480

aactctggtg ctctgacttc tggtgtccac actttccctg ctgtgctgca gtctagtgga    540

ctgtactctc tgtcatctgt ggtcactgtg ccctcttcat ctctgggaac ccagacctac    600

atttgtaatg tgaaccacaa accatccaac actaaagtgg acaaaaaagt ggaacccaaa    660

tcctgtgaca aaacccacac ctgcccacct tgtcctgccc ctgaactgct gggaggacct    720

tctgtgtttc tgttcccccc caaaccaaag gataccctga tgatctctag aacccctgag    780

gtgacatgtg tggtggtgga tgtgtctcat gaggaccctg aggtcaaatt caactggtac    840

gtggatggag tggaagtcca caatgccaaa accaagccta gagaggaaca gtacaattca    900

acctacagag tggtcagtgt gctgactgtg ctgcatcagg attggctgaa tggcaaggaa    960

tacaagtgta aagtctcaaa caaggccctg cctgctccaa ttgagaaaac aatctcaaag   1020

gccaagggac agcctaggga accccaggtc tacaccctgc caccttcaag agaggaaatg   1080

accaaaaacc aggtgtccct gacatgcctg gtcaaaggct tctacccttc tgacattgct   1140

gtggagtggg agtcaaatgg acagcctgag aacaactaca aaacaacccc ccctgtgctg   1200

gattctgatg gctctttctt tctgtactcc aaactgactg tggacaagtc tagatggcag   1260

caggggaatg tcttttcttg ctctgtcatg catgaggctc tgcataacca ctacactcag   1320

aaatccctgt ctctgtctcc tggcaaatga tagtaaaagc tt                      1362
```

<210> SEQ ID NO 332
<211> LENGTH: 657
<212> TYPE: DNA
<213> ORGANISM: Artificial sequence
<220> FEATURE:
<223> OTHER INFORMATION: Anti-HER2 antibody 1 (light chain) (coding for amino acids shown in SEQ ID NO:155)

<400> SEQUENCE: 332

```
gatatccaga tgacccagag ccctagtagt ctgagcgcaa gcgtcgggga ccgtgtgacc     60

attacctgta aagcaagcca ggatgtgtct atcggtgtgg catggtatca gcagaagccc    120

ggcaaagccc ctaagctgct gatctactct gctagttaca gatatactgg agtcccaagt    180

cggttctcag gctccggaag cgggaccgac tttaccctga caatctcctc cctgcaaccc    240

gaggatttcg ccacatacta ttgccagcag tactacatct atccttatac attcgggcag    300

gggacaaaag tggaaatcaa acggactgtg gcggcgcctt ctgtgttcat tttcccccca    360

tctgatgaac agctgaaatc tggcactgct tctgtggtct gtctgctgaa caacttctac    420

cctagagagg ccaaagtcca gtggaaagtg gacaatgctc tgcagagtgg gaattcccag    480

gaatctgtca ctgagcagga ctctaaggat agcacatact ccctgtcctc tactctgaca    540

ctgagcaagg ctgattacga gaaacacaaa gtgtacgcct gtgaagtcac acatcagggg    600

ctgtctagtc ctgtgaccaa atccttcaat aggggagagt gctgatagta aaagctt       657
```

<210> SEQ ID NO 333
<211> LENGTH: 891
<212> TYPE: DNA
<213> ORGANISM: Artificial sequence
<220> FEATURE:
<223> OTHER INFORMATION: N-terminal fusion of C12 to light chain of anti-HER2 antibody 1 (coding for amino acids shown in SEQ ID NO: 159)

<400> SEQUENCE: 333

```
ggggtgactc tgttcgtcgc tctgtatgat tacacttcct ataacaccag agacctgagc     60
```

```
ttccacaagg gcgagaaatt tcagatcctg aggatggagg atggagtgtg gtgggaagcc    120

cggtctctga ccacagggga gacaggttac attccttcaa actacgtcgc tcccgtggac    180

agcattcagg gtggtggggg atccggcgga ggaggaagtg gcggaggagg aagtgatatc    240

cagatgaccc agagccctag tagtctgagc gcaagcgtcg gggaccgtgt gaccattacc    300

tgtaaagcaa gccaggatgt gtctatcggt gtggcatggt atcagcagaa gcccggcaaa    360

gcccctaagc tgctgatcta ctctgctagt tacagatata ctggagtccc aagtcggttc    420

tcaggctccg gaagcgggac cgactttacc ctgacaatct cctccctgca acccgaggat    480

ttcgccacat actattgcca gcagtactac atctatcctt atacattcgg gcaggggaca    540

aaagtggaaa tcaaacggac tgtggcggcg ccttctgtgt tcattttccc cccatctgat    600

gaacagctga aatctggcac tgcttctgtg gtctgtctgc tgaacaactt ctaccctaga    660

gaggccaaag tccagtggaa agtggacaat gctctgcaga gtgggaattc ccaggaatct    720

gtcactgagc aggactctaa ggatagcaca tactccctgt cctctactct gacactgagc    780

aaggctgatt acgagaaaca caaagtgtac gcctgtgaag tcacacatca ggggctgtct    840

agtcctgtga ccaaatcctt caatagggga gagtgctgat agtaaaagct t             891
```

```
<210> SEQ ID NO 334
<211> LENGTH: 1365
<212> TYPE: DNA
<213> ORGANISM: Artificial sequence
<220> FEATURE:
<223> OTHER INFORMATION: Anti-HER2 antibody 2 (heavy chain) (coding for
      amino acids shown in SEQ ID NO: 160)

<400> SEQUENCE: 334
```

```
gaagtccagc tggtcgaatc tggtggtggc ctggtccagc ctggtggatc actgagactg     60

tcctgtgctg cttctggttt caacatcaag gacacctaca tccattgggt cagacaggca    120

cctggcaagg gactggaatg ggtcgcccga atctacccta caaacggcta cactcgctac    180

gccgactccg tcaagggacg ctttaccatc tccgccgaca cctctaaaaa caccgcctac    240

ctgcagatga atagtctgag ggccgaggat actgctgtgt actactgctc acgatgggga    300

ggcgacggct tttacgctat ggattactgg ggacagggaa ctctggtcac tgtgtctagc    360

gctagcacaa agggccctag tgtgtttcct ctggctccct cttccaaatc cacttctggt    420

ggcactgctg ctctgggatg cctggtgaag gattactttc ctgaacctgt gactgtctca    480

tggaactctg gtgctctgac ttctggtgtc cacactttcc ctgctgtgct gcagtctagt    540

ggactgtact ctctgtcatc tgtggtcact gtgccctctt catctctggg aacccagacc    600

tacatttgta atgtgaacca caaaccatcc aacactaaag tggacaaaaa agtggaaccc    660

aaatcctgtg acaaaaccca cacctgccca ccttgtcctg cccctgaact gctgggagga    720

ccttctgtgt ttctgttccc ccccaaacca aaggataccc tgatgatctc tagaacccct    780

gaggtgacat gtgtggtggt ggatgtgtct catgaggacc ctgaggtcaa attcaactgg    840

tacgtggatg gagtggaagt ccacaatgcc aaaaccaagc ctagagagga acagtacaat    900

tcaacctaca gagtggtcag tgtgctgact gtgctgcatc aggattggct gaatggcaag    960

gaatacaagt gtaaagtctc aaacaaggcc ctgcctgctc caattgagaa aacaatctca   1020

aaggccaagg gacagcctag ggaaccccag gtctacaccc tgccaccttc aagagaggaa   1080

atgaccaaaa accaggtgtc cctgacatgc ctggtcaaag gcttctaccc ttctgacatt   1140

gctgtggagt gggagtcaaa tggacagcct gagaacaact acaaaacaac ccccccctgtg   1200
```

ctggattctg atggctcttt ctttctgtac tccaaactga ctgtggacaa gtctagatgg 1260
cagcagggga atgtcttttc ttgctctgtc atgcatgagg ctctgcataa ccactacact 1320
cagaaatccc tgtctctgtc tcctggcaaa tgatagtaaa agctt 1365

<210> SEQ ID NO 335
<211> LENGTH: 657
<212> TYPE: DNA
<213> ORGANISM: Artificial sequence
<220> FEATURE:
<223> OTHER INFORMATION: Anti-HER2 antibody 2 (light chain) (coding for amino acids shown in SEQ ID NO: 163)

<400> SEQUENCE: 335
gacatccaga tgacacagtc tccctcttcc ctgtccgctt ctgtgggcga tcgagtgaca 60
atcacctgta gggctagtca ggatgtgaat actgctgttg cttggtacca gcagaaacca 120
ggaaaagccc ctaaactgct gatctactct gcctcattcc tgtactctgg ggtgccttct 180
cgattcagtg gttctagatc tggcaccgat ttcacactga ccatttcttc actgcaacct 240
gaggattttg ccacctacta ctgtcagcag cactacacaa cacctcccac atttggccag 300
ggcacaaaag tggagatcaa acggaccgtg gcggcgcctt ctgtgttcat tttcccccca 360
tctgatgaac agctgaaatc tggcactgct tctgtggtct gtctgctgaa caacttctac 420
cctagagagg ccaaagtcca gtggaaagtg gacaatgctc tgcagagtgg gaattcccag 480
gaatctgtca ctgagcagga ctctaaggat agcacatact ccctgtcctc tactctgaca 540
ctgagcaagg ctgattacga gaaacacaaa gtgtacgcct gtgaagtcac acatcagggg 600
ctgtctagtc ctgtgaccaa atccttcaat aggggagagt gctgatagta aaagctt 657

<210> SEQ ID NO 336
<211> LENGTH: 891
<212> TYPE: DNA
<213> ORGANISM: Artificial sequence
<220> FEATURE:
<223> OTHER INFORMATION: N-terminal C12 fusion to anti-HER2 antibody 2 light chain (coding for amino acids shown in SEQ ID NO: 161)

<400> SEQUENCE: 336
ggggtgactc tgttcgtcgc tctgtatgat tacacttcct ataacaccag agacctgagc 60
ttccacaagg gcgagaaatt tcagatcctg aggatggagg atggagtgtg gtgggaagcc 120
cggtctctga ccacagggga gacaggttac attccttcaa actacgtcgc tcccgtggac 180
agcattcagg gtggtggggg atccggcgga ggaggaagtg gcggaggagg aagtgacatc 240
cagatgacac agtctccctc ttccctgtcc gcttctgtgg gcgatcgagt gacaatcacc 300
tgtagggcta gtcaggatgt gaatactgct gttgcttggt accagcagaa accaggaaaa 360
gcccctaaac tgctgatcta ctctgcctca ttcctgtact ctggggtgcc ttctcgattc 420
agtggttcta gatctggcac cgatttcaca ctgaccattt cttcactgca acctgaggat 480
tttgccacct actactgtca gcagcactac acaacacctc ccacatttgg ccagggcaca 540
aaagtggaga tcaaacggac cgtggcggcg ccttctgtgt tcattttccc cccatctgat 600
gaacagctga aatctggcac tgcttctgtg gtctgtctgc tgaacaactt ctaccctaga 660
gaggccaaag tccagtggaa agtggacaat gctctgcaga gtgggaattc ccaggaatct 720
gtcactgagc aggactctaa ggatagcaca tactccctgt cctctactct gacactgagc 780
aaggctgatt acgagaaaca caaagtgtac gcctgtgaag tcacacatca ggggctgtct 840
agtcctgtga ccaaatcctt caatagggga gagtgctgat agtaaaagct t 891

<210> SEQ ID NO 337
<211> LENGTH: 1255
<212> TYPE: PRT
<213> ORGANISM: Homo sapiens

<400> SEQUENCE: 337

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
```

```
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800
```

```
Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Pro Ala Phe Ser Pro Ala
                1205                1210                1215
```

```
Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255


<210> SEQ ID NO 338
<211> LENGTH: 217
<212> TYPE: PRT
<213> ORGANISM: Homo sapiens

<400> SEQUENCE: 338

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg
    210                 215


<210> SEQ ID NO 339
<211> LENGTH: 63
<212> TYPE: PRT
<213> ORGANISM: Homo sapiens

<400> SEQUENCE: 339

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 340
<211> LENGTH: 64
<212> TYPE: PRT
<213> ORGANISM: Artificial sequence
<220> FEATURE:
<223> OTHER INFORMATION: C1

<400> SEQUENCE: 340

Gly Val Thr Leu Phe Val Ala Leu Tyr Asp Tyr His Ala His Leu Gly
1 5 10 15

Tyr Asp Leu Ser Phe His Lys Gly Glu Lys Phe Gln Ile Leu Gln Asp
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 341
<211> LENGTH: 64
<212> TYPE: PRT
<213> ORGANISM: Artificial sequence
<220> FEATURE:
<223> OTHER INFORMATION: 17H

<400> SEQUENCE: 341

Gly Val Thr Leu Phe Val Ala Leu Tyr Asp Tyr Gln Ser Arg His Gly
1 5 10 15

Phe Asp Leu Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 342
<211> LENGTH: 64
<212> TYPE: PRT
<213> ORGANISM: Artificial sequence
<220> FEATURE:
<223> OTHER INFORMATION: AB15F3

<400> SEQUENCE: 342

Gly Val Thr Leu Phe Val Ala Leu Tyr Asp Tyr Val Ser Asn Thr Gly
1 5 10 15

Phe Asp Leu Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 343
<211> LENGTH: 64
<212> TYPE: PRT
<213> ORGANISM: Artificial sequence
<220> FEATURE:
<223> OTHER INFORMATION: AB19C4

<400> SEQUENCE: 343

Gly Val Thr Leu Phe Val Ala Leu Tyr Asp Tyr Thr Ala Ser Tyr Gly
1 5 10 15

```
Tyr Asp Leu Ser Phe His Lys Gly Glu Lys Phe Gln Ile Leu Asp Asp
            20                  25                  30

Ile Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 344
<211> LENGTH: 64
<212> TYPE: PRT
<213> ORGANISM: Artificial sequence
<220> FEATURE:
<223> OTHER INFORMATION: SAM5H5

<400> SEQUENCE: 344

Gly Val Thr Leu Phe Val Ala Leu Tyr Asp Tyr Leu Arg Arg Asn Ser
1               5                   10                  15

Pro Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 345
<211> LENGTH: 64
<212> TYPE: PRT
<213> ORGANISM: Artificial sequence
<220> FEATURE:
<223> OTHER INFORMATION: SAM7G4

<400> SEQUENCE: 345

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Gln Asp
            20                  25                  30

Leu Trp Thr Gly Ala Leu Trp Arg Ala Arg Ser Leu Thr Thr Gly Arg
        35                  40                  45

Met Gly Ser Ile Pro Ser Asn Tyr Val Ala Pro Val Asp Ser Ile Gln
    50                  55                  60


<210> SEQ ID NO 346
<211> LENGTH: 64
<212> TYPE: PRT
<213> ORGANISM: Artificial sequence
<220> FEATURE:
<223> OTHER INFORMATION: SAM23C5

<400> SEQUENCE: 346

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30

Leu Trp Thr Gly Glu Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 347
<211> LENGTH: 64
<212> TYPE: PRT
```

<213> ORGANISM: Artificial sequence
<220> FEATURE:
<223> OTHER INFORMATION: SAM22A2

<400> SEQUENCE: 347

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30

Leu Trp Thr Gly Ser Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 348
<211> LENGTH: 64
<212> TYPE: PRT
<213> ORGANISM: Artificial sequence
<220> FEATURE:
<223> OTHER INFORMATION: SAM23F4

<400> SEQUENCE: 348

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30

Leu Trp Thr Gly Lys Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 349
<211> LENGTH: 64
<212> TYPE: PRT
<213> ORGANISM: Artificial sequence
<220> FEATURE:
<223> OTHER INFORMATION: SAM11C1

<400> SEQUENCE: 349

Gly Val Thr Leu Phe Val Ala Leu Tyr Asp Tyr Glu Lys Gln His Ala
1               5                   10                  15

Trp Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 350
<211> LENGTH: 64
<212> TYPE: PRT
<213> ORGANISM: Artificial sequence
<220> FEATURE:
<223> OTHER INFORMATION: SAM11E6

<400> SEQUENCE: 350

Gly Val Thr Leu Phe Val Ala Leu Tyr Asp Tyr Arg Ser Ser Tyr Glu
1               5                   10                  15

Trp Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu

```
        35                  40                  45

Thr Gly Tyr Ile Pro Ser Asn Tyr Val Ala Pro Val Asp Ser Ile Gln
    50                  55                  60


<210> SEQ ID NO 351
<211> LENGTH: 64
<212> TYPE: PRT
<213> ORGANISM: Artificial sequence
<220> FEATURE:
<223> OTHER INFORMATION: SAM23C9

<400> SEQUENCE: 351

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30

Leu Trp Thr Gly Asn Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 352
<211> LENGTH: 64
<212> TYPE: PRT
<213> ORGANISM: Artificial sequence
<220> FEATURE:
<223> OTHER INFORMATION: SAM19G2

<400> SEQUENCE: 352

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 353
<211> LENGTH: 64
<212> TYPE: PRT
<213> ORGANISM: Artificial sequence
<220> FEATURE:
<223> OTHER INFORMATION: SAM19F9

<400> SEQUENCE: 353

Gly Val Thr Leu Phe Val Ala Leu Tyr Asp Tyr Gly Asn Phe Arg Trp
1               5                   10                  15

Arg Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 354
<211> LENGTH: 64
<212> TYPE: PRT
<213> ORGANISM: Artificial sequence
<220> FEATURE:
<223> OTHER INFORMATION: SAM20F11
```

<400> SEQUENCE: 354

Gly Val Thr Leu Phe Val Ala Leu Tyr Asp Tyr Gln Ser Arg His Gly
1 5 10 15

Phe Asp Leu Ser Phe His Lys Gly Glu Lys Phe Gln Ile Leu Gln Asn
20 25 30

Leu Trp Thr Gly Trp Gly Trp Val Ala Arg Ser Leu Thr Thr Gly Leu
35 40 45

Ser Gly Tyr Ile Pro Ser Asn Tyr Val Ala Pro Val Asp Ser Ile Gln
50 55 60

<210> SEQ ID NO 355
<211> LENGTH: 64
<212> TYPE: PRT
<213> ORGANISM: Artificial sequence
<220> FEATURE:
<223> OTHER INFORMATION: SAM21D10

<400> SEQUENCE: 355

Gly Val Thr Leu Phe Val Ala Leu Tyr Asp Tyr Thr Ser Met Arg Gly
1 5 10 15

Tyr Asp Leu Ser Phe His Lys Gly Glu Lys Phe Gln Ile Leu Gln Asp
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 356
<211> LENGTH: 64
<212> TYPE: PRT
<213> ORGANISM: Artificial sequence
<220> FEATURE:
<223> OTHER INFORMATION: SAM21E1

<400> SEQUENCE: 356

Gly Val Thr Leu Phe Val Ala Leu Tyr Asp Tyr Gln Ser Lys His Gly
1 5 10 15

Tyr Asp Leu Ser Phe His Lys Gly Glu Lys Phe Gln Ile Leu Gln Asp
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 357
<211> LENGTH: 64
<212> TYPE: PRT
<213> ORGANISM: Artificial sequence
<220> FEATURE:
<223> OTHER INFORMATION: SAM21G3

<400> SEQUENCE: 357

Gly Val Thr Leu Phe Val Ala Leu Tyr Asp Tyr Leu Met Lys Thr Leu
1 5 10 15

Ala Asp Leu Ser Phe His Lys Gly Glu Lys Phe Gln Ile Leu Gln Asp
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 358
<211> LENGTH: 64
<212> TYPE: PRT
<213> ORGANISM: Artificial sequence
<220> FEATURE:
<223> OTHER INFORMATION: SAM22B3

<400> SEQUENCE: 358

```
Gly Val Thr Leu Phe Val Ala Leu Tyr Asp Tyr Thr Leu Arg Gln Trp
1               5                   10                  15

Lys Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 359
<211> LENGTH: 64
<212> TYPE: PRT
<213> ORGANISM: Artificial sequence
<220> FEATURE:
<223> OTHER INFORMATION: SAM22B8

<400> SEQUENCE: 359

```
Gly Val Thr Leu Phe Val Ala Leu Tyr Asp Tyr Glu Arg Gln His Gly
1               5                   10                  15

Phe Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 360
<211> LENGTH: 64
<212> TYPE: PRT
<213> ORGANISM: Artificial sequence
<220> FEATURE:
<223> OTHER INFORMATION: SAM22B7

<400> SEQUENCE: 360

```
Gly Val Thr Leu Phe Val Ala Leu Tyr Asp Tyr Glu Ser Arg His Gly
1               5                   10                  15

Tyr Asp Leu Ser Phe His Lys Gly Glu Lys Phe Gln Ile Leu Gln Asn
            20                  25                  30

Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 361
<211> LENGTH: 64
<212> TYPE: PRT
<213> ORGANISM: Artificial sequence
<220> FEATURE:
<223> OTHER INFORMATION: SAM22E3

<400> SEQUENCE: 361

```
Gly Val Thr Leu Phe Val Ala Leu Tyr Asp Tyr Gln Ser Lys Gln Gly
1               5                   10                  15
```

Phe Asp Leu Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 362
<211> LENGTH: 64
<212> TYPE: PRT
<213> ORGANISM: Artificial sequence
<220> FEATURE:
<223> OTHER INFORMATION: SAM28B1

<400> SEQUENCE: 362

Gly Val Thr Leu Phe Val Ala Leu Tyr Asp Tyr Leu Leu Gln Trp Arg
1 5 10 15

Gln Asp Leu Ser Phe His Lys Gly Glu Lys Phe Gln Ile Leu Gln Asp
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 363
<211> LENGTH: 64
<212> TYPE: PRT
<213> ORGANISM: Artificial sequence
<220> FEATURE:
<223> OTHER INFORMATION: SAM28B9

<400> SEQUENCE: 363

Gly Val Thr Leu Phe Val Ala Leu Tyr Asp Tyr Thr Ser Ser His Gly
1 5 10 15

Phe Asp Leu Ser Phe His Lys Gly Glu Lys Phe Gln Ile Leu Gln Asp
20 25 30

Leu Trp Thr Gly Asp Trp Trp Glu Val Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 364
<211> LENGTH: 64
<212> TYPE: PRT
<213> ORGANISM: Artificial sequence
<220> FEATURE:
<223> OTHER INFORMATION: SAM30H2

<400> SEQUENCE: 364

Gly Val Thr Leu Phe Val Ala Leu Tyr Asp Tyr Glu Ala His Leu Gly
1 5 10 15

Tyr Asp Leu Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 365
<211> LENGTH: 64

<212> TYPE: PRT
<213> ORGANISM: Artificial sequence
<220> FEATURE:
<223> OTHER INFORMATION: SAM30D6

<400> SEQUENCE: 365

Gly Val Thr Leu Phe Val Ala Leu Tyr Asp Tyr Thr Ala Val His Gly
1 5 10 15

Tyr Asp Leu Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 366
<211> LENGTH: 64
<212> TYPE: PRT
<213> ORGANISM: Artificial sequence
<220> FEATURE:
<223> OTHER INFORMATION: SAM30B8

<400> SEQUENCE: 366

Gly Val Thr Leu Phe Val Ala Leu Tyr Asp Tyr Leu Thr Lys Gln Leu
1 5 10 15

Pro Asp Arg Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 367
<211> LENGTH: 64
<212> TYPE: PRT
<213> ORGANISM: Artificial sequence
<220> FEATURE:
<223> OTHER INFORMATION: SAM30B12

<400> SEQUENCE: 367

Gly Val Thr Leu Phe Val Ala Leu Tyr Asp Tyr Met Ser Gln Met Gly
1 5 10 15

Tyr Asp Leu Ser Phe His Lys Gly Glu Lys Phe Gln Ile Leu Gln Asn
20 25 30

Leu Trp Thr Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 368
<211> LENGTH: 64
<212> TYPE: PRT
<213> ORGANISM: Artificial sequence
<220> FEATURE:
<223> OTHER INFORMATION: SAM31H9

<400> SEQUENCE: 368

Gly Val Thr Leu Phe Val Ala Leu Tyr Asp Tyr Gln Ala Ser His Gly
1 5 10 15

Tyr Asp Leu Ser Phe His Lys Gly Glu Lys Phe Gln Ile Leu Gln Asn
20 25 30

```
Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 369
<211> LENGTH: 64
<212> TYPE: PRT
<213> ORGANISM: Artificial sequence
<220> FEATURE:
<223> OTHER INFORMATION: AB8F11

<400> SEQUENCE: 369

Gly Val Thr Leu Phe Val Ala Leu Tyr Asp Tyr Thr Ala Arg Thr Gly
1               5                   10                  15

Tyr Asp Leu Ser Phe His Lys Gly Glu Lys Phe Gln Ile Leu Asp Ala
            20                  25                  30

Val Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 370
<211> LENGTH: 64
<212> TYPE: PRT
<213> ORGANISM: Artificial sequence
<220> FEATURE:
<223> OTHER INFORMATION: AB18G9

<400> SEQUENCE: 370

Gly Val Thr Leu Phe Val Ala Leu Tyr Asp Tyr Gln Ser Arg Glu Lys
1               5                   10                  15

Phe Asp Leu Ser Phe His Lys Gly Glu Lys Phe Gln Ile Leu Asp Gln
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 371
<211> LENGTH: 64
<212> TYPE: PRT
<213> ORGANISM: Artificial sequence
<220> FEATURE:
<223> OTHER INFORMATION: SAM14D1

<400> SEQUENCE: 371

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Asp Asn
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 372
<211> LENGTH: 64
<212> TYPE: PRT
<213> ORGANISM: Artificial sequence
<220> FEATURE:
<223> OTHER INFORMATION: SAM14C3
```

<400> SEQUENCE: 372

Gly Val Thr Leu Phe Val Ala Leu Tyr Asp Tyr His Ala His Leu Gly
1 5 10 15

Tyr Asp Leu Ser Phe His Lys Gly Glu Lys Phe Gln Ile Leu Asp Asp
20 25 30

Leu Arg Phe Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 373
<211> LENGTH: 64
<212> TYPE: PRT
<213> ORGANISM: Artificial sequence
<220> FEATURE:
<223> OTHER INFORMATION: SAM17F1

<400> SEQUENCE: 373

Gly Val Thr Leu Phe Val Ala Leu Tyr Asp Tyr Gln Ser Arg His Gly
1 5 10 15

Phe Asp Leu Ser Phe His Lys Gly Glu Lys Phe Gln Ile Leu Asp Trp
20 25 30

Leu Arg Phe Gly Asp Trp Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 374
<211> LENGTH: 64
<212> TYPE: PRT
<213> ORGANISM: Artificial sequence
<220> FEATURE:
<223> OTHER INFORMATION: SAM17B3

<400> SEQUENCE: 374

Gly Val Thr Leu Phe Val Ala Leu Tyr Asp Tyr Gln Ser Arg His Gly
1 5 10 15

Phe Asp Leu Ser Phe His Lys Gly Glu Lys Phe Gln Ile Leu Asp Ala
20 25 30

Ile Arg Phe Gly Asp Arg Trp Glu Ala Arg Ser Leu Thr Thr Gly Glu
35 40 45

Thr Gly Tyr Ile Pro Ser Asn Tyr Val Ala Pro Val Asp Ser Ile Gln
50 55 60

<210> SEQ ID NO 375
<211> LENGTH: 64
<212> TYPE: PRT
<213> ORGANISM: Artificial sequence
<220> FEATURE:
<223> OTHER INFORMATION: SAM17F3

<400> SEQUENCE: 375

Gly Val Thr Leu Phe Val Ala Leu Tyr Asp Tyr Gln Ser Arg His Gly
1 5 10 15

Phe Asp Leu Ser Phe His Lys Gly Glu Lys Phe Gln Ile Leu Asp Ala
20 25 30

Met Leu Arg Phe Gly Asp Trp Trp Glu Ala Arg Ser Leu Thr Thr Gly
35 40 45

Glu Thr Gly Tyr Ile Pro Ser Asn Tyr Val Ala Pro Val Asp Ser Ile

```
    50                  55                  60


<210> SEQ ID NO 376
<211> LENGTH: 64
<212> TYPE: PRT
<213> ORGANISM: Artificial sequence
<220> FEATURE:
<223> OTHER INFORMATION: SAM17H4

<400> SEQUENCE: 376

Gly Val Thr Leu Phe Val Ala Leu Tyr Asp Tyr His Ala His Leu Gly
1               5                   10                  15

Tyr Asp Leu Ser Phe His Lys Gly Glu Lys Phe Gln Ile Leu Asp Ser
            20                  25                  30

Leu Arg Phe Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60


<210> SEQ ID NO 377
<211> LENGTH: 15
<212> TYPE: PRT
<213> ORGANISM: Artificial sequence
<220> FEATURE:
<223> OTHER INFORMATION: linker

<400> SEQUENCE: 377

Gly Gly Gly Gly Ser Gly Gly Gly Gly Ser Gly Gly Gly Gly Ser
1               5                   10                  15


<210> SEQ ID NO 378
<211> LENGTH: 498
<212> TYPE: PRT
<213> ORGANISM: Artificial sequence
<220> FEATURE:
<223> OTHER INFORMATION: BITE protein

<400> SEQUENCE: 378

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Asn Val Asp Thr Asn Val Ala Trp Tyr Gln Gln Lys Pro
                165                 170                 175
```

```
Gly Gln Ala Pro Lys Ser Leu Ile Tyr Ser Ala Thr Tyr Arg Tyr Ser
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asn Ser Tyr Pro Tyr Thr Phe Gly Gly Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu


<210> SEQ ID NO 379
<211> LENGTH: 578
<212> TYPE: PRT
<213> ORGANISM: Artificial sequence
<220> FEATURE:
<223> OTHER INFORMATION: COVA406

<400> SEQUENCE: 379

Gly Val Thr Leu Phe Val Ala Leu Tyr Asp Tyr Gln Ser Arg His Gly
1               5                   10                  15

Phe Asp Leu Ser Phe His Lys Gly Glu Lys Phe Gln Ile Leu Gln Asn
            20                  25                  30
```

-continued

```
Leu Trp Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

Gly Gly Gly Gly Gly Ser Gly Gly Gly Gly Ser Gly Gly Gly Gly Ser
65                  70                  75                  80

Gln Val Gln Leu Val Glu Ser Gly Gly Gly Leu Val Lys Pro Gly Glu
                85                  90                  95

Ser Leu Arg Leu Ser Cys Ala Ala Ser Gly Phe Thr Phe Ser Asp Tyr
            100                 105                 110

Tyr Met Tyr Trp Val Arg Gln Ala Pro Gly Lys Gly Leu Glu Trp Val
        115                 120                 125

Ala Ile Ile Ser Asp Gly Gly Tyr Tyr Thr Tyr Tyr Ser Asp Ile Ile
    130                 135                 140

Lys Gly Arg Phe Thr Ile Ser Arg Asp Asn Ala Lys Asn Ser Leu Tyr
145                 150                 155                 160

Leu Gln Met Asn Ser Leu Lys Ala Glu Asp Thr Ala Val Tyr Tyr Cys
                165                 170                 175

Ala Arg Gly Phe Pro Leu Leu Arg His Gly Ala Phe Asp Tyr Trp Gly
            180                 185                 190

Gln Gly Thr Leu Val Thr Val Ser Ser Gly Gly Gly Gly Ser Gly Gly
        195                 200                 205

Gly Gly Ser Gly Gly Gly Gly Ser Asp Ile Gln Met Thr Gln Ser Pro
    210                 215                 220

Ser Ser Leu Ser Ala Ser Val Gly Asp Arg Val Thr Ile Thr Cys Arg
225                 230                 235                 240

Ala Ser Gln Asn Val Asp Thr Asn Val Ala Trp Tyr Gln Gln Lys Pro
                245                 250                 255

Gly Gln Ala Pro Lys Ser Leu Ile Tyr Ser Ala Thr Tyr Arg Tyr Ser
            260                 265                 270

Asp Val Pro Ser Arg Phe Ser Gly Ser Ala Ser Gly Thr Asp Phe Thr
        275                 280                 285

Leu Thr Ile Ser Ser Val Gln Ser Glu Asp Phe Ala Thr Tyr Tyr Cys
    290                 295                 300

Gln Gln Tyr Asn Ser Tyr Pro Tyr Thr Phe Gly Gly Gly Thr Lys Leu
305                 310                 315                 320

Glu Ile Lys Ser Gly Gly Gly Gly Ser Glu Val Gln Leu Val Glu Ser
                325                 330                 335

Gly Gly Gly Leu Val Gln Pro Gly Gly Ser Leu Lys Leu Ser Cys Ala
            340                 345                 350

Ala Ser Gly Phe Thr Phe Asn Lys Tyr Ala Met Asn Trp Val Arg Gln
        355                 360                 365

Ala Pro Gly Lys Gly Leu Glu Trp Val Ala Arg Ile Arg Ser Lys Tyr
    370                 375                 380

Asn Asn Tyr Ala Thr Tyr Tyr Ala Asp Ser Val Lys Asp Arg Phe Thr
385                 390                 395                 400

Ile Ser Arg Asp Asp Ser Lys Asn Thr Ala Tyr Leu Gln Met Asn Asn
                405                 410                 415

Leu Lys Thr Glu Asp Thr Ala Val Tyr Tyr Cys Val Arg His Gly Asn
            420                 425                 430

Phe Gly Asn Ser Tyr Ile Ser Tyr Trp Ala Tyr Trp Gly Gln Gly Thr
        435                 440                 445

Leu Val Thr Val Ser Ser Gly Gly Gly Gly Ser Gly Gly Gly Gly Ser
```

```
    450                 455                 460

Gly Gly Gly Gly Ser Gln Thr Val Val Thr Gln Glu Pro Ser Leu Thr
465                 470                 475                 480

Val Ser Pro Gly Gly Thr Val Thr Leu Thr Cys Gly Ser Ser Thr Gly
                485                 490                 495

Ala Val Thr Ser Gly Asn Tyr Pro Asn Trp Val Gln Gln Lys Pro Gly
            500                 505                 510

Gln Ala Pro Arg Gly Leu Ile Gly Gly Thr Lys Phe Leu Ala Pro Gly
        515                 520                 525

Thr Pro Ala Arg Phe Ser Gly Ser Leu Leu Gly Gly Lys Ala Ala Leu
    530                 535                 540

Thr Leu Ser Gly Val Gln Pro Glu Asp Glu Ala Glu Tyr Tyr Cys Val
545                 550                 555                 560

Leu Trp Tyr Ser Asn Arg Trp Val Phe Gly Gly Gly Thr Lys Leu Thr
                565                 570                 575

Val Leu


<210> SEQ ID NO 380
<211> LENGTH: 27
<212> TYPE: PRT
<213> ORGANISM: Artificial sequence
<220> FEATURE:
<223> OTHER INFORMATION: sequence of peptide derived
      from CD3

<400> SEQUENCE: 380

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25


<210> SEQ ID NO 381
<211> LENGTH: 449
<212> TYPE: PRT
<213> ORGANISM: Artificial Sequence
<220> FEATURE:
<223> OTHER INFORMATION: anti-CD3 antibody

<400> SEQUENCE: 381

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Ala Ala Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 382
<211> LENGTH: 213
<212> TYPE: PRT
<213> ORGANISM: Artificial Sequence
<220> FEATURE:
<223> OTHER INFORMATION: anti-CD3 antibody

<400> SEQUENCE: 382

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

Asn Trp Tyr Gln Gln Thr Pro Gly Lys Ala Pro Lys Arg Trp Ile Tyr
35 40 45

Asp Thr Ser Lys Leu Ala Ser Gly Val Pro Ser Arg Phe Ser Gly Ser

```
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 383
<211> LENGTH: 63
<212> TYPE: PRT
<213> ORGANISM: Artificial Sequence
<220> FEATURE:
<223> OTHER INFORMATION: anti-HER2 Fynomer C12

<400> SEQUENCE: 383

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60


<210> SEQ ID NO 384
<211> LENGTH: 67
<212> TYPE: PRT
<213> ORGANISM: Artificial Sequence
<220> FEATURE:
<223> OTHER INFORMATION: anti-HER2 Fynomer

<400> SEQUENCE: 384

Gly Val Thr Leu Phe Val Ala Leu Tyr Asp Tyr Glu Ala Arg Pro Tyr
1               5                   10                  15

Leu Gly Gly Gln Asp Leu Ser Phe His Lys Gly Glu Lys Phe Gln Ile
            20                  25                  30

Leu His Ala Ser Met Leu Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65
```

<210> SEQ ID NO 385
<211> LENGTH: 63
<212> TYPE: PRT
<213> ORGANISM: Artificial Sequence
<220> FEATURE:
<223> OTHER INFORMATION: anti-HER2 Fynomer

<400> SEQUENCE: 385

Gly Val Thr Leu Phe Val Ala Leu Tyr Asp Tyr Thr Ser Tyr Asn Gln
1 5 10 15

His Asp Leu Ser Phe His Lys Gly Glu Lys Phe Gln Ile Leu Gly Asp
20 25 30

Asn Ile Gly Asp Trp Trp Glu Ala Arg Ser Leu Thr Thr Gly Glu Thr
35 40 45

Gly Tyr Ile Pro Ser Asn Tyr Val Ala Pro Val Asp Ser Ile Gln
50 55 60

<210> SEQ ID NO 386
<211> LENGTH: 15
<212> TYPE: PRT
<213> ORGANISM: Artificial Sequence
<220> FEATURE:
<223> OTHER INFORMATION: GS-linker

<400> SEQUENCE: 386

Gly Gly Gly Gly Ser Gly Gly Gly Gly Ser Gly Gly Gly Gly Ser
1 5 10 15

<210> SEQ ID NO 387
<211> LENGTH: 527
<212> TYPE: PRT
<213> ORGANISM: Artificial Sequence
<220> FEATURE:
<223> OTHER INFORMATION: COVA420 Heavy Chain

<400> SEQUENCE: 387

Gly Val Thr Leu Phe Val Ala Leu Tyr Asp Tyr Thr Ser Tyr Asn Thr
1 5 10 15

Arg Asp Leu Ser Phe His Lys Gly Glu Lys Phe Gln Ile Leu Arg Met
20 25 30

Glu Asp Gly Val Trp Trp Glu Ala Arg Ser Leu Thr Thr Gly Glu Thr
35 40 45

Gly Tyr Ile Pro Ser Asn Tyr Val Ala Pro Val Asp Ser Ile Gln Gly
50 55 60

Gly Gly Gly Ser Gly Gly Gly Gly Ser Gly Gly Gly Gly Ser Gln Val
65 70 75 80

Gln Leu Val Gln Ser Gly Gly Gly Val Val Gln Pro Gly Arg Ser Leu
85 90 95

Arg Leu Ser Cys Lys Ala Ser Gly Tyr Thr Phe Thr Arg Tyr Thr Met
100 105 110

His Trp Val Arg Gln Ala Pro Gly Lys Gly Leu Glu Trp Ile Gly Tyr
115 120 125

Ile Asn Pro Ser Arg Gly Tyr Thr Asn Tyr Asn Gln Lys Val Lys Asp
130 135 140

Arg Phe Thr Ile Ser Arg Asp Asn Ser Lys Asn Thr Ala Phe Leu Gln
145 150 155 160

Met Asp Ser Leu Arg Pro Glu Asp Thr Gly Val Tyr Phe Cys Ala Arg
165 170 175

Tyr Tyr Asp Asp His Tyr Cys Leu Asp Tyr Trp Gly Gln Gly Thr Pro

```
            180                 185                 190

Val Thr Val Ser Ser Ala Ser Thr Lys Gly Pro Ser Val Phe Pro Leu
        195                 200                 205

Ala Pro Ser Ser Lys Ser Thr Ser Gly Gly Thr Ala Ala Leu Gly Cys
    210                 215                 220

Leu Val Lys Asp Tyr Phe Pro Glu Pro Val Thr Val Ser Trp Asn Ser
225                 230                 235                 240

Gly Ala Leu Thr Ser Gly Val His Thr Phe Pro Ala Val Leu Gln Ser
                245                 250                 255

Ser Gly Leu Tyr Ser Leu Ser Ser Val Val Thr Val Pro Ser Ser Ser
            260                 265                 270

Leu Gly Thr Gln Thr Tyr Ile Cys Asn Val Asn His Lys Pro Ser Asn
        275                 280                 285

Thr Lys Val Asp Lys Lys Val Glu Pro Lys Ser Cys Asp Lys Thr His
    290                 295                 300

Thr Cys Pro Pro Cys Pro Ala Pro Glu Ala Ala Gly Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Glu Glu Met Thr Lys Asn Gln Val Ser Leu Thr Cys Leu
        435                 440                 445

Val Lys Gly Phe Tyr Pro Ser Asp Ile Ala Val Glu Trp Glu Ser Asn
    450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
            500                 505                 510

His Asn His Tyr Thr Gln Lys Ser Leu Ser Leu Ser Pro Gly Lys
        515                 520                 525
```

<210> SEQ ID NO 388
<211> LENGTH: 213
<212> TYPE: PRT
<213> ORGANISM: Artificial Sequence
<220> FEATURE:
<223> OTHER INFORMATION: COVA420 Light Chain

<400> SEQUENCE: 388

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
```

```
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 389
<211> LENGTH: 527
<212> TYPE: PRT
<213> ORGANISM: Artificial Sequence
<220> FEATURE:
<223> OTHER INFORMATION: COVA422 Heavy Chain

<400> SEQUENCE: 389

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

-continued

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gly Val Thr Leu Phe Val Ala Leu Tyr Asp Tyr Thr Ser Tyr Asn Thr
465                 470                 475                 480

Arg Asp Leu Ser Phe His Lys Gly Glu Lys Phe Gln Ile Leu Arg Met
                485                 490                 495

Glu Asp Gly Val Trp Trp Glu Ala Arg Ser Leu Thr Thr Gly Glu Thr
            500                 505                 510

Gly Tyr Ile Pro Ser Asn Tyr Val Ala Pro Val Asp Ser Ile Gln
        515                 520                 525


<210> SEQ ID NO 390
<211> LENGTH: 213
<212> TYPE: PRT
<213> ORGANISM: Artificial Sequence
<220> FEATURE:
<223> OTHER INFORMATION: COVA422 Light Chain

<400> SEQUENCE: 390

Asp Ile Gln Met Thr Gln Ser Pro Ser Ser Leu Ser Ala Ser Val Gly
```

```
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 391
<211> LENGTH: 495
<212> TYPE: PRT
<213> ORGANISM: Artificial Sequence
<220> FEATURE:
<223> OTHER INFORMATION: COVA446: anti-HER2 x anti CD3 single chain Fv

<400> SEQUENCE: 391

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
```

```
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Trp Val Arg Gln Ala Pro Gly
        275                 280                 285

Lys Gly Leu Glu Trp Val Ala Arg Ile Arg Ser Lys Tyr Asn Asn Tyr
    290                 295                 300

Ala Thr Tyr Tyr Ala Asp Ser Val Lys Asp Arg Phe Thr Ile Ser Arg
305                 310                 315                 320

Asp Asp Ser Lys Asn Thr Ala Tyr Leu Gln Met Asn Asn Leu Lys Thr
                325                 330                 335

Glu Asp Thr Ala Val Tyr Tyr Cys Val Arg His Gly Asn Phe Gly Asn
            340                 345                 350

Ser Tyr Ile Ser Tyr Trp Ala Tyr Trp Gly Gln Gly Thr Leu Val Thr
        355                 360                 365

Val Ser Ser Gly Gly Gly Gly Ser Gly Gly Gly Gly Ser Gly Gly Gly
    370                 375                 380

Gly Ser Gln Thr Val Val Thr Gln Glu Pro Ser Leu Thr Val Ser Pro
385                 390                 395                 400

Gly Gly Thr Val Thr Leu Thr Cys Gly Ser Ser Thr Gly Ala Val Thr
                405                 410                 415

Ser Gly Asn Tyr Pro Asn Trp Val Gln Gln Lys Pro Gly Gln Ala Pro
            420                 425                 430

Arg Gly Leu Ile Gly Gly Thr Lys Phe Leu Ala Pro Gly Thr Pro Ala
        435                 440                 445

Arg Phe Ser Gly Ser Leu Leu Gly Gly Lys Ala Ala Leu Thr Leu Ser
    450                 455                 460

Gly Val Gln Pro Glu Asp Glu Ala Glu Tyr Tyr Cys Val Leu Trp Tyr
465                 470                 475                 480

Ser Asn Arg Trp Val Phe Gly Gly Gly Thr Lys Leu Thr Val Leu
                485                 490                 495
```

<210> SEQ ID NO 392
<211> LENGTH: 66
<212> TYPE: PRT
<213> ORGANISM: Artificial Sequence
<220> FEATURE:
<223> OTHER INFORMATION: anti-EGFR Fynomer ER7L2D6

<400> SEQUENCE: 392

```
Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
```

```
            20                  25                  30

Leu Ser Phe Glu Thr Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 393
<211> LENGTH: 532
<212> TYPE: PRT
<213> ORGANISM: Artificial Sequence
<220> FEATURE:
<223> OTHER INFORMATION: COVA493 HC

<400> SEQUENCE: 393

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Ser Phe Glu Thr Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln Gly Gly Gly Gly Ser Gly Gly Gly Gly Ser Gly Gly Gly Gly
65                  70                  75                  80

Ser Gln Val Gln Leu Gln Gln Ser Gly Ala Glu Leu Ala Arg Pro Gly
                85                  90                  95

Ala Ser Val Lys Met Ser Cys Lys Ala Ser Gly Tyr Thr Phe Thr Arg
            100                 105                 110

Ser Thr Met His Trp Val Lys Gln Arg Pro Gly Gln Gly Leu Glu Trp
        115                 120                 125

Ile Gly Tyr Ile Asn Pro Ser Ser Ala Tyr Thr Asn Tyr Asn Gln Lys
    130                 135                 140

Phe Lys Asp Lys Ala Thr Leu Thr Ala Asp Lys Ser Ser Ser Thr Ala
145                 150                 155                 160

Tyr Met Gln Leu Ser Ser Leu Thr Ser Glu Asp Ser Ala Val Tyr Tyr
                165                 170                 175

Cys Ala Ser Pro Gln Val His Tyr Asp Tyr Asn Gly Phe Pro Tyr Trp
            180                 185                 190

Gly Gln Gly Thr Leu Val Thr Val Ser Ala Ala Ser Thr Lys Gly Pro
        195                 200                 205

Ser Val Phe Pro Leu Ala Pro Ser Ser Lys Ser Thr Ser Gly Gly Thr
    210                 215                 220

Ala Ala Leu Gly Cys Leu Val Lys Asp Tyr Phe Pro Glu Pro Val Thr
225                 230                 235                 240

Val Ser Trp Asn Ser Gly Ala Leu Thr Ser Gly Val His Thr Phe Pro
                245                 250                 255

Ala Val Leu Gln Ser Ser Gly Leu Tyr Ser Leu Ser Ser Val Val Thr
            260                 265                 270

Val Pro Ser Ser Ser Leu Gly Thr Gln Thr Tyr Ile Cys Asn Val Asn
        275                 280                 285

His Lys Pro Ser Asn Thr Lys Val Asp Lys Lys Val Glu Pro Lys Ser
    290                 295                 300

Cys Asp Lys Thr His Thr Cys Pro Pro Cys Pro Ala Pro Glu Leu Leu
```

```
305                 310                 315                 320

Gly Gly Pro Ser Val Phe Leu Phe Pro Pro Lys Pro Lys Asp Thr Leu
                325                 330                 335

Met Ile Ser Arg Thr Pro Glu Val Thr Cys Val Val Val Ala Val Ser
            340                 345                 350

His Glu Asp Pro Glu Val Lys Phe Asn Trp Tyr Val Asp Gly Val Glu
        355                 360                 365

Val His Asn Ala Lys Thr Lys Pro Arg Glu Glu Gln Tyr Asn Ser Thr
    370                 375                 380

Tyr Arg Val Val Ser Val Leu Thr Val Leu His Gln Asp Trp Leu Asn
385                 390                 395                 400

Gly Lys Glu Tyr Lys Cys Lys Val Ser Asn Lys Ala Leu Ala Ala Pro
                405                 410                 415

Ile Glu Lys Thr Ile Ser Lys Ala Lys Gly Gln Pro Arg Glu Pro Gln
            420                 425                 430

Val Tyr Thr Leu Pro Pro Ser Arg Glu Glu Met Thr Lys Asn Gln Val
        435                 440                 445

Ser Leu Thr Cys Leu Val Lys Gly Phe Tyr Pro Ser Asp Ile Ala Val
    450                 455                 460

Glu Trp Glu Ser Asn Gly Gln Pro Glu Asn Asn Tyr Lys Thr Thr Pro
465                 470                 475                 480

Pro Val Leu Asp Ser Asp Gly Ser Phe Phe Leu Tyr Ser Lys Leu Thr
                485                 490                 495

Val Asp Lys Ser Arg Trp Gln Gln Gly Asn Val Phe Ser Cys Ser Val
            500                 505                 510

Met His Glu Ala Leu His Asn His Tyr Thr Gln Lys Ser Leu Ser Leu
        515                 520                 525

Ser Pro Gly Lys
    530


<210> SEQ ID NO 394
<211> LENGTH: 451
<212> TYPE: PRT
<213> ORGANISM: Artificial Sequence
<220> FEATURE:
<223> OTHER INFORMATION: COVA489 HC, anti-CD3 antibody

<400> SEQUENCE: 394

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
```

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Ala Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 395
<211> LENGTH: 213
<212> TYPE: PRT
<213> ORGANISM: Artificial Sequence
<220> FEATURE:
<223> OTHER INFORMATION: COVA489 LC, anti-CD3 antibody

<400> SEQUENCE: 395

Gln Val Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
```

```
        35                  40                  45

Asp Ser Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 396
<211> LENGTH: 501
<212> TYPE: PRT
<213> ORGANISM: Artificial Sequence
<220> FEATURE:
<223> OTHER INFORMATION: COVA445, anti-EGFR/CD3 scFv control

<400> SEQUENCE: 396

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Gly Ser Gln Val Gln Leu Lys Gln
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Asn Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Asn Thr Asp Tyr Asn Thr Pro Phe Thr Ser Arg Leu Ser Ile Asn
```

```
            180                 185                 190

Lys Asp Asn Ser Lys Ser Gln Val Phe Phe Lys Met Asn Ser Leu Gln
        195                 200                 205

Ser Asn Asp Thr Ala Ile Tyr Tyr Cys Ala Arg Ala Leu Thr Tyr Tyr
    210                 215                 220

Asp Tyr Glu Phe Ala Tyr Trp Gly Gln Gly Thr Leu Val Thr Val Ser
225                 230                 235                 240

Ser Gly Gly Gly Gly Ser Glu Val Gln Leu Val Glu Ser Gly Gly Gly
                245                 250                 255

Leu Val Gln Pro Gly Gly Ser Leu Lys Leu Ser Cys Ala Ala Ser Gly
            260                 265                 270

Phe Thr Phe Asn Lys Tyr Ala Met Asn Trp Val Arg Gln Ala Pro Gly
        275                 280                 285

Lys Gly Leu Glu Trp Val Ala Arg Ile Arg Ser Lys Tyr Asn Asn Tyr
    290                 295                 300

Ala Thr Tyr Tyr Ala Asp Ser Val Lys Asp Arg Phe Thr Ile Ser Arg
305                 310                 315                 320

Asp Asp Ser Lys Asn Thr Ala Tyr Leu Gln Met Asn Asn Leu Lys Thr
                325                 330                 335

Glu Asp Thr Ala Val Tyr Tyr Cys Val Arg His Gly Asn Phe Gly Asn
            340                 345                 350

Ser Tyr Ile Ser Tyr Trp Ala Tyr Trp Gly Gln Gly Thr Leu Val Thr
        355                 360                 365

Val Ser Ser Gly Gly Gly Gly Ser Gly Gly Gly Gly Ser Gly Gly Gly
    370                 375                 380

Gly Ser Gln Thr Val Val Thr Gln Glu Pro Ser Leu Thr Val Ser Pro
385                 390                 395                 400

Gly Gly Thr Val Thr Leu Thr Cys Gly Ser Ser Thr Gly Ala Val Thr
                405                 410                 415

Ser Gly Asn Tyr Pro Asn Trp Val Gln Gln Lys Pro Gly Gln Ala Pro
            420                 425                 430

Arg Gly Leu Ile Gly Gly Thr Lys Phe Leu Ala Pro Gly Thr Pro Ala
        435                 440                 445

Arg Phe Ser Gly Ser Leu Leu Gly Gly Lys Ala Ala Leu Thr Leu Ser
    450                 455                 460

Gly Val Gln Pro Glu Asp Glu Ala Glu Tyr Tyr Cys Val Leu Trp Tyr
465                 470                 475                 480

Ser Asn Arg Trp Val Phe Gly Gly Gly Thr Lys Leu Thr Val Leu His
                485                 490                 495

His His His His His
            500


<210> SEQ ID NO 397
<211> LENGTH: 63
<212> TYPE: PRT
<213> ORGANISM: Artificial Sequence
<220> FEATURE:
<223> OTHER INFORMATION: anti-CD33 Fynomer EE1L1B3

<400> SEQUENCE: 397

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Asn Ser
            20                  25                  30

Ser Glu Gly Pro Phe Trp Glu Ala His Ser Leu Thr Thr Gly Glu Thr
```

-continued 35 40 45

Gly Trp Ile Pro Ser Asn Tyr Val Ala Pro Val Asp Ser Ile Gln
50 55 60

<210> SEQ ID NO 398
<211> LENGTH: 291
<212> TYPE: PRT
<213> ORGANISM: Artificial Sequence
<220> FEATURE:
<223> OTHER INFORMATION: COVA467 LC

<400> SEQUENCE: 398

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

Asn Trp Tyr Gln Gln Thr Pro Gly Lys Ala Pro Lys Arg Trp Ile Tyr
35 40 45

Asp Thr Ser Lys Leu Ala Ser Gly Val Pro Ser Arg Phe Ser Gly Ser
50 55 60

Gly Ser Gly Thr Asp Tyr Thr Phe Thr Ile Ser Ser Leu Gln Pro Glu
65 70 75 80

Asp Ile Ala Thr Tyr Tyr Cys Gln Gln Trp Ser Ser Asn Pro Phe Thr
85 90 95

Phe Gly Gln Gly Thr Lys Leu Gln Ile Thr Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys Gly Gly Gly Gly Ser Gly Gly Gly Gly Ser Gly
210 215 220

Gly Gly Gly Ser Gly Val Thr Leu Phe Val Ala Leu Tyr Asp Tyr Glu
225 230 235 240

Ala Leu Gly Ala His Glu Leu Ser Phe His Lys Gly Glu Lys Phe Gln
245 250 255

Ile Leu Asn Ser Ser Glu Gly Pro Phe Trp Glu Ala His Ser Leu Thr
260 265 270

Thr Gly Glu Thr Gly Trp Ile Pro Ser Asn Tyr Val Ala Pro Val Asp
275 280 285

Ser Ile Gln
290

<210> SEQ ID NO 399
<211> LENGTH: 511
<212> TYPE: PRT
<213> ORGANISM: Artificial Sequence
<220> FEATURE:
<223> OTHER INFORMATION: COVA463, anti-CD3/CD33 scFv control

<400> SEQUENCE: 399

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Lys Gln Ala Pro Gly Gln Gly Leu Lys Trp Met
35 40 45

Gly Trp Ile Asn Thr Tyr Thr Gly Glu Pro Thr Tyr Ala Asp Asp Phe
50 55 60

Lys Gly Arg Val Thr Met Thr Ser Asp Thr Ser Thr Ser Thr Ala Tyr
65 70 75 80

Leu Glu Leu His Asn Leu Arg Ser Asp Asp Thr Ala Val Tyr Tyr Cys
85 90 95

Ala Arg Trp Ser Trp Ser Asp Gly Tyr Tyr Val Tyr Phe Asp Tyr Trp
100 105 110

Gly Gln Gly Thr Thr Val Thr Val Ser Ser Gly Gly Gly Gly Ser Gly
115 120 125

Gly Gly Gly Ser Gly Gly Gly Gly Ser Asp Ile Val Met Thr Gln Ser
130 135 140

Pro Asp Ser Leu Thr Val Ser Leu Gly Glu Arg Thr Thr Ile Asn Cys
145 150 155 160

Lys Ser Ser Gln Ser Val Leu Asp Ser Ser Lys Asn Lys Asn Ser Leu
165 170 175

Ala Trp Tyr Gln Gln Lys Pro Gly Gln Pro Pro Lys Leu Leu Leu Ser
180 185 190

Trp Ala Ser Thr Arg Glu Ser Gly Ile Pro Asp Arg Phe Ser Gly Ser
195 200 205

Gly Ser Gly Thr Asp Phe Thr Leu Thr Ile Asp Ser Leu Gln Pro Glu
210 215 220

Asp Ser Ala Thr Tyr Tyr Cys Gln Gln Ser Ala His Phe Pro Ile Thr
225 230 235 240

Phe Gly Gln Gly Thr Arg Leu Glu Ile Lys Ser Gly Gly Gly Gly Ser
245 250 255

Glu Val Gln Leu Val Glu Ser Gly Gly Gly Leu Val Gln Pro Gly Gly
260 265 270

Ser Leu Lys Leu Ser Cys Ala Ala Ser Gly Phe Thr Phe Asn Lys Tyr
275 280 285

Ala Met Asn Trp Val Arg Gln Ala Pro Gly Lys Gly Leu Glu Trp Val
290 295 300

Ala Arg Ile Arg Ser Lys Tyr Asn Asn Tyr Ala Thr Tyr Tyr Ala Asp
305 310 315 320

Ser Val Lys Asp Arg Phe Thr Ile Ser Arg Asp Asp Ser Lys Asn Thr
325 330 335

Ala Tyr Leu Gln Met Asn Asn Leu Lys Thr Glu Asp Thr Ala Val Tyr
340 345 350

Tyr Cys Val Arg His Gly Asn Phe Gly Asn Ser Tyr Ile Ser Tyr Trp
355 360 365

Ala Tyr Trp Gly Gln Gly Thr Leu Val Thr Val Ser Ser Gly Gly Gly
370 375 380

Gly Ser Gly Gly Gly Gly Ser Gly Gly Gly Gly Ser Gln Thr Val Val
385 390 395 400

Thr Gln Glu Pro Ser Leu Thr Val Ser Pro Gly Gly Thr Val Thr Leu

```
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Ala Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu His His His His His His
            500                 505                 510


<210> SEQ ID NO 400
<211> LENGTH: 63
<212> TYPE: PRT
<213> ORGANISM: Artificial Sequence
<220> FEATURE:
<223> OTHER INFORMATION: anti-CD33 Fynomer EE3L11B4

<400> SEQUENCE: 400

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Arg Gly
            20                  25                  30

Ser Lys Gly Pro Phe Trp Glu Ala His Ser Leu Thr Thr Gly Glu Thr
        35                  40                  45

Gly Trp Ile Pro Ser Asn Tyr Val Ala Pro Val Asp Ser Ile Gln
    50                  55                  60


<210> SEQ ID NO 401
<211> LENGTH: 64
<212> TYPE: PRT
<213> ORGANISM: Artificial Sequence
<220> FEATURE:
<223> OTHER INFORMATION: anti-CD33 Fynomer EE4L12D5

<400> SEQUENCE: 401

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Ser Ser
            20                  25                  30

Leu Ala Val Gly Pro Phe Trp Glu Ala His Ser Leu Thr Thr Gly Glu
        35                  40                  45

Thr Gly Trp Ile Pro Ser Asn Tyr Val Ala Pro Val Asp Ser Ile Gln
    50                  55                  60


<210> SEQ ID NO 402
<211> LENGTH: 64
<212> TYPE: PRT
<213> ORGANISM: Artificial Sequence
<220> FEATURE:
<223> OTHER INFORMATION: anti-CD33 Fynomer EE4L12D3

<400> SEQUENCE: 402

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Met Met
            20                  25                  30
```

```
Ser Asp Glu Gly Pro Phe Trp Glu Ala His Ser Leu Thr Thr Gly Glu
        35                  40                  45

Thr Gly Trp Ile Pro Ser Asn Tyr Val Ala Pro Val Asp Ser Ile Gln
    50                  55                  60


<210> SEQ ID NO 403
<211> LENGTH: 64
<212> TYPE: PRT
<213> ORGANISM: Artificial Sequence
<220> FEATURE:
<223> OTHER INFORMATION: anti-CD33 Fynomer EE4L12G1

<400> SEQUENCE: 403

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Ser Pro
            20                  25                  30

Arg Ser Glu Gly Pro Phe Trp Glu Ala His Ser Leu Thr Thr Gly Glu
        35                  40                  45

Thr Gly Trp Ile Pro Ser Asn Tyr Val Ala Pro Val Asp Ser Ile Gln
    50                  55                  60


<210> SEQ ID NO 404
<211> LENGTH: 64
<212> TYPE: PRT
<213> ORGANISM: Artificial Sequence
<220> FEATURE:
<223> OTHER INFORMATION: anti-CD33 Fynomer EE6L12C6

<400> SEQUENCE: 404

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Ser Ser
            20                  25                  30

Leu Leu Gln Gly Pro Phe Trp Glu Ala His Ser Leu Thr Thr Gly Glu
        35                  40                  45

Thr Gly Trp Ile Pro Ser Asn Tyr Val Ala Pro Val Asp Ser Ile Gln
    50                  55                  60


<210> SEQ ID NO 405
<211> LENGTH: 65
<212> TYPE: PRT
<213> ORGANISM: Artificial Sequence
<220> FEATURE:
<223> OTHER INFORMATION: anti-CD33 Fynomer EE23L59C1

<400> SEQUENCE: 405

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Asp Val
            20                  25                  30

Thr Leu Ala Gly Gly Pro Phe Trp Glu Ala His Ser Leu Thr Thr Gly
        35                  40                  45

Glu Thr Gly Trp Ile Pro Ser Asn Tyr Val Ala Pro Val Asp Ser Ile
    50                  55                  60

Gln
65


<210> SEQ ID NO 406
<211> LENGTH: 65
```

```
<212> TYPE: PRT
<213> ORGANISM: Artificial Sequence
<220> FEATURE:
<223> OTHER INFORMATION: anti-CD33 Fynomer EE23L59A6A

<400> SEQUENCE: 406

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Tyr Val
            20                  25                  30

Ala Leu Glu Gly Gly Pro Phe Trp Glu Ala His Ser Leu Thr Thr Gly
        35                  40                  45

Glu Thr Gly Trp Ile Pro Ser Asn Tyr Val Ala Pro Val Asp Ser Ile
    50                  55                  60

Gln
65


<210> SEQ ID NO 407
<211> LENGTH: 64
<212> TYPE: PRT
<213> ORGANISM: Artificial Sequence
<220> FEATURE:
<223> OTHER INFORMATION: anti-CD33 Fynomer EE23L62E1

<400> SEQUENCE: 407

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Leu Arg
            20                  25                  30

Val Gln Leu Gly Pro Phe Trp Glu Ala His Ser Leu Thr Thr Gly Glu
        35                  40                  45

Thr Gly Trp Ile Pro Ser Asn Tyr Val Ala Pro Val Asp Ser Ile Gln
    50                  55                  60


<210> SEQ ID NO 408
<211> LENGTH: 65
<212> TYPE: PRT
<213> ORGANISM: Artificial Sequence
<220> FEATURE:
<223> OTHER INFORMATION: anti-CD33 Fynomer EE23L62D6

<400> SEQUENCE: 408

Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Asp Val
            20                  25                  30

Gly Leu Arg Gly Gly Pro Phe Trp Glu Ala His Ser Leu Thr Thr Gly
        35                  40                  45

Glu Thr Gly Trp Ile Pro Ser Asn Tyr Val Ala Pro Val Asp Ser Ile
    50                  55                  60

Gln
65


<210> SEQ ID NO 409
<211> LENGTH: 65
<212> TYPE: PRT
<213> ORGANISM: Artificial Sequence
<220> FEATURE:
<223> OTHER INFORMATION: anti-CD33 Fynomer EE23L62H7

<400> SEQUENCE: 409
```

-continued

```
Gly Val Thr Leu Phe Val Ala Leu Tyr Asp Tyr Glu Ala Leu Gly Ala
1               5                   10                  15

His Glu Leu Ser Phe His Lys Gly Glu Lys Phe Gln Ile Leu Leu Arg
            20                  25                  30

Leu Val Leu Leu Gly Pro Phe Trp Glu Ala His Ser Leu Thr Thr Gly
        35                  40                  45

Glu Thr Gly Trp Ile Pro Ser Asn Tyr Val Ala Pro Val Asp Ser Ile
    50                  55                  60

Gln
65


<210> SEQ ID NO 410
<211> LENGTH: 66
<212> TYPE: PRT
<213> ORGANISM: Artificial Sequence
<220> FEATURE:
<223> OTHER INFORMATION: anti-EGFR Fynomer ER9L3D7

<400> SEQUENCE: 410

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Ser Thr Glu Asn Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 411
<211> LENGTH: 66
<212> TYPE: PRT
<213> ORGANISM: Artificial Sequence
<220> FEATURE:
<223> OTHER INFORMATION: anti-EGFR Fynomer ER5L1E2

<400> SEQUENCE: 411

Gly Val Thr Leu Phe Val Ala Val Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Asn Arg Glu Ser Glu Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 412
<211> LENGTH: 66
<212> TYPE: PRT
<213> ORGANISM: Artificial Sequence
<220> FEATURE:
<223> OTHER INFORMATION: anti-EGFR Fynomer ER5L1E5

<400> SEQUENCE: 412

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
```

```
            20                  25                  30

Leu Gln Phe Glu Thr Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 413
<211> LENGTH: 66
<212> TYPE: PRT
<213> ORGANISM: Artificial Sequence
<220> FEATURE:
<223> OTHER INFORMATION: anti-EGFR Fynomer ER5L1H3

<400> SEQUENCE: 413

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Ala Phe Glu Thr Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 414
<211> LENGTH: 66
<212> TYPE: PRT
<213> ORGANISM: Artificial Sequence
<220> FEATURE:
<223> OTHER INFORMATION: anti-EGFR Fynomer ER6L1A9

<400> SEQUENCE: 414

Gly Val Thr Leu Phe Val Ala Leu Tyr Asp Tyr Glu Ala Arg Gly Leu
1               5                   10                  15

Asn Arg Leu Phe Asp Leu Ser Phe His Lys Gly Glu Lys Phe Gln Ile
            20                  25                  30

Leu Asp Arg Thr Asn Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 415
<211> LENGTH: 66
<212> TYPE: PRT
<213> ORGANISM: Artificial Sequence
<220> FEATURE:
<223> OTHER INFORMATION: anti-EGFR Fynomer ER6L1C10

<400> SEQUENCE: 415

Gly Val Thr Leu Phe Val Ala Leu Tyr Asp Tyr Glu Ala Arg Gly Leu
1               5                   10                  15

His Arg Met Phe Asp Leu Ser Phe His Lys Gly Glu Lys Phe Gln Ile
            20                  25                  30

Leu Asn Arg Glu Thr Gly Asp Trp Trp Glu Ala Arg Ser Leu Thr Thr
        35                  40                  45
```

```
Gly Glu Thr Gly Tyr Ile Pro Ser Asn Tyr Val Ala Pro Val Asp Ser
    50                  55                  60

Ile Gln
65


<210> SEQ ID NO 416
<211> LENGTH: 66
<212> TYPE: PRT
<213> ORGANISM: Artificial Sequence
<220> FEATURE:
<223> OTHER INFORMATION: anti-EGFR Fynomer ER6L1F9

<400> SEQUENCE: 416

Gly Val Thr Leu Phe Val Ala Leu Tyr Asp Tyr Glu Ala Arg Gly Leu
1               5                   10                  15

Asn Arg Leu Phe Asp Leu Ser Phe His Lys Gly Glu Lys Phe Gln Ile
            20                  25                  30

Leu Asp Arg Thr Asn Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 417
<211> LENGTH: 66
<212> TYPE: PRT
<213> ORGANISM: Artificial Sequence
<220> FEATURE:
<223> OTHER INFORMATION: anti-EGFR Fynomer ER7L2E8

<400> SEQUENCE: 417

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Thr Arg Glu Thr Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65


<210> SEQ ID NO 418
<211> LENGTH: 67
<212> TYPE: PRT
<213> ORGANISM: Artificial Sequence
<220> FEATURE:
<223> OTHER INFORMATION: anti-EGFR Fynomer ER8L3G1

<400> SEQUENCE: 418

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Asp Thr Ser Glu Ser Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60
```

Ser Ile Gln
65

<210> SEQ ID NO 419
<211> LENGTH: 66
<212> TYPE: PRT
<213> ORGANISM: Artificial Sequence
<220> FEATURE:
<223> OTHER INFORMATION: anti-EGFR Fynomer 3D5

<400> SEQUENCE: 419

Gly Val Thr Leu Phe Val Ala Leu Tyr Asp Tyr Glu Ala Arg Gly Leu
1 5 10 15

Asn Arg Met Phe Asp Leu Ser Phe His Lys Gly Glu Lys Phe Gln Ile
20 25 30

Leu Leu Pro Gln Glu Gly Asp Trp Trp Glu Ala Arg Ser Leu Thr Thr
35 40 45

Gly Glu Thr Gly Tyr Ile Pro Ser Asn Tyr Val Ala Pro Val Asp Ser
50 55 60

Ile Gln
65

<210> SEQ ID NO 420
<211> LENGTH: 66
<212> TYPE: PRT
<213> ORGANISM: Artificial Sequence
<220> FEATURE:
<223> OTHER INFORMATION: anti-EGFR Fynomer 1C6

<400> SEQUENCE: 420

Gly Val Thr Leu Phe Val Ala Leu Tyr Asp Tyr Glu Ala Arg Gly Leu
1 5 10 15

His Arg Met Phe Asp Leu Ser Phe His Lys Gly Glu Lys Phe Gln Ile
20 25 30

Leu Asp Arg Thr Asn Gly Asp Trp Trp Glu Ala Arg Ser Leu Thr Thr
35 40 45

Gly Glu Thr Gly Tyr Ile Pro Ser Asn Tyr Val Ala Pro Val Asp Ser
50 55 60

Ile Gln
65

<210> SEQ ID NO 421
<211> LENGTH: 294
<212> TYPE: PRT
<213> ORGANISM: Artificial Sequence
<220> FEATURE:
<223> OTHER INFORMATION: COVA494 LC

<400> SEQUENCE: 421

Gly Val Thr Leu Phe Val Ala Leu Tyr Asp Tyr Glu Ala Arg Gly Leu
1 5 10 15

Asn Arg Met Phe Asp Leu Ser Phe His Lys Gly Glu Lys Phe Gln Ile
20 25 30

Leu Ser Phe Glu Thr Gly Asp Trp Trp Glu Ala Arg Ser Leu Thr Thr
35 40 45

Gly Glu Thr Gly Tyr Ile Pro Ser Asn Tyr Val Ala Pro Val Asp Ser
50 55 60

Ile Gln Gly Gly Gly Gly Ser Gly Gly Gly Gly Ser Gly Gly Gly Gly
65 70 75 80

Ser Gln Val Val Leu Thr Gln Ser Pro Ala Ile Met Ser Ala Phe Pro

```
                85                  90                  95

Gly Glu Lys Val Thr Met Thr Cys Ser Ala Ser Ser Ser Val Ser Tyr
            100                 105                 110

Met Asn Trp Tyr Gln Gln Lys Ser Gly Thr Ser Pro Lys Arg Trp Ile
        115                 120                 125

Tyr Asp Ser Ser Lys Leu Ala Ser Gly Val Pro Ala Arg Phe Ser Gly
    130                 135                 140

Ser Gly Ser Gly Thr Ser Tyr Ser Leu Thr Ile Ser Ser Met Glu Thr
145                 150                 155                 160

Glu Asp Ala Ala Thr Tyr Tyr Cys Gln Gln Trp Ser Arg Asn Pro Pro
                165                 170                 175

Thr Phe Gly Gly Gly Thr Lys Leu Gln Ile Thr Arg Thr Val Ala Ala
            180                 185                 190

Pro Ser Val Phe Ile Phe Pro Pro Ser Asp Glu Gln Leu Lys Ser Gly
        195                 200                 205

Thr Ala Ser Val Val Cys Leu Leu Asn Asn Phe Tyr Pro Arg Glu Ala
    210                 215                 220

Lys Val Gln Trp Lys Val Asp Asn Ala Leu Gln Ser Gly Asn Ser Gln
225                 230                 235                 240

Glu Ser Val Thr Glu Gln Asp Ser Lys Asp Ser Thr Tyr Ser Leu Ser
                245                 250                 255

Ser Thr Leu Thr Leu Ser Lys Ala Asp Tyr Glu Lys His Lys Val Tyr
            260                 265                 270

Ala Cys Glu Val Thr His Gln Gly Leu Ser Ser Pro Val Thr Lys Ser
        275                 280                 285

Phe Asn Arg Gly Glu Cys
    290


<210> SEQ ID NO 422
<211> LENGTH: 532
<212> TYPE: PRT
<213> ORGANISM: Artificial Sequence
<220> FEATURE:
<223> OTHER INFORMATION: COVA497 HC

<400> SEQUENCE: 422

Gly Val Thr Leu Phe Val Ala Leu Tyr Asp Tyr Glu Ala Arg Gly Leu
1               5                   10                  15

Asn Arg Met Phe Asp Leu Ser Phe His Lys Gly Glu Lys Phe Gln Ile
            20                  25                  30

Leu Ser Thr Glu Asn Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln Gly Gly Gly Gly Ser Gly Gly Gly Gly Ser Gly Gly Gly Gly
65                  70                  75                  80

Ser Gln Val Gln Leu Gln Gln Ser Gly Ala Glu Leu Ala Arg Pro Gly
                85                  90                  95

Ala Ser Val Lys Met Ser Cys Lys Ala Ser Gly Tyr Thr Phe Thr Arg
            100                 105                 110

Ser Thr Met His Trp Val Lys Gln Arg Pro Gly Gln Gly Leu Glu Trp
        115                 120                 125

Ile Gly Tyr Ile Asn Pro Ser Ser Ala Tyr Thr Asn Tyr Asn Gln Lys
    130                 135                 140

Phe Lys Asp Lys Ala Thr Leu Thr Ala Asp Lys Ser Ser Ser Thr Ala
```

-continued

```
145                 150                 155                 160

Tyr Met Gln Leu Ser Ser Leu Thr Ser Glu Asp Ser Ala Val Tyr Tyr
                165                 170                 175

Cys Ala Ser Pro Gln Val His Tyr Asp Tyr Asn Gly Phe Pro Tyr Trp
            180                 185                 190

Gly Gln Gly Thr Leu Val Thr Val Ser Ala Ala Ser Thr Lys Gly Pro
        195                 200                 205

Ser Val Phe Pro Leu Ala Pro Ser Ser Lys Ser Thr Ser Gly Gly Thr
    210                 215                 220

Ala Ala Leu Gly Cys Leu Val Lys Asp Tyr Phe Pro Glu Pro Val Thr
225                 230                 235                 240

Val Ser Trp Asn Ser Gly Ala Leu Thr Ser Gly Val His Thr Phe Pro
                245                 250                 255

Ala Val Leu Gln Ser Ser Gly Leu Tyr Ser Leu Ser Ser Val Val Thr
            260                 265                 270

Val Pro Ser Ser Ser Leu Gly Thr Gln Thr Tyr Ile Cys Asn Val Asn
        275                 280                 285

His Lys Pro Ser Asn Thr Lys Val Asp Lys Lys Val Glu Pro Lys Ser
    290                 295                 300

Cys Asp Lys Thr His Thr Cys Pro Pro Cys Pro Ala Pro Glu Leu Leu
305                 310                 315                 320

Gly Gly Pro Ser Val Phe Leu Phe Pro Pro Lys Pro Lys Asp Thr Leu
                325                 330                 335

Met Ile Ser Arg Thr Pro Glu Val Thr Cys Val Val Val Ala Val Ser
            340                 345                 350

His Glu Asp Pro Glu Val Lys Phe Asn Trp Tyr Val Asp Gly Val Glu
        355                 360                 365

Val His Asn Ala Lys Thr Lys Pro Arg Glu Glu Gln Tyr Asn Ser Thr
    370                 375                 380

Tyr Arg Val Val Ser Val Leu Thr Val Leu His Gln Asp Trp Leu Asn
385                 390                 395                 400

Gly Lys Glu Tyr Lys Cys Lys Val Ser Asn Lys Ala Leu Ala Ala Pro
                405                 410                 415

Ile Glu Lys Thr Ile Ser Lys Ala Lys Gly Gln Pro Arg Glu Pro Gln
            420                 425                 430

Val Tyr Thr Leu Pro Pro Ser Arg Glu Glu Met Thr Lys Asn Gln Val
        435                 440                 445

Ser Leu Thr Cys Leu Val Lys Gly Phe Tyr Pro Ser Asp Ile Ala Val
    450                 455                 460

Glu Trp Glu Ser Asn Gly Gln Pro Glu Asn Asn Tyr Lys Thr Thr Pro
465                 470                 475                 480

Pro Val Leu Asp Ser Asp Gly Ser Phe Phe Leu Tyr Ser Lys Leu Thr
                485                 490                 495

Val Asp Lys Ser Arg Trp Gln Gln Gly Asn Val Phe Ser Cys Ser Val
            500                 505                 510

Met His Glu Ala Leu His Asn His Tyr Thr Gln Lys Ser Leu Ser Leu
        515                 520                 525

Ser Pro Gly Lys
    530
```

<210> SEQ ID NO 423
<211> LENGTH: 294
<212> TYPE: PRT
<213> ORGANISM: Artificial Sequence

<220> FEATURE:
<223> OTHER INFORMATION: COVA499 LC

<400> SEQUENCE: 423

Gln Val Val Leu Thr Gln Ser Pro Ala Ile Met Ser Ala Phe Pro Gly
1 5 10 15

Glu Lys Val Thr Met Thr Cys Ser Ala Ser Ser Ser Val Ser Tyr Met
20 25 30

Asn Trp Tyr Gln Gln Lys Ser Gly Thr Ser Pro Lys Arg Trp Ile Tyr
35 40 45

Asp Ser Ser Lys Leu Ala Ser Gly Val Pro Ala Arg Phe Ser Gly Ser
50 55 60

Gly Ser Gly Thr Ser Tyr Ser Leu Thr Ile Ser Ser Met Glu Thr Glu
65 70 75 80

Asp Ala Ala Thr Tyr Tyr Cys Gln Gln Trp Ser Arg Asn Pro Pro Thr
85 90 95

Phe Gly Gly Gly Thr Lys Leu Gln Ile Thr Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys Gly Gly Gly Gly Ser Gly Gly Gly Gly Ser Gly
210 215 220

Gly Gly Gly Ser Gly Val Thr Leu Phe Val Ala Leu Tyr Asp Tyr Glu
225 230 235 240

Ala Arg Gly Leu Asn Arg Met Phe Asp Leu Ser Phe His Lys Gly Glu
245 250 255

Lys Phe Gln Ile Leu Ser Thr Glu Asn Gly Asp Trp Trp Glu Ala Arg
260 265 270

Ser Leu Thr Thr Gly Glu Thr Gly Tyr Ile Pro Ser Asn Tyr Val Ala
275 280 285

Pro Val Asp Ser Ile Gln
290

<210> SEQ ID NO 424
<211> LENGTH: 65
<212> TYPE: PRT
<213> ORGANISM: Artificial Sequence
<220> FEATURE:
<223> OTHER INFORMATION: 1B-G10

<400> SEQUENCE: 424

Gly Val Thr Leu Phe Val Ala Leu Tyr Asp Tyr Glu Ala Arg Pro Asn
1 5 10 15

Arg Pro Leu Asp Leu Ser Phe His Lys Gly Glu Lys Phe Gln Ile Leu
20 25 30

Ala Pro Pro Arg Gly Asp Trp Trp Glu Ala Arg Ser Leu Thr Thr Gly

```
        35                  40                  45

Glu Thr Gly Tyr Ile Pro Ser Asn Tyr Val Ala Pro Val Asp Ser Ile
    50                  55                  60

Gln
65


<210> SEQ ID NO 425
<211> LENGTH: 65
<212> TYPE: PRT
<213> ORGANISM: Artificial Sequence
<220> FEATURE:
<223> OTHER INFORMATION: 2B-D2

<400> SEQUENCE: 425

Gly Val Thr Leu Phe Val Ala Leu Tyr Asp Tyr Glu Ala Arg Gly Glu
1               5                   10                  15

Gln Asp Leu Ser Phe His Lys Gly Glu Lys Phe Gln Ile Leu Asn Trp
            20                  25                  30

Trp His Val Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 426
<211> LENGTH: 65
<212> TYPE: PRT
<213> ORGANISM: Artificial Sequence
<220> FEATURE:
<223> OTHER INFORMATION: 1B-H10

<400> SEQUENCE: 426

Gly Val Thr Leu Phe Val Ala Leu Tyr Asp Tyr Glu Ala Arg Gly Glu
1               5                   10                  15

Tyr Asp Leu Ser Phe His Lys Gly Glu Lys Phe Gln Ile Leu Asn Trp
            20                  25                  30

Trp His Val Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65


<210> SEQ ID NO 427
<211> LENGTH: 65
<212> TYPE: PRT
<213> ORGANISM: Artificial Sequence
<220> FEATURE:
<223> OTHER INFORMATION: 1B-B11

<400> SEQUENCE: 427

Gly Val Thr Leu Phe Val Ala Leu Tyr Asp Tyr Glu Ala Arg His Thr
1               5                   10                  15

Phe Asp Leu Ser Phe His Lys Gly Glu Lys Phe Gln Ile Leu Asn Trp
            20                  25                  30

Trp His Val Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60
```

Gln
65

<210> SEQ ID NO 428
<211> LENGTH: 67
<212> TYPE: PRT
<213> ORGANISM: Artificial Sequence
<220> FEATURE:
<223> OTHER INFORMATION: 2B-E9

<400> SEQUENCE: 428

Gly Val Thr Leu Phe Val Ala Leu Tyr Asp Tyr Glu Ala Arg Pro Gly
1 5 10 15

Arg Lys His Asp Leu Ser Phe His Lys Gly Glu Lys Phe Gln Ile Leu
20 25 30

Asn Trp Trp His Val Arg Gly Asp Trp Trp Glu Ala Arg Ser Leu Thr
35 40 45

Thr Gly Glu Thr Gly Tyr Ile Pro Ser Asn Tyr Val Ala Pro Val Asp
50 55 60

Ser Ile Gln
65

<210> SEQ ID NO 429
<211> LENGTH: 67
<212> TYPE: PRT
<213> ORGANISM: Artificial Sequence
<220> FEATURE:
<223> OTHER INFORMATION: 2B-H11

<400> SEQUENCE: 429

Gly Val Thr Leu Phe Val Ala Leu Tyr Asp Tyr Glu Ala Arg Pro Asn
1 5 10 15

Arg Pro Leu Asp Leu Ser Phe His Lys Gly Glu Lys Phe Gln Ile Leu
20 25 30

Asn Trp Trp His Val Arg Gly Asp Trp Trp Glu Ala Arg Ser Leu Thr
35 40 45

Thr Gly Glu Thr Gly Tyr Ile Pro Ser Asn Tyr Val Ala Pro Val Asp
50 55 60

Ser Ile Gln
65

<210> SEQ ID NO 430
<211> LENGTH: 67
<212> TYPE: PRT
<213> ORGANISM: Artificial Sequence
<220> FEATURE:
<223> OTHER INFORMATION: 2B-B12

<400> SEQUENCE: 430

Gly Val Thr Leu Phe Val Ala Leu Tyr Asp Tyr Glu Ala Arg Ser Asp
1 5 10 15

Arg Pro Leu Asp Leu Ser Phe His Lys Gly Glu Lys Phe Gln Ile Leu
20 25 30

Asn Trp Trp His Val Arg Gly Asp Trp Trp Glu Ala Arg Ser Leu Thr
35 40 45

Thr Gly Glu Thr Gly Tyr Ile Pro Ser Asn Tyr Val Ala Pro Val Asp
50 55 60

Ser Ile Gln
65